United States Patent
Jayaram et al.

(10) Patent No.: US 11,113,535 B2
(45) Date of Patent: Sep. 7, 2021

(54) DETERMINING TACTICAL RELEVANCE AND SIMILARITY OF VIDEO SEQUENCES

(71) Applicant: Second Spectrum, Inc., Los Angeles, CA (US)

(72) Inventors: Vivek Jayaram, Los Gatos, CA (US); Nikhil Mitra, Los Angeles, CA (US); Kevin Squire, Pacific Palisades, CA (US)

(73) Assignee: Second Spectrum, Inc., Los Angeles, CA (US)

( * ) Notice: Subject to any disclaimer, the term of this patent is extended or adjusted under 35 U.S.C. 154(b) by 107 days.

(21) Appl. No.: 16/678,520

(22) Filed: Nov. 8, 2019

(65) Prior Publication Data

US 2021/0142066 A1 May 13, 2021

(51) Int. Cl.
| | |
|---|---|
| G06K 9/00 | (2006.01) |
| H04N 21/44 | (2011.01) |
| G06K 9/62 | (2006.01) |

(52) U.S. Cl.
CPC ..... *G06K 9/00724* (2013.01); *G06K 9/00744* (2013.01); *G06K 9/6215* (2013.01); *H04N 21/44008* (2013.01)

(58) Field of Classification Search
CPC ........... G06K 9/00724; G06K 9/00744; G06K 9/6215; H04N 21/44008
See application file for complete search history.

(56) References Cited

U.S. PATENT DOCUMENTS

| | | | |
|---|---|---|---|
| 5,060,171 A | 10/1991 | Steir et al. | |
| 6,959,253 B2 | 10/2005 | Jackson et al. | |
| 7,085,322 B2 | 8/2006 | Ngai et al. | |
| 7,143,083 B2 | 11/2006 | Carlbom et al. | |
| 7,657,836 B2 | 2/2010 | Pan et al. | |
| 7,699,707 B2 | 4/2010 | Bahou | |
| 7,796,155 B1 | 9/2010 | Neely et al. | |
| 7,932,923 B2 | 4/2011 | Lipton et al. | |
| 8,238,662 B2 | 8/2012 | Banerjee et al. | |
| 8,275,672 B1 | 9/2012 | Nguyen et al. | |

(Continued)

FOREIGN PATENT DOCUMENTS

| | | |
|---|---|---|
| CN | 101271527 A | 9/2008 |
| CN | 102750695 A | 10/2012 |

(Continued)

OTHER PUBLICATIONS

PCT/US2017/051768, "International Application Serial No. PCT/US2017/051768, International Preliminary Report on Patentability dated Mar. 28, 2019", 24 pages.

(Continued)

*Primary Examiner* — Dhaval V Patel

(74) *Attorney, Agent, or Firm* — GTC Law Group PC & Affiliates

(57) ABSTRACT

Methods and systems for finding and ranking video sequences that contain tactical sequences (e.g., an uninterrupted portion of a sporting event) that are similar to tactical event content in a target video sequence, such as those occurring in sports, include learning and labelling (e.g., through use of metadata and the like) tactically significant sequences in a plurality of video segments, including a plurality of such tactically significant sequences in a single video segment.

16 Claims, 69 Drawing Sheets

(56) References Cited

U.S. PATENT DOCUMENTS

| | | |
|---|---|---|
| 8,295,683 B2 | 10/2012 | Widdowson |
| 8,453,027 B2 | 5/2013 | Bartz et al. |
| 8,597,133 B2 | 12/2013 | Priester |
| 8,620,077 B1 | 12/2013 | Kwatra et al. |
| 8,810,408 B2 | 8/2014 | Hanson et al. |
| 8,856,030 B2 | 10/2014 | Russek |
| 8,965,172 B2 | 2/2015 | Yu et al. |
| 9,110,988 B1 | 8/2015 | Tan |
| 9,124,856 B2 | 9/2015 | Deshpande et al. |
| 9,141,258 B2 | 9/2015 | Sundstrom |
| 9,168,452 B2 | 10/2015 | Walker et al. |
| 9,171,369 B2 | 10/2015 | Leal et al. |
| 9,294,710 B2 | 3/2016 | Lim et al. |
| 9,339,710 B2 | 5/2016 | Thurman et al. |
| 9,342,785 B2 | 5/2016 | Lucey et al. |
| 9,440,152 B2 | 9/2016 | Thompson et al. |
| 9,596,399 B2 | 3/2017 | Eledath et al. |
| 9,600,717 B1 * | 3/2017 | Dai .................. G06K 9/00342 |
| 9,609,373 B2 | 3/2017 | Rango et al. |
| 9,613,661 B2 | 4/2017 | Matsunaga et al. |
| 9,740,977 B1 | 8/2017 | Moon et al. |
| 9,740,984 B2 | 8/2017 | Lucey et al. |
| 9,744,457 B2 | 8/2017 | Ibrahim et al. |
| 9,750,433 B2 | 9/2017 | Hu et al. |
| 9,814,977 B2 | 11/2017 | Stafford et al. |
| 9,881,221 B2 | 1/2018 | Bala et al. |
| 9,992,470 B1 | 6/2018 | Hofmann |
| 10,231,787 B2 | 3/2019 | Schmidt et al. |
| 10,248,812 B2 | 4/2019 | Pinpin et al. |
| 10,360,685 B2 | 7/2019 | Marty et al. |
| 10,460,176 B2 | 10/2019 | Chang et al. |
| 10,460,177 B2 | 10/2019 | Chan et al. |
| 10,521,671 B2 | 12/2019 | Chang et al. |
| 10,650,442 B2 | 5/2020 | Shihadah et al. |
| 10,713,494 B2 | 7/2020 | Chang et al. |
| 10,748,008 B2 | 8/2020 | Chang et al. |
| 10,755,102 B2 | 8/2020 | Chang et al. |
| 10,755,103 B2 | 8/2020 | Chang et al. |
| 10,762,351 B2 | 9/2020 | Chang et al. |
| 10,769,446 B2 | 9/2020 | Chang et al. |
| 10,832,057 B2 | 11/2020 | Chan et al. |
| 2003/0093810 A1 | 5/2003 | Taniguchi et al. |
| 2003/0172346 A1 | 9/2003 | Gould et al. |
| 2003/0225536 A1 | 12/2003 | Jackson et al. |
| 2004/0017389 A1 | 1/2004 | Pan et al. |
| 2004/0199923 A1 | 10/2004 | Russek |
| 2005/0107159 A1 | 5/2005 | Sato |
| 2005/0160458 A1 | 7/2005 | Baumgartner |
| 2006/0252476 A1 | 11/2006 | Bahou |
| 2006/0256210 A1 | 11/2006 | Ryall et al. |
| 2007/0167216 A1 | 7/2007 | Walker et al. |
| 2007/0238538 A1 | 10/2007 | Priester |
| 2007/0250901 A1 | 10/2007 | McIntire et al. |
| 2008/0193016 A1 | 8/2008 | Lim et al. |
| 2008/0225130 A1 | 9/2008 | Paaaho et al. |
| 2008/0260347 A1 | 10/2008 | Widdowson |
| 2008/0312010 A1 | 12/2008 | Marty et al. |
| 2009/0022394 A1 | 1/2009 | Banerjee et al. |
| 2009/0077503 A1 | 3/2009 | Sundstrom |
| 2009/0183103 A1 | 7/2009 | McCartie et al. |
| 2011/0013087 A1 | 1/2011 | House et al. |
| 2011/0044602 A1 | 2/2011 | Lim et al. |
| 2011/0066908 A1 | 3/2011 | Bartz et al. |
| 2011/0112665 A1 | 5/2011 | Roberts et al. |
| 2011/0202397 A1 | 8/2011 | Lam et al. |
| 2011/0275045 A1 | 11/2011 | Bhupathi et al. |
| 2012/0017236 A1 | 1/2012 | Stafford et al. |
| 2012/0265758 A1 | 10/2012 | Han et al. |
| 2012/0313785 A1 | 12/2012 | Hanson et al. |
| 2013/0027757 A1 | 1/2013 | Lee et al. |
| 2013/0182119 A1 | 7/2013 | Eledath et al. |
| 2013/0208963 A1 | 8/2013 | Leal et al. |
| 2013/0266286 A1 | 10/2013 | Yu et al. |
| 2014/0029921 A1 | 1/2014 | Warren et al. |
| 2014/0037140 A1 | 2/2014 | Benhimane et al. |
| 2014/0058992 A1 * | 2/2014 | Lucey .................. G06N 5/043 |
| | | 706/46 |
| 2014/0064693 A1 | 3/2014 | Deshpande et al. |
| 2014/0085443 A1 * | 3/2014 | Sathish ............ H04N 21/23418 |
| | | 348/61 |
| 2014/0135959 A1 | 5/2014 | Thurman et al. |
| 2014/0245152 A1 | 8/2014 | Carter et al. |
| 2014/0286621 A1 | 9/2014 | Matsunaga et al. |
| 2015/0086072 A1 | 3/2015 | Kompalli et al. |
| 2015/0116493 A1 | 4/2015 | Bala et al. |
| 2015/0121436 A1 | 4/2015 | Rango et al. |
| 2015/0131845 A1 | 5/2015 | Forouhar et al. |
| 2015/0142716 A1 | 5/2015 | Lucey et al. |
| 2015/0248917 A1 * | 9/2015 | Chang .................. G11B 27/28 |
| | | 386/282 |
| 2015/0332465 A1 | 11/2015 | Schmidt et al. |
| 2015/0375117 A1 | 12/2015 | Thompson et al. |
| 2016/0007912 A1 | 1/2016 | Hu et al. |
| 2016/0080830 A1 | 3/2016 | Kim et al. |
| 2016/0148650 A1 | 5/2016 | Laksono |
| 2016/0234566 A1 | 8/2016 | Suoknuuti et al. |
| 2016/0378861 A1 | 12/2016 | Eledath et al. |
| 2017/0001118 A1 | 1/2017 | Ibrahim et al. |
| 2017/0046967 A1 | 2/2017 | Sundquist et al. |
| 2017/0132264 A1 | 5/2017 | Li et al. |
| 2017/0238055 A1 | 8/2017 | Chang et al. |
| 2017/0255826 A1 | 9/2017 | Chang et al. |
| 2017/0255827 A1 | 9/2017 | Chang et al. |
| 2017/0255828 A1 | 9/2017 | Chang et al. |
| 2017/0255829 A1 | 9/2017 | Chang et al. |
| 2017/0269819 A1 | 9/2017 | Pinpin et al. |
| 2018/0025078 A1 | 1/2018 | Quennesson |
| 2019/0075176 A1 | 3/2019 | Nguyen et al. |
| 2019/0114485 A1 | 4/2019 | Chan et al. |
| 2019/0205651 A1 | 7/2019 | Chang et al. |
| 2019/0294631 A1 | 9/2019 | Alcantara et al. |
| 2019/0354765 A1 | 11/2019 | Chan et al. |
| 2019/0392219 A1 | 12/2019 | Chang et al. |
| 2020/0012861 A1 | 1/2020 | Chan et al. |
| 2020/0074181 A1 | 3/2020 | Chang et al. |
| 2020/0074182 A1 | 3/2020 | Chang et al. |
| 2020/0193163 A1 | 6/2020 | Chang et al. |
| 2020/0218902 A1 | 7/2020 | Chang et al. |
| 2020/0342233 A1 | 10/2020 | Chang et al. |
| 2020/0401809 A1 | 12/2020 | Chang et al. |
| 2021/0089779 A1 | 3/2021 | Chan et al. |
| 2021/0089780 A1 | 3/2021 | Chang et al. |

FOREIGN PATENT DOCUMENTS

| | | |
|---|---|---|
| CN | 102985926 A | 3/2013 |
| CN | 103294716 A | 9/2013 |
| WO | 9631047 A2 | 10/1996 |
| WO | 02071334 A2 | 9/2002 |
| WO | 2013166456 A2 | 11/2013 |
| WO | 2015060691 A1 | 4/2015 |
| WO | 2015/131084 A1 | 9/2015 |
| WO | 2016057844 A1 | 4/2016 |
| WO | 2018053257 A1 | 3/2018 |
| WO | 2019183235 A1 | 9/2019 |
| WO | 2019183235 A8 | 10/2019 |

OTHER PUBLICATIONS

PCT/US2019/023192 , "International Application Serial No. PCT/US2019/023192, International Preliminary Report on Patentability dated Oct. 1, 2020", Second Spectrum, Inc., 18 pages.

15754985.8, "European Application Serial No. 15754985.8, Extended European Search Report dated Nov. 15, 2017", Second Spectrum, Inc., 10 Pages.

17851597.9, "European Application Serial No. 17851597.9, Extended European Search Report dated Aug. 9, 2019", Second Spectrum, Inc., 8 pages.

Kim, "Automatic Classification of Offensive Patterns for Soccer Game Highlights Using Neural Networks", Malaysian Journal of Computer Science, XP055422797, Retrieved from the Internet:

(56) References Cited

OTHER PUBLICATIONS

URL:http://citeseerx.ist.psu.edujviewdocjdownload?doi=I0.1.1.630. 7271&rep=rep1&type=pdf, Jun. 1, 2002, p. 57-67.

PCT/US2015/018077, "International Application Serial No. PCT/US2015/018077, International Preliminary Report on Patentability and Written Opinion dated Sep. 15, 2016", Second Spectrum, Inc., 9 Pages.

PCT/US2015/018077, "International Application Serial No. PCT/US2015/018077, International Search Report and Written Opinion dated May 27, 2015", Second Spectrum, Inc., 13 pages.

PCT/US2017/051768, "International Application Serial No. PCT/US2017/051768, International Search Report and Written Opinion dated Feb. 28, 2018", Second Spectrum, Inc., 33 Pages.

PCT/US2017/051768, "International Application Serial No. PCT/US2017/051768, Invitation to Pay Additional Fees and, Where Applicable, Protest Fee mailed Nov. 29, 2017", Second Spectrum, Inc., 7 Pages.

PCT/US2019/023192, "International Application Serial No. PCT/US2019/023192, International Search Report and Written Opinion dated Jul. 2, 2019", Second Spectrum, Inc., 22 pages.

U.S. Appl. No. 16/677,972, filed Nov. 8, 2019, Pending, Yu-Han Chang et al.

\* cited by examiner

| 100 | | |
|---|---|---|
| EAGLE STACK | CUSTOMIZATION 102 | TEAM-SPECIFIC ANALYTICS, VISUALIZATIONS AND TOOLS ANALYTICS EXPORTS, CROWD-SOURCED FEEDBACK |
| | INTERACTION 104 | REAL-TIME INTERACTIVE TOOLS TO SLICE AND DICE DATA SHOT MATRIX, SCREEN BREAKDOWN, POSSESSION DETECTIVE |
| | VISUALIZATIONS 108 | DYNAMIC VISUALIZATIONS OF PATTERNS AND ANALYTICS SCATTER RANK, SHOT COMPARISON, CLIP VIEW |
| | ANALYTICS 110 | NEW METRICS BASED ON AI, MACHINE LEARNING SITUATIONAL EFG, VORONOI-BASED RB% |
| | PATTERNS 112 | INFRASTRUCTURE FOR RAPID DISCOVERY OF NEW PATTERNS SCREENS, DEFENSE, FACE-UP, POST-UP, TRANSITION,.... |
| | EVENTS 114 | CREATE NEW EVENTS AND CORRECT CURRENT ERRORS ANALYZE ACCURACY OF MARKINGS [FGA, DRB,...] |
| | DATA 118 | CATALOGUE, CORRECT AND ADAPT RAW DATA [X,Y,Z,T] MANAGE ONLINE WAREHOUSING IN THE CLOUD |

*FIG. 1*

EAGLE - RANKINGS

RANKINGS / BREAKDOWNS / COURT VIEW / COURT COMPARISON / VIDEO / REPORTS / PLAYS / GAMES / SIGN OUT

RANK [SHOOTING ⇵] FOR [PLAYERS ⇵] ON [OFFENSE ⇵]     [CUSTOMIZE]
              402              404              408

— TISFY FILTERS AND 176 MEET MINIMUM REQUIREMENTS.                    [EXPORT]

POSITION: [▽]                                                    MIN OPPORTUNITIES: [500]

| TER | TEAM | PLAYER POS | PG | SG | SF | PF | CTR | SHOTS | ▽EFG | SEFG | EFG+ |
|---|---|---|---|---|---|---|---|---|---|---|---|
| PLAYER1 | TEAM1 | C | | | | | | 147 | 54.4 | 53.0 | 9 |
| PLAYER2 | TEAM2 | SG, SF | | | | | | 85 | 59.1 | 56.0 | 8 |
| PLAYER3 | TEAM1 | C | | | | | | 63 | 63.2 | 62.1 | 7 |
| PLAYER4 | TEAM3 | SF, PF | | | | | | 123 | 47.2 | 46.3 | 7 |
| PLAYER5 | TEAM3 | C | | | | | | 131 | 48.0 | 45.0 | 6 |
| PLAYER6 | TEAM4 | SG | | | | | | 65 | 49.0 | 47.0 | 6 |
| PLAYER7 | TEAM5 | PF | | | | | | 231 | 51.2 | 50.3 | 7 |
| PLAYER8 | TEAM8 | PG, SG | | | | | | 147 | 53.6 | 52.4 | 9 |
| PLAYER9 | TEAM2 | SF | | | | | | 151 | 55.0 | 53.3 | 8 |
| PLAYER10 | TEAM3 | SG, SF | | | | | | 220 | 47.3 | 45.2 | 9 |

410 ⟶
✓ SHOOTING
REBOUNDING
ISOS (CHANCE)
ISOS (DIRECT)
PICKS (CHANCE)
PICKS (DIRECT)
POSTUPS (CHANCE)
POSTUPS (DIRECT)
HANDOFFS (CHANCE)
HANDOFFS (DIRECT)
LINEUPS (CHANCE)
MATCHUPS (CHANCE)
POSSESSIONS (METRICS)
POSSESSIONS (ACTIONS)
TRANSITIONS (CHANCES)
PLAYS (CHANCE)
CHANCES

FIG. 4

FILTERS=%7B" SEASONS"%3A%5B"2013"%5D%7D

RANKINGS / REPORTS / OTHER ▽ / ▽ ACCOUNT

CHANCE
CHARGES (IN PROGRESS)
CLOSEOUTS
DRIVES
FREQUENCIES
HANDOFFS
ISOS
LINEUPS
MATCHUPS
PICKS
PLAYS
POSSESSIONS
POSTUPS
PRIMARY DEFENDERS (IN PROGRESS)
REBOUNDING (MAIN)
REBOUNDING (REW)
OFF BALL SCREENS (IN PROGRESS)
SHOOTING
SPEED/LOAD
TRANSITIONS

...TION ⇅ FOR PLAYERS ⇅ ON OFFENSE ⇅ CUSTOMIZE

...MUM REQUIREMENTS.

EXPORT

MIN OPPORTUNITIES: 200

| | BALLHANDLER | SCREENER | TEAM | ACTI... | D | DA% | DPT... | I | IA% | IPTS/A | V | VA% | PTS/A | GAMES | DP/G | P/G | VIDEO |
|---|---|---|---|---|---|---|---|---|---|---|---|---|---|---|---|---|---|
| 1 | PLAYER1 | PLAYER1' | 1 | 250 | 168 | 67.200 | 1.244 | 67 | 26.800 | 0.940 | 235 | 94.000 | 1.157 | 56 | 3.000 | 4.464 | WATCH |
| 2 | PLAYER2 | PLAYER2' | 2 | 851 | 606 | 71.210 | 1.144 | 170 | 19.976 | 0.871 | 776 | 91.187 | 1.084 | 76 | 7.974 | 11.197 | WATCH |
| 3 | PLAYER3 | PLAYER3' | 3 | 372 | 293 | 78.763 | 1.126 | 65 | 17.473 | 0.908 | 358 | 96.237 | 1.087 | 80 | 3.663 | 4.650 | WATCH |
| 4 | PLAYER4 | PLAYER4' | 4 | 305 | 214 | 70.164 | 1.117 | 68 | 22.295 | 0.853 | 282 | 92.459 | 1.053 | 74 | 2.892 | 4.122 | WATCH |

FIG. 5A

| 5 | PLAYER5 | PLAYER5' | 5 | 334 | 153 | 45.808 | 1.098 | 154 | 46.108 | 0.916 | 307 | 91.916 | 1.007 | 67 | 2.284 | 4.985 | WATCH |
|---|---|---|---|---|---|---|---|---|---|---|---|---|---|---|---|---|---|
| 6 | PLAYER6 | PLAYER6' | 3 | 205 | 159 | 77.561 | 1.094 | 31 | 15.122 | 0.868 | 190 | 92.683 | 1.074 | 63 | 2.524 | 3.254 | WATCH |
| 7 | PLAYER7 | PLAYER7' | 6 | 208 | 134 | 64.423 | 1.090 | 61 | 29.327 | 0.820 | 195 | 93.750 | 1.005 | 23 | 5.826 | 9.043 | WATCH |
| 8 | PLAYER8 | PLAYER8' | 7 | 367 | 229 | 62.398 | 1.087 | 114 | 31.063 | 0.930 | 343 | 93.460 | 1.035 | 52 | 4.404 | 7.058 | WATCH |
| 9 | PLAYER9 | PLAYER9' | 8 | 330 | 236 | 71.515 | 1.085 | 71 | 21.515 | 0.789 | 307 | 93.030 | 1.016 | 64 | 3.688 | 5.156 | WATCH |
| 10 | PLAYER10 | PLAYER10' | 9 | 294 | 189 | 64.286 | 1.085 | 86 | 29.252 | 0.930 | 275 | 93.537 | 1.036 | 46 | 4.109 | 6.391 | WATCH |
| 11 | PLAYER11 | PLAYER11' | 10 | 206 | 133 | 64.563 | 1.083 | 61 | 29.612 | 0.967 | 194 | 94.175 | 1.046 | 24 | 5.542 | 8.538 | WATCH |
| 12 | PLAYER12 | PLAYER12' | 5 | 253 | 160 | 63.241 | 1.063 | 78 | 30.830 | 1.141 | 238 | 94.071 | 1.088 | 52 | 3.077 | 4.865 | WATCH |
| 13 | PLAYER13 | PLAYER13' | 1 | 263 | 150 | 57.034 | 1.060 | 96 | 36.502 | 0.813 | 246 | 93.536 | 0.963 | 51 | 2.941 | 5.157 | WATCH |
| 14 | PLAYER14 | PLAYER14' | 11 | 216 | 151 | 69.907 | 1.060 | 55 | 25.463 | 1.109 | 206 | 95.370 | 1.073 | 49 | 3.082 | 4.408 | WATCH |
| 15 | PLAYER15 | PLAYER15' | 8 | 272 | 188 | 69.118 | 1.059 | 65 | 23.897 | 0.692 | 253 | 93.015 | 0.964 | 49 | 3.837 | 5.551 | WATCH |

*FIG. 5B*

| | VIDEO | BREAKDOWNS | RANKINGS | REPORTS | OTHERS ▽ | | | ▽ ACCOUNT |
|---|---|---|---|---|---|---|---|---|

RANK [PICKS] ⇅ ACTION ⇅ FOR [PLAYERS] ⇅ ON [OFFENSE] ⇅ [CUSTOMIZE]

FILTERS  (RESET)  (EXPORT)

| GAME|TEAM|LOCATION|OTHER|OFFENSE|DEFENSE |
|---|

BALLHANDLER POSITION
[SELECT SOME OPTIONS]

SCREENER POSITION
[SELECT SOME OPTIONS]

BALLHANDLER OUTCOME  SCREENER OUTCOME
[SELECT SOME OPTIONS]  [SELECT SOME OPTIONS]

DIRECT  PICK TYPE
[ALL ▽]  [SELECT SOME OPTIONS]

MIN OPPORTUNITIES: [200]

| O | DA% | DPT... | I | IA% | IPTS/A | V | VA% | PTS/A | GAMES | DP/G | P/G | VIDEO |
|---|---|---|---|---|---|---|---|---|---|---|---|---|
| 168 | 67.200 | 1.244 | 67 | 26.800 | 0.940 | 235 | 94.000 | 1.157 | 56 | 3.000 | 4.464 | WATCH |
| 606 | 71.210 | 1.144 | 170 | 19.976 | 0.871 | 776 | 91.187 | 1.084 | 76 | 7.974 | 11.197 | WATCH |
| 293 | 78.763 | 1.126 | 65 | 17.473 | 0.908 | 358 | 96.237 | 1.087 | 80 | 3.663 | 4.650 | WATCH |
| 214 | 70.164 | 1.117 | 68 | 22.295 | 0.853 | 282 | 92.459 | 1.053 | 74 | 2.892 | 4.122 | WATCH |
| 153 | 45.808 | 1.098 | 154 | 46.108 | 0.916 | 307 | 91.916 | 1.007 | 67 | 2.284 | 4.985 | WATCH |
| 159 | 77.561 | 1.094 | 31 | 15.122 | 0.968 | 190 | 92.683 | 1.074 | 63 | 2.524 | 3.254 | WATCH |
| 134 | 64.423 | 1.090 | 61 | 29.327 | 0.820 | 195 | 93.750 | 1.005 | 23 | 5.826 | 9.043 | WATCH |

*FIG. 6A*

| POP/ROLL | DIRECTION | | | | | | | | | | | | |
|---|---|---|---|---|---|---|---|---|---|---|---|---|---|
| SELECT SOME OPTIONS ▽ | EITHER ▽ | 229 | 62.398 | 1.087 | 114 | 31.063 | 0.930 | 343 | 93.460 | 1.035 | 52 | 4.404 | 7.058 WATCH |
| WING/MIDDLE | | 236 | 71.515 | 1.085 | 71 | 21.515 | 0.789 | 307 | 93.030 | 1.016 | 64 | 3.688 | 5.156 WATCH |
| ALL ▽ | | 189 | 64.286 | 1.085 | 86 | 29.252 | 0.930 | 275 | 93.537 | 1.036 | 46 | 4.109 | 6.391 WATCH |
| | | 133 | 64.563 | 1.083 | 61 | 29.612 | 0.967 | 194 | 94.175 | 1.046 | 24 | 5.542 | 8.538 WATCH |
| | (UPDATE) | 160 | 63.241 | 1.063 | 78 | 30.830 | 1.141 | 238 | 94.071 | 1.088 | 52 | 3.077 | 4.865 WATCH |
| | | 150 | 57.034 | 1.060 | 96 | 36.502 | 0.813 | 246 | 93.536 | 0.963 | 51 | 2.941 | 5.157 WATCH |
| 14 PLAYER14 | 11 | 216 | 151 | 69.907 | 1.060 | 55 | 25.463 | 1.109 | 206 | 95.370 | 1.073 | 49 | 3.082 | 4.408 WATCH |
| 15 PLAYER15 | 12 | 272 | 188 | 69.118 | 1.059 | 65 | 23.897 | 0.692 | 253 | 93.015 | 0.964 | 49 | 3.837 | 5.551 WATCH |
| 16 PLAYER16 | 13 | 241 | 172 | 71.389 | 1.058 | 52 | 21.577 | 0.885 | 224 | 92.946 | 1.018 | 71 | 2.423 | 3.384 WATCH |
| 17 PLAYER17 | 4 | 895 | 541 | 60.447 | 1.059 | 299 | 33.408 | 0.953 | 840 | 93.855 | 1.018 | 86 | 6.291 | 10.407 WATCH |

*FIG. 6B*

RANKINGS / BREAKDOWNS / COURT VIEW / COURT COMPARISON / VIDEO / REPORTS / PLAYS / GAMES / SIGN OUT

702

BREAKDOWN [SPURS ▲▼] [PICK AND ROLL/POP ▲▼] [OFFENSE ▲▼] BY [BALLHANDLER, SCREENER ▲▼]  [CUSTOMIZE]

| ALL PICKS | BALLHANDLER | SCREENER | SCREENER DEFENSE TYPE |
|---|---|---|---|
| ALL PICKS ..... DIRECT PTS/ACT II..... | PLAYER1 ..... DIRECT PTS/ACT II..... | | SOFT (... DIRECT PTS/ACT I ..... DIRECT ACT..... |
| | | PLAYER2 (..... DIRECT PTS/ACT I..... DIR... | SHOW (..... DIRECT PTS/ ACT II..... DIRECT AC.... |
| | | PLAYER3 (..... DIRECT PTS/ACT I..... | ICE (...DIRECT PTS/ACT I.... DIRECT ACTIONS |
| | | PLAYER4 (..... DIRECT PTS/ ACT I..... | SOFT (... DIRECT PTS/ACT I... DIRECT ACT I... |
| | | | ICE (...DIRECT PTS/ACT I.... DIRECT ACTIONS |
| | | PLAYER5 (1,127 DIRECT PTS/ ACT I.....) | SOFT (... DIRECT PTS/ACT II ... DIRECT ACT..... |
| | | | SOFT (... DIRECT PTS/ACT II ... DIRECT ACT I... |

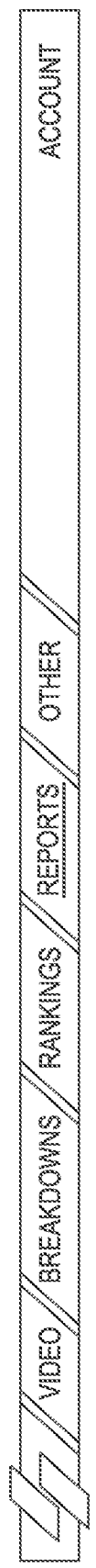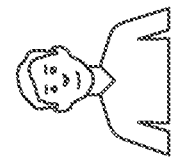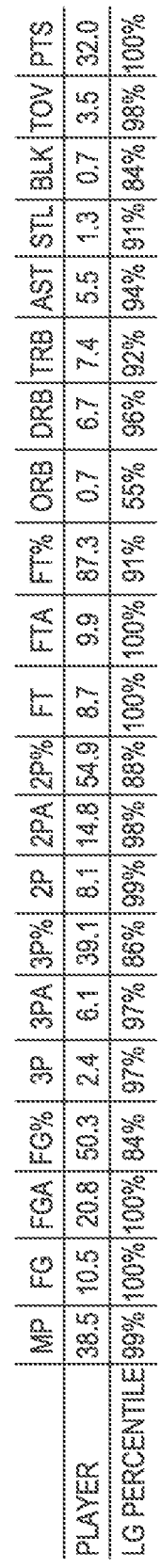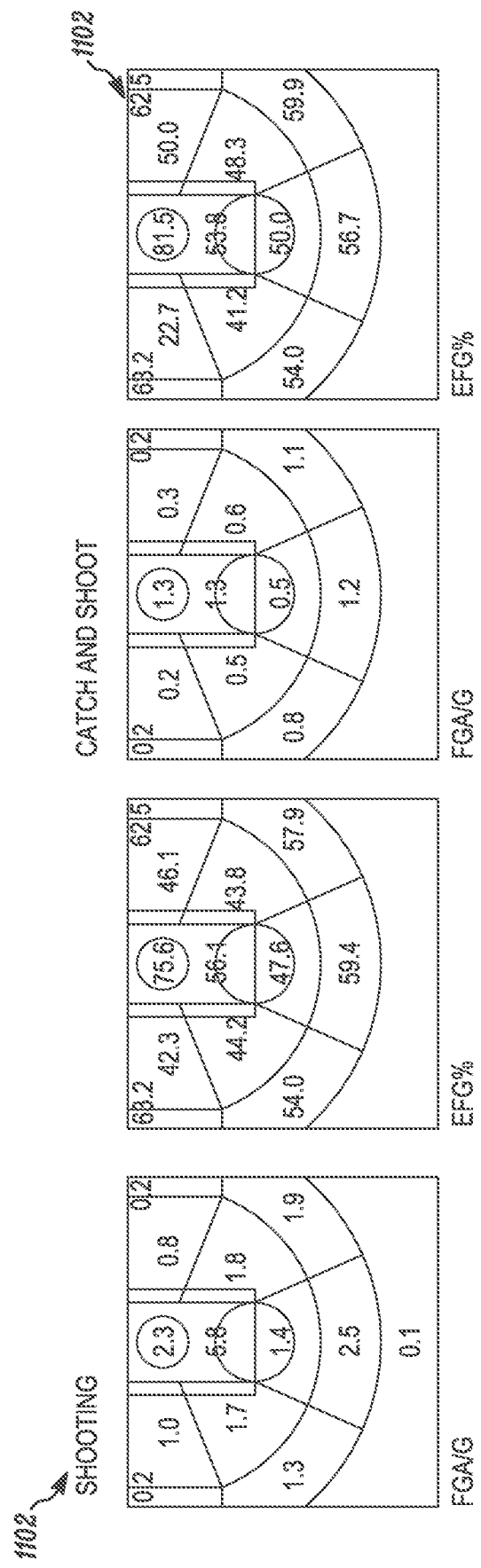
FIG. 11

| VIDEO | BREAKDOWNS | RANKINGS | REPORTS | OTHER ▾ | play by play

NOTE: CHANGES WILL ONLY BE SAVED WHEN YOU CLICK "SUBMIT MARKINGS".

| FIND & REPLACE TAGS | FIND & REPLACE TAGS |

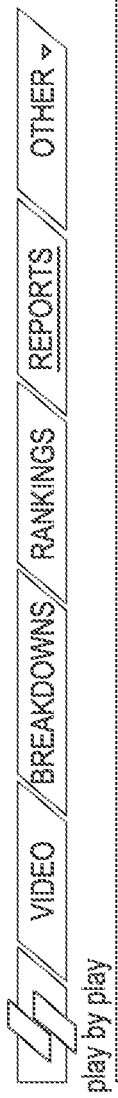

| DATE | PERIOD | HOME TEAM | AWAY TEAM | CLOCK | INDEX | PTS | EVENTS | DESCRIPTION | TAGS |
|---|---|---|---|---|---|---|---|---|---|
| 2014/6/15 | 2 | 1 | 4 | 11:49 | 0 | 2 | FGM | PLAYER1 MAKES AN ALLEY OOP DUNK 2 FEET OUT. PLAYER3 WITH THE ASSIST. | |
| 2014/6/15 | 2 | 1 | 4 | 11:32 | 1 | 0 | TO | PLAYER4 STEALS THE BALL FROM PLAYER3. | |
| 2014/6/15 | 2 | 1 | 4 | 11:32 | 2 | 2 | JMP | JUMP BALL: PLAYER2 VS PLAYER4 PLAYER6 GAINS POSSESSION. | |
| 2014/6/15 | 2 | 1 | 4 | 11:09 | 2 | 2 | FGM | PLAYER4 MAKES A JUMP SHOT FROM 20 FEET OUT. | |
| 2014/6/15 | 2 | 1 | 4 | 10:48 | 3 | 2 | FGM | PLAYER3 MAKES A JUMP SHOT FROM 23 FEET OUT. PLAYER5 WITH THE ASSIST. | |
| 2014/6/15 | 2 | 1 | 4 | 10:30 | 4 | 0 | FGX | PLAYER4 MISSES A 3 POINT JUMP SHOT FROM 23 FEET OUT. | |
| 2014/6/15 | 2 | 1 | 4 | 10:29 | 4 | 0 | DRB | PLAYER1 WITH A DEFENSIVE REBOUND. | |
| 2014/6/15 | 2 | 1 | 4 | 10:15 | 5 | 0 | FGX | PLAYER1 MISSES A 3 POINT JUMP SHOT FROM 25 FEET OUT. | |

*FIG. 14*

| TEAM COMPARISON | | | | | |
|---|---|---|---|---|---|
| SHOOTING | | TEAM 4 OFFENSE | | TEAM 7 DEFENSE | |
| FIELD GOAL PERCENTAGE | | | | | |
| FG% | 44.91 | #16 | #1 MIA (52.80) (42.36) #1 MIL | #30 DET (47.00) (41.47) #1 IND | #19 45.86 |
| EFFECTIVE FIELD GOAL PRECENTAGE | | | | | |
| EFG | 49.96 | #13 | #1 MIA (56.05) (42.46) #30 CLI | #30 PHI (52.05) (45.19) #1 IND | #14 49.47 |
| SHOT QUALITY | | | | | |
| SHOT QUALITY | 47.55 | #25 | #1 HOU (50.82) (46.95) #30 CLI | #30 UTA (49.53) (46.73) #1 SAS | #5 47.66 |
| EFG ABOVE SHOT QUALITY | | | | | |
| EFG+(SHOOTING ABILITY) | 2.41 | #8 | #1 MIA (5.28) (-2.59) #30 PHI | #30 MIN (2.91) (-1.75) #1 IND | #16 1.81 |
| FGX REBOUNDING | | TEAM 4 OFFENSE | | TEAM 7 DEFENSE | |
| PERCENT OF FGX ... | | | | | |
| FB% | 22.13 | #26 | #1 DET (31.04) (20.36) #30 MIA | #30 LAL (62.66) (69.46) #1 WAS | #6 68.12 |
| RB... | | | #1 MEM (30.05) (23.34) #30 LAL | #30 MIA (70.72) (75.88) #1 ORL | |
| RB POSITIONING (SHOT) | 24.68 | #25 | | | #6 74.66 |
| SHOT QUALITY | | | | | |
| RB POSITIONING (RIM) | 28.33 | #24 | #1 DET (32.52) (25.69) #30 MIA | #30 DET (67.64) (72.09) #1 ORL | #6 70.83 |
| RB... | | | #1 POR (5.26) (1.75) #30 ORL | #30 SAS (-4.47) (-1.98) #1 MIA | |
| RB CRASH | 3.64 | #11 | | | #22 -3.83 |
| PRO... | | | #1 DET (67.93) (59.46) #30 ORL | #30 MIL (83.69) (88.34) #1 GSW | |

*FIG. 24A*

| | | | | | |
|---|---|---|---|---|---|
| FB OPP % | | 62.60 | #22 | | #3 | 88.19 |
| FB OPP %... | | | | #1 MIL (40.24) (32.70) #30 MEM #30 MIL (10.88) (15.57) #1 MIA | | |
| RB HUSTLE PERSENT... | | 37.92 | #12 | | #13 | 13.53 |
| RB CONVERSION % | | 35.34 | #27 | | #1 PRO (46.09) (34.01) #30 MIA #30 LAL (73.38) (79.17) #1 MEM | #14 | 77.24 |
| RB PERSENT ... | | | | #1 POR (2.39) (-4.67) #30 ATL #30 MIL (-9.43) (-3.23) #1 WAS | | |
| RB %+ | | -2.56 | #26 | | #11 | -6.54 |

| BASIC | TEAM 4 OFFENSE | | | TEAM 7 DEFENSE | | |
|---|---|---|---|---|---|---|
| DEEF... | | 0.20 | #7 | #1 HOU (0.23) (0.18) #30 LAL #30 NOP (0.22) (0.17) #1 CHA | #7 | 0.18 |
| DEFFOULS PER POSSENSIVE | | | | | | |
| ASS... | | | | #1 ATL (0.27) (0.20) #30 PHX #30 PHI (0.27) (0.19) #1 IND | | |
| ASSISTS PER POSS... | | 0.22 | #18 | | #4 | 0.21 |
| BLOCK... | | | | #1 MIA (0.03) (0.07) #30 PHI #30 MIN (0.04) (0.07) #1 NOP | | |
| BLOCK PER POSS. | | 0.04 | #9 | | #12 | 0.05 |
| STEALS PER POSSE... | | | | #1 CHA (0.07) (0.10) #30 LAL #30 POR (0.06) (0.10) #1 MIA | | |
| STEALS PER POSS. | | 0.08 | #15 | | #30 | 0.06 |

JSONS

3002

CAMERA.JSON [CHOOSE FILE] N...n ✓  VORONOI-POLS.JSON [CHOOSE FILE] N...n ⊙
COURT.JSON [CHOOSE FILE] N...n ⊙  PLAYERS-3D-ALL.JSON [CHOOSE FILE] N...n ✓
                                  PLAYER-POS.JSON [CHOOSE FILE] N...n ⊙
                                  HEATMAP-POLS.JSON [CHOOSE FILE] N...n ⊙

✓ UPDATE
⚐ CAMERA.JSON
⚐ COURT.JSON
⚐ VORONOI-POLS.JSON
⚐ PLAYERS-3D-ALL.JSON
⚐ PLAYER-POS.JSON

CLIP

GAME ID [2014000001]
UNIQUE ID [1]
CLIP [CHOOSE FILE] N...n ✓

WIDTH [1280]
HEIGHT [720]
FRAME RATE [29.97]

⬆ UPLOAD
⚐ CLIP.MP4

PROJECT

| TYPE | START AT | DURATION | |
|------|----------|----------|---|
| PAUSE | 0.867 | 15 | 🗑 |
| PAUSE | 2.266 | 15 | 🗑 |
| PAUSE | 3.066 | 15 | 🗑 |

⟳ GENERATE
⚐ SCRIPT.JSX

*FIG. 30A*

PLAYER CIRCLES

| FRAME ID | START AT | DURATION | PLAYER | COLOR | GET BALLS | BALL TIME | |
|---|---|---|---|---|---|---|---|
| 27 | 1.367 | | 1 | RE ⇵ | ☐ | 0 | 🗑 |
| 27 | 1.617 | 14.25 | 2 | WH ⇵ | ☐ | 0 | 🗑 |

+ ADD CIRCLE
↻ GENERATE
⇩ SCRIPT.JSX

SCREEN ARROWS

| FRAME ID | START AT | DURATION | PLAYER | C/CC | ROTATION | FLICKER AT |
|---|---|---|---|---|---|---|

+ ADD ARROW
↻ GENERATE
⇩ SCRIPT.JSX

SCREEN CALLOUTS

| FRAME ID | START AT | DURATION | PLAYER | TEXT | NUMBER | ARROW |
|---|---|---|---|---|---|---|

+ ADD ARROW
↻ GENERATE
⇩ SCRIPT.JSX

*FIG. 30C*

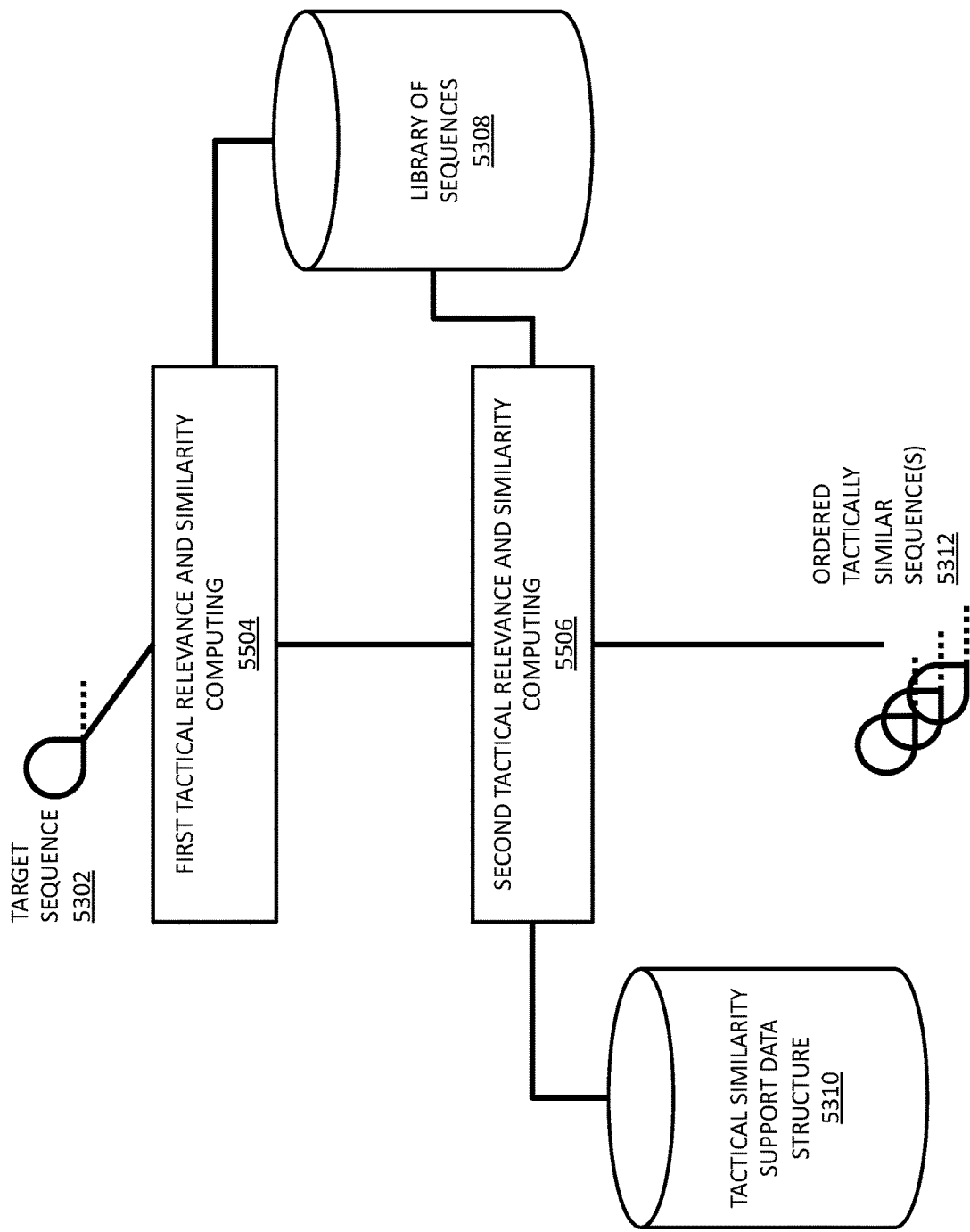

DETERMINING TACTICAL RELEVANCE AND SIMILARITY OF VIDEO SEQUENCES

RELATED MATTERS

This application relates to the following applications: U.S. application Ser. No. 16/229,457, filed Dec. 21, 2018, U.S. provisional patent application Ser. No. 62/646,012, filed Mar. 21, 2018, International Application serial number PCT/US2017/051768, filed Sep. 15, 2017, and published as WO 2018/053257 on Mar. 22, 2018, U.S. provisional patent application Ser. No. 62/532,744 filed Jul. 14, 2017, U.S. patent application Ser. No. 15/586,379, filed on May 4, 2017, and published as US 2017/0238055 on Aug. 17, 2017, U.S. provisional patent application Ser. No. 62/395,886, filed Sep. 16, 2016, U.S. patent application Ser. No. 14/634,070 filed Feb. 27, 2015, U.S. provisional patent application Ser. No. 62/072,308 filed Oct. 29, 2014, and U.S. provisional patent application Ser. No. 61/945,899 filed Feb. 28, 2014.

Each of the applications listed above and elsewhere herein is hereby incorporated by reference in its entirety as if fully set forth herein.

BACKGROUND

Field of the Invention

This disclosure pertains to methods and systems for finding and ranking video sequences that contain tactical sequences (e.g., an uninterrupted portion of a sporting event) that are similar to tactical event content in a target video sequence, such as those occurring in sports. This can be used, for example, for finding and recommending content, such as from a library of content that is tactically similar to a sequence for which a user has indicated a preference. The methods and systems disclosed herein may also facilitate learning and labelling (e.g., through use of metadata and the like) tactically significant sequences in a plurality of video segments, including a plurality of such tactically significant sequences in one video segment and the like.

Description of the Related Art

Live events, such as sports, especially at the college and professional levels, continue to grow in popularity and revenue as individual colleges and franchises reap billions in revenue each year. To provide valuable insights and gain a competitive advantage in such endeavors, quantitative methodologies, such as Sabermetrics, have grown in importance and ubiquity as a valuable augmentation to traditional scouting methods. However, as no one person can evaluate and accurately store all of the information available from the vast volumes of sporting information generated on a daily basis, there seldom exists a storehouse of properly coded and stored information reflecting such large volumes of sports information and, even were such information available, there is lacking the provision of tools capable of mining and analyzing such information.

Systems are now available for capturing and encoding event information, such as sporting event information, such as "X, Y, Z" motion data captured by imaging cameras deployed in National Basketball Association (NBA) arenas. However, there are many challenges with such systems, including difficulty handling the data, difficulty transforming X, Y, Z data into meaningful and existing sports terminology, difficulty identifying meaningful insights from the data, difficulty visualizing results, and others. Also, there are opportunities to identify and extract novel insights from the data. Accordingly, a need exists for methods and systems that can take event data captured in video feeds and enable discovery and ranking of video sequences that contain tactical sequences.

SUMMARY

This disclosure pertains to methods and systems for finding and ranking video sequences that contain tactical sequences (e.g., an uninterrupted portion of a sporting event) that are similar to tactical event content in a target video sequence, such as those occurring in sports. This can be used, for example, for finding and recommending content, such as from a library of content that is tactically similar to a sequence for which a user has indicated a preference. The methods and systems disclosed herein may also facilitate learning and labelling (e.g., through use of metadata and the like) tactically significant sequences in a plurality of video segments, including a plurality of such tactically significant sequences in one video segment and the like.

In many sports, analyzing and understanding offensive and defensive tactics (e.g., commonly called tactical plays) is relevant and interesting to coaches, players and fans. A play essentially consists of a sequence of actions taken by one or more players on or in conjunction with a playing field/court. A simple example of a play in basketball could consist of the following actions: a screener sets a pick at the top of the key, the pick is taken, the screener rolls to the basket, receives a pass and shoots. At least some portions of the actions in this example may include tactical significance that may be captured, detected, labelled, and used for, among other things, determining if a new sequence is tactically similar thereto.

In embodiments, methods and systems disclosed herein may include a method of steps including: receiving a first client device consumable video feed comprising a first filmed occurrence as a sequence of video frames captured by a camera; detecting at least one game chance sequence from the sequence of video frames based on spatiotemporal analysis that identifies game chance boundary events; determining at least one semantic label and associated location data of at least one tactically relevant event in the at least one game chance sequence; concatenating the at least one semantic label and associated location data as a first labeled tactical sequence; and identifying from a library of stored game chance sequences at least one stored game chance sequence that is similar to the at least one game chance sequence from the first video feed based on tactical similarity of a stored labeled tactical sequence of the at least one stored game chance with the first labeled tactical sequence. In embodiments, the tactical similarity may be further based on similarity of a semantic label for the stored tactical sequence and associated location data with the semantic label and location data of the first labeled tactical sequence. In embodiments, a spatiotemporal pattern analysis of the at least one game chance sequence from the sequence of video frames and of the at least one stored game chance sequence indicates a substantive difference in spatiotemporal patterns therein. Also, in embodiments, identifying game chance boundary events includes detecting actions that occur between labeled tactical sequences. In embodiments, a game chance boundary event includes at least one of a game clock stoppage, a scoring attempt, a scoring deflection, an event occurring in a region of a field of play, and an event occurring outside of a field of play. Further, game change boundary events facilitate partitioning the first broadcast video feed into one or more labeled tactical subsequences. In embodiments, tactical similarity of two sequences comprises each of the two sequences occurring proximal to a common location. Yet further in embodiments a location characteristic of a first sequence that is determined by a first level of tactical relevance and similarity computing informs a second level of tactical relevance and similarity computing performing tactical similarity comparison of the first sequence with at least one other sequence. In embodiments, tactical similarity of two sequences is responsive to outcomes of the two sequences. Also in embodiments, two sequences that produce different outcomes are not tactically similar. In embodiments, tactical similarity is determined by use of a VP tree algorithm that applies a distance metric based at least in part on one or more tactical characteristics of the first labeled tactical sequence and of the stored labeled tactical sequence. Further, tactical similarity is determined by use of multi-dimensional distance metric that is based on a plurality of tactical characteristics of the first labeled tactical sequence and of the stored labeled tactical sequence. Also, tactical similarity is determined by application of distance metric values for a plurality of tactical sequence characteristics via a VP tree algorithm. Yet further, the plurality of tactical sequence characteristics includes a player identity characteristic.

In embodiments, methods and systems disclosed herein may include a method that involves receiving a first video feed capturing a first filmed occurrence, the first video feed comprising a sequence of video frames captured by a camera, wherein the first video feed is a video feed that is consumable by a client device; processing the captured first video feed with a first tactical relevance and similarity computing circuit, wherein the first tactical relevance and similarity computing circuit determines, during processing, portions of the video feed that comprise location-event data for one or more semantic events; accessing with a second tactical relevance and similarity computing circuit a tactical similarity support data structure; and determining similarity of the one or more semantic events with tactical video sequences in a library of video sequences by determining for a plurality of tactical similarity characteristic types accessed in the tactical similarity support data structure a concurrence of instances of each of the plurality of tactical similarity characteristic types associated with at least one semantic event of the one or more semantic events and corresponding instances of tactical similarity characteristics associated with tactical video sequences in the library of video sequences. Yet further in embodiments, location-event data indicates at least one of a play, a part of a chance, an event and a chance demarcation.

BRIEF DESCRIPTION OF THE FIGURES

The following detailed description of certain embodiments may be understood by reference to the following figures:

FIG. 1 illustrates a technology stack according to an exemplary and non-limiting embodiment.

FIG. 4 illustrates a ranking user interface according to an exemplary and non-limiting embodiment.

FIGS. 5A and 5B illustrate a ranking user interface according to an exemplary and non-limiting embodiment.

FIGS. 6A and 6B illustrate a filters user interface according to an exemplary and non-limiting embodiment.

FIG. 7 illustrates a breakdown user interface according to an exemplary and non-limiting embodiment.

FIG. 8 illustrates a breakdown user interface according to an exemplary and non-limiting embodiment.

FIG. 11 illustrates an alternative report according to an exemplary and non-limiting embodiment.

FIG. 14 illustrates a report according to an exemplary and non-limiting embodiment.

FIGS. 24A and 24B illustrate reports according to an exemplary and non-limiting embodiment.

FIG. 26 illustrates a quality assurance user interface according to an exemplary and non-limiting embodiment.

FIGS. 30A, 30B, and 30C illustrate scripted storytelling with assets according to an exemplary and non-limiting embodiment.

FIG. 56 depicts a flow diagram of embodiments of methods and systems for determining tactical relevance of a sequence.

DETAILED DESCRIPTION

Figure 2:
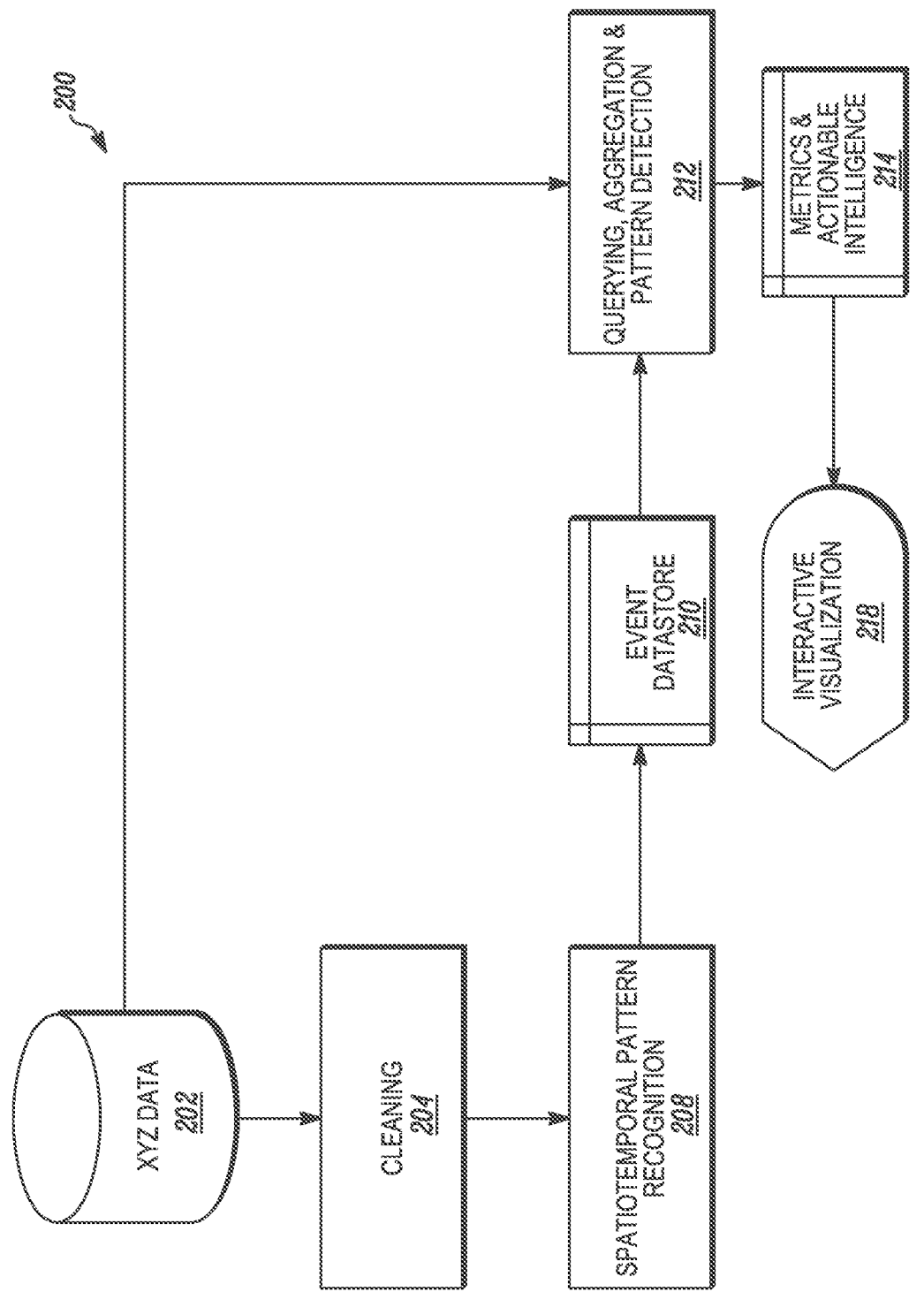
FIG. 2 illustrates a stack flow according to an exemplary and non-limiting embodiment.

FIG. 1 illustrates a technology stack 100 indicative of technology layers configured to execute a set of capabilities, in accordance with an embodiment of the present invention. The technology stack 100 may include a customization layer 102, an interaction layer 104, a visualizations layer 108, an analytics layer 110, a patterns layer 112, an events layer 114, and a data layer 118, without limitations. The different technology layers or the technology stack 100 may be referred to as an "Eagle" Stack 100, which should be understood to encompass the various layers allow precise monitoring, analytics, and understanding of spatiotemporal data associated with an event, such as a sports event and the like, For example, the technology stack may provide an analytic platform that may take spatiotemporal data (e.g., 3D motion capture "XYZ" data) from National Basketball Association (NBA) arenas or other sports arenas and, after cleansing, may perform spatiotemporal pattern recognition to extract certain "events". The extracted events may be for example (among many other possibilities) events that correspond to particular understandings of events within the overall sporting event, such as "pick and roll" or "blitz." Such events may correspond to real events in a game, and may, in turn, be subject to various metrics, analytic tools, and visualizations around the events. Event recognition may be based on pattern recognition by machine learning, such as spatiotemporal pattern recognition, and in some cases, may be augmented, confirmed, or aided by human feedback.

The customization layer 102 may allow performing custom analytics and interpretation using analytics, visualization, and other tools, as well as optional crowd-sourced feedback for developing team-specific analytics, models, exports, and related insights. For example, among many other possibilities, the customization layer 102 may facilitate in generating visualizations for different spatiotemporal movements of a football player, or group of players and counter movements associated with other players or groups of players during a football event.

The interaction layer 104 may facilitate generating real-time interactive tasks, visual representations, interfaces, videos clips, images, screens, and other such vehicles for allowing viewing of an event with enhanced features or allowing interaction of a user with a virtual event derived from an actual real-time event. For example, the interaction layer 104 may allow a user to access features or metrics such as a shot matrix, a screens breakdown, possession detection, and many others using real-time interactive tools that may slice, dice, and analyze data obtained from the real-time event such as a sports event.

The visualizations layer 108 may allow dynamic visualizations of patterns and analytics developed from the data obtained from the real-time event. The visualizations may be presented in the form of a scatter rank, shot comparisons, a clip view, and many others. The visualizations layer 108 may use various types of visualizations and graphical tools for creating visual depictions. The visuals may include various types of interactive charts, graphs, diagrams, comparative analytical graphs, and the like. The visualizations layer 108 may be linked with the interaction layer so that the visual depictions may be presented in an interactive fashion for a user interaction with real-time events produced on a virtual platform such as the analytic platform of the present invention.

The analytics layer 110 may involve various analytics and Artificial Intelligence (AI) tools to perform analysis and interpretation of data retrieved from the real-time event such as a sports event so that the analyzed data results in insights that make sense out of the pulled big data from the real-time event. The analytics and AI tools may comprise such as search and optimization tools, inference rules engines, algorithms, learning algorithms, logic modules, probabilistic tools and methods, decision analytics tools, machine learning algorithms, semantic tools, expert systems, and the like without limitations.

Output from the analytics layer 110 and patterns layer 112 is exportable by the user as a database that enables the customer to configure their own machines to read and access the events and metrics stored in the system. In accordance with various exemplary and non-limiting embodiments, patterns and metrics are structured and stored in an intuitive way. In general, the database utilized for storing the events and metric data is designed to facilitate easy export and to enable integration with a team's internal workflow. In one embodiment, there is a unique file corresponding to each individual game. Within each file, individual data structures may be configured in accordance with included structure definitions for each data type indicative of a type of event for which data may be identified and stored. For example, types of events that may be recorded for a basketball game include, but are not limited to, isos, handoffs, posts, screens, transitions, shots, closeouts, and chances. With reference to, for example, the data type "screens", Table 1 is an exemplary listing of the data structure for storing information related to each occurrence of a screen. As illustrated, each data type is comprised of a plurality of component variable definitions each comprised of a data type and a description of the variable.

TABLE 1 screens
id
  INT
  Internal ID of this screen,
possession_id
  STRING
  Internal ID of the possession in which this event took place,
frame
  INT
  Frame ID, denoting frame number from the start of the current period. Currently, this marks the frame at which the screener and ballhandler are closest,
frame_time
  INT
  Time stamp provided in SportVU data for a frame, measured in milliseconds in the current epoch (i.e., from 00:00:00 UTC on 1 January 1970),
game_code
  INT
  Game code provided in SportVU data,
period
  INT
  Regulation periods 1-4, overtime periods 5 and up,
game_clock
  NUMBER
  Number of seconds remaining in period, from 720.00 to 0.00,
location_x
  NUMBER
  Location along length of court, from 0 to 94.
location_y
  NUMBER
  Location along baseline of court, from 0 to 50,
screener
  INT
  ID of screener, matches SportVU ID,
ballhandler
  INT
  ID of the ballhandler, matches SportVU ID,
screener_defender
  INT
  ID of the screener's defender, matches SportVU ID,
ballhandler_defender
  INT
  ID of the ballhandler's defender, matches SportVU ID,
oteam
  INT
  ID of team on offense, matches IDs in SportVU data,
dteam
  INT
  ID of team on defense, matches IDs in SportVU data,
rdef
  STRING
  String representing the observed actions of the ballhandler's defender,
sdef
  STRING
  String representing the observed actions of the screener's defender,
scr_type TABLE 1-continued STRING
  Classification of the screen into take, reject, or slip.
outcomes_bhr
  ARRAY
  Actions by the ballhandler, taken from the outcomes described at the end of the document, such as FGX or FGM,
outcomes_scr
  ARRAY
  Actions by the screener, taken from the outcomes described at the end of the document, such as FGX or FGM, These exported files, one for each game, enable other machines to read the stored understanding of the game and build further upon that knowledge. In accordance with various embodiments, the data extraction and/or export is optionally accomplished via a JSON schema.

The patterns layer 112 may provide a technology infrastructure for rapid discovery of new patterns arising out of the retrieved data from the real-time event such as a sports event. The patterns may comprise many different patterns that corresponding to an understanding of the event, such as a defensive pattern (e.g., blitz, switch, over, under, up to touch, contain-trap, zone, man-to-man, or face-up pattern), various offensive patterns (e.g., pick-and-roll, pick-and-pop, horns, dribble-drive, off-ball screens, cuts, post-up, and the like), patterns reflecting plays (scoring plays, three-point plays, "red zone" plays, pass plays, running plays, fast break plays, etc.) and various other patterns associated with a player in the game or sports, in each case corresponding to distinct spatiotemporal events.

The events layer 114 may allow creating new events or editing or correcting current events. For example, the events layer may allow for the analyzing of the accuracy of markings or other game definitions and may comment on whether they meet standards and sports guidelines. For example, specific boundary markings in an actual real-time event may not be compliant with the guidelines and there may exist some errors, which may be identified by the events layers through analysis and virtual interactions possible with the platform of the present invention. Events may correspond to various understandings of a game, including offensive and defensive plays, matchups among players or groups of players, scoring events, penalty or foul events, and many others.

The data layer 118 facilitates management of the big data retrieved from the real-time event such as a sports event. The data layer 118 may allow creating libraries that may store raw data, catalogs, corrected data, analyzed data, insights, and the like. The data layer 118 may manage online warehousing in a cloud storage setup or in any other manner in various embodiments.

FIG. 2 illustrates a process 200 as shown in the flow diagram, in accordance with an embodiment of the present invention. The process 200 may include retrieving spatiotemporal data associated with a sports or game and storing in a data library at step 202. The spatiotemporal data may relate to a video feed that was captured by a 3D camera, such as one positioned in a sports arena or other venue, or it may come from another source.

The process 200 may further include cleaning of the rough spatiotemporal data at data cleaning step 204 through analytical and machine learning tools and utilizing various technology layers as discussed in conjunction with FIG. 1 so as to generate meaningful insights from the cleansed data.

The process 200 may further include recognizing spatiotemporal patterns through analysis of the cleansed data at step 208. Spatiotemporal patterns may comprise a wide range of patterns that are associated with types of events. For example, a particular pattern in space, such as the ball bouncing off the rim, then falling below it, may contribute toward recognizing a "rebound" event in basketball. Patterns in space and time may lead to recognition of single events or multiple events that comprise a defined sequence of recognized events (such as in types of plays that have multiple steps).

The recognized patterns may define a series of events associated with the sports that may be stored in a canonical event datastore 210. These events may be organized according to the recognized spatiotemporal patterns; for example, a series of events may have been recognized as "pick," "rebound," "shot," or like events in basketball, and they may be stored as such in the canonical event datastore 210. The canonical event datastore 210 may store a wide range of such events, including individual patterns recognized by spatiotemporal pattern recognition and aggregated patterns, such as when one pattern follows another in an extended, multi-step event (such as in plays where one event occurs and then another occurs, such as "pick and roll" or "pick and pop" events in basketball, football events that involve setting an initial block, then springing out for a pass, and many others).

The process 200 may further include querying or aggregation or pattern detection at step 212. The querying of data or aggregation may be performed with the use of search tools that may be operably and communicatively connected with the data library or the events datastore for analyzing, searching, aggregating the rough data, cleansed, or analyzed data, or events data or the events patterns.

At metrics and actionable intelligence 214 may be used for developing insights from the searched or aggregated data through artificial intelligence and machine learning tools.

At interactive visualization 218, for example, the metrics and actionable intelligence may convert the data into interactive visualization portals or interfaces for use by a user in an interactive manner.

In embodiments, an interactive visualization portal or interface may produce a 3D reconstruction of an event, such as a game. In embodiments, a 3D reconstruction of a game may be produced using a process that presents the reconstruction from a point of view, such as a first person point of view of a participant in an event, such as a player in a game.

Raw input XYZ data obtained from various data sources is frequently noisy, missing, or wrong. XYZ data is sometimes delivered with attached basic events already identified in it, such as possession, pass, dribble, and shot events; however, these associations are frequently incorrect. This is important because event identification further down the process (in Spatiotemporal Pattern Recognition) sometimes depends on the correctness of these basic events. For example, if two players' XY positions are switched, then "over" vs "under" defense would be incorrectly characterized, since the players' relative positioning is used as a critical feature for the classification. Even player-by-player data sources are occasionally incorrect, such as associating identified events with the wrong player.

First, validation algorithms are used to detect all events, including the basic events such as possession, pass, dribble, shot, and rebound that are provided with the XYZ data. Possession/Non-possession models may use a Hidden Markov Model to best fit the data to these states. Shots and rebounds may use the possession model outputs, combined with 1) projected destination of the ball, and 2) player by player information (PBP) information. Dribbles may be identified using a trained ML algorithm and also using the output of the possession model. These algorithms may decrease the basic event labeling error rate by approximately 50% or more.

Second, the system has a library of anomaly detection algorithms to identify potential problems in the data including, but not limited to, temporal discontinuities (intervals of missing data are flagged), spatial discontinuities (objects traveling is a non-smooth motion, "jumping") and interpolation detection (data that is too smooth, indicating that post-processing was done by the data supplier to interpolate between known data points in order to fill in missing data). This problem data is flagged for human review so that events detected during these periods are subject to further scrutiny.

Spatiotemporal Pattern Recognition

Spatiotemporal pattern recognition (step 208) is used to automatically identify relationships between physical and temporal patterns and various types of events. In the example of basketball, one challenge is how to turn x, y, z positions of ten players and one ball at twenty-five frames per second into usable input for machine learning and pattern recognition algorithms. For patterns, one is trying to detect (e.g., pick & rolls), the raw inputs may not suffice. The instances within each pattern category can look very different from each other. One, therefore, may benefit from a layer of abstraction and generality. Features that relate multiple actors in time are key components to the input. Examples include, but are not limited to, the motion of player one (P1) towards player two (P2), for at least T seconds, a rate of motion of at least V m/s for at least T seconds and at the projected point of intersection of paths A and B, and a separation distance less than D.

In embodiments, an algorithm for spatiotemporal pattern recognition can use relative motion of visible features within a feed, duration of relative motion of such features, rate of motion of such features with respect to each other, rate of acceleration of such features with respect to each other, a projected point of intersection of such features, the separation distance of such features, and the like to identify or recognize a pattern with respect to visible features in a feed, which in turn can be used for various other purposes disclosed herein, such as recognition of a semantically relevant event or feature that relates to the pattern. In embodiments, these factors may be based on a pre-existing model or understanding of the relevance of such features, such as where values or thresholds may be applied within the pattern recognition algorithm to aid pattern recognition. Thus, thresholds or values may be applied to rates of motion, durations of motion, and the like to assist in pattern recognition. However, in other cases, pattern recognition may occur by adjusting weights or values of various input features within a machine learning system, without a pre-existing model or understanding of the significance of particular values and without applying thresholds or the like. Thus, the spatiotemporal pattern recognition algorithm may be based on at least one pattern recognized by adjusting at least one of an input type and a weight within a machine learning system. This recognition may occur independently of any a priori model or understanding of the significance of particular input types, features, or characteristics. In embodiments, an input type may be selected from the group consisting of relative direction of motion of at least two visible features, duration of relative motion of visible features with respect to each other, rate of motion of at least two visible features with respect to each other, acceleration of motion of at least two visible feature with respect to each other, projected point of intersection of at least two visible features with respect to each other and separation distance between at least two visible features with respect to each other, and the like.

In embodiments of the present disclosure, there is provided a library of such features involving multiple actors over space and time. In the past machine learning (ML) literature, there has been relatively little need for such a library of spatiotemporal features, because there were few datasets with these characteristics on which learning could have been considered as an option. The library may include relationships between actors (e.g., players one through ten in basketball), relationships between the actors and other objects such as the ball, and relationships to other markers, such as designated points and lines on the court or field, and to projected locations based on predicted motion.

Another key challenge is there has not been a labeled dataset for training the ML algorithms. Such a labeled dataset may be used in connection with various embodiments disclosed herein. For example, there has previously been no XYZ player-tracking dataset that already has higher level events, such as pick and roll (P&R) events) labeled at each time frame they occur. Labeling such events, for many different types of events and sub-types, is a laborious process, Also, the number of training examples required to adequately train the classifier may be unknown. One may use a variation of active learning to solve this challenge. Instead of using a set of labeled data as training input for a classifier trying to distinguish A and B, the machine finds an unlabeled example that is closest to the boundary between As and Bs in the feature space. The machine then queries a human operator/labeler for the label for this example. It uses this labeled example to refine its classifier and then repeats.

In one exemplary embodiment of active learning, the system also incorporates human input in the form of new features. These features are either completely devised by the human operator (and inputted as code snippets in the active learning framework), or they are suggested in template form by the framework. The templates use the spatiotemporal pattern library to suggest types of features that may be fruitful to test. The operator can choose a pattern, and test a particular instantiation of it, or request that the machine test a range of instantiations of that pattern.

Multi-Loop Iterative Process

Some features are based on outputs of the machine learning process itself. Thus, multiple iterations of training are used to capture this feedback and allow the process to converge. For example, a first iteration of the ML process may suggest that the Bulls tend to ice the P&R. This fact is then fed into the next iteration of ML training as a feature, which biases the algorithm to label Bulls' P&R defense as ices. The process converges after multiple iterations. In practice, two iterations have typically been sufficient to yield good results.

In accordance with exemplary embodiments, a canonical event datastore 210 may contain a definitive list of events that the system knows occurred during a game. This includes events extracted from the XYZ data, as well as those specified by third-party sources, such as PBP data from various vendors. The events in the canonical event datastore 210 may have game clock times specified for each event. The canonical event datastore 210 may be fairly large. To maintain efficient processing, it is shared and stored in-memory across many machines in the cloud. This is similar in principle to other methods such as Hadoop™; however, it is much more efficient, because in embodiments involving events, such as sporting events, where there is some predetermined structure that is likely to be present (e.g., the 24-second shot clock, or quarters or halves in a basketball game), it makes key structural assumptions about the data. Because the data is from sports games, for example, in embodiments one may enforce that no queries will run across multiple quarters/periods. Aggregation steps can occur across quarters/periods, but query results will not. This is one instantiation of this assumption. Any other domain in which locality of data can be enforced will also fall into this category.

Such a design allows rapid and complex querying across all of the data, allowing arbitrary filters, rather than relying on either 1) long-running processes, or 2) summary data, or 3) pre-computed results on pre-determined filters.

In accordance with exemplary and non-limiting embodiments, data is divided into small enough shards that each worker shard has a low latency response time. Each distributed machine may have multiple workers corresponding to the number of processes the machine can support concurrently. Query results do not rely on more than one shard, since we enforce that events not cross quarter/period boundaries. Aggregation functions all run incrementally rather than in batch process so that as workers return results, these are incorporated into the final answer immediately. To handle results such as rankings pages, where many rows may be returned, the aggregator uses hashes to keep track of the separate rows and incrementally updates them.

Figure 3:
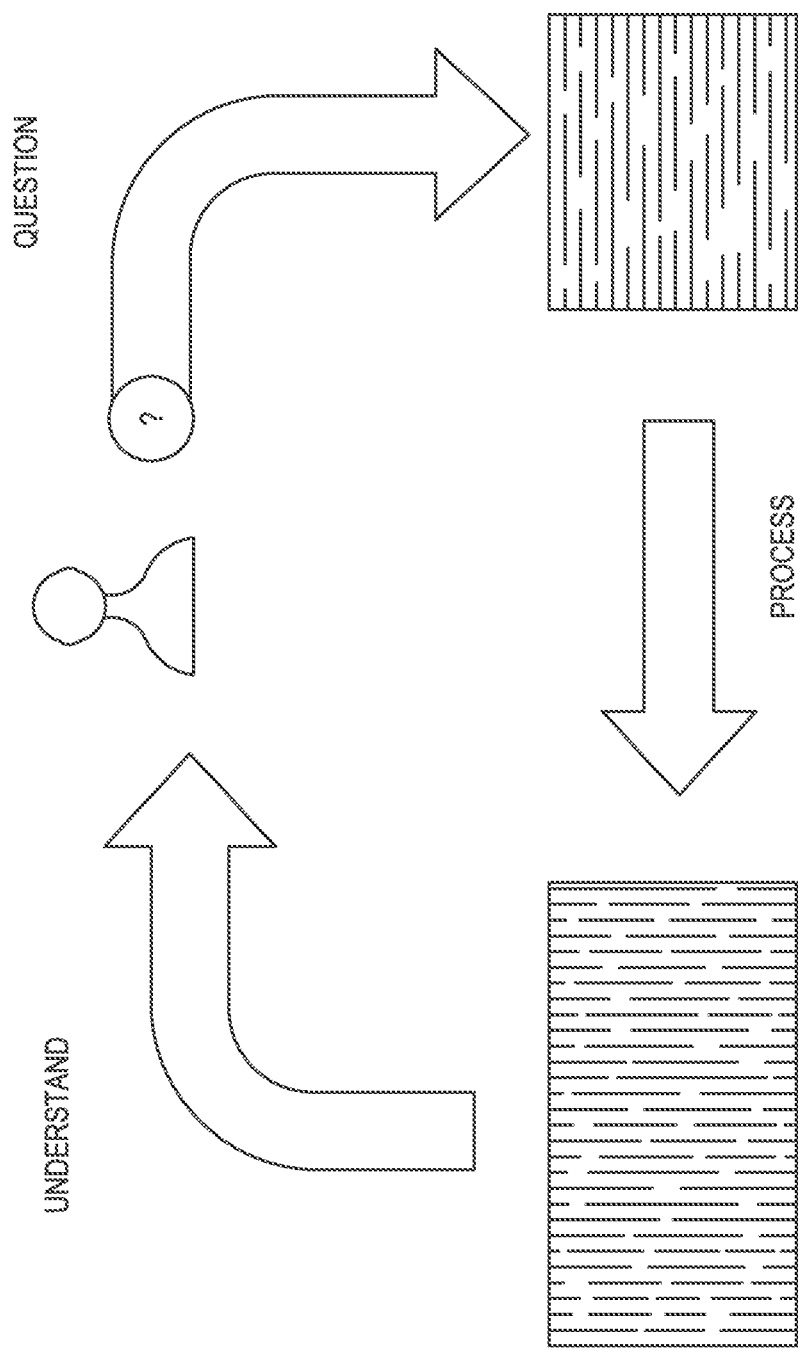
FIG. 3 illustrates an exploration loop according to an exemplary and non-limiting embodiment.

Referring to FIG. 3, an exploration loop may be enabled by the methods and systems disclosed herein, where questioning and exploration can occur, such as using visualizations (e.g., data effects, referred to as DataFX in this disclosure), processing can occur, such as to identify new events and metrics, and understanding emerges, leading to additional questions, processing and understanding.

Referring to FIG. 4, the present disclosure provides an instant player rankings feature as depicted in the illustrated user interface. A user can select among various types of available rankings 402, as indicated in the drop down list 410, such as rankings relating to shooting, rebounding, rebound ratings, isolations (Isos), picks, postups, handoffs, lineups, matchups, possessions (including metrics and actions), transitions, plays and chances. Rankings can be selected in a menu element 404 for players, teams, or other entities. Rankings can be selected for different types of play in the menu element 408, such as for offense, defense, transition, special situations, and the like. The ranking interface allows a user to quickly query the system to answer a particular question instead of thumbing through pages of reports. The user interface lets a user locate essential factors and evaluate talent of a player to make more informed decisions.

FIGS. 5A and 5B show certain basic, yet quite in-depth, pages in the systems described herein, referred to in some cases as the "Eagle system." This user interface may allow the user to rank players and teams by a wide variety of metrics. This may include identified actions, metrics derived from these actions, and other continuous metrics. Metrics may relate to different kinds of events, different entities (players and teams), different situations (offense and defense) and any other patterns identified in the spatiotemporal pattern recognition system. Examples of items on which various entities can be ranked in the case of basketball include chances, charges, closeouts, drives, frequencies, handoffs, isolations, lineups, matches, picks, plays, possessions, postups, primary defenders, rebounding (main and raw), off ball screens, shooting, speed/load and transitions.

The Rankings UI makes it easy for a user to understand relative quality of one row item versus other row items, along any metric. Each metric may be displayed in a column, and that row's ranking within the distribution of values for that metrics may be displayed for the user. Color coding makes it easy for the user to understand relative goodness.

FIGS. 6A and 6B show a set of filters in the UI, which can be used to filter particular items to obtain greater levels of detail or selected sets of results. Filters may exist for seasons, games, home teams, away teams, earliest and latest date, postseason/regular season, wins/losses, offense home/away, offensive team, defensive team, layers on the court for offense/defense, players off court for offense/defense, locations, offensive or defensive statistics, score differential, periods, time remaining, after timeout play start, transition/no transition, and various other features. The filters 602 for offense may include selections for the ballhandler, the ballhandler position, the screener, the screener position, the ballhandler outcome, the screener outcome, the direction, the type of pick, the type of pop/roll, the direction of the pop/roll, and presence of the play (e.g., on the wing or in the middle). Many other examples of filters are possible, as a filter can exist for any type of parameter that is tracked with respect to an event that is extracted by the system or that is in the spatiotemporal data set used to extract events. The present disclosure also allows situational comparisons. The user interface allows a user to search for a specific player that may fit into the offense. The highly accurate dataset and easy to use interface allow the user to compare similar players in similar situations. The user interface may allow the user to explore player tendencies. The user interface may allow locating shot locations and also may provide advanced search capabilities.

Filters enable users to subset the data in a large number of ways and immediately receive metrics calculated on the subset. Using multiple loops for convergence in machine learning enables the system to return the newly filtered data and metrics in real-time, whereas existing methods would require minutes to re-compute the metrics given the filters, leading to inefficient exploration loops (FIG. 3). Given that the data exploration and investigation process often require many loops, these inefficiencies can otherwise add up quickly.

As illustrated with reference to FIGS. 6A and 6B, there are many filters that may enable a user to select specific situations of interest to analyze. These filters may be categorized into logical groups, including, but not limited to, Game, Team, Location, Offense, Defense, and Other. The possible filters may automatically change depending on the type of event being analyzed, for example, Shooting, Rebounding, Picks, Handoffs, Isolations, Postups, Transitions, Closeouts, Charges, Drives, Lineups, Matchups, Play Types, Possessions.

For all event types, under the Game category, filters may include Season, specific Games, Earliest Date, Latest Date, Home Team, Away Team, where the game is being played Home/Away, whether the outcome was Wins/Losses, whether the game was a Playoff game, and recency of the game, For all event types, under the Team category, filters may include Offensive Team, Defensive Team, Offensive Players on Court, Defenders Players on Court, Offensive Players Off Court, Defenders Off Court, For all event types, under the Location category, the user may be given a clickable court map that is segmented into logical partitions of the court. The user may then select any number of these partitions in order to filter only events that occurred in those partitions.

For all event types, under the Other category, the filters may include Score Differential, Play Start Type (Multi-Select: Field Goal ORB, Field Goal DRB, Free Throw ORB, Free Throw DRB, Jump Ball, Live Ball Turnover, Defensive Out of Bounds, Sideline Out of Bounds), Periods, Seconds Remaining, Chance After Timeout (T/F/ALL), Transition (T/F/ALL).

For Shooting, under the Offense category, the filters may include Shooter, Position, Outcome (Made/Missed/All), Shot Value, Catch and Shoot (T/F/ALL), Shot Distance, Simple Shot Type (Multi-Select: Heave, Angle Layup, Driving Layup, Jumper, Post), Complex Shot Type (Multi-Select: Heave, Lob, Tip, Standstill Layup, Cut Layup, Driving Layup, Floater, Catch and Shoot), Assisted (T/F/ALL), Pass From (Player), Blocked (T/F/ALL), Dunk (T/F/ALL), Bank (T/F/ALL), Goaltending (T/F/ALL), Shot Attempt Type (Multi-select: FGA No Foul, FGM Foul, FGX Foul), Shot SEFG (Value Range), Shot Clock (Range), Previous Event (Multi-Select: Transition, Pick, Isolation, Handoff, Post, None).

For Shooting, under the Defense category, the filters may include Defender Position (Multi-Select: PG, SG, SF, PF, CTR), Closest Defender, Closest Defender Distance, Blocked By, Shooter Height Advantage.

For Picks, under the Offense category, the filters may include Ballhandler, Ballhandler Position, Screener, Screener Position, Ballhandler Outcome (Pass, Shot, Foul, Turnover), Screener Outcome (Pass, Shot, Foul, Turnover), Direct or Indirect Outcome, Pick Type (Reject, Slip, Pick), Pop/Roll, Direction, Wing/Middle, Middle/Wing/Step-Up.

For Picks, under the Defense category, the filters may include Ballhandler Defender, Ballhandler Defender Position, Screener Defender, Screener Defender Position, Ballhandler Defense Type (Over, Under, Blitz, Switch, Ice), Screener Defense Type (Soft, Show, Ice, Blitz, Switch), Ballhandler Defense (Complex) (Over, Under, Blitz, Switch, Ice, Contain Trap, Weak), Screener Defense (Complex) (Over, Under, Blitz, Switch, Ice, Contain Trap, Weak, Up to Touch), For Drives, under the Offense category, the filters may include Ballhandler, Ballhandler Position, Ballhandler Outcome, Direct or Indirect, Drive Category (Handoff, Iso, Pick, Closeout, Misc.), Drive End (Shot Near Basket, Pullup, Interior Pass, Kickout, Pullout, Turnover, Stoppage, Other), Direction, Blowby (T/F).

For Drives, under the Defense category, the filters may include Ballhandler Defender, Ballhandler Defender Position, Help Defender Present (T/F), Help Defenders.

For most other events, under the Offense category, the filters may include Ballhandler, Ballhandler Position, Ballhandler Outcome, Direct or Indirect.

For most other events, under the Defense category, the filters may include Ballhandler Defender, Ballhandler Defender Position.

For Postups, under the Offense category, the filters may additionally include Area (Left, Right, Middle).

For Postups, under the Defense category, the filters may additionally include Double Team (T/F).

The present disclosure provides detailed analysis capabilities, such as through the depicted user interface embodiment of FIG. 7. In an example depicted in FIG. 7, the user interface may be used to know if a player should try and ice the pick and roll or not between two players. Filters can go from all picks, to picks involving a selected player as ballhandler, to picks involving that ballhandler with a certain screener, to the type of defense played by that screener. By filtering down to particular matchups (by player combinations and actions taken), the system allows rapid exploration of the different options for coaches and players, and selection of preferred actions that had the best outcomes in the past. Among other things, the system may give a detailed breakdown of a player's opponent and a better idea of what to expect during a game. The user interface may be used to know and highlight opponent capabilities. A breakdowns UI may make it easy for a user to drill down to a specific situation, all while gaining insight regarding frequency and efficacy of relevant slices through the data.

Figure 8:
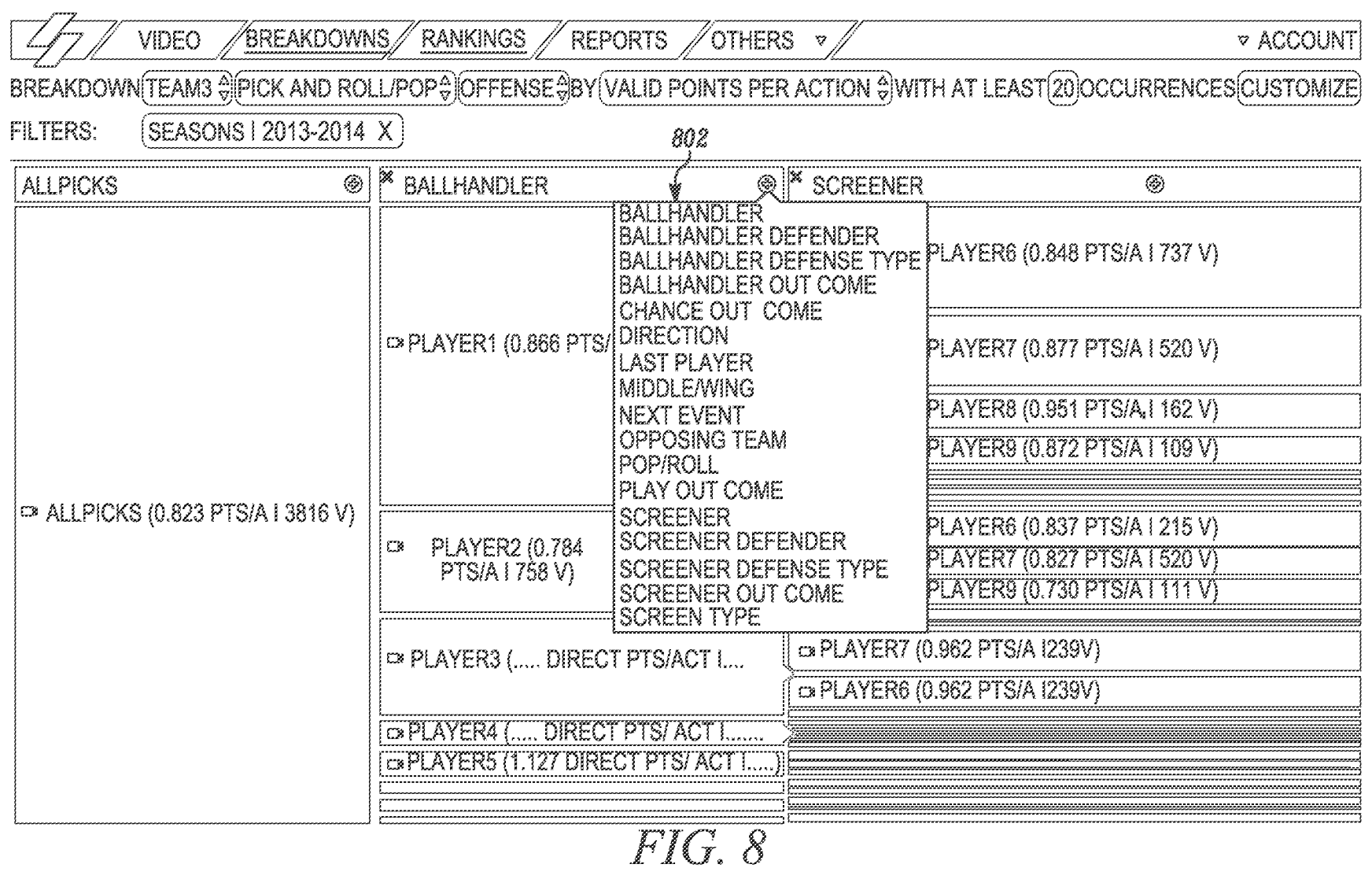

The events captured by the present system may be capable of being manipulated using the UI. FIG. 8 shows a visualization, where a drop-down feature 802 allows a user to select various parameters related to the ballhandler, such as to break down to particular types of situations involving that ballhandler. These types of "breakdowns" facilitate improved interactivity with video data, including enhanced video data created with the methods and systems disclosed herein. Most standard visualizations are static images. For large and complex datasets, especially in cases where the questions to be answered are unknown beforehand, interactivity enables the user to explore the data, ask new questions, get new answers. Visualizations may be color coded good (e.g., orange) to bad (e.g., blue) based on outcomes in particular situations for easy understanding without reading the detailed numbers. Elements like the sizes of partitions can be used, such as to denote frequency. Again, a user can comprehend significance from a glance. In embodiments, each column represents a variable for partitioning the dataset. It is easy for a user to add, remove, and re-arrange columns by clicking and dragging. This makes it easy to experiment with different visualizations. Furthermore, the user can drill into a particular scenario by clicking on the partition of interest, which zooms into that partition, and redraws the partitions in the columns to the right so that they are re-scaled appropriately. This enables the user to view the relative sample sizes of the partitions in columns to the right, even when they are small relative to all possible scenarios represented in columns further to the left. In embodiments, a video icon takes a user to video clips of the set of plays that correspond to a given partition. Watching the video gives the user ideas for other variables to use for partitioning.

Various interactive visualizations may be created to allow users to better understand insights that arise from the classification and filtering of events, such as ones that emphasize color coding for easy visual inspection and detection of anomalies (e.g., a generally good player with lots of orange but is bad/blue in one specific dimension). Conventionally, most standard visualizations are static images. However, for large and complex datasets, especially in cases where the questions to be answered are unknown beforehand, interactivity enables the user to explore the data, ask new questions, get new answers. For example, a breakdown view may be color coded good (orange) to bad (blue) for easy understanding without reading the numbers. Sizes of partitions may denote the frequency of events. Again, one can comprehend from a glance at the events that occur most frequently. Each column of a visualization may represent a variable for partitioning the dataset. It may be easy to add, remove, and re-arrange columns by clicking and dragging. This makes it easy to experiment with possible visualizations. In embodiments, a video icon may take a user to video clips, such as of the set of plays that correspond to that partition. Watching the video gives the user ideas for other variables to use for partitioning.

In embodiments, a ranking view is provided. Upon mousing over each row of a ranking view, histograms above each column may give the user a clear contextual understanding that row's performance for each column variable. The shape of a distribution is often informative. Color-coded bars within each cell may also provide a view of each cell's performance that is available, without mousing over. Alternatively, the cells themselves may be color-coded.

Figure 9:
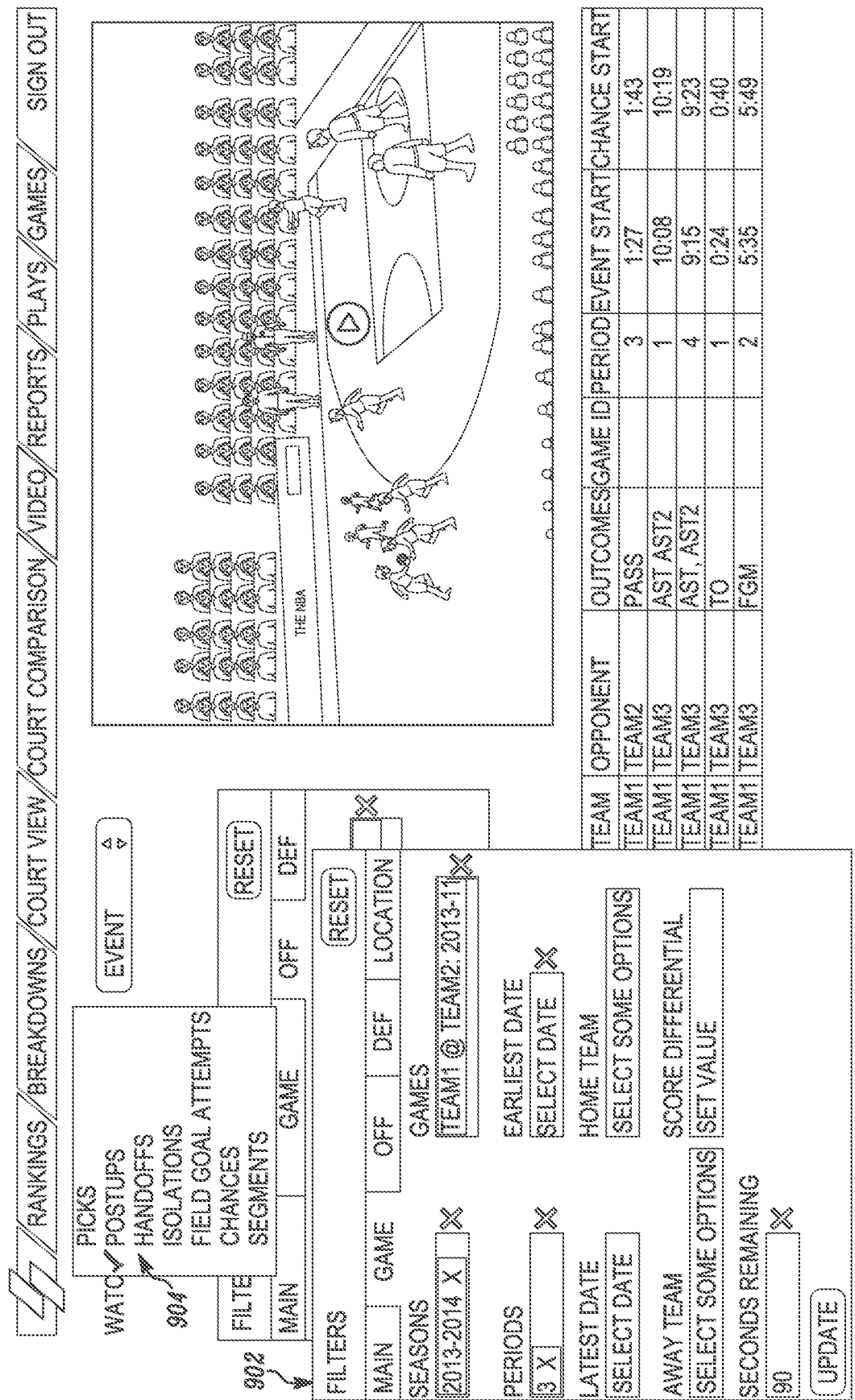
FIG. 9 illustrates a personalized user interface according to an exemplary and non-limiting embodiment.
Figure 10:
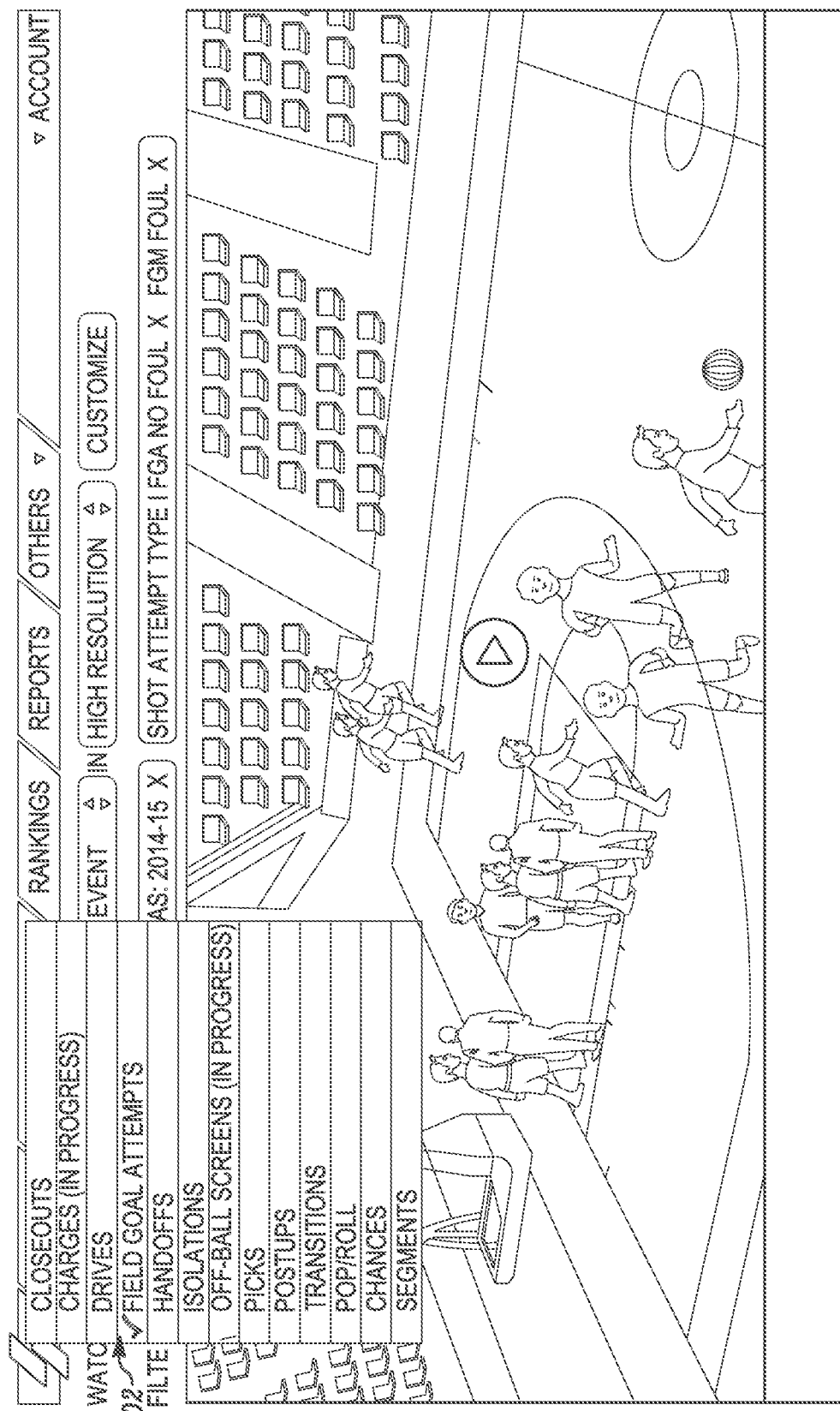
FIG. 10 illustrates an alternative video user interface according to an exemplary and non-limiting embodiment.

Referring to FIGS. 9 and 10, a system may provide a personalized video in embodiments of the methods and systems described herein. For example, with little time to scout the opposition, the system can provide a user with relevant information to quickly prepare the team. The team may rapidly retrieve the most meaningful plays, cut, and compiled to specific needs of players. The system may provide immediate video cut-ups. In embodiments, the present disclosure provides a video that is synchronized with identified actions. For example, if spatiotemporal machine learning identifies a segment of a video as showing a pick and roll involving two players, then that video segment may be tagged, so that when that event is found (either by browsing or by filtering to that situation), the video can be displayed. Because the machine understands the precise moment that an event occurs in the video, a user-customizable segment of video can be created. For example, the user can retrieve video corresponding to x seconds before, and y seconds after, each event occurrence. Thus, the video may be tagged and associated with events. The present disclosure may provide a video that may allow customization by numerous filters of the type disclosed above, relating to finding a video that satisfies various parameters, that displays various events, or combinations thereof. For example, in embodiments, an interactive interface provided by the present disclosure allows watching videos clips for specific game situations or actions.

Reports may provide a user with easy access to printable pages summarizing pre-game information about an opponent, scouting report for a particular player, or a post-game summary. For example, the reports may collect actionable useful information in one to two easy-to-digest pages. These pages may be automatically scheduled to be sent to other staff members, e.g., post-game reports sent to coaches after each game. Referring to FIG. 11, a report may include statistics for a given player, as well as visual representations, such as of locations 1102 where shots were taken, including shots of a particular type (such as catch and shoot shots).

Figure 12:
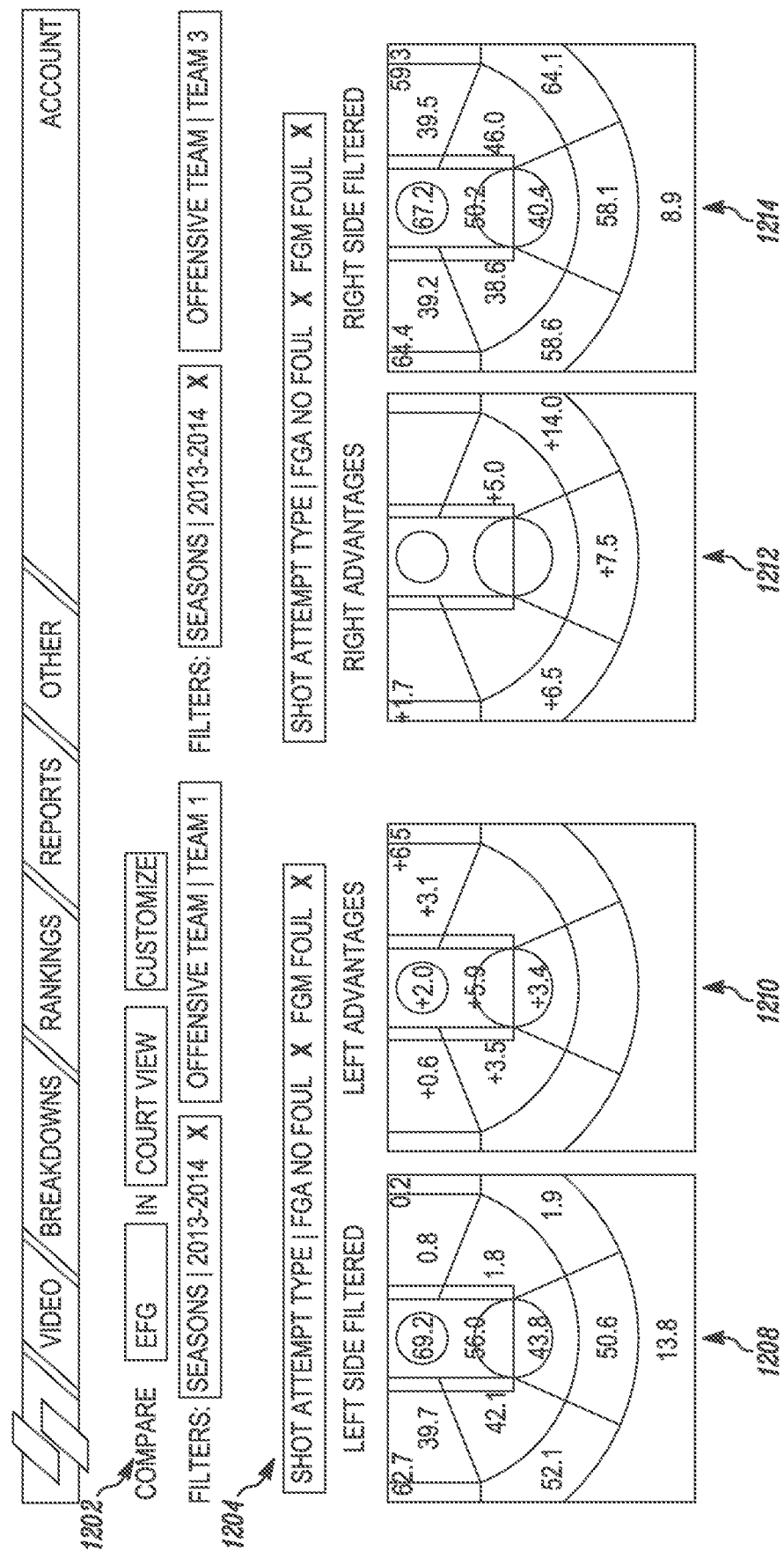
FIG. 12 illustrates a court comparison view according to an exemplary and non-limiting embodiment.

The UI as illustrated in FIG. 12 provides a court comparison view 1202 among several parts of a sports court (and can be provided among different courts as well). For example, filters 1204 may be used to select the type of statistic to show for a court. The statistics can be filtered to show results filtered by left side 1208 or right side 1214. Where the statistics indicate an advantage, the advantages can be shown, such as the advantages of left center FIG. 1210 and advantages of right center FIG. 1212.

In sports, the field of play is an important domain constant or elements. Many aspects of the game are best represented for comparison on a field of play. In embodiments, a four court comparison view 1202 is a novel way to compare two players, two teams, or other entities, to gain an overview view of each player/team (Leftmost and Rightmost figures) 1208, 1214 and understand each one's strengths/weaknesses (Left and Right Center figures 1210, 1212).

Figure 13:
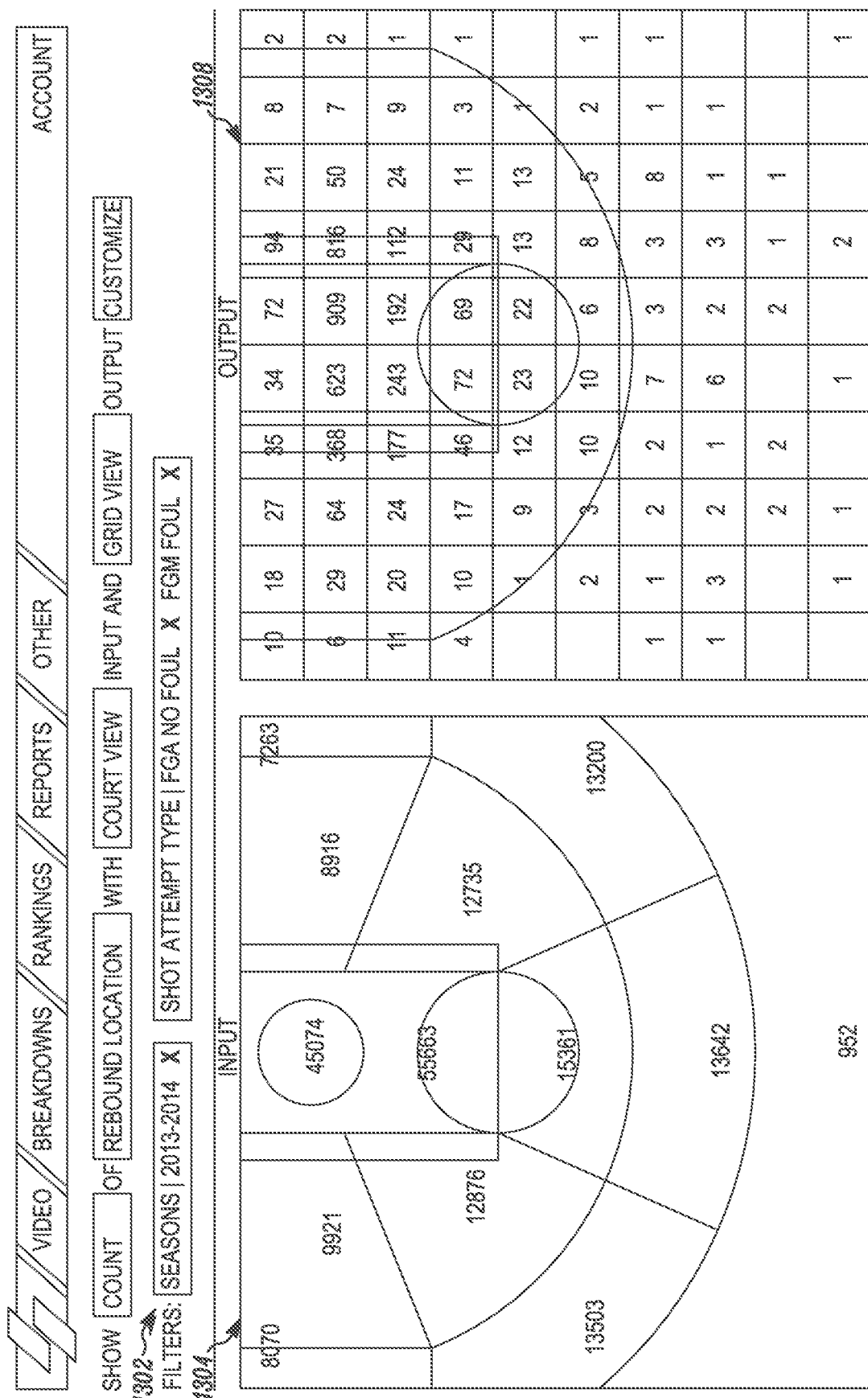
FIG. 13 illustrates a court view according to an exemplary and non-limiting embodiment.

The court view UI 1302 as illustrated in FIG. 13 provides a court view 1304 of a sport arena, in accordance with an embodiment of the present disclosure. Statistics for very specific court locations can be presented on a portion 1308 of the court view. The UI may provide a view of custom markings, in accordance with an embodiment of the present invention.

Referring to FIG. 14, filters may enable users to subset the data in a large number of ways, and immediately receive metrics calculated on the subset. Descriptions of particular events may be captured and made available to users.

Figure 15:
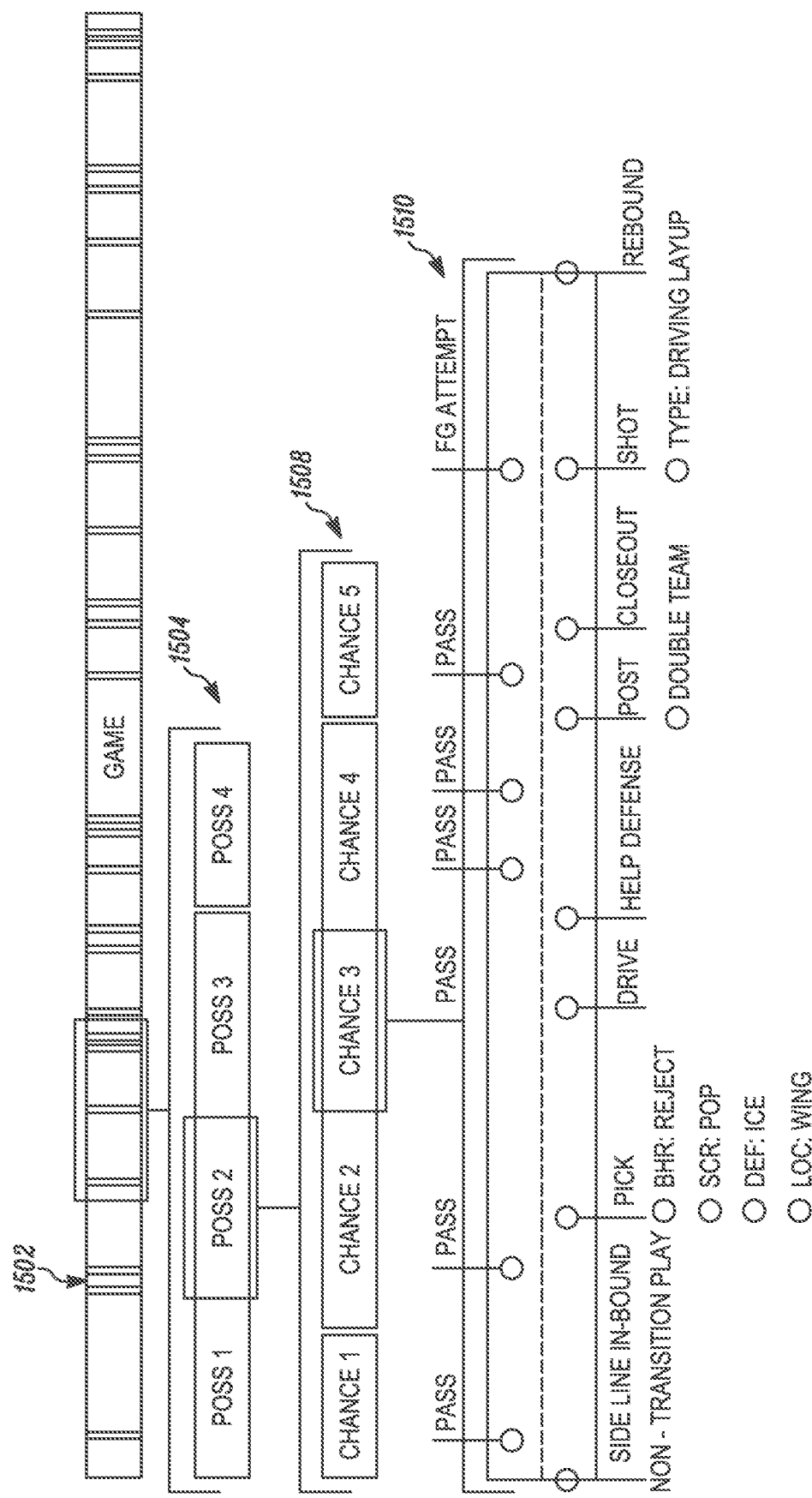
FIG. 15 illustrates a detailed depiction of a game according to an exemplary and non-limiting embodiment.

Various events may be labeled in a game, as reflected in FIG. 15, which provides a detailed view of a timeline 1502 of a game, broken down by possession 1504, by chances 1508, and by specific events 1510 that occurred along the timeline 1502, such as determined by spatiotemporal pattern recognition, by human analysis, or by a combination of the two. Filter categories available by a user interface of the present disclosure may include ones based on seasons, games, home teams, away teams, earliest date, latest date, postseason/regular season, wins/losses, offense home/away, offensive team, defensive team, players on the court for offense/defense, players off court for offense/defense, location, score differential, periods, time remaining, play type (e.g., after timeout play) and transition/no transition, Events may include ones based on primitive markings, such as shots, shots with a corrected shot clock, rebounds, passes, possessions, dribbles, and steals, and various novel event types, such as SEFG (shot quality), EFG+, player adjusted SEFG, and various rebounding metrics, such as positioning, opportunity percentage, attack, conversion percentage, rebounding above position (RAP), attack+, conversion+ and RAP+. Offensive markings may include simple shot types (e.g., angled layup, driving layup, heave, post shot, jumper), complex shot types (e.g., post shot, heave, cut layup, standstill layup, lob, tip, floater, driving layup, catch and shoot stationary, catch and shoot on the move, shake & raise, over screen, pullup and stepback), and other information relating to shots (e.g., catch and shoot, shot clock, 2/3S, assisted shots, shooting foul/not shooting foul, made/missed, blocked/not blocked, shooter/defender, position/defender position, defender distance and shot distance). Other events that may be recognized, such as through the spatiotemporal learning system, may include ones related to picks (ballhandler/screener, ballhandler/screener defender, pop/roll, wing/middle, step-up screens, reject/slip/take, direction (right/left/none), double screen types (e.g., double, horns, L, and handoffs into pick), and defense types (ice, blitz, switch, show, soft, over, under, weak, contain trap, and up to touch), ones related to handoffs (e.g., receive/setter, receiver/setter defender, handoff defense (ice, blitz, switch, show, soft, over, or under), handback/dribble handoff, and wing/step-up/middle), ones related to isolations (e.g., ballhandler/defender and double team), and ones related to post-ups (e.g., ballhandler/defender, right/middle/left and double teams).

Defensive markings are also available, such as ones relating to closeouts (e.g., ballhandler/defender), rebounds (e.g., players going for rebounds (defense/offense)), pick/handoff defense, post double teams, drive blow-bys and help defender on drives), ones relating to off ball screens (e.g., screener/cutter and screener/cutter defender), ones relating to transitions (e.g., when transitions/fast breaks occur, players involved on offense and defense, and putback/no putback), ones relating to how plays start (e.g., after timeout/not after timeout, sideline out of bounds, baseline out of bounds, field goal offensive rebound/defensive rebound, free throw offensive rebound/defensive rebound and live ball turnovers), and ones relating to drives, such as ballhandler/defender, right/left, blowby/no blowby, help defender presence, identity of help defender, drive starts (e.g., handoff, pick, isolation or closeout) and drive ends (e.g., shot near basket, interior pass, kickout, pullup, pullout, stoppage, and turnover). These examples and many others from basketball and other sports may be defined, based on any understanding of what constitutes a type of event during a game. Markings may relate to off ball screens (screener/cutter), screener/cutter defender, screen types (down, pro cut, UCLA, wedge, wide pin, back, flex, clip, zipper, flare, cross, and pin in).

Figure 16:
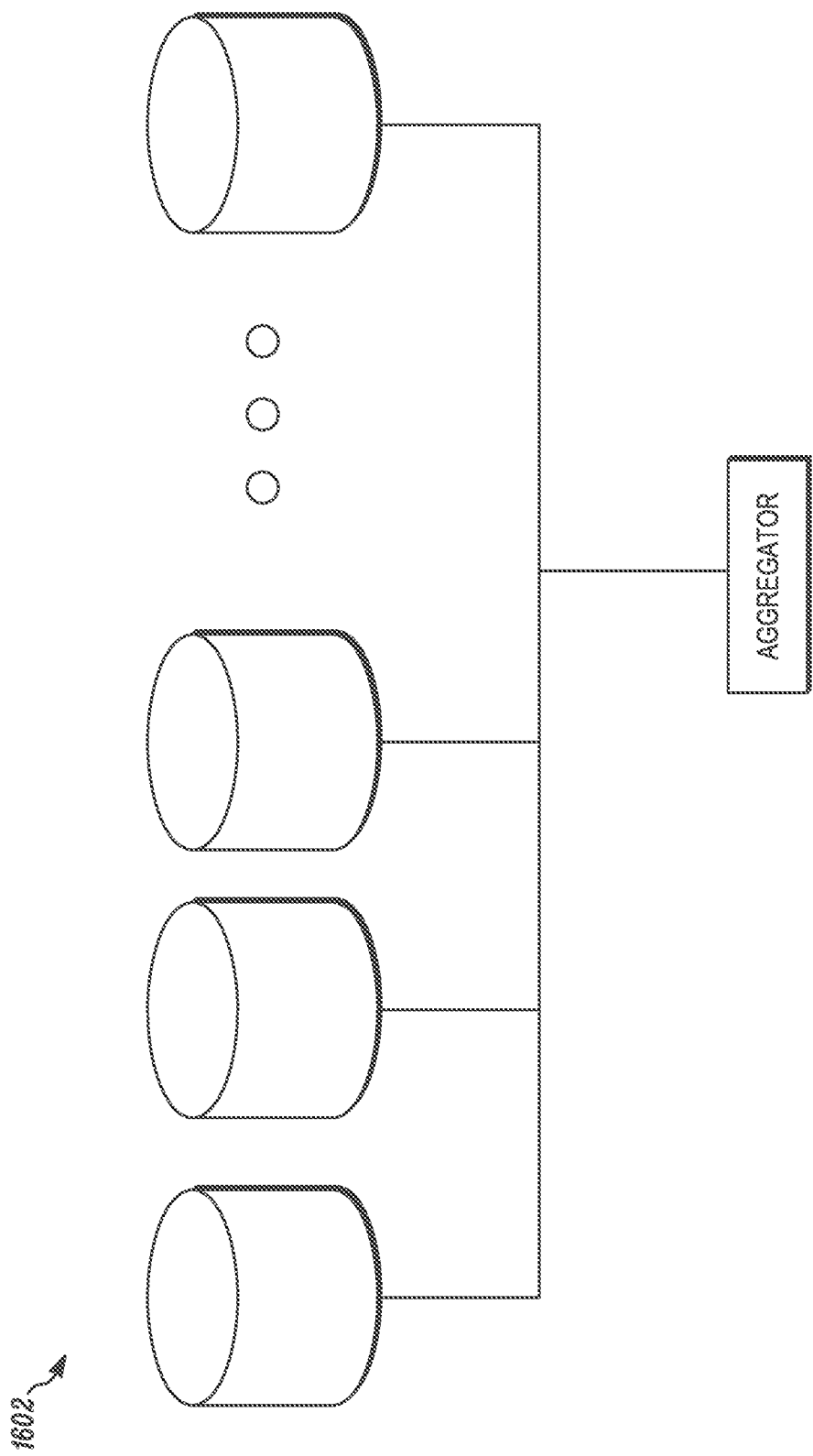
FIG. 16 illustrates querying and aggregation according to an exemplary and non-limiting embodiment.

FIG. 16 shows a system 1602 for querying and aggregation. In embodiments, data is divided into small enough shards that each worker has low latency response time. Each distributed machine may have multiple workers corresponding to the number of processes the machine can support concurrently. Query results do not rely on more than one shard, since we enforce that events not cross quarter/period boundaries. Aggregation functions all run incrementally rather than in batch process, so that as workers return results, these are incorporated into the final answer immediately. To handle results such as rankings pages, where many rows may be returned, the aggregator uses hashes to keep track of the separate rows and incrementally updates them.

Figure 17:
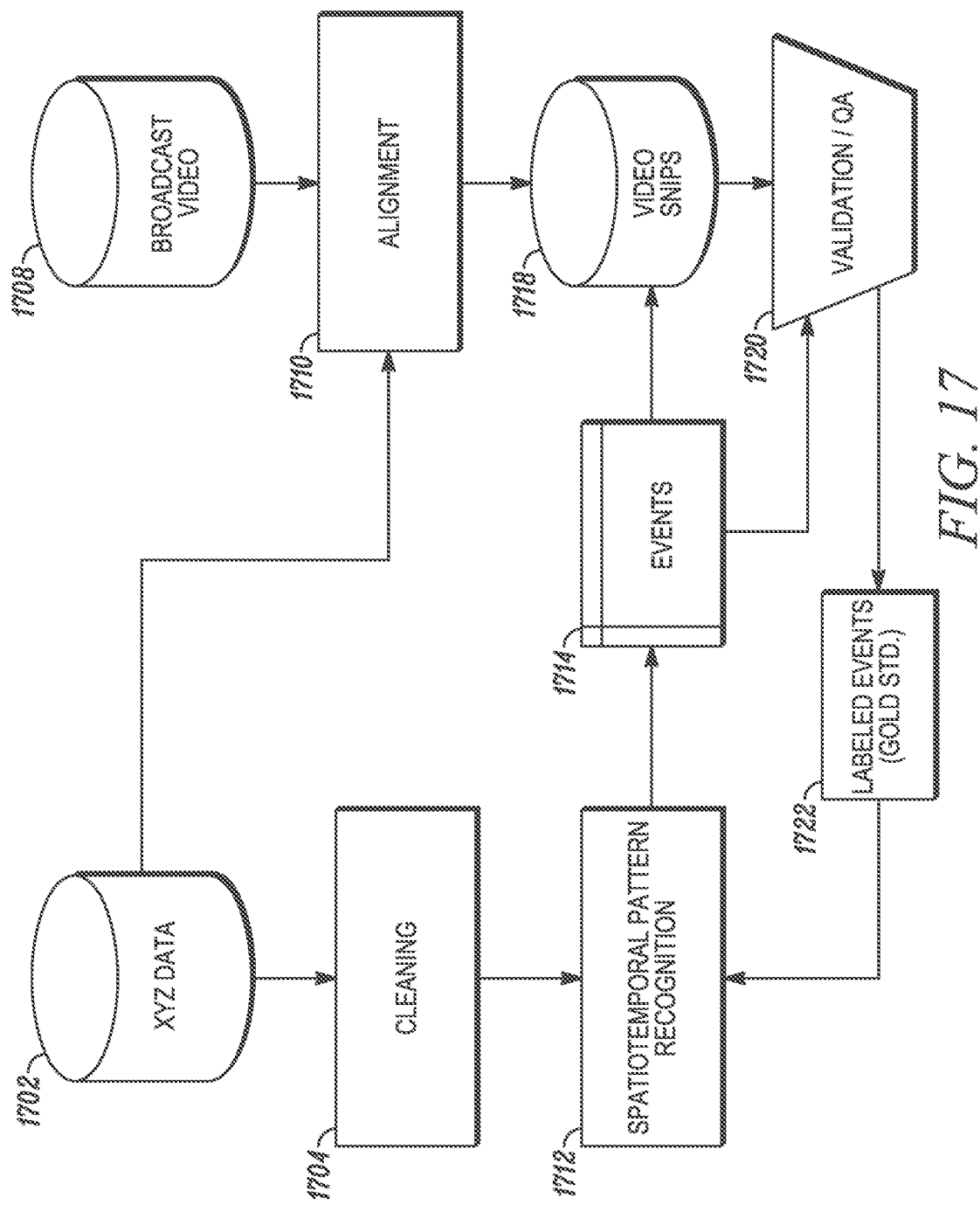
FIG. 17 illustrates a hybrid classification process flow according to an exemplary and non-limiting embodiment.

FIG. 17 shows a process flow for a hybrid classification process that uses human labelers together with machine learning algorithms to achieve high accuracy. This is similar to the flow described above in connection with FIG. 2, except with the explicit inclusion of the human-machine validation process. By taking advantage of aligned video as described herein, one may provide an optimized process for human validation of machine labeled data. Most of the components are similar to those described in connection with FIG. 2 and in connection with the description of aligned video, such as the XYZ data source 1702, cleaning process 1704, spatiotemporal pattern recognition module 1712, event processing system 1714, video source 1708, alignment facility 1710 and video snippets facility 1718. Additional components include a validation and quality assurance process 1720 and an event-labeling component 1722. Machine learning algorithms are designed to output a measure of confidence. For the most part, this corresponds to the distance from a separating hyperplane in the feature space. In embodiments, one may define a threshold for confidence. If an example is labeled by the machine and has confidence above the threshold, the event goes into the canonical event datastore 210 and nothing further is done. If an example has a confidence score below the threshold, then the system may retrieve the video corresponding to this candidate event, and ask a human operator to provide a judgment. The system asks two separate human operators for labels. If the given labels agree, the event goes into the canonical event datastore 210, If they do not, a third person, known as the supervisor, is contacted for a final opinion. The supervisor's decision may be final. The canonical event datastore 210 may contain both human marked and completely automated markings. The system may use both types of marking to further train the pattern recognition algorithms. Event labeling is similar to the canonical event datastore 210, except that sometimes one may either 1) develop the initial gold standard set entirely by hand, potentially with outside experts, or 2) limit the gold standard to events in the canonical event datastore 210 that were labeled by hand, since biases may exist in the machine labeled data.

Figure 18:
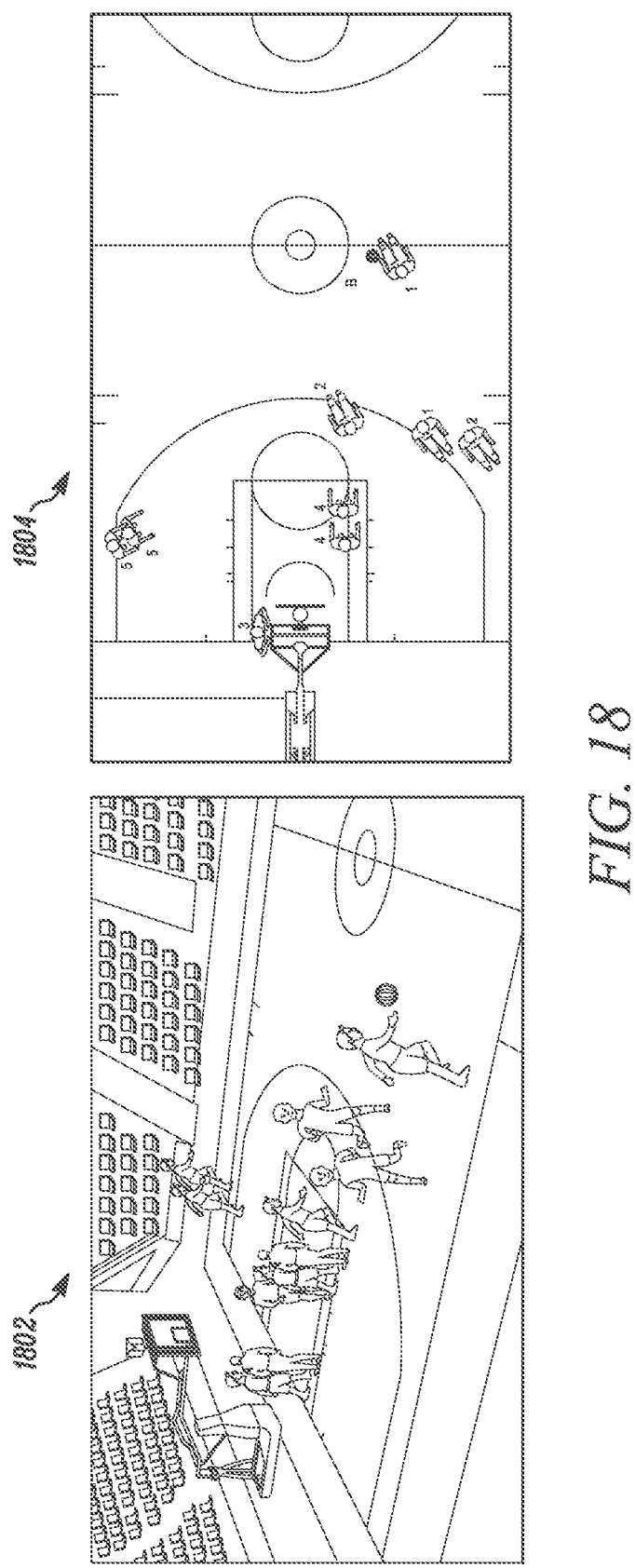
FIG. 18 illustrates test inputs according to an exemplary and non-limiting embodiment.

FIG. 18 shows test video input for use in the methods and systems disclosed herein, including views of a basketball court from simulated cameras, both simulated broadcast camera views 1802, as well as purpose-mounted camera views 1804.

Figure 19:
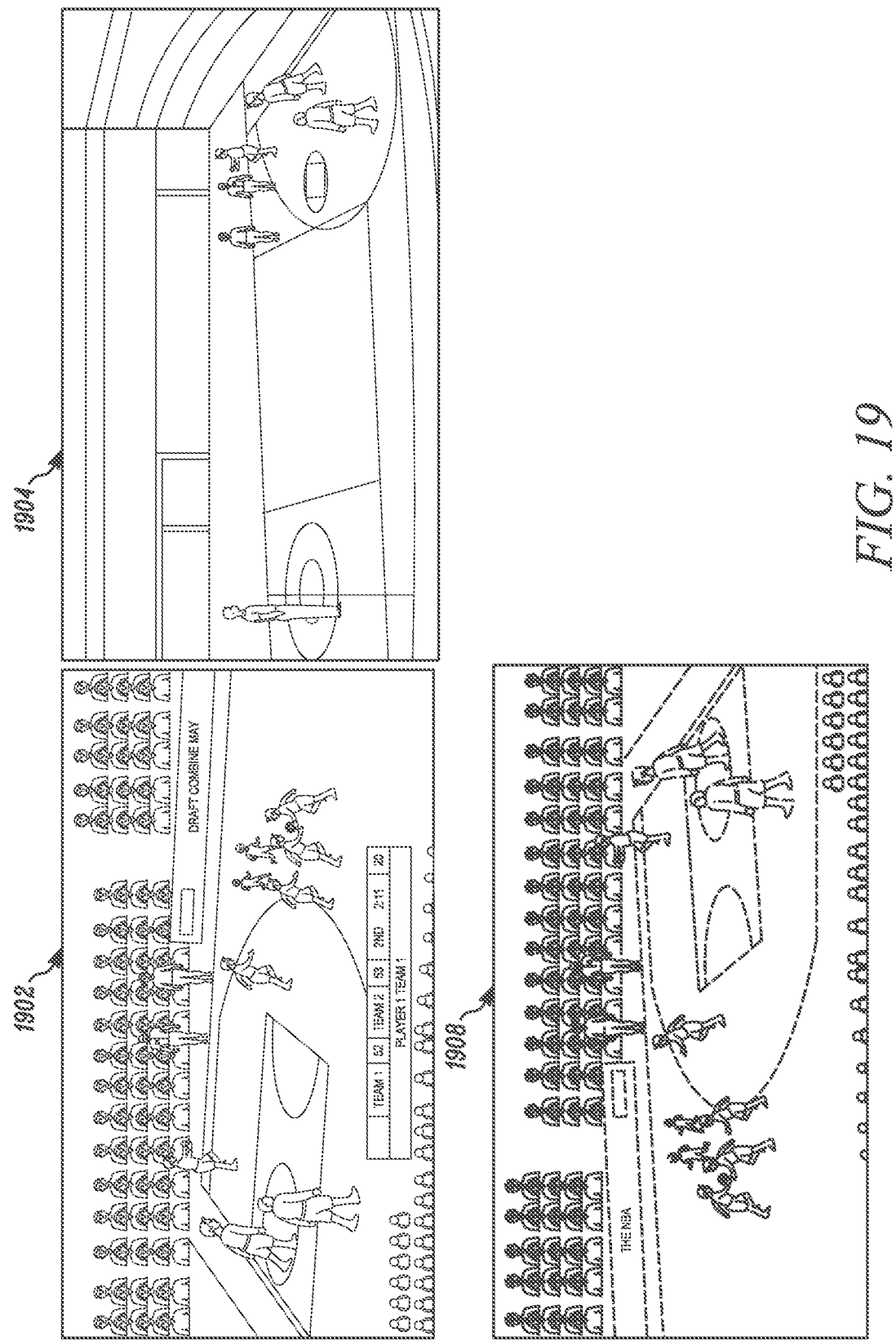
FIG. 19 illustrates test inputs according to an exemplary and non-limiting embodiment.
Figure 20:
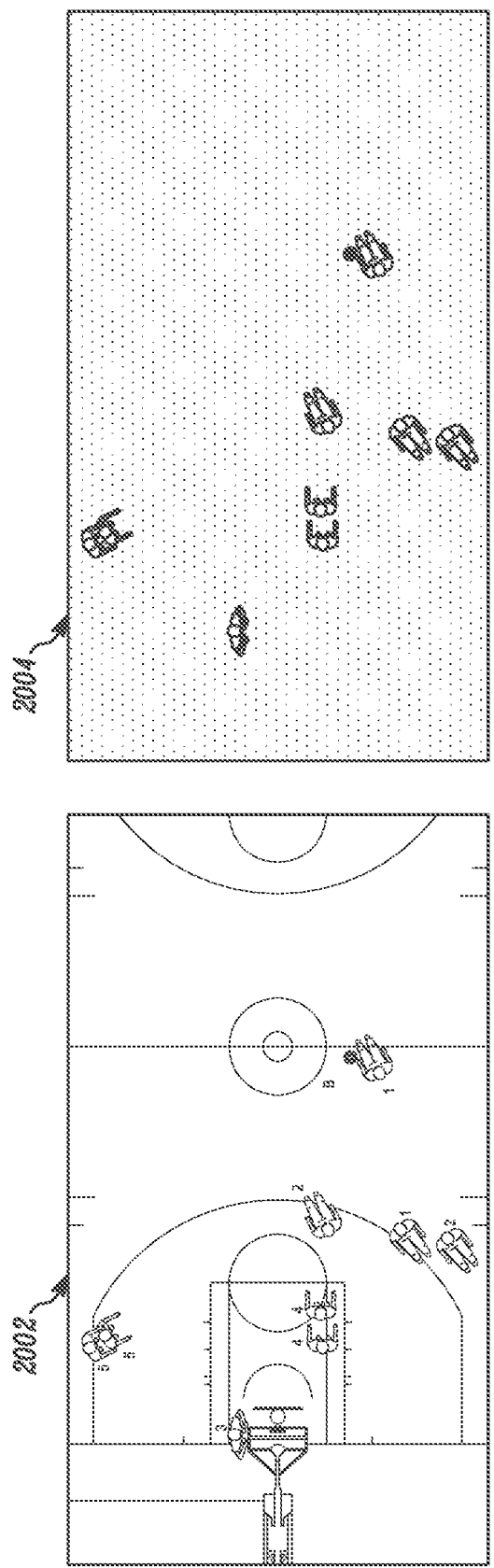
FIG. 20 illustrates player detection according to an exemplary and non-limiting embodiment.

FIG. 19 shows additional test video input for use in the methods and systems disclosed herein, including input from broadcast video 1902 and from purpose-mounted cameras 1904 in a venue. Referring to FIG. 20, probability maps 2004 may be computed based on likelihood there is a person standing at each x, y location.

Figure 21:
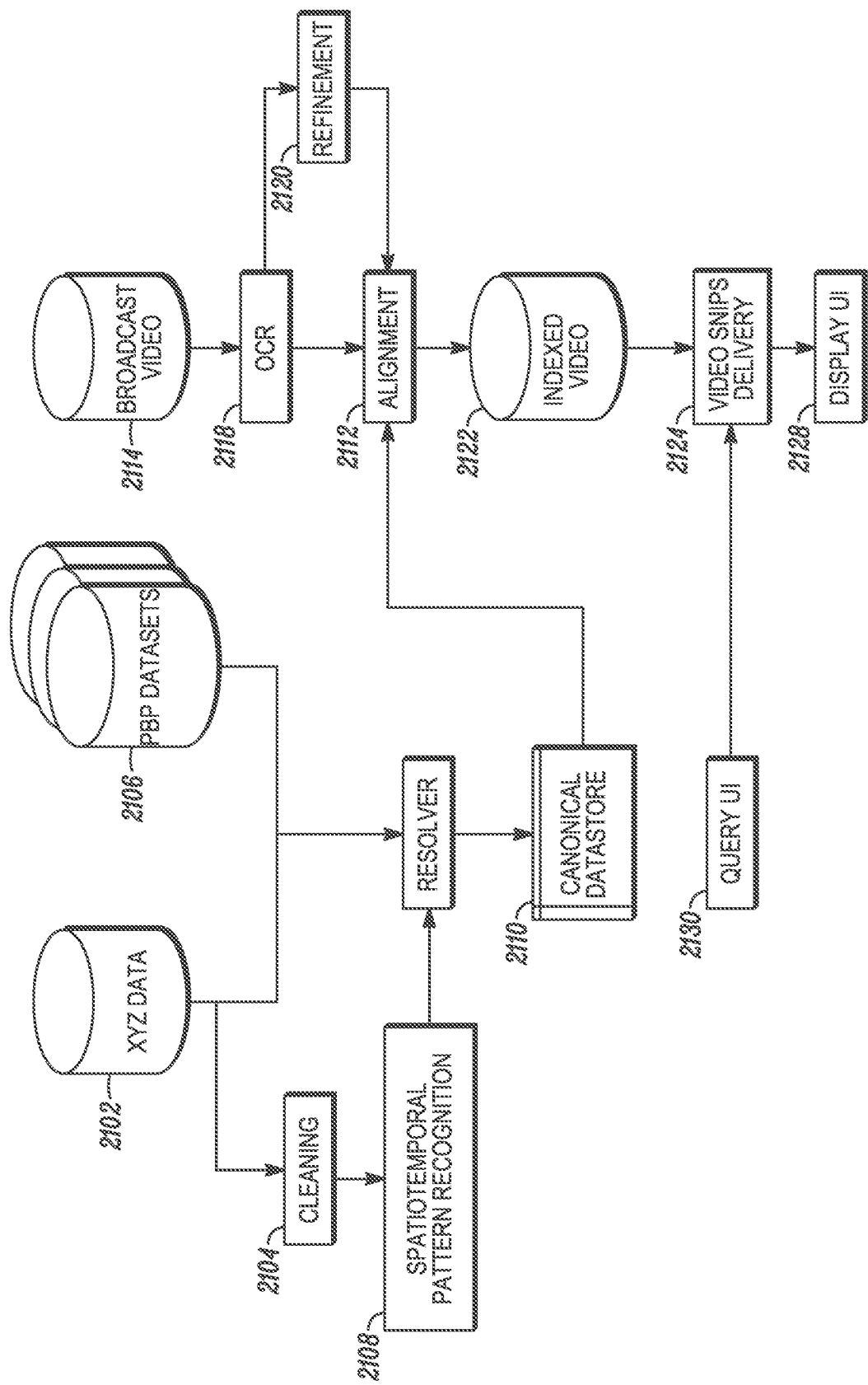
FIG. 21 illustrates a process flow according to an exemplary and non-limiting embodiment.

FIG. 21 shows a process flow of an embodiment of the methods and systems described herein. Initially, in an OCR process 2118, machine vision techniques are used to automatically locate the "score bug" and determine the location of the game clock, score, and quarter information. This information is read and recognized by OCR algorithms. Post-processing algorithms using various filtering techniques are used to resolve issues in the OCR. Kalman filtering/HMMs used to detect errors and correct them. Probabilistic outputs (which measure the degree of confidence) assist in this error detection/correction. Next, in a refinement process 2120, sometimes, a score bug is nonexistent or cannot be detected automatically (e.g., sometimes during PIP or split screens). In these cases, remaining inconsistencies or missing data is resolved with the assistance of human input. Human input is designed to be sparse so that labelers do not have to provide input at every frame. Interpolation and other heuristics are used to fill in the gaps. Consistency checking is done to verify the game clock. Next, in an alignment process, 2112 the Canonical Datastore 2110 (referred to elsewhere in this disclosure alternatively as the event datastore) contains a definitive list of events that the system knows occurred during a game. This includes events extracted from the XYZ data 2102, such as after cleansing 2104 and spatiotemporal pattern recognition 2108, as well as those specified by third-party sources such as player-by-player data sets 2106, such as available from various vendors. Differences among the data sources can be resolved, such as by a resolver process. The events in the canonical datastore 2110 may have game clock times specified for each event. Depending on the type of event, the system knows that the user will be most likely to be interested in a certain interval of game play tape before and after that game clock. The system can thus retrieve the appropriate interval of video for the user to watch.

One challenge pertains to the handling of dead ball situations and other game clock stoppages. The methods and systems disclosed herein include numerous novel heuristics to enable computation of the correct video frame that shows the desired event, which has a specified game clock, and which could be before or after the dead ball since those frames have the same game clock. The game clock is typically specified only at the one-second level of granularity, except in the final minute of each quarter.

Another advance is to use machine vision techniques to verify some of the events. For example, video of a made shot will typically show the score being increased, or will show a ball going through a hoop. Either kind of automatic observation serves to help the alignment process result in the correct video frames being shown to the end user.

Next, in a query UI component 2130, the UI enables a user to quickly and intuitively request all video clips associated with a set of characteristics: player, team, play type, ballhandler, ballhandler velocity, time remaining, quarter, defender, etc. In addition, when a user is watching a video clip, the user can request all events that are similar to whatever just occurred in the video. The system uses a series of cartoon-like illustration to depict possible patterns that represent "all events that are similar." This enables the user to choose the intended pattern, and quickly search for other results that match that pattern.

Next, the methods and systems may enable delivery of enhanced video, or video snips 2124, which may include rapid transmission of clips from stored data in the cloud. The system may store video as chunks (e.g., one-minute chunks), such as in AWS S3, with each subsequent file overlapping with a previous file, such as by 30 seconds. Thus, each video frame may be stored twice, Other instantiations of the system may store the video as different sized segments, with different amounts of overlap, depending on the domain of use. In embodiments, each video file is thus kept at a small size. The 30-second duration of overlap may be important because most basketball possessions (or chances in our terminology) do not last more than 24 seconds. Thus, each chance can be found fully contained in one video file, and in order to deliver that chance, the system does not need to merge content from multiple video files. Rather, the system simply finds the appropriate file that contains the entire chance (which in turn contains the event that is in the query result), and returns that entire file, which is small. With the previously computed alignment index, the system is also able to inform the UI to skip ahead to the appropriate frame of the video file in order to show the user the query result as it occurs in that video file. This delivery may occur using AWS S3 as the file system, the Internet as transport, and a browser-based interface as the UI. It may find other instantiations with other storage, transport, and UI components.

Figure 22:
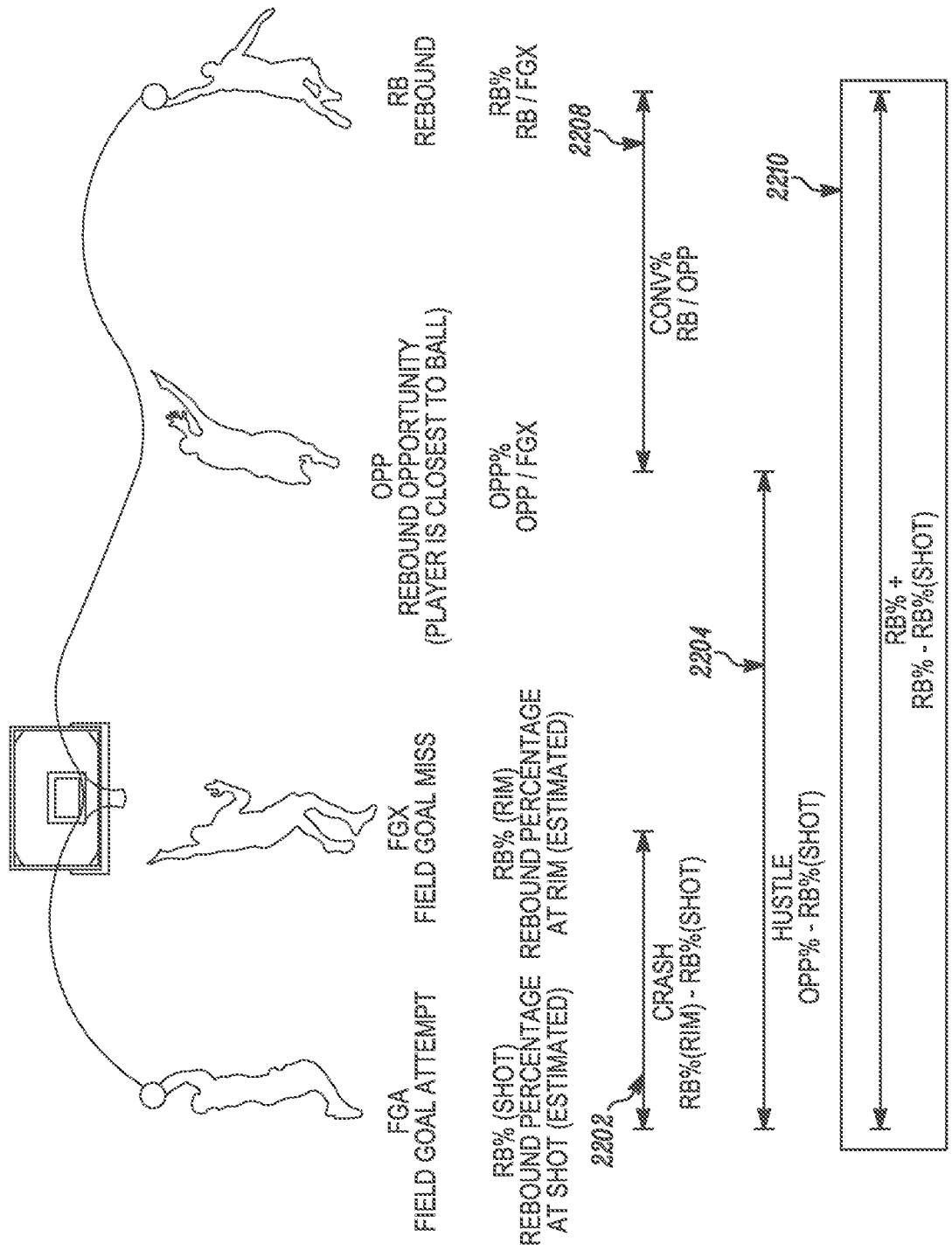
FIG. 22 illustrates rebounding according to an exemplary and non-limiting embodiment.

FIG. 22 shows certain metrics that can be extracted using the methods and systems described herein, relating to rebounding in basketball. These metrics include positioning metrics, attack metrics, and conversion metrics. For positioning, the methods and systems described herein first address how to value the initial position of the players when the shot is taken. This is a difficult metric to establish. The methods and systems disclosed herein may give a value to the real estate that each player owns at the time of the shot. This breaks down into two questions: (1) what is the real estate for each player? (2) what is it worth? To address the first question, one may apply the technique of using Voronoi (or Dirichlet) tessellations. Voronoi tessellations are often applied to problems involving spatial allocation. These tessellations partition a space into Voronoi cells given a number of points in that space. For any point, it is the intersection of the self-containing half-spaces defined by hyper-planes equidistant from that point to all other points. That is, a player's cell is all the points on the court that are closer to the player than any other player. If all players were equally capable they should be able to control any rebound that occurred in this cell. One understands that players are not equally capable however this establishment of real estate is to set a baseline for performance. Over performance or under performance of this baseline will be indicative of their ability. To address the second question, one may condition based on where the shot was taken and calculate a spatial probability distribution of where all rebounds for similar shots were obtained. For each shot attempt, one may choose a collection of shots closest to the shot location that provides enough samples to construct a distribution. This distribution captures the value of the real estate across the court for a given shot. To assign each player a value for initial positioning, i.e., the value of the real estate at the time of the shot, one may integrate the spatial distribution over the Voronoi cell for that player. This yields the likelihood of that player getting the rebound if no one moved when the shot was taken and they controlled their cell. We note that because we use the distribution of locations of the rebound conditioned on the shot, it is not a matter of controlling more area or even necessarily area close to the basket, but the most valuable area for that shot. While the most valuable areas are typically close to the basket, there are some directional effects.

For an attack or hustle metric, one may look at phases following a shot, such as an initial crash phase. To analyze this, one may look at the trajectory of the ball and calculate the time that it gets closest to the center of the rim. At this point, one may reapply the Voronoi-based analysis and calculate the rebound percentages of each player, i.e., the value of the real the estate that each player has at the time the ball hits the rim. The change in this percentage from the time the shot is taken to the time it hits the rim is the value or likelihood the player had added during the phase. Players can add value by crashing the boards, i.e., moving closer to the basket towards places where the rebound is likely to go, or by blocking out, i.e., preventing other players by taking valuable real estate that is already established. A useful, novel metric for the crash phase is generated by subtracting the rebound probability at the shot from the rebound probability at the rim. The issue is that the ability to add probability is not independent of the probability at the shot. Consider a case of a defensive player who plays close to the basket. The player is occupying high-value real estate, and once the shot is taken, other players are going to start coming into this real estate. It is difficult for players with high initial positioning value to have positive crash deltas. Now consider a player out by the three-point line. Their initial value is very low and moving any significant distance toward the rim will give them a positive crash delta. Thus, it is not fair to compare these players on the same scale. To address this, one may look at the relationship of the raw crash deltas (the difference between the probability at rim and probability at shot) compared to the probability at shot. In order to normalize for this effect, one may subtract the value of the regression at the player's initial positioning value from the raw crash delta to form the player's Crash value. Intuitively, the value indicates how much more probability is added by this player beyond what a player with similar initial positioning would add. One may apply this normalization methodology to all the metrics the initial positioning affects the other dimensions and it can be beneficial to control for it.

A player has an opportunity to rebound the ball if they are the closest player to the ball once the ball gets below ten feet (or if they possess the ball while it is above ten feet). The player with the first opportunity may not get the rebound so multiple opportunities could be created after a single field goal miss. One may tally the number of field goal misses for which a player generated an opportunity for themselves and divided by the number of field goals to create an opportunity percentage metric. This indicates the percentage of field goal misses for which that player ended up being closest to the ball at some point. The ability for a player to generate opportunities beyond his initial position is the second dimension of rebounding: Hustle. Again, one may then apply the same normalization process as described earlier for Crash.

The reason that there are often multiple opportunities for rebounds for every missed shot is that being closest to the ball does not mean that a player will convert it into a rebound. Thus, the third dimension of rebounding, conversion. The raw conversion metric for players is calculated simply by dividing the number of rebounds obtained by the number of opportunities generated.

Formally, given a shot is described by its 2D coordinates on the court, s_x and s_y, which is followed by a rebound r, also described by its coordinates on the court of r_x and r_y, one may estimate P(r_y, r_x|s_x, s_y), the probability density of the rebound occurring at each position on the court given its shot location.

This may be accomplished by first discretizing the court into, for example, 156 bins, created by separating the court into 13 equally spaced columns, and 12 equally spaced rows. Then, given some set S of shots from a particular bin, the rebounds from S will be distributed in the bins of the court according to a multinomial distribution. One may then apply maximum likelihood estimation to determine the probability of a rebound in each of the bins of the court, given the training set S. This process may be performed for bins that shots may fall in, giving 156 distributions for the court.

Using these distributions, one may determine P(r_y, r_x|s_x, s_y). First, the shot is mapped to an appropriate bin. The probability distribution determined in the previous step is then utilized to determine the probability of the shot being rebounded in every bin of the court. One assumes that within a particular bin, the rebound is uniformly likely to occur in any coordinate. Thus, a probability density of the probability of the rebound falling in the bin is assigned to all points in the bin.

Using the probability density P(r_y, r_x|s_x, s_y), one may determine the probability that each particular player grabs the rebound given their location and the position of the other players on the court.

To accomplish this, one may first create a Voronoi diagram of the court, where the set of points is the location (p_x, p_y) for each player on the court. In such a diagram, each player is given a set of points that they control. Formally one may characterize the set of points that player P_k controls in the following manner, where X is all points on the court, and d denotes the Cartesian distance between 2 points.

$$R_k = \{x \in X | d(x, P_k) \leq d(x, P_j) \text{ for all } j \neq k\}$$

Now there exist the two components for determining the probability that each player gets the rebound given their location, specifically, the shot's location, and the location of all the other players on the court. One may determine this value by assuming that if a ball is rebounded, it will be rebounded by the closest available player. Therefore, by integrating the probability of a rebound over each location in the player's Voronoi cell, we determine their rebound probability:

$$\int_R P(r_x, r_y | s_x, s_y) dx dy$$

The preceding section describes a method for determining the players rebounding probability, assuming that the players are stationary. However, players often move in order to get into better positions for the rebound, especially when they begin in poor positions. One may account for these phenomena. Let the player's raw rebound probability be denoted $r_p$ and let d be an indicator variable denoting whether the player is on defense.

On may then attempt to estimate the player's probability of getting a rebound, which we express in the following manner:

$$P(r|r_p, d)$$

One does this by performing two linear regressions, one for the offensive side of the ball and one for the defensive. One may attempt to estimate $p(r|r_p, d)$ in the following manner:

$$P(r|r_p, d=0) = A_o * r_p + B_o$$

$$P(r|r_p, d=1) = A_d * r_p + B_d$$

This results in four quantities to estimate. One may do this by performing an ordinary least squares regression for offensive and defensive players' overall rebounds in the test set. One may use 1 as a target variable when the player rebounds the ball, and 0 when he does not. This regression is performed for offense to determine $A_o$ and $B_o$ and for defense to determine $A_d$ and $B_d$. One can then use the values to determine the final probability of each player getting the rebound given the shots location and the other players on the court. Novel shooting metrics can also be created using this system. One is able to determine the probability of a shot being made given various features of the shot s, denoted as F. Formally each shot can be characterized by a feature vector of the following form.

[dist (hoop, shooter), dist(shooter, defender$_0$), |angle (hoop, shooter, defender$_0$)|,|angle(shooter, hoop, hoop$_{other}$), I(shot=catchAndShoot), dist(shooter, defender$_1$)]

Here, the hoop represents the basket the shooter is shooting at, defender$_0$ refers to the closest defender to the shooter, defender$_1$ refers to the second closest defender, and hoop$_{other}$ refers to the hoop on the other end of the court. The angle function refers to the angle between three points, with the middle point serving as the vertex. I(shot=catchAndShoot) is an indicator variable, set to 1 if the shooter took no dribbles in the individual possession before shooting the shot, otherwise set to 0.

Given these features, one seeks to estimate P(s=make). To do this, one may first split the shots into 2 categories, one for where dist (hoop, shooter) is less than 10, and the other for the remaining shots. Within each category one may find coefficients $\beta_0, \beta_1, \ldots, \beta_5$ for the following equation:

$$1/(1+e^{\wedge}(-t))$$

where $$t=F_0*\beta_0+F_1*\beta_1+\ldots+F_5*\beta_5$$

Here, $F_0$ through $F_5$ denote the feature values for the particular shot. One may find the coefficient values $\beta_0, \beta_1, \ldots, \beta_5$ using logistic regression on the training set of shots S. The target for the regression is 0 when the shot is missed and 1 when the shot is made. By performing two regressions, one is able to find appropriate values for the coefficients, for both shots within 10 feet, and longer shots outside 10 feet.

Figure 23:
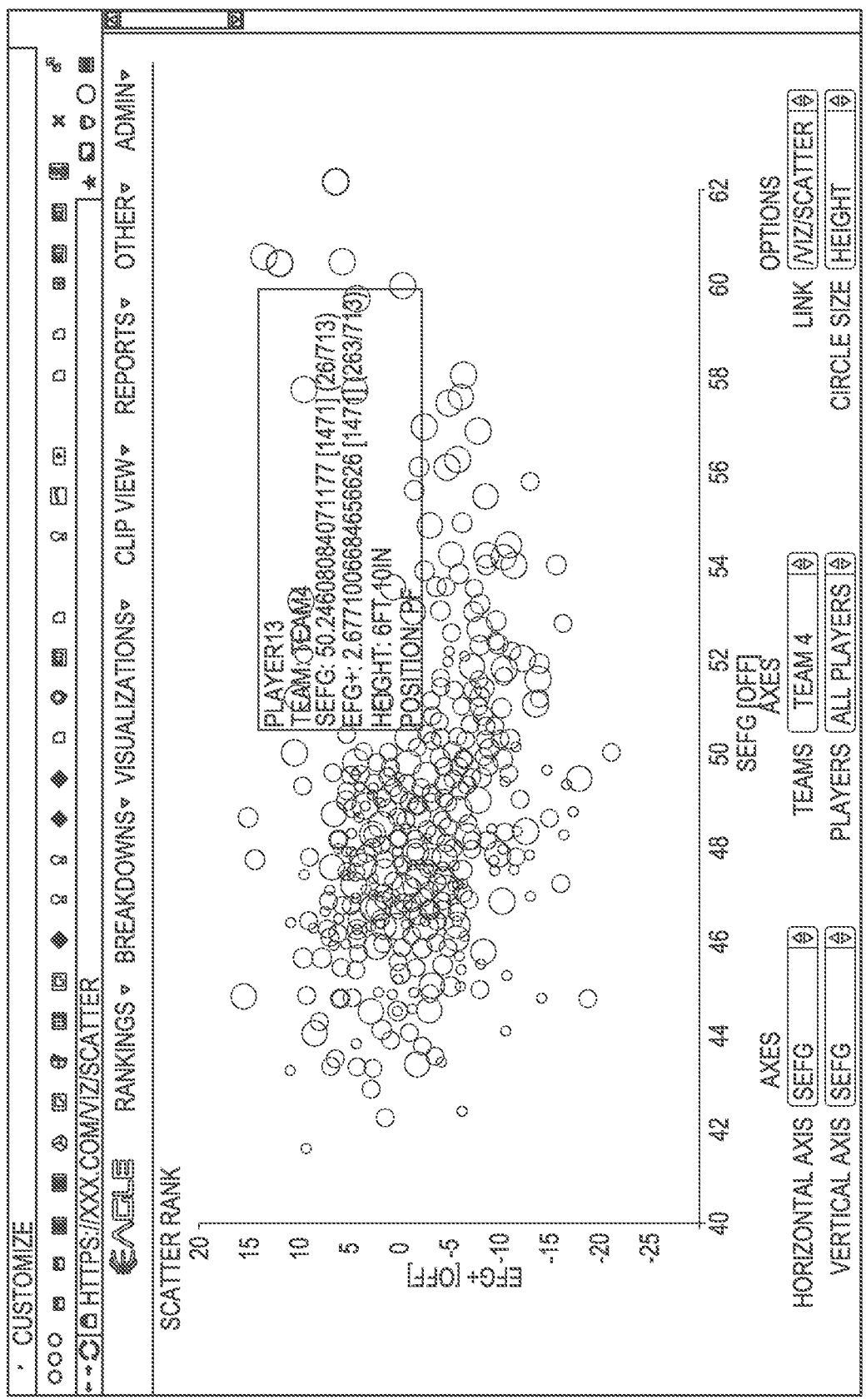
FIG. 23 illustrates scatter rank according to an exemplary and non-limiting embodiment.

As depicted in FIG. 23, three or four dimensions can be dynamically displayed on a 2-D graph scatter rank view 2302, including the x, y, size of the icon, and changes over time. Each dimension may be selected by the user to represent a variable of the user's choice. Also, on mouseover, related icons may highlight, e.g., mousing over one player may highlight all players on the same team.

As depicted in FIGS. 24A and 24B, reports 2402 can be customized by the user so that a team can create a report that is specifically tailored to that team's process and workflow, Another feature is that the report may visually display not only the advantages and disadvantages for each category shown but also the size of that advantage or disadvantage, along with the value and rank of each side being compared. This visual language enables a user to quickly scan the report and understanding the most important points.

Figure 25:
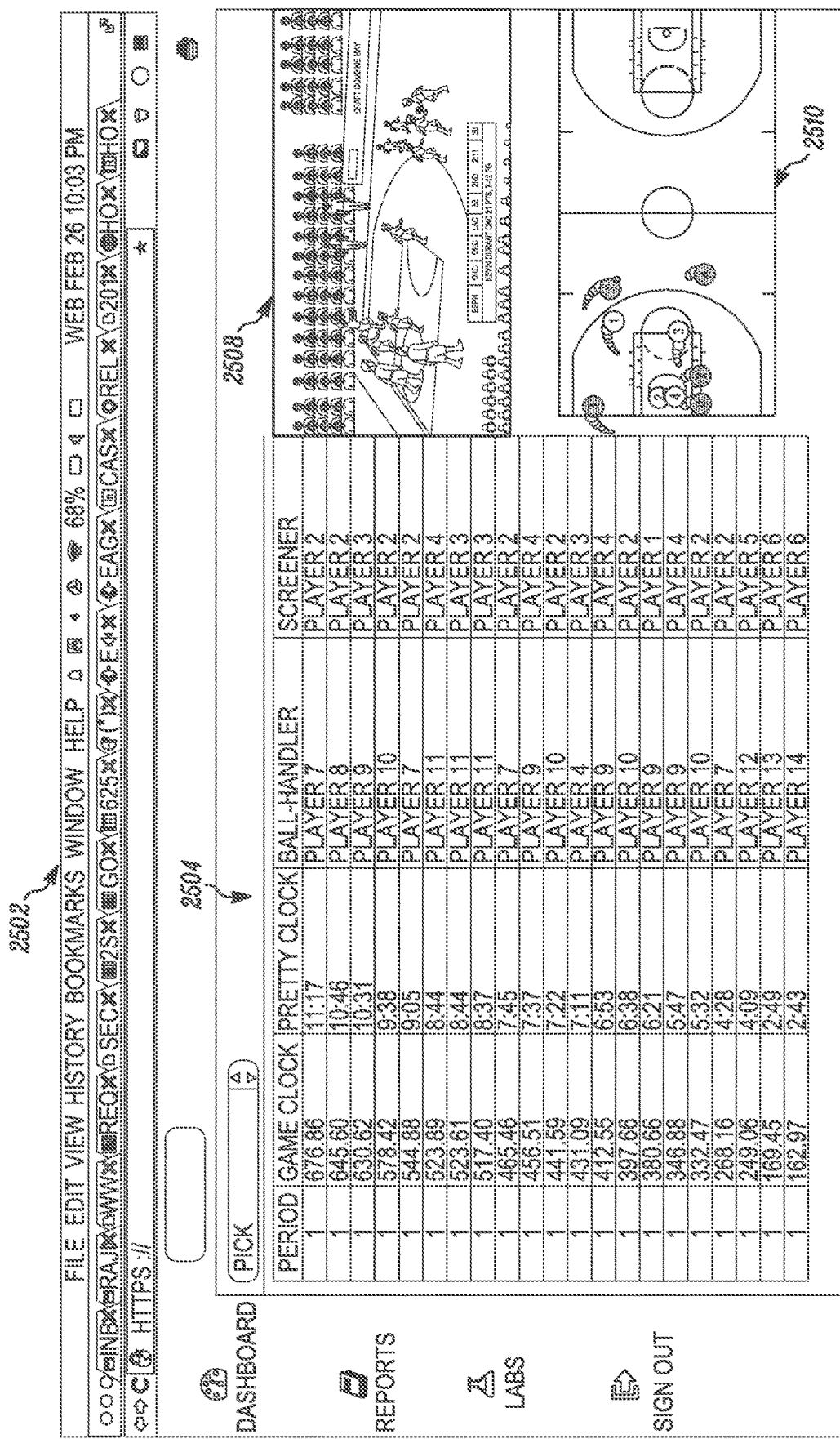
FIG. 25 illustrates a quality assurance user interface according to an exemplary and non-limiting embodiment.
Figure 26:
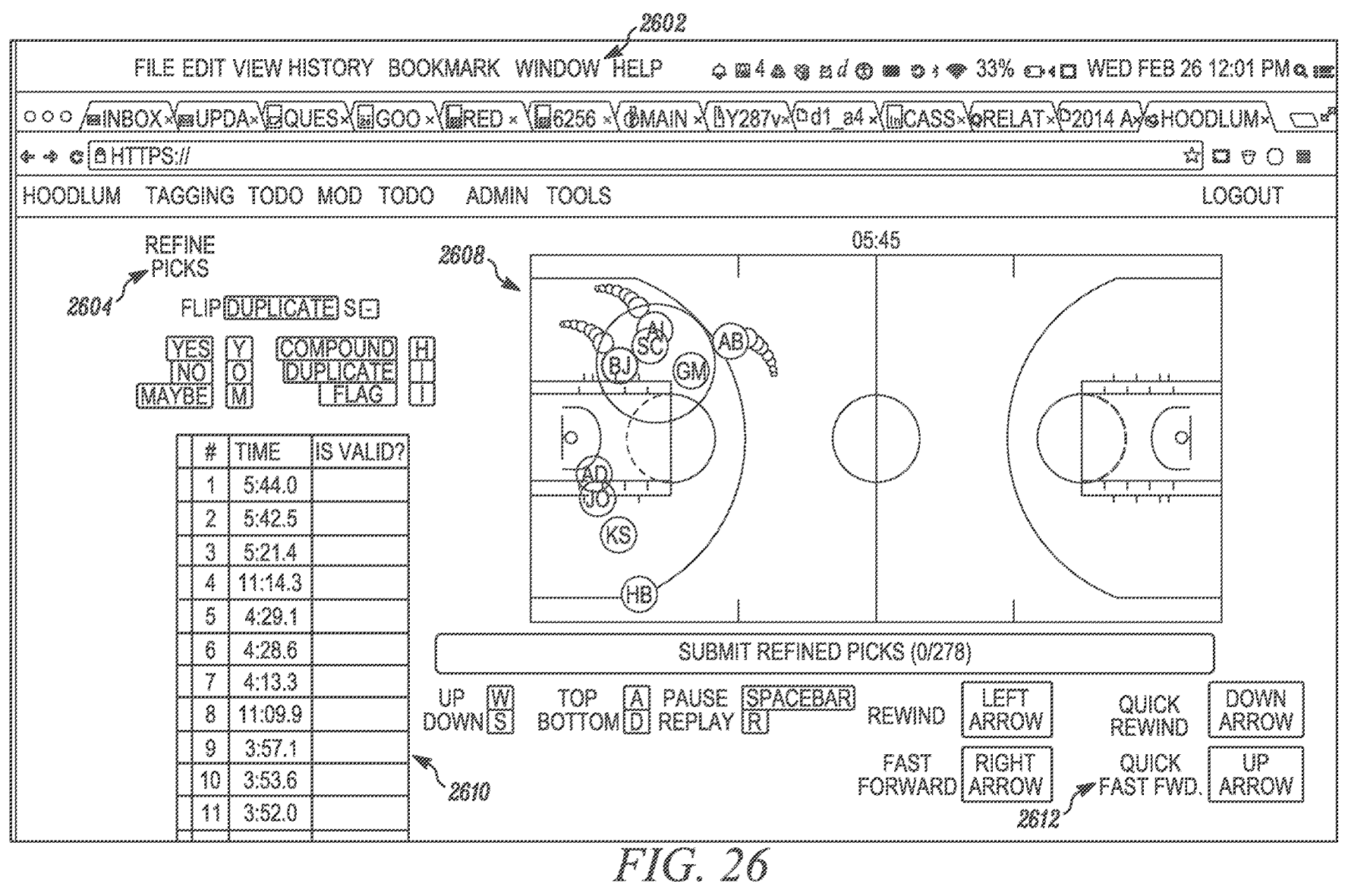

Referring to FIG. 25, an embodiment of a quality assurance UI 2502 is provided. The QA UI 2502 presents the human operator with both an animated 2D overhead view 2510 of the play, as well as a video clip 2508 of the play. A key feature is that as only the few seconds relevant to that play are shown to the operator, instead of an entire possession, which might be over 20 seconds long, or even worse, requiring the human operator to fast forward in the game tape to find the event herself, Keyboard shortcuts are used for all operations, to maximize efficiency. Referring to FIG. 26, the operator's task is simplified to its core, so that we lighten the cognitive load as much as possible: if the operator is verifying a category of plays X, the operator has to simply choose, in an interface element 2604 of the embodiment of the QA UI 2602 whether the play shown in the view 2608 is valid (Yes or No), or (Maybe). She can also deem the play to be a (Duplicate), a (Compound) play that means it is just one type-X action in a consecutive sequence of type-X actions, or choose to (Flag) the play for supervisor review for any reason. Features of the UI 2602 include the ability to fast word, rewind, submit and the like, as reflected in the menu element 2612. A table 2610 can allow a user to indicate the validity of plays occurring at designated times.

Figure 27:
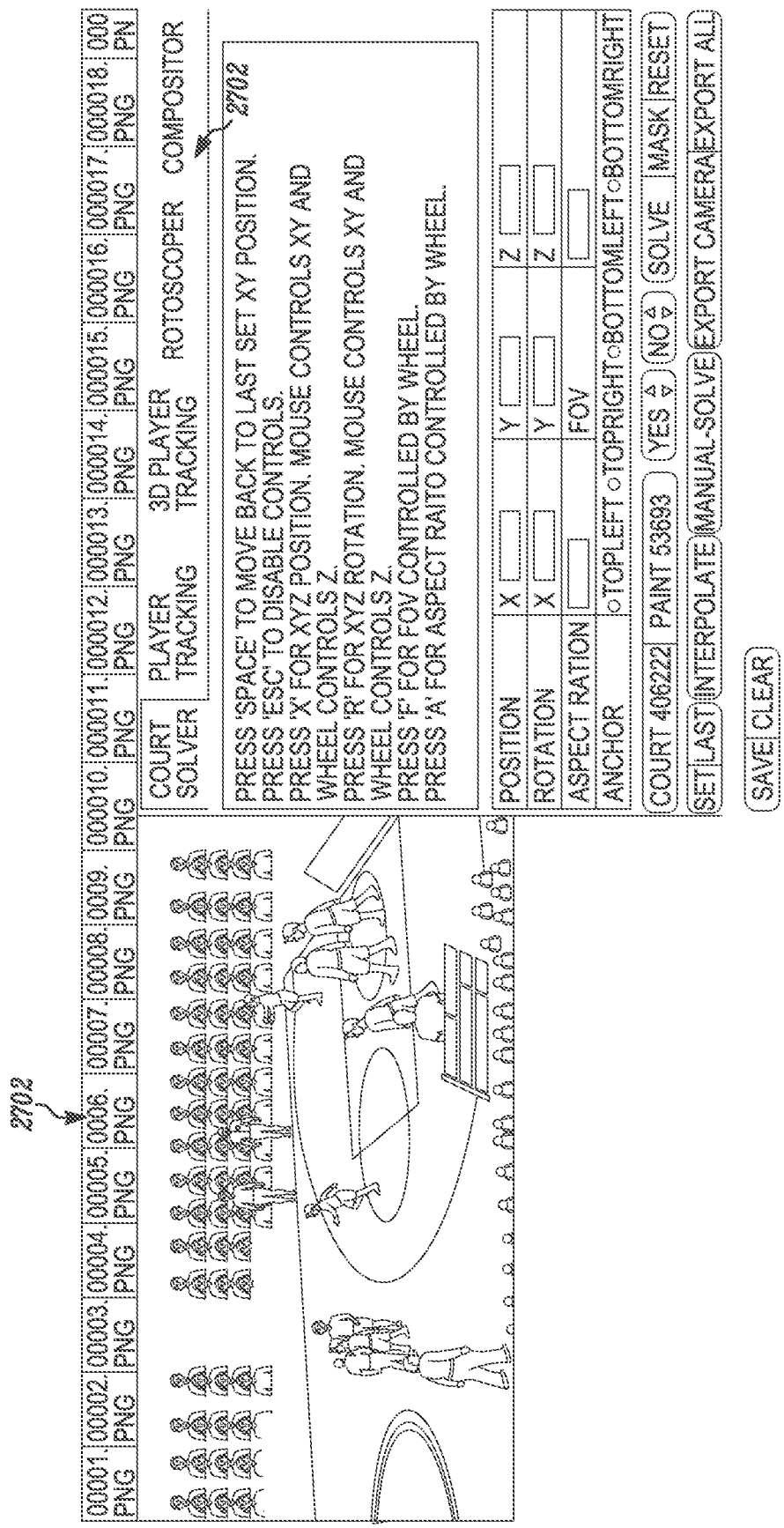
FIG. 27 illustrates camera pose detection according to an exemplary and non-limiting embodiment.
Figure 46:
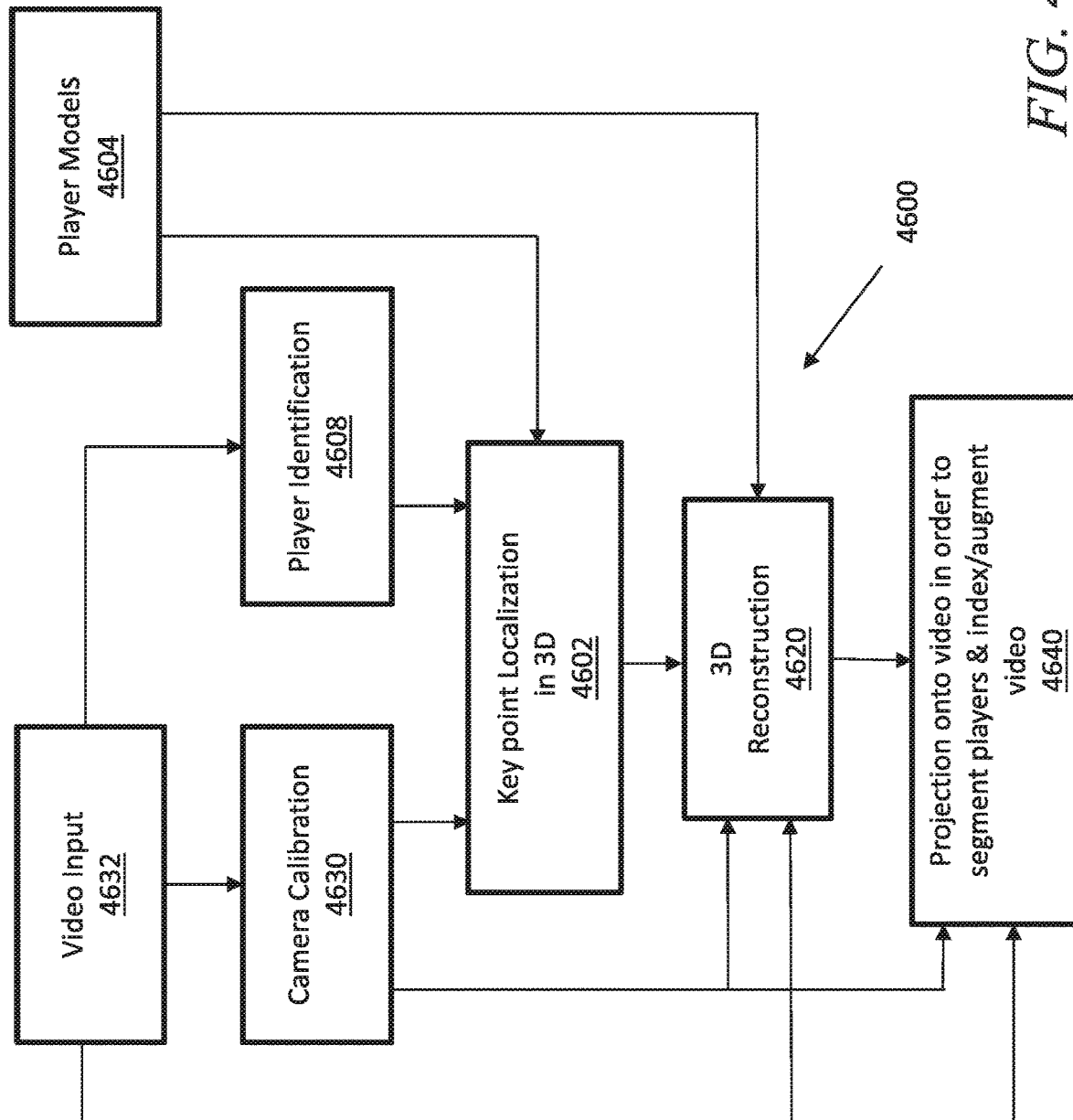
FIG. 46 illustrates systems and methods for player-specific information in three-dimensional position identification and reconstruction in accordance with the various embodiments.

FIG. 27 shows a method of camera pose detection, also known as "court solving." FIG. 27 also shows the result of automatic detection of the "paint," and use of the boundary lines to solve for the camera pose. The court lines and hoop location, given the solved camera pose, are then shown projected back onto the original image, This projection is from the first iteration of the solving process, and one can see that the projected court and the actual court do not yet align perfectly. One may use machine vision techniques to find the hoop and to find the court lines (e.g., paint boundaries), then use found lines to solve for the camera pose. Multiple techniques may be used to determine court lines, including detecting the paint area. Paint area detection can be done automatically. One method involves automatically removing the non-paint area of the court by automatically executing a series of "flood fill" type actions across the image, selecting for court-colored pixels. This leaves the paint area in the image, and it is then straightforward to find the lines/points. One may also detect all lines on the court that are visible, e.g., background or 3-point arc. In either case, intersections provide points for camera solving. A human interface 2702 may be provided for providing points or lines to assist algorithms, to fine-tune the automatic solver. Once all inputs are provided, the camera pose solver is essentially a randomized hill climber that uses the mathematical models as a guide (since it may be under-constrained). It may use multiple random initializations. It may advance a solution if it is one of the best in that round. When an iteration is done, it may repeat until the error is small. FIG. 46 shows the result of automatic detection of the "paint," and use of the boundary lines to solve for the camera pose. The court lines and hoop location, given the solved camera pose, are then shown projected back onto the original image. This projection is from the first iteration of the solving process, and one can see that the projected court and the actual court do not yet align perfectly.

Figure 28:
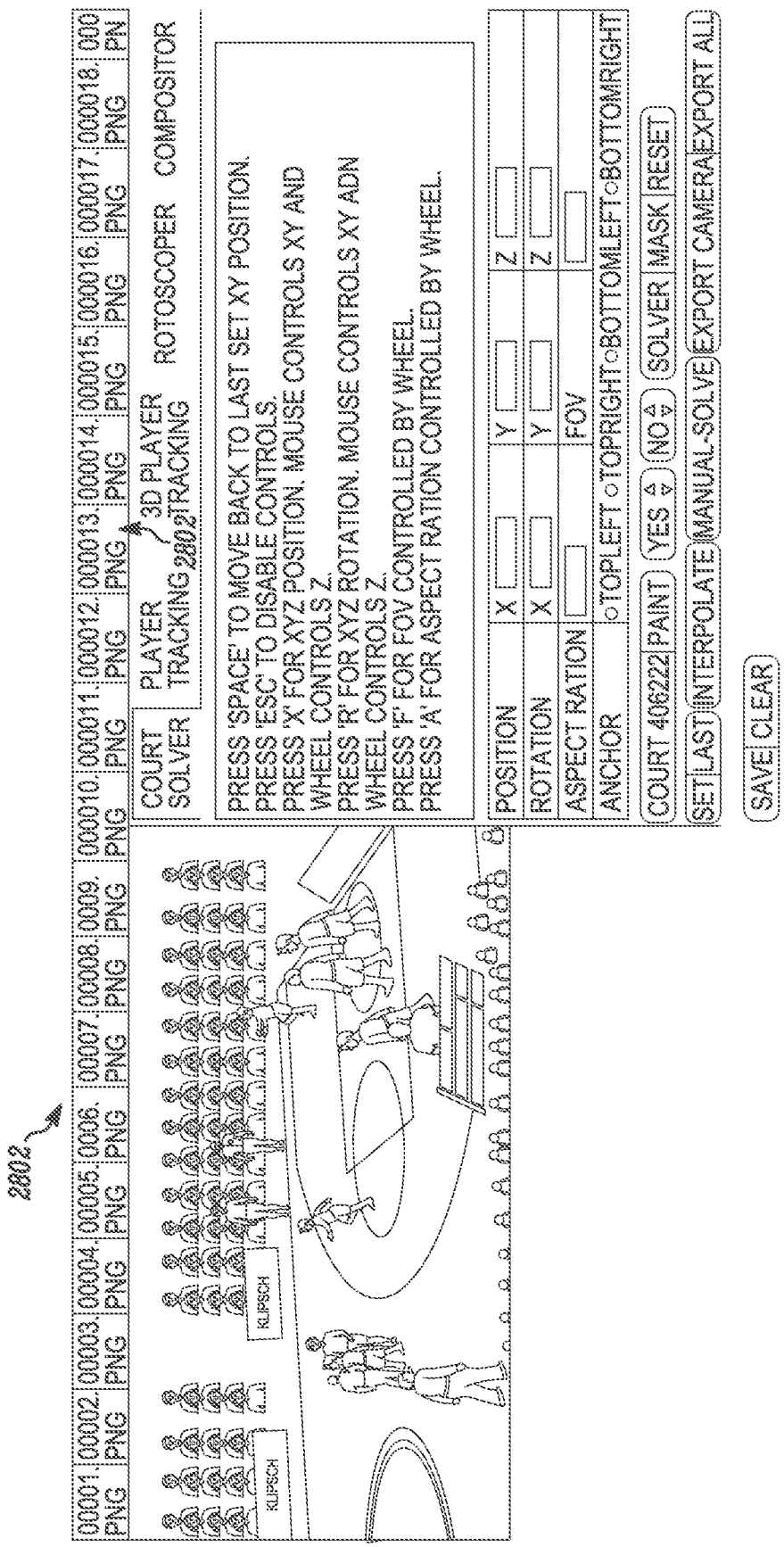
FIG. 28 illustrates camera pose detection according to an exemplary and non-limiting embodiment.

FIG. 28 relates to camera pose detection. The second step 2802 shown in the Figure shows how the human can use this GUI to manually refine camera solutions that remain slightly off.

Figure 29:
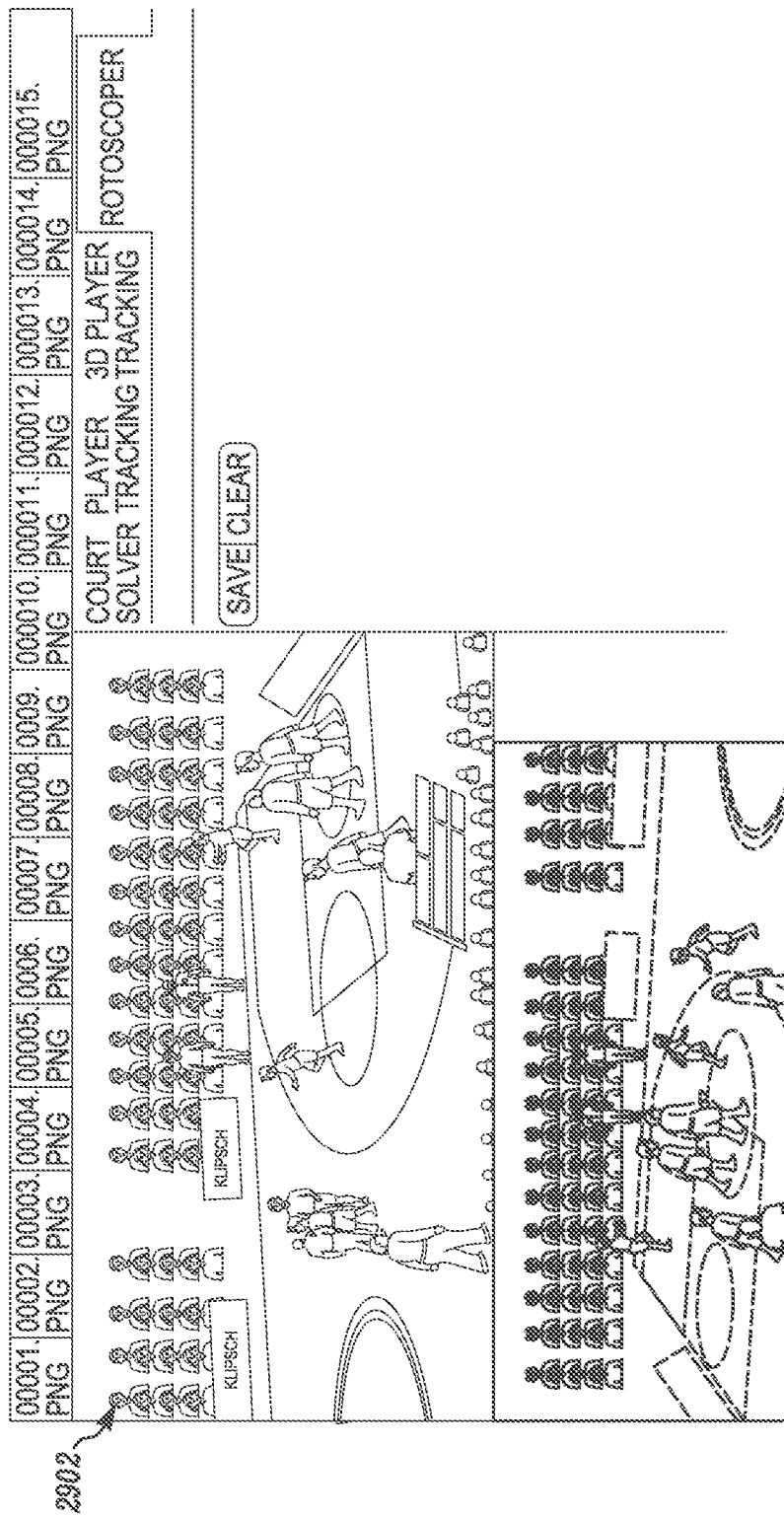
FIG. 29 illustrates auto-rotoscoping according to an exemplary and non-limiting embodiment.

FIG. 29 relates to auto-rotoscoping. Rotoscoping 2902 is required in order to paint graphics around players without overlapping the players' bodies. Rotoscoping is partially automated by selecting out the parts of the image with similar color as the court. Masses of color left in the image can be detected to be human silhouettes. The patch of color can be "vectorized" by finding a small number of vectors that surround the patch, but without capturing too many pixels that might not represent a player's body.

Figure 30B:
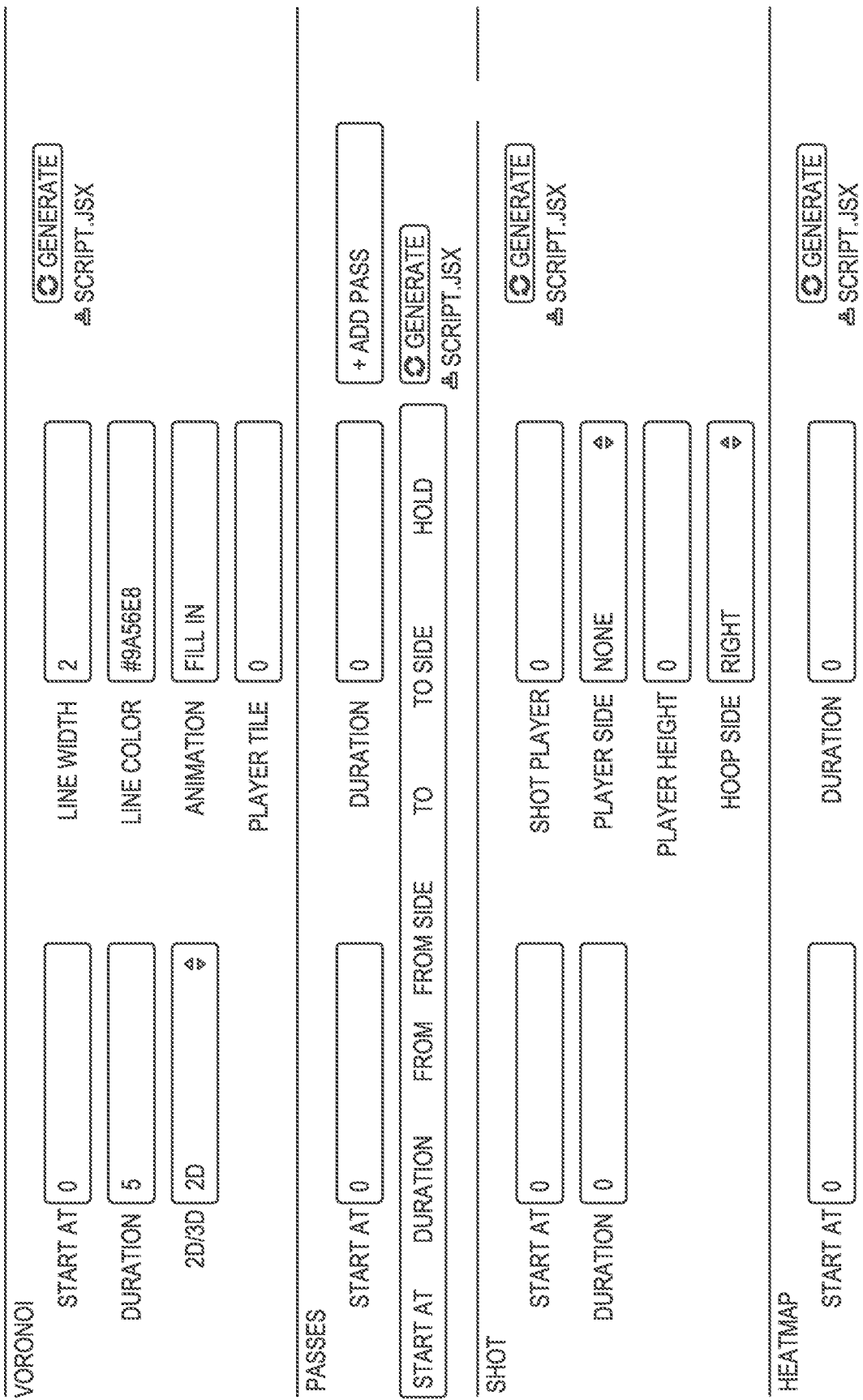
Figure 31:
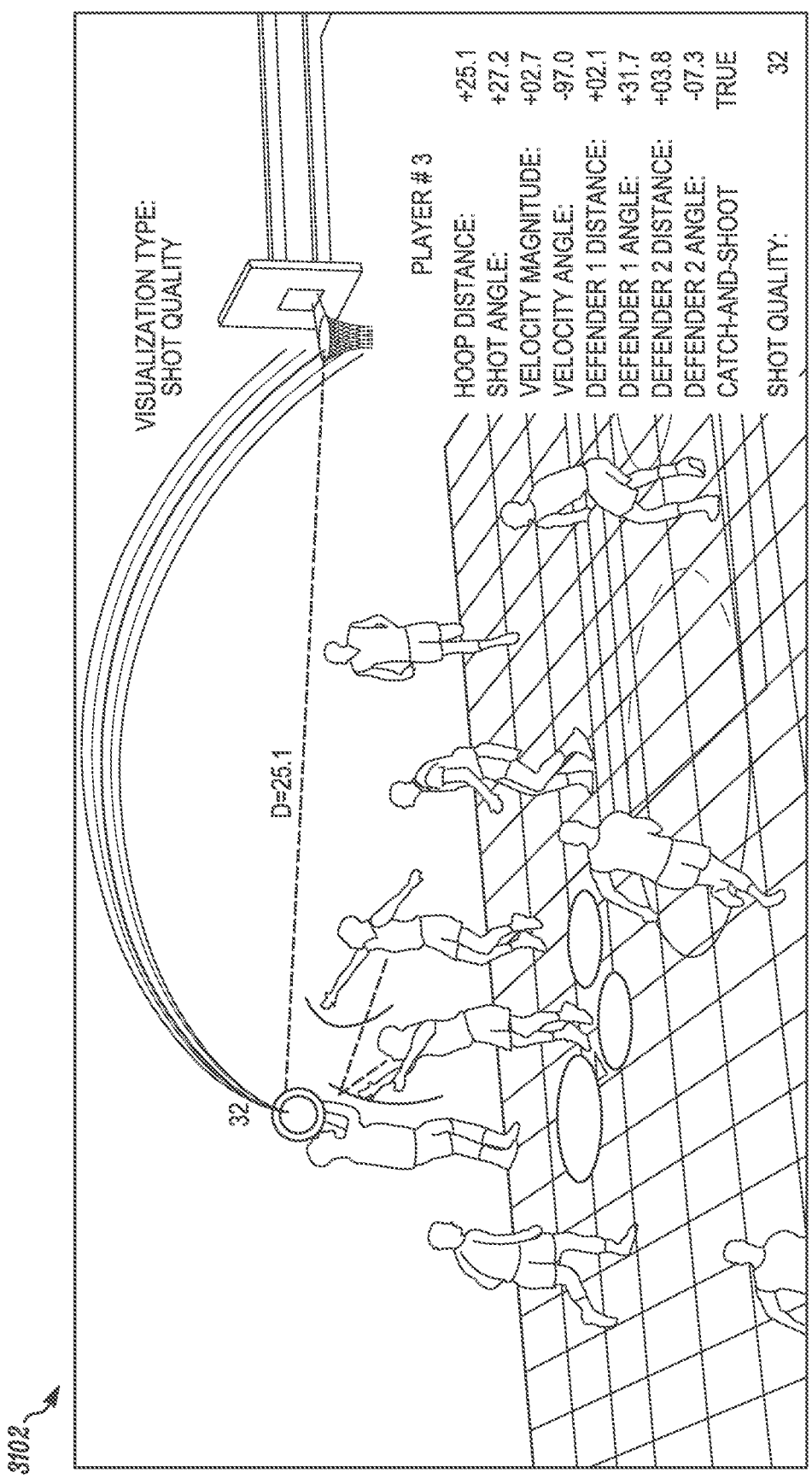
FIG. 31 illustrates an example according to an exemplary and non-limiting embodiment.

FIGS. 30A, 30B, and 30C relate to scripted storytelling with an asset library 3002. To produce the graphics-augmented clips, a company may either lean heavily on a team of artists, or a company may determine how best to handle scripting based on a library of assets. For example, instead of manually tracing a player's trajectory and increasing the shot probability in each frame as the player gets closer to the ball, a scripting language allows the methods and systems described herein to specify this augmentation in a few lines of code. In another example, for rebound clips, the Voronoi partition and the associated rebound positioning percentages can be difficult to compute for every frame. A library of story element effects may list each of these current and future effects. Certain combinations of scripted story element effects may be best suited for certain types of clips. For example, a rebound and putback will likely make use of the original shot probability, the rebound probabilities including Voronoi partitioning, and then go back to the shot probability of the player going for the rebound, This entire script can be learned as being well-associated with the event type in the video, Over time, the system can automatically infer the best, or at least retrieve an appropriate, storyline to match up with a selected video clip containing certain events. This enables augmented video clips, referred to herein as DataFX clips, to be auto-generated and delivered throughout a game.

Figure 32:
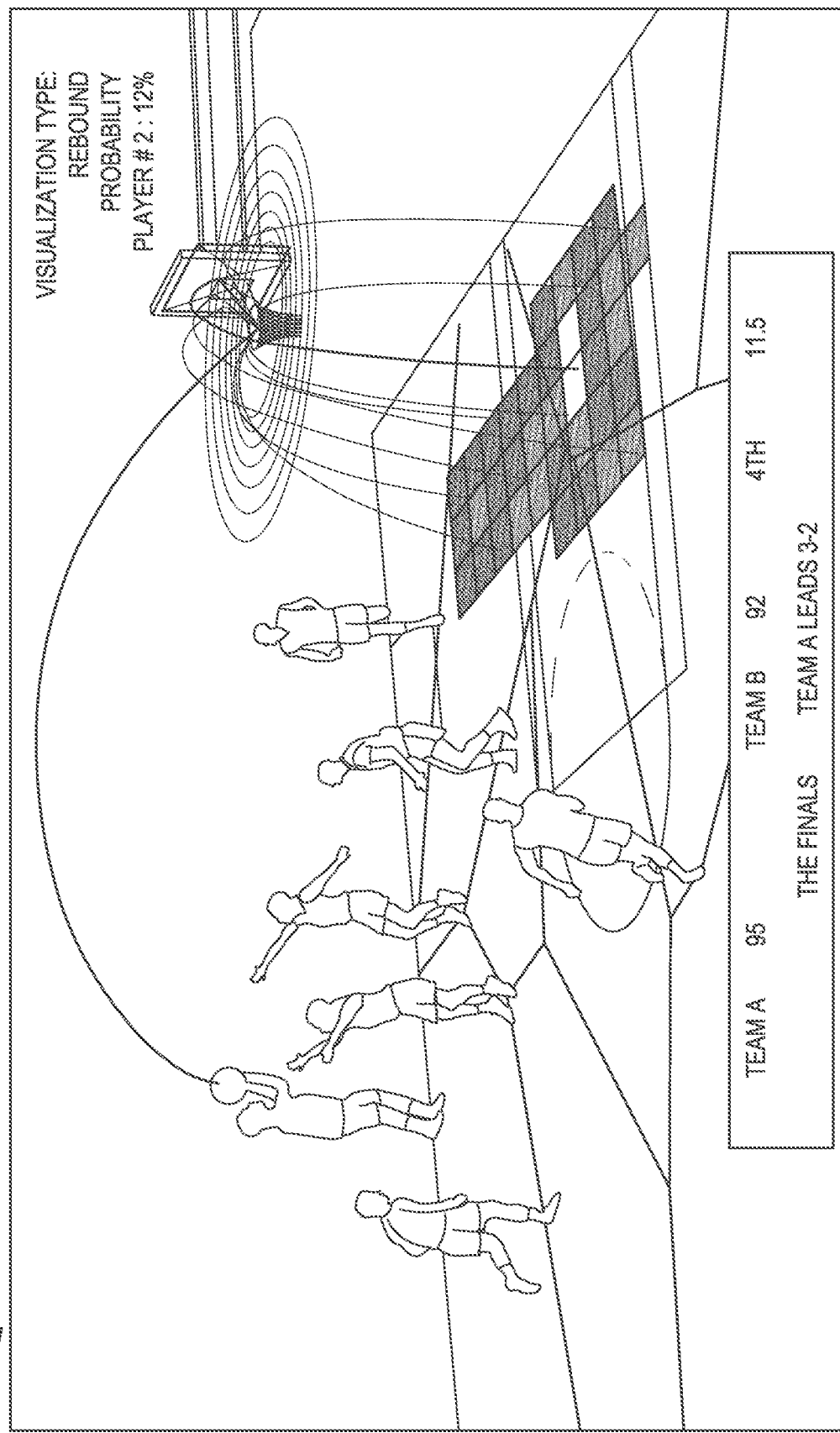
FIG. 32 illustrates an example according to an exemplary and non-limiting embodiment.
Figure 33:
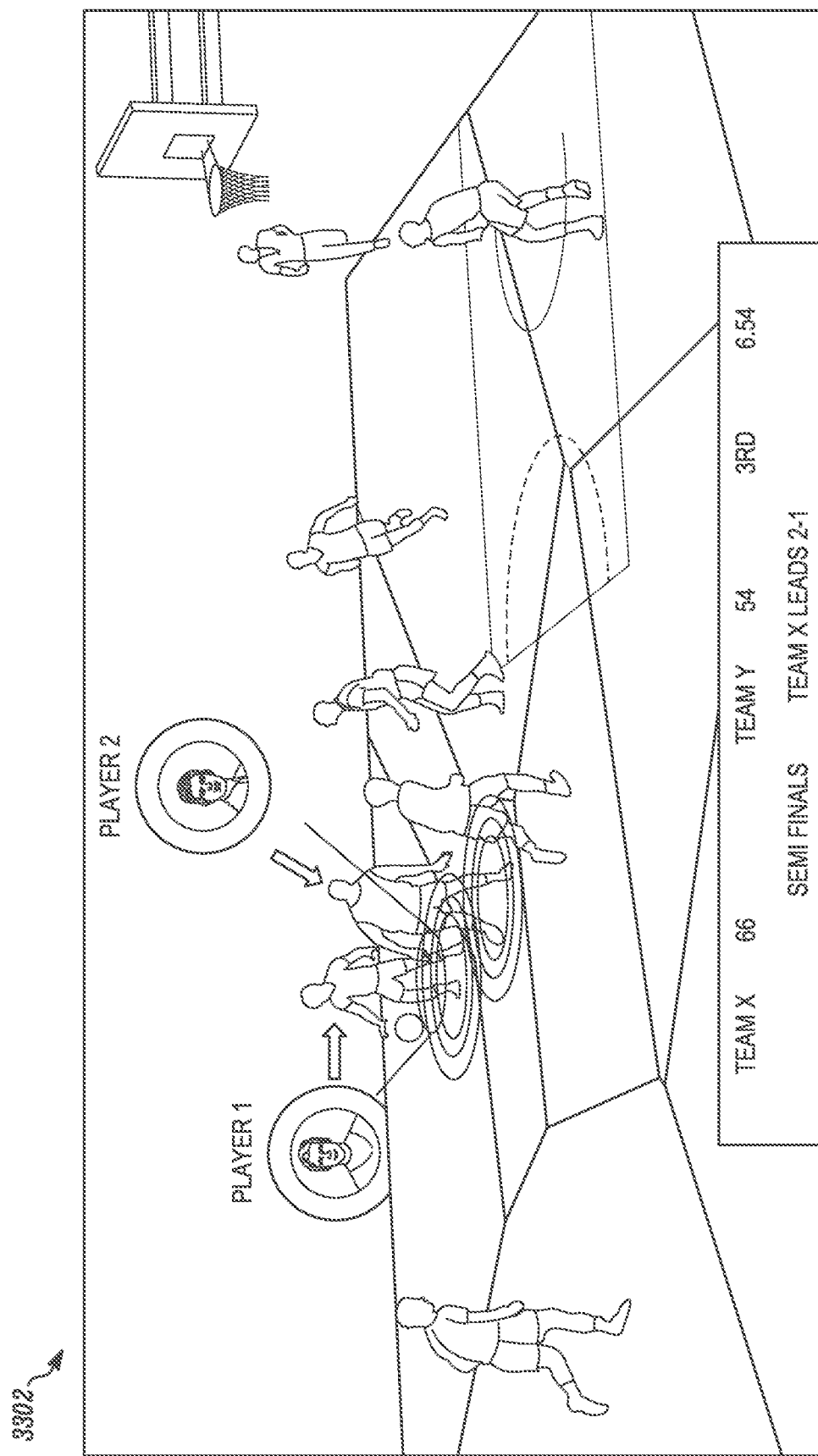
FIG. 33 illustrates an example according to an exemplary and non-limiting embodiment.
Figure 34:
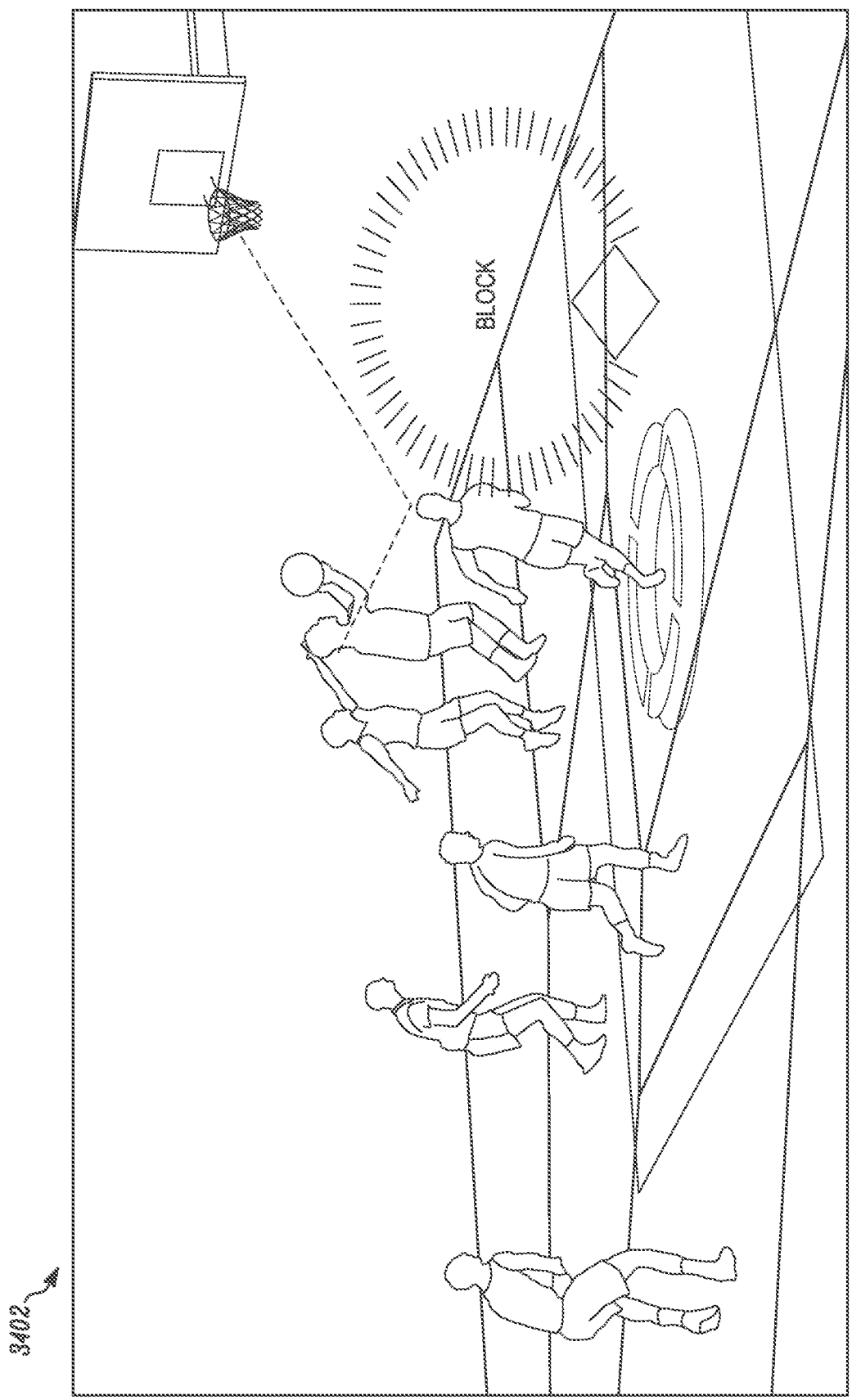
FIG. 34 illustrates an example according to an exemplary and non-limiting embodiment.
Figure 35:
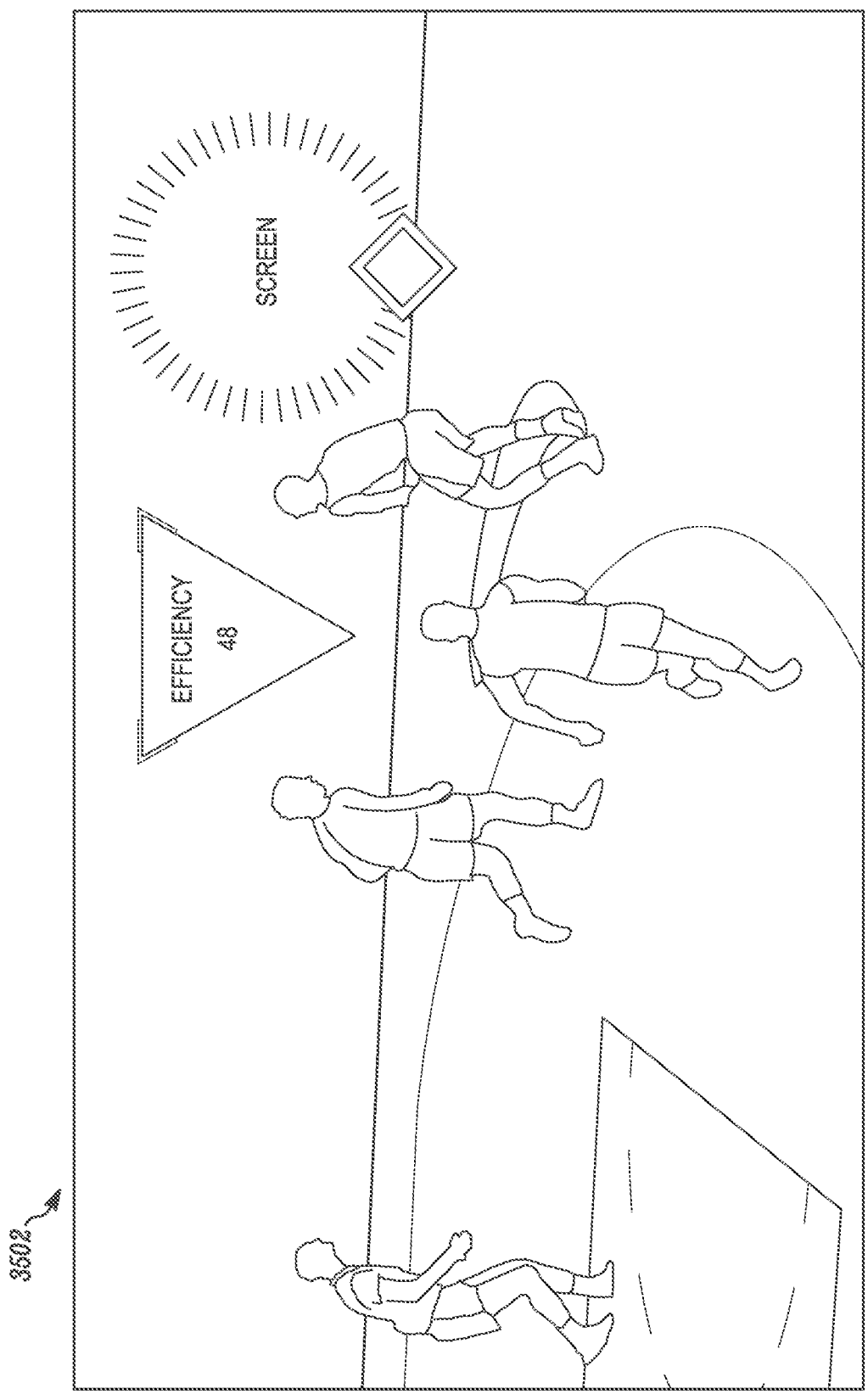
FIG. 35 illustrates an example according to an exemplary and non-limiting embodiment.
Figure 36:
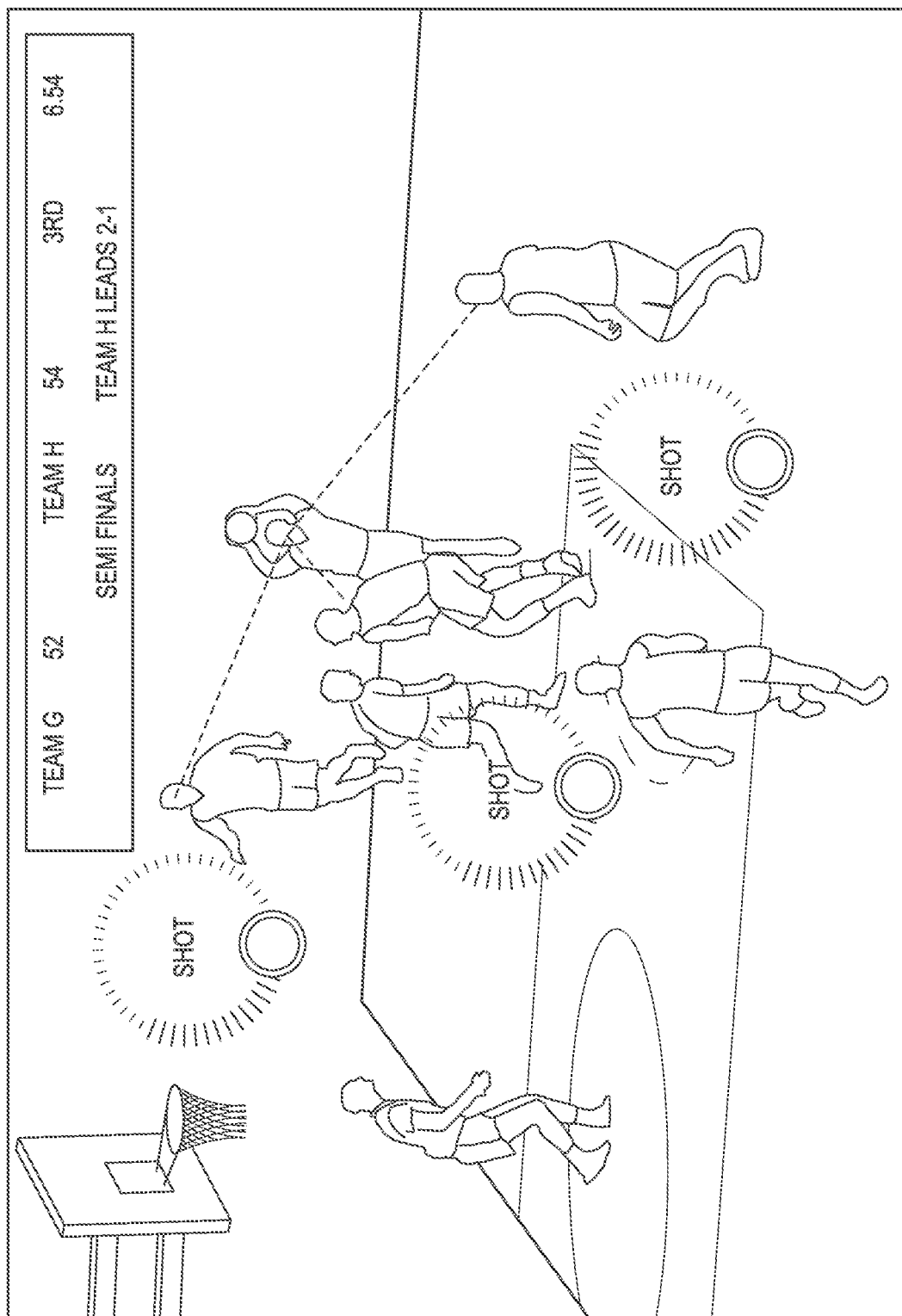
FIG. 36 illustrates an example according to an exemplary and non-limiting embodiment.
Figure 37:
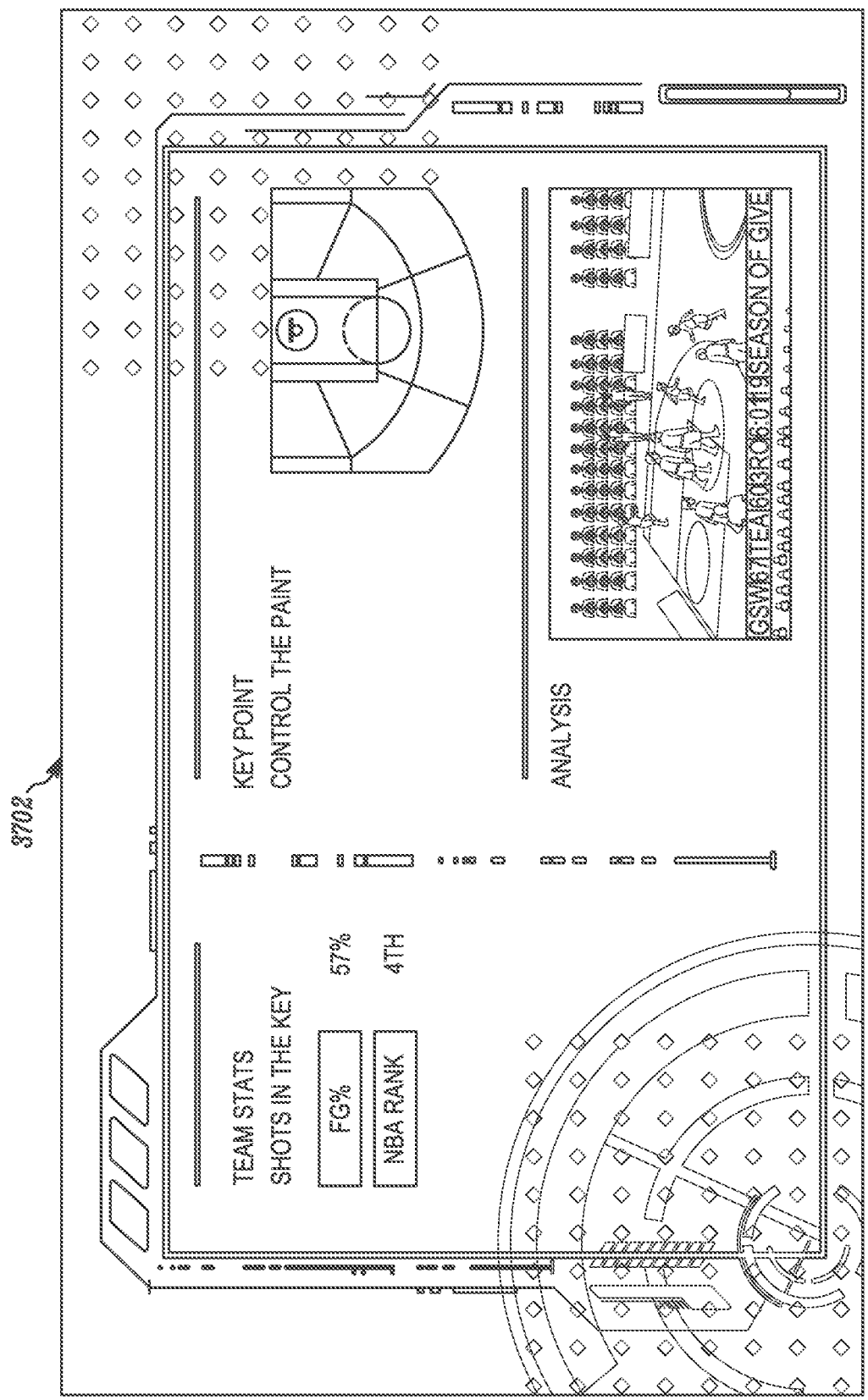
FIG. 37 illustrates an example according to an exemplary and non-limiting embodiment.
Figure 38:
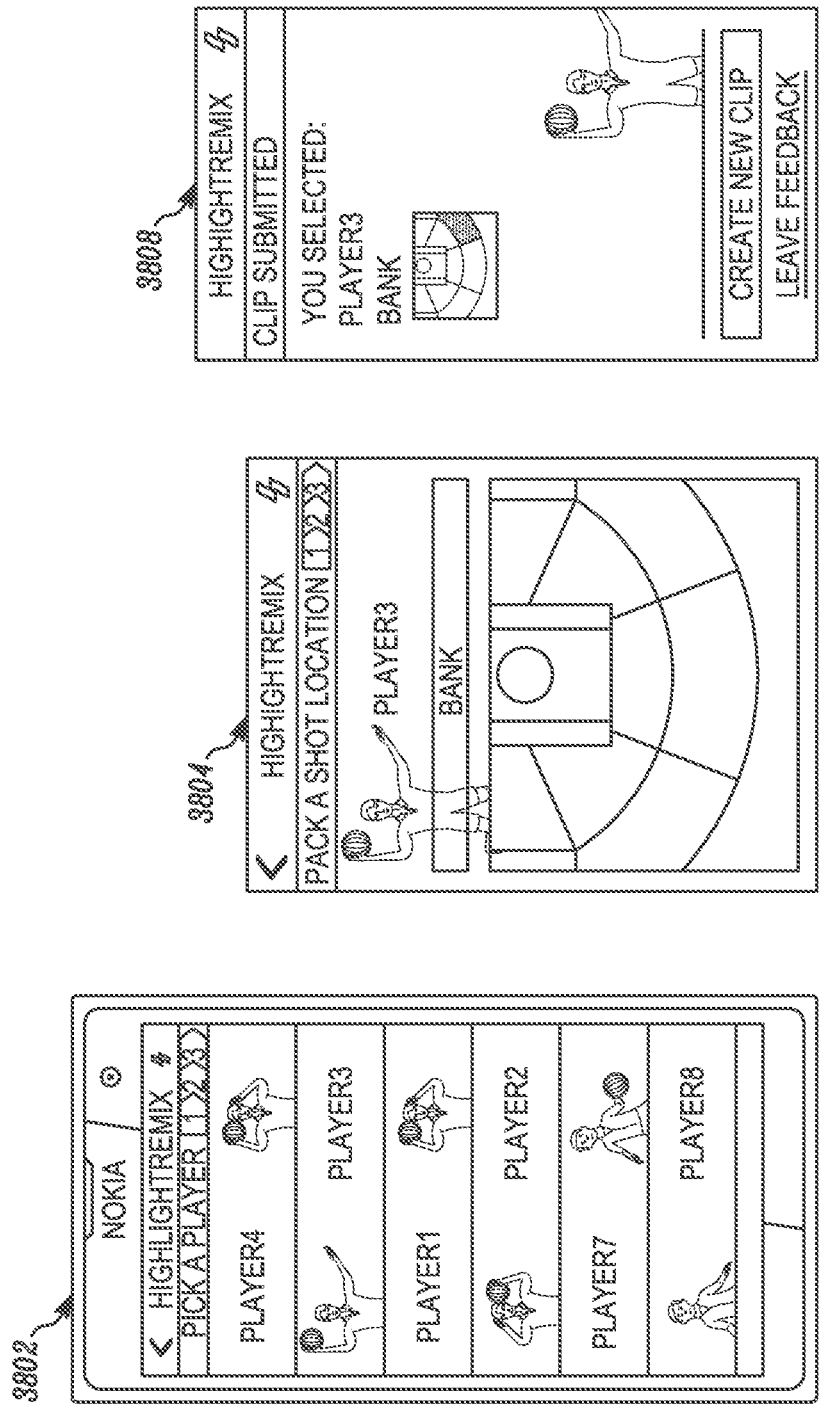
FIG. 38 illustrates a screen shot according to an exemplary and non-limiting embodiment.

FIGS. 31-38 show examples of DataFX visualizations. The visualization of FIG. 31 requires court position to be solved in order to lay down grid, player "puddles". Shot arc also requires backboard/hoop solution. In FIG. 32, Voronoi tessellation, heat map, shot and rebound arcs all require the camera pose solution. The highlight of the player uses rotoscoping. In FIG. 33, in addition to the above, players are rotoscoped for highlighting. FIGS. 34-38 show additional visualizations that are based on the use of the methods and systems disclosed herein.

In embodiments, DataFX (video augmented with data-driven special effects) may be provided for pre-, during, or post-game viewing, for analytic and entertainment purposes. DataFX may combine advanced data with Hollywood-style special effects. Pure numbers can be boring, while pure special effects can be silly, but the combination of the two and the results can be very powerful. Example features used alone or in combination in DataFX can include use of a Voronoi overlay on court, a Grid overlay on court, a Heatmap overlay on court, a Waterfall effect showing likely trajectories of the ball after a missed field goal attempt, a Spray effect on a shot, showing likely trajectories of the shot to the hoop, Circles and glows around highlighted players, Statistics and visual cues over or around players, Arrows and other markings denoting play actions, Calculation overlays on court, and effects showing each variable taken into account.

Figure 39A:
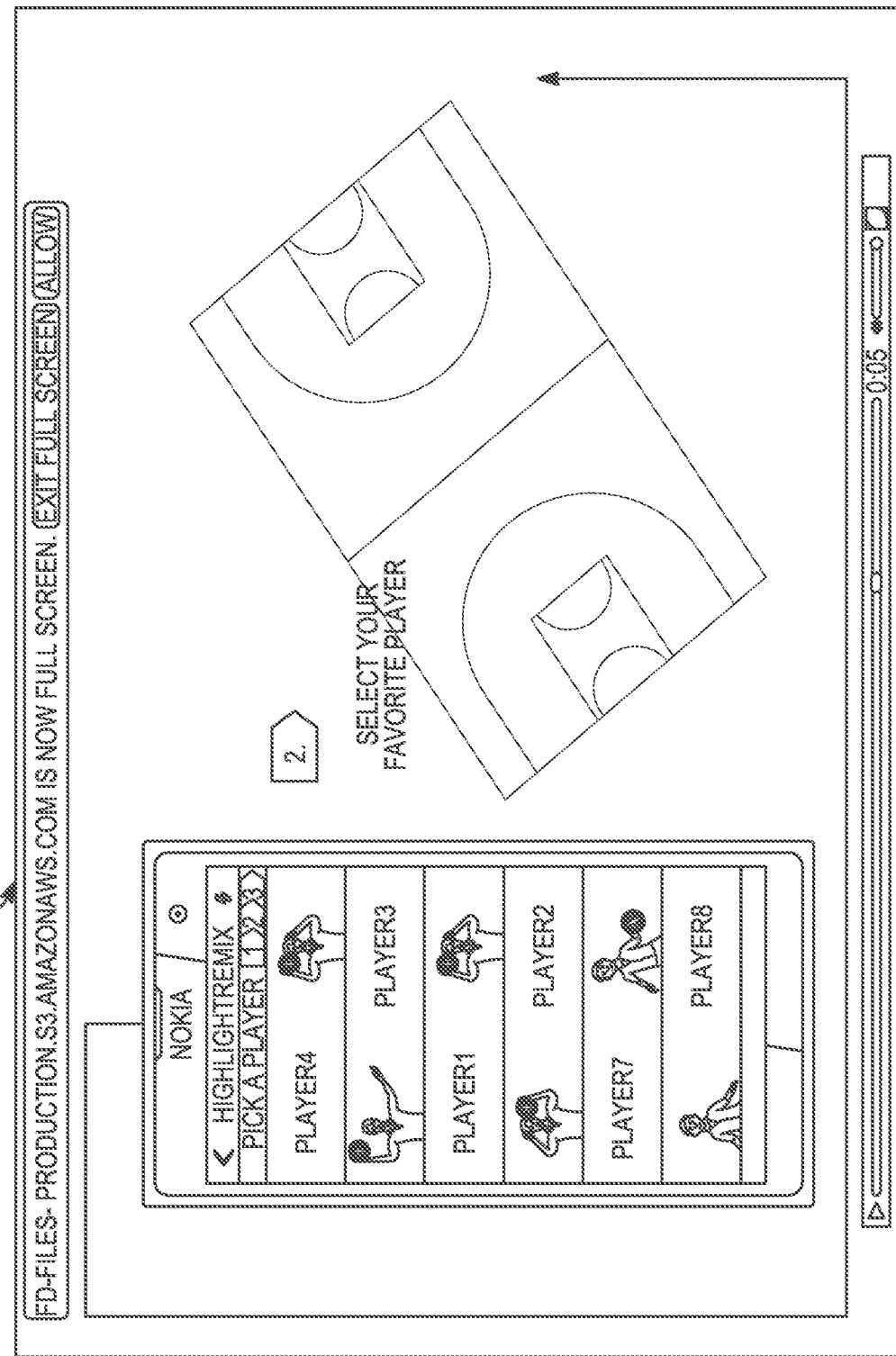
FIGS. 39A, 39B, 39C, 39D, and 39E illustrate a screen shot according to an exemplary and non-limiting embodiment.
Figure 39B:
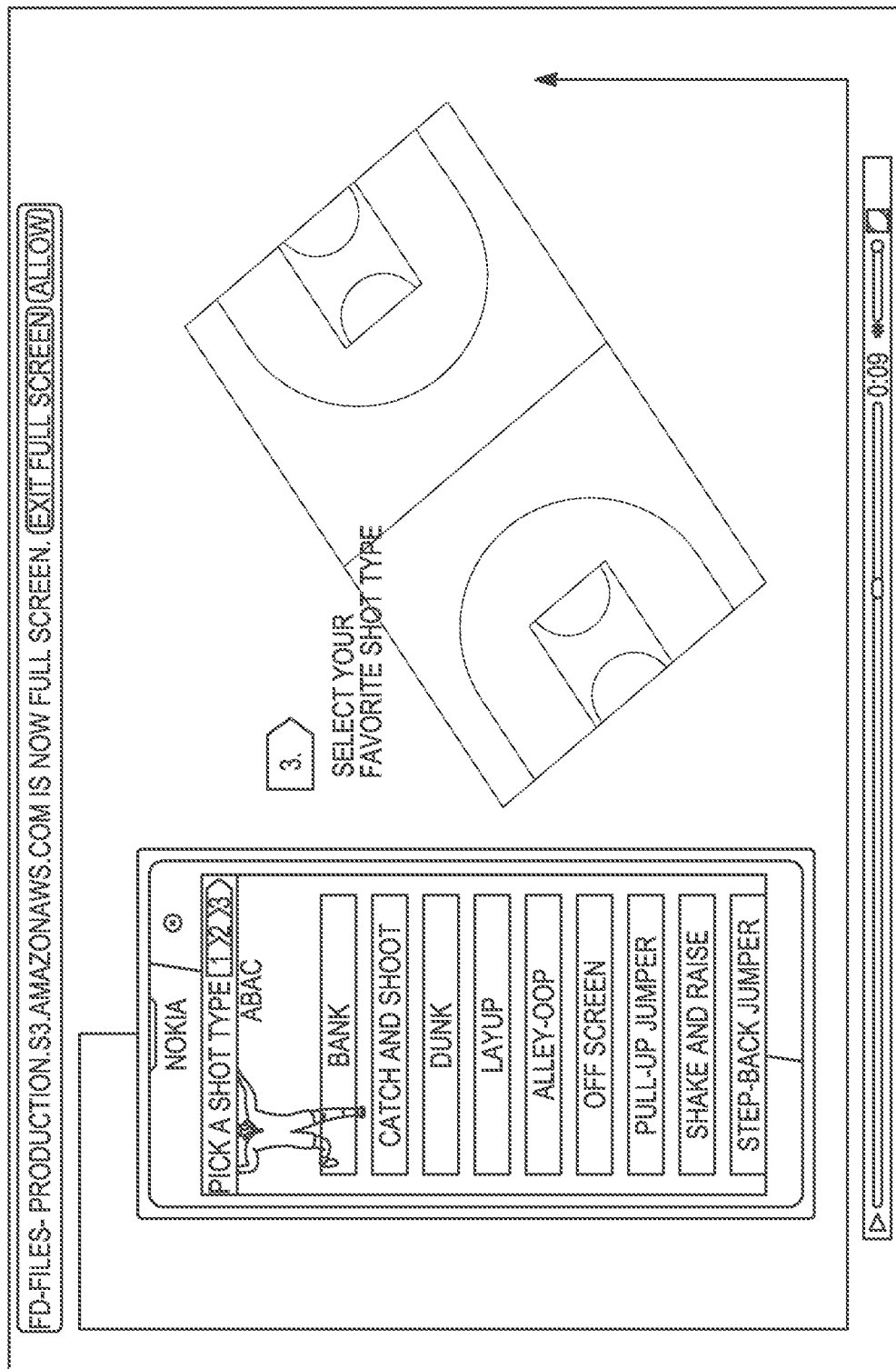
Figure 39C:
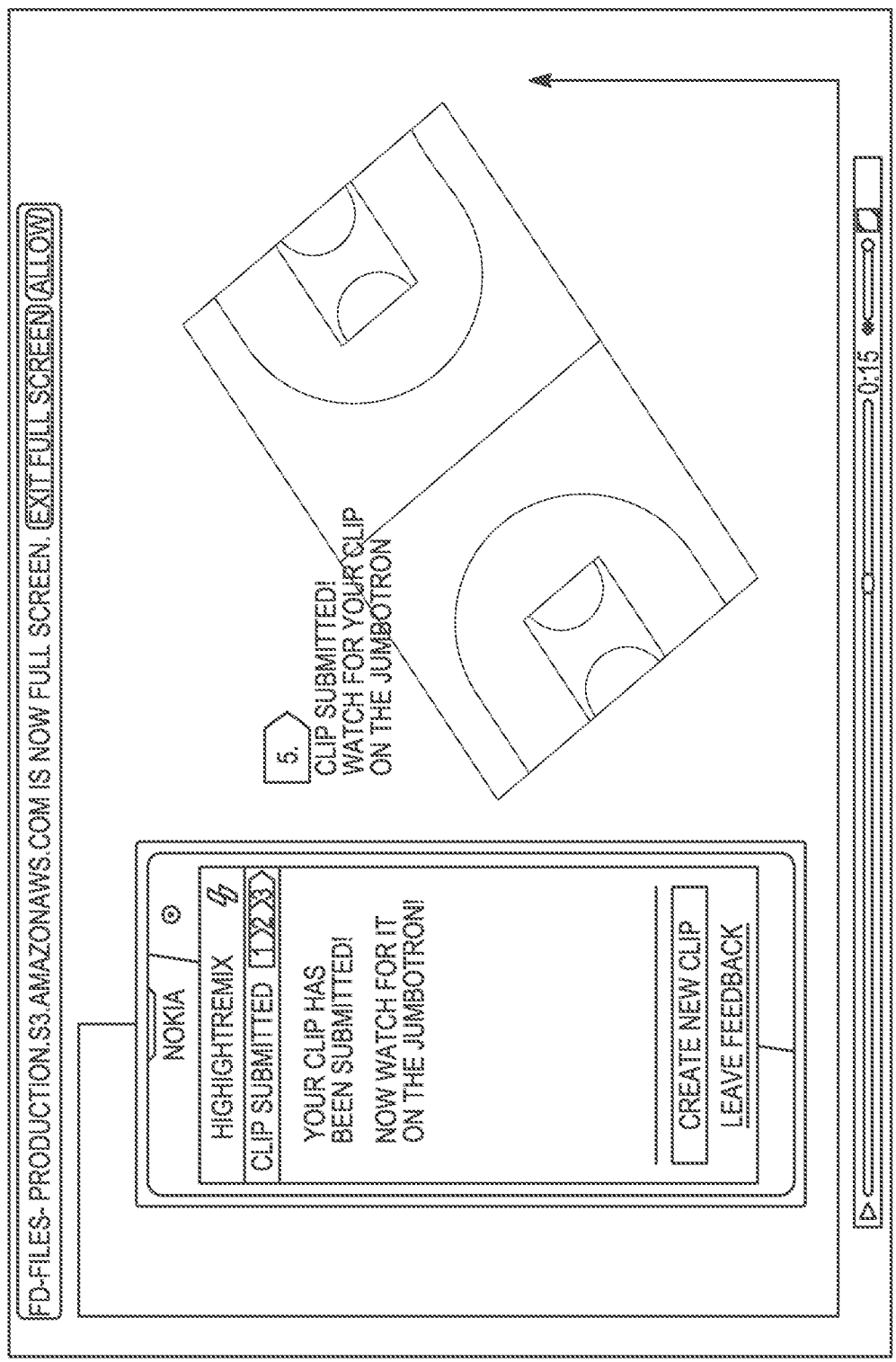
Figure 39D:
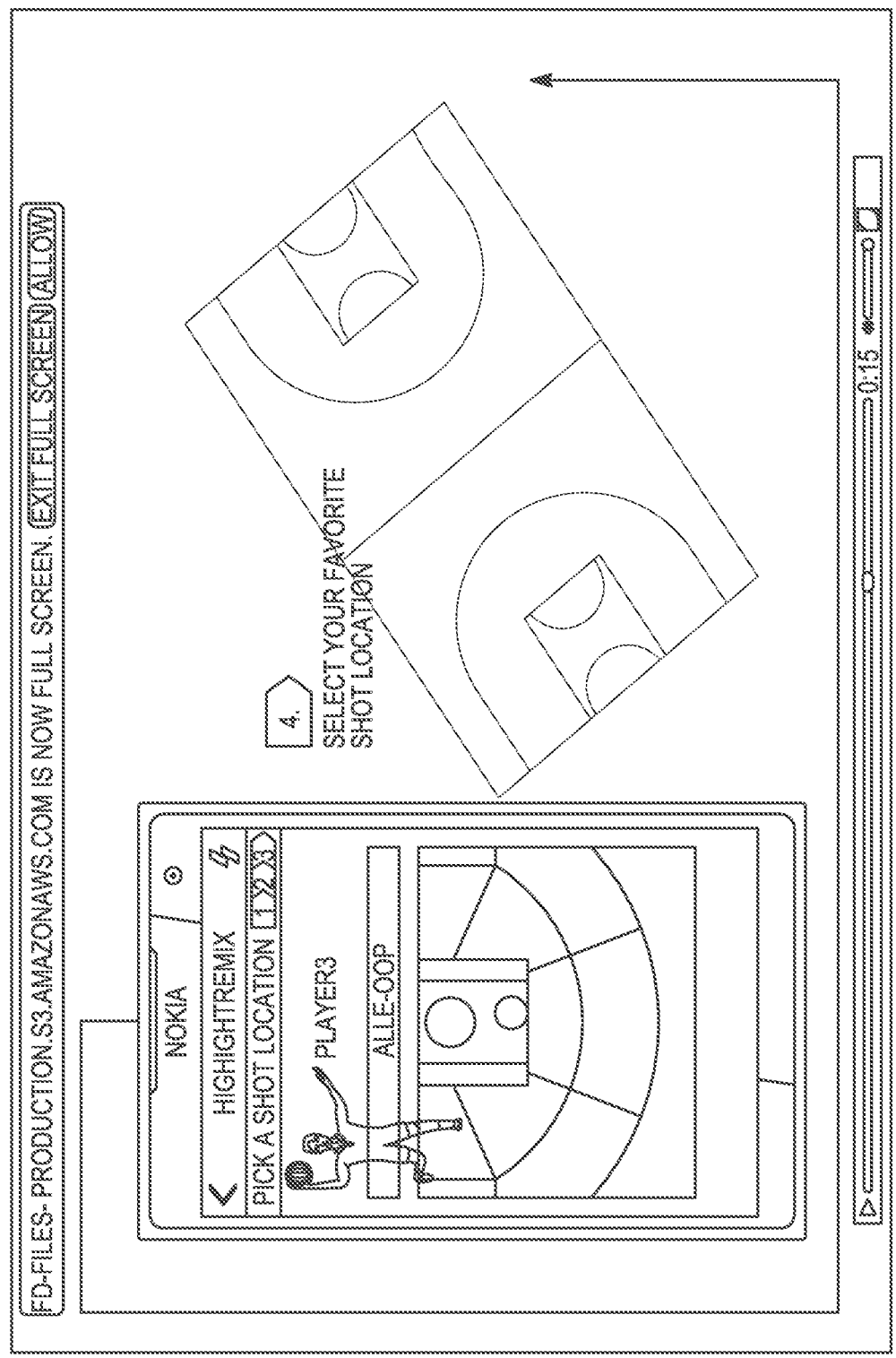
Figure 39E:
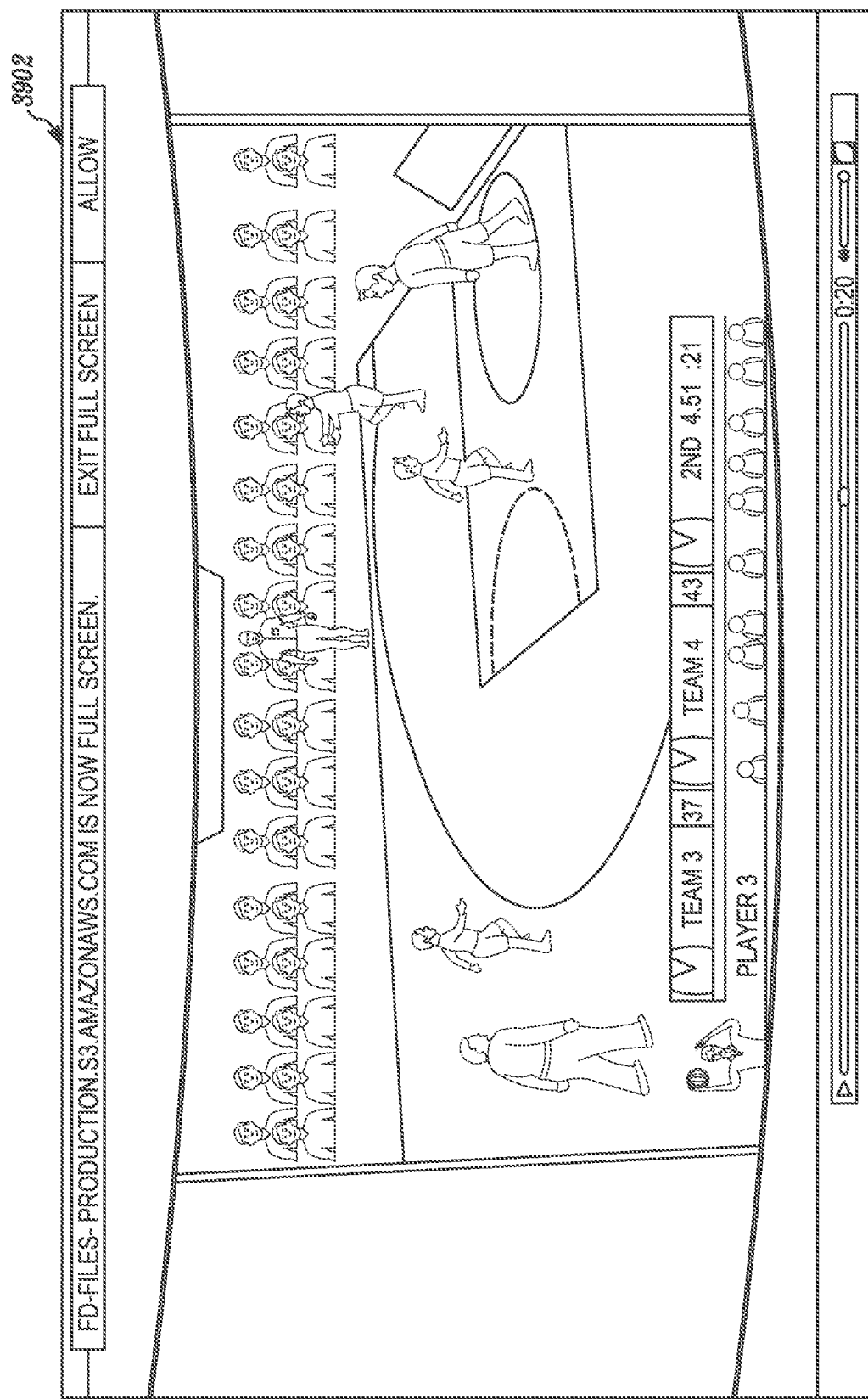
Figure 39F:
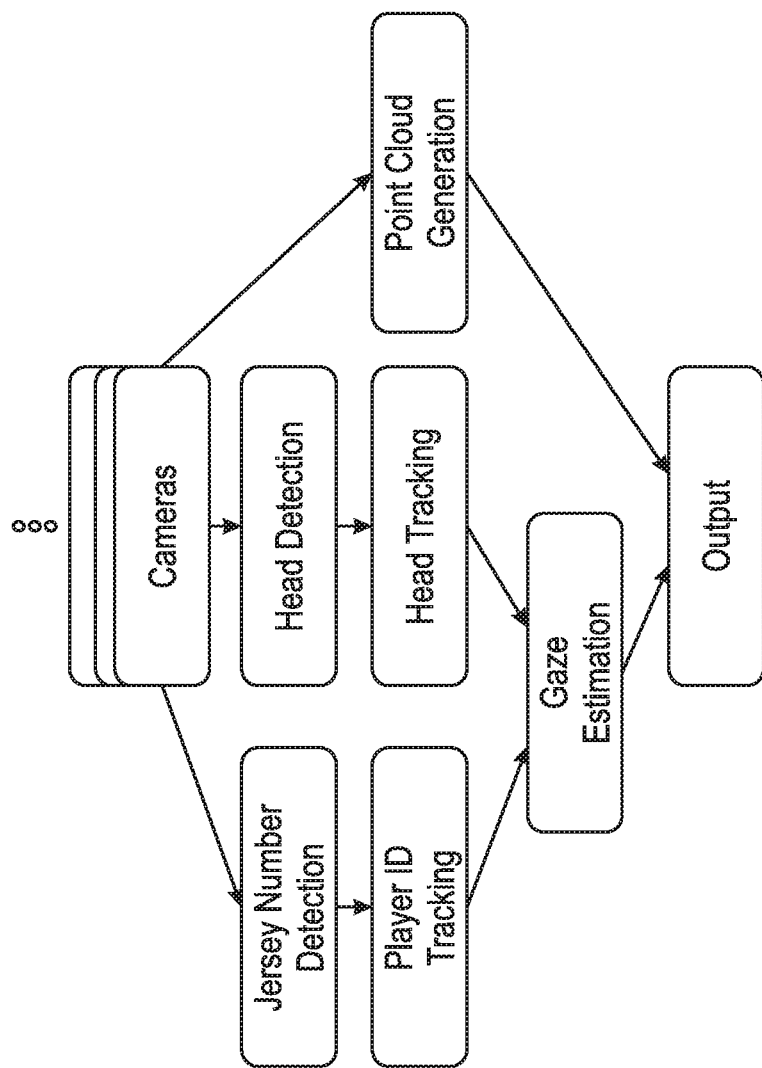
FIG. 39F illustrates a first person process according to an exemplary and non-limiting embodiment.
Figure 40:
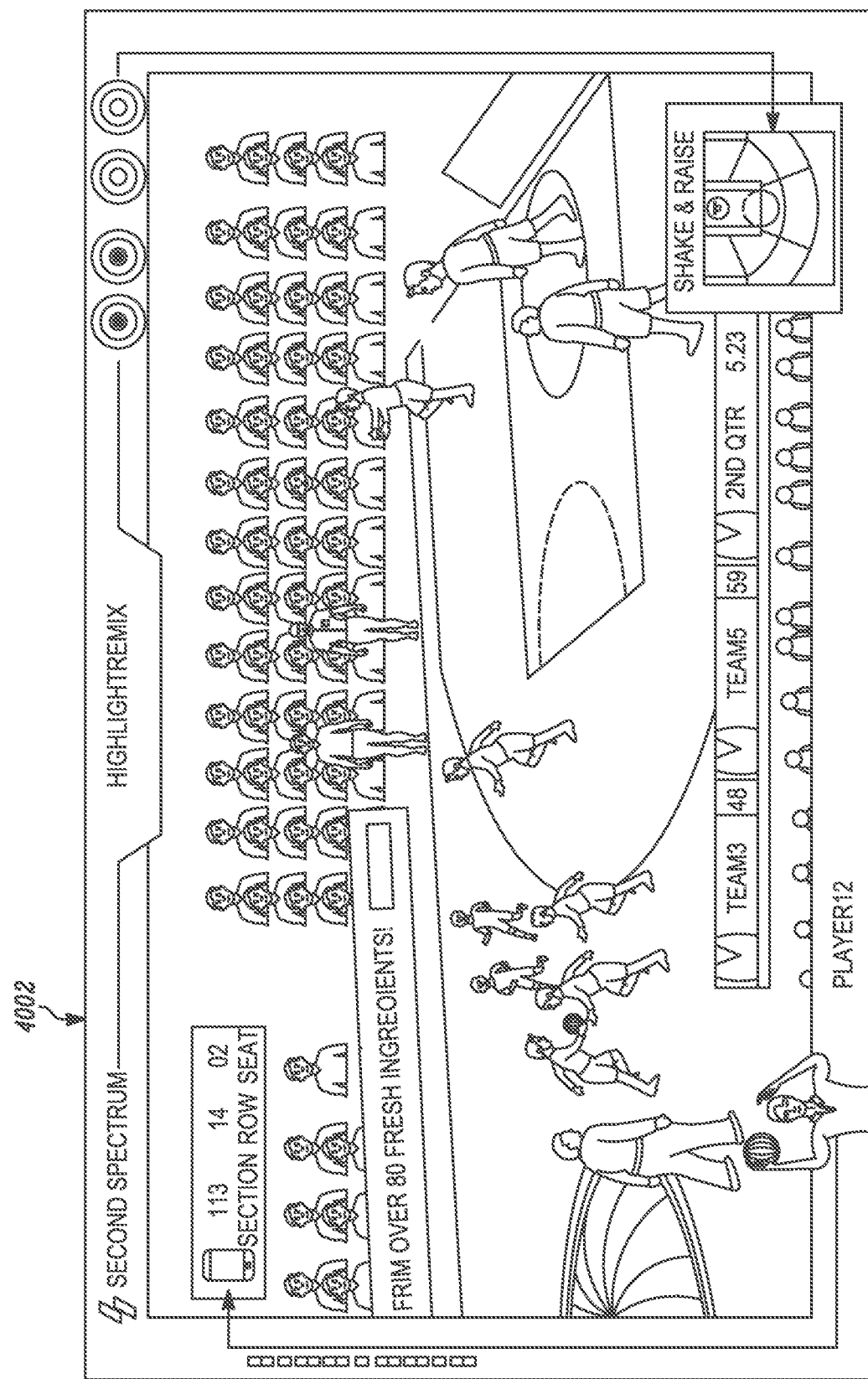
FIG. 40 illustrates a screen shot according to an exemplary and non-limiting embodiment.

FIGS. 39A through 41B show a product referred to as "Clippertron." Provided is a method and system whereby fans can use their distributed mobile devices to control individually and/or collectively what is shown on the Jumbotron or video board(s). An embodiment enables the fan to go through mobile application dialogs in order to choose the player (FIG. 39A), shot type (FIG. 39B), and shot location (FIG. 39D) to be shown on the video board (FIG. 39C). The fan can also enter in his or her own name so that it is displayed alongside the highlight clip, Clips are shown on the Video Board in real time or queued up for display. Variations include getting information about the fan's seat number (FIG. 40). This could be used to show a live video feed of the fan while their selected highlight is being shown on the video board. Referred to as "FanMix" is a web-based mobile application that enables in-stadium fans to control the Jumbotron and choose highlight clips to push to the Jumbotron. An embodiment of FanMix enables fans to choose their favorite player, shot type, and shot location using a mobile device web interface. Upon pressing the submit button, a highlight showing this particular shot is sent to the Jumbotron and displayed according to placement order in a queue. Enabling this capability is that video is lined up to each shot within a fraction of a second. This allows many clips to be shown in quick succession, each showing video from the moment of release to the ball going through the hoop. In some cases, the video may start from the beginning of a play, instead of when a play begins.

The methods and systems disclosed herein may include methods and systems for allowing a user or group of users to control presentation of a large scale display in an event venue, where the options for control are based on a context of the content as determined by machine extraction of semantically relevant events from the content The methods and systems disclosed herein may include methods and systems for enabling interaction with a large scale display system and may include taking a video feed; using machine learning to develop an understanding of an event within the video feed, the understanding including identifying context information relating to the event; automatically, under computer control, extracting the content displaying the event and associating the extracted content with the context information; producing a video content data structure that includes the associated context information; and providing an application by which at least one user can interact with the video content data structure, wherein the options for user interaction are based on the context information, wherein the interaction with the video content data structure controls the presentation of the content on a large scale display.

In embodiments, one or more users may interact with menus on an application, such as a smart phone application, in an arena or other location that has a large-scale display. The users may express preferences, such as by voting, for what content should be displayed, including selecting preferred types of events and/or contexts (which may be organized as noted above based on semantically relevant filters), selecting what metrics should be displayed (options for which may be offered based on context information for particular extracted video events), and the like. In embodiments, a large scale display in a venue where a live event is taking place may offer games, quizzes, or the like, where users may respond by text, SMS, or the like. The content of such games or quizzes may be constructed at least in part based on a machine semantic understanding of the live event, such as asking users which player has the most rebounds in the first quarter, or the like.

The methods and systems disclosed herein may include methods and systems for a user to control Jumbotron clips based on contextualized content filters. The methods and systems disclosed herein may include methods and systems for a Jumbotron fan quiz based on machine semantic understanding of a live game. The methods and systems disclosed herein may include methods and systems wherein the application comprises a quiz for a user, wherein the quiz is constructed based at least in part on a machine semantic understanding of a live game that is taking place in a venue where the large-scale display is located. In embodiments, a fan quiz may ask questions based on proprietary machine learned metrics such as "which player took the hardest shots in this quarter." The methods and systems disclosed herein may include methods and systems for embedding a machine extracted video cut in an application, where the selection of the embedded cut for the application is based on the context of the video cut.

First Person Point of View (POV)

In embodiments, interactive visualization 218, as illustrated in FIG. 2, may include producing a reconstruction of an event, such as a game, such as a 3D reconstruction or rendering. In embodiments, a 3D reconstruction or rendering of an event may be produced using a process that presents the event from a defined point of view, such as the first person point of view of a participant in the event, such as a player. FIG. 39F illustrates an embodiment of such as process, referred to herein in some cases as a first person POV process, or simply a first person process.

A first person process may allow the user to select a player's view to follow. A first person process may automatically pin a user's view to the head of the selected player. The end result of a first person process may be dynamically rendered from the view of the selected player as a play occurs.

A first person process may be an automated first person process. An automated first person process may produce a 3D reconstruction or rendering of a game and render each frame from the view of a player selected by a user.

A first person process may be a virtual reality-based first person process. A virtual reality-based first person process may produce a 3D reconstruction or rendering of a game that allows a user to control the orientation of a view from the head movements of a user. In embodiments, the point of view may be controlled by, for example, player head tracking.

In embodiments, users may choose a player whose point of view will be presented. Location of a view may be controlled automatically via head tracking data. View orientation may be controlled by the head movements of a user. In embodiments, the head movements of a user may be recorded by virtual reality (VR) technology. VR technology may be Oculus Rift™ technology and the like.

Point Cloud Construction

As illustrated in FIG. 39F, a first person process may include constructing a point cloud that provides a 3D model of a real world scene.

Point cloud construction may begin by producing binary, background-subtracted images for each time-synchronized frame on each camera. Using these binary images and the calibrations of each camera, a 3D convex hull may be produced by discretizing the scene into voxels and filling each voxel, if the voxel is contained within the ray projected from the camera through the image visual hull. The image visual hull may be the silhouette of the scene, for example. The silhouette of the scene may be a shape-form silhouette.

The resulting convex hull may contain voxels that may not actually be present in the world, due to reconstructing only of the visual hull. In order to achieve a more precise point cloud, the 3D convex hull may be carved using photo consistency methods.

Photo consistency methods may back-project the surface of a 3D reconstructed visual hull onto each visible camera. Photo consistency methods may also check to ensure the color of the pixels is consistent with the same pixel from another camera, or with nearby pixels, such as to avoid unrealistic discontinuities. If the colors from each visible camera do not agree, the voxel may be carved. This process may be repeated for the entire convex hull, producing the final carved point cloud.

Point cloud construction may estimate the skeletal pose of all participants in a real world scene. Point cloud construction may fit a hand-made participant model to the estimated pose of each participant in a real world scene. In an example, the real world scene could be a sports court and the participants could be all the players on the sports court. In this example, point cloud construction could fit a hand-made player model to the estimated pose of each player on the sports court.

Point cloud construction may include meshing techniques, which may be used to improve the quality of a final visualization for a user. Meshing techniques may be used to mesh multiple point counts. Meshing techniques may be used to provide a view that may be very close to a point cloud, for example.

Player Identification

A first person process may use player identification to enable the user to select from which player's view to render the 3D reconstruction. Player identification may involve multiple steps in order to produce reliable results.

Player identification may start by performing jersey number detection, as illustrated in FIG. 39F. Jersey numbers may be mapped to player names. Jersey numbers may then be mapped to player names using official rosters and the like.

Jersey number detection may be performed frame-by-frame. Frame-by-frame jersey number detection may be performed by scanning and classifying each window as a number or as nothing, such as using a support vector machine (SVM), a supervised machine learning model used for classification. The SVM may be trained, such as using training sets of manually marked jersey numbers from the game video, for example.

Results from individual frame-by-frame detection may be stitched together to form temporal tracks. Individual frame by frame detection may be stitched together to form temporal tracks using a k-shortest paths algorithm, as illustrated in Fig. Y. Jersey number tracks may be associated with existing, more continuous player tracking data. Associating jersey number tracks with existing, more continuous player tracking data may produce robust tracks of identifiable players.

Head Tracking

A first person process may use head tracking in order to control the location of the view within a 3D reconstruction, as illustrated in FIG. 39F. Head tracking may involve multiple steps in order to produce reliable results.

The first step of head tracking may be the same as for player identification. The first step of head tracking may include head detection. Head detection may create a model on heads instead of on jersey numbers. Head detection may be performed frame by frame.

Head detection may include frame by frame head detection. Frame-by-frame head detection may be performed by scanning each image. Frame-by-frame head detection may be performed by scanning each image and classifying each window as a head or not.

Classifying each window as a head or not may be performed using an SVM. An SVM may be trained. An SVM may be trained using manually marked head samples from previously recorded games. An SVM maybe be a team-dk-SVM.

The results of the detection may then be used in 2D tracking to produce temporal 2D tracklets of each head within a camera's frame. 2D tracklets may then be triangulated using the results of all cameras to produce a 3D estimation of the location of all heads on the court. A 3D estimation of the location of all heads on the court may be 3D tracklets.

3D tracklets may then be stitched together. 3D tracklets may then be stitched together using an algorithm. An algorithm may be a k-shortest paths (KSP) algorithm. 3D tracklets may be stitched together to produce potential final head tracking results. Linear programming may be used to choose optimal head paths.

Gaze Estimation

As illustrated in FIG. 39F, a first person process may use gaze estimation. Gaze estimation may be used to control the orientation of a view mounted on the player's head within the 3D reconstruction. Gaze estimation may be computed by assuming a player is looking in the direction opposite the numbers on the back of the player.

Jersey number detection may be performed frame by frame. Frame by frame jersey number detection may be performed by scanning and classifying each window as a number or nothing using an SVM. The SVM may be trained using manually marked jersey numbers from an existing game video.

An assumption may be made to determine the angle of a jersey number located on the back or front of a player's jersey. An assumption may be that a jersey number is only visible when the jersey number is perfectly aligned with a camera that made the detection.

Cameras may have a known location in space. Because the cameras have a known location in space, the vector between the jersey and the camera may be computed using the known location of the camera in space.

Frame-by-frame estimation may be performed after a vector is calculated. The results of the frame-by-frame estimation may be filtered to provide a smoothed experience for a first person process.

Figure 41A:
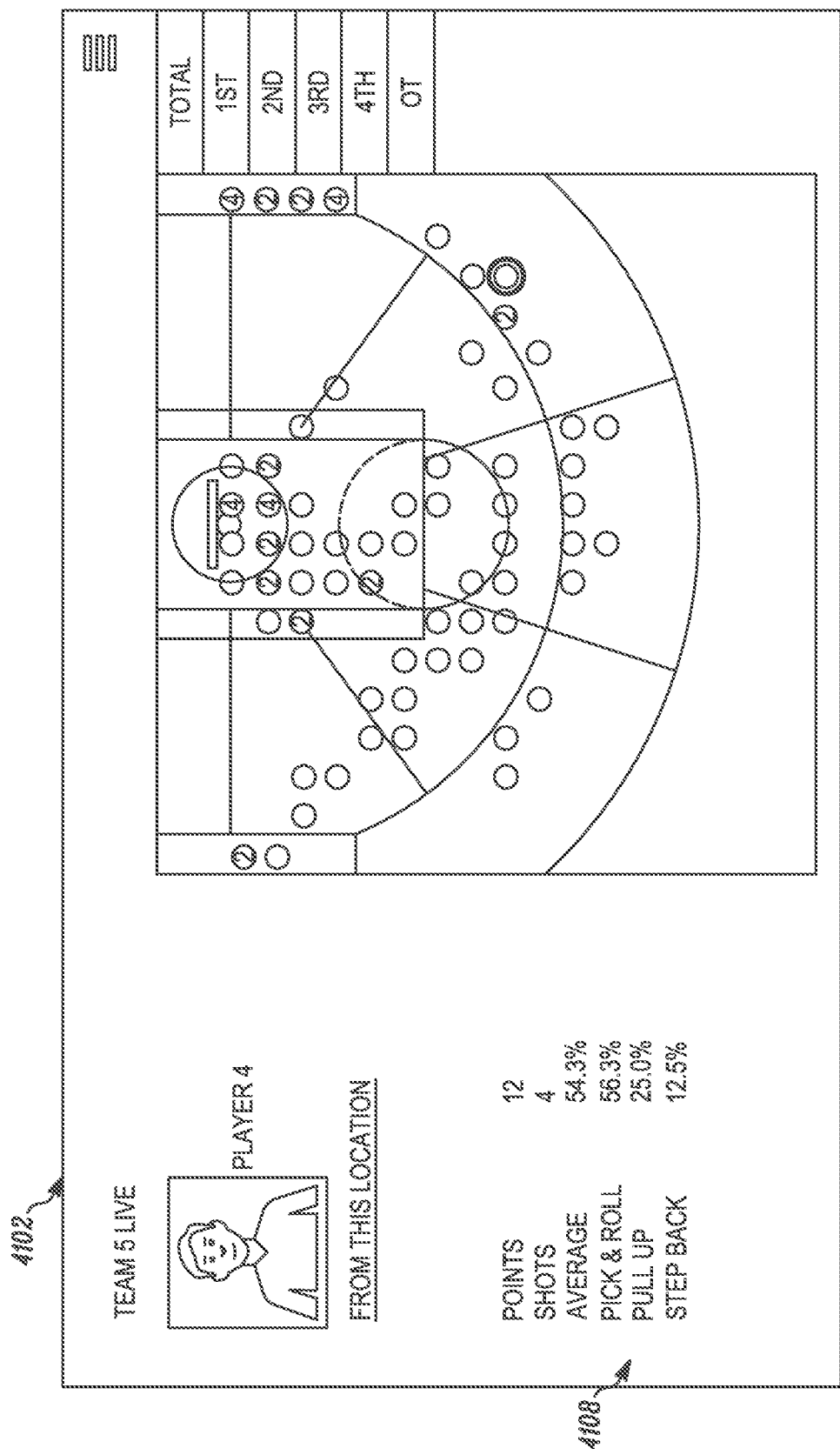
FIGS. 41A and 41B illustrate a screen shot according to an exemplary and non-limiting embodiment.
Figure 41B:
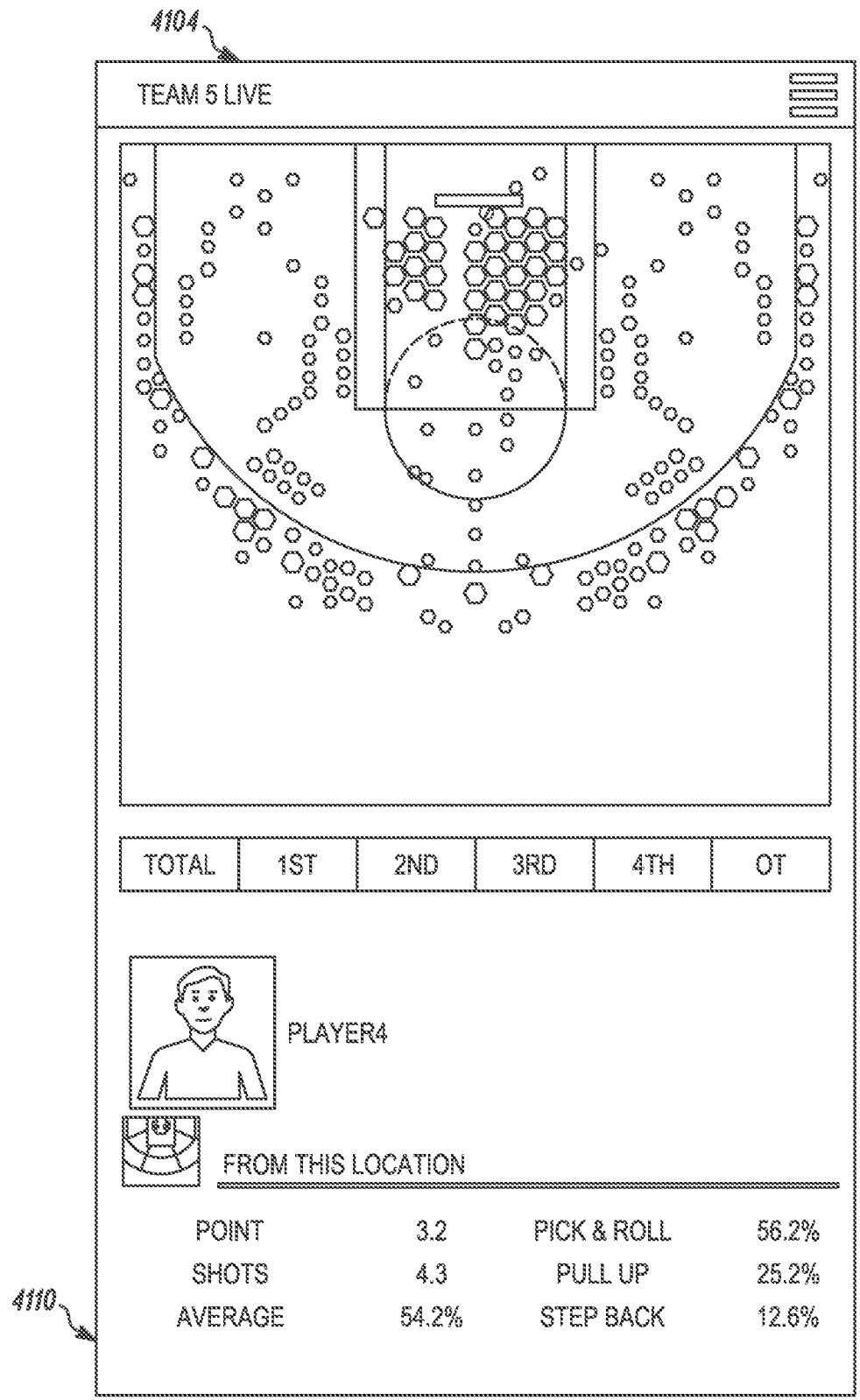
Figure 42A:
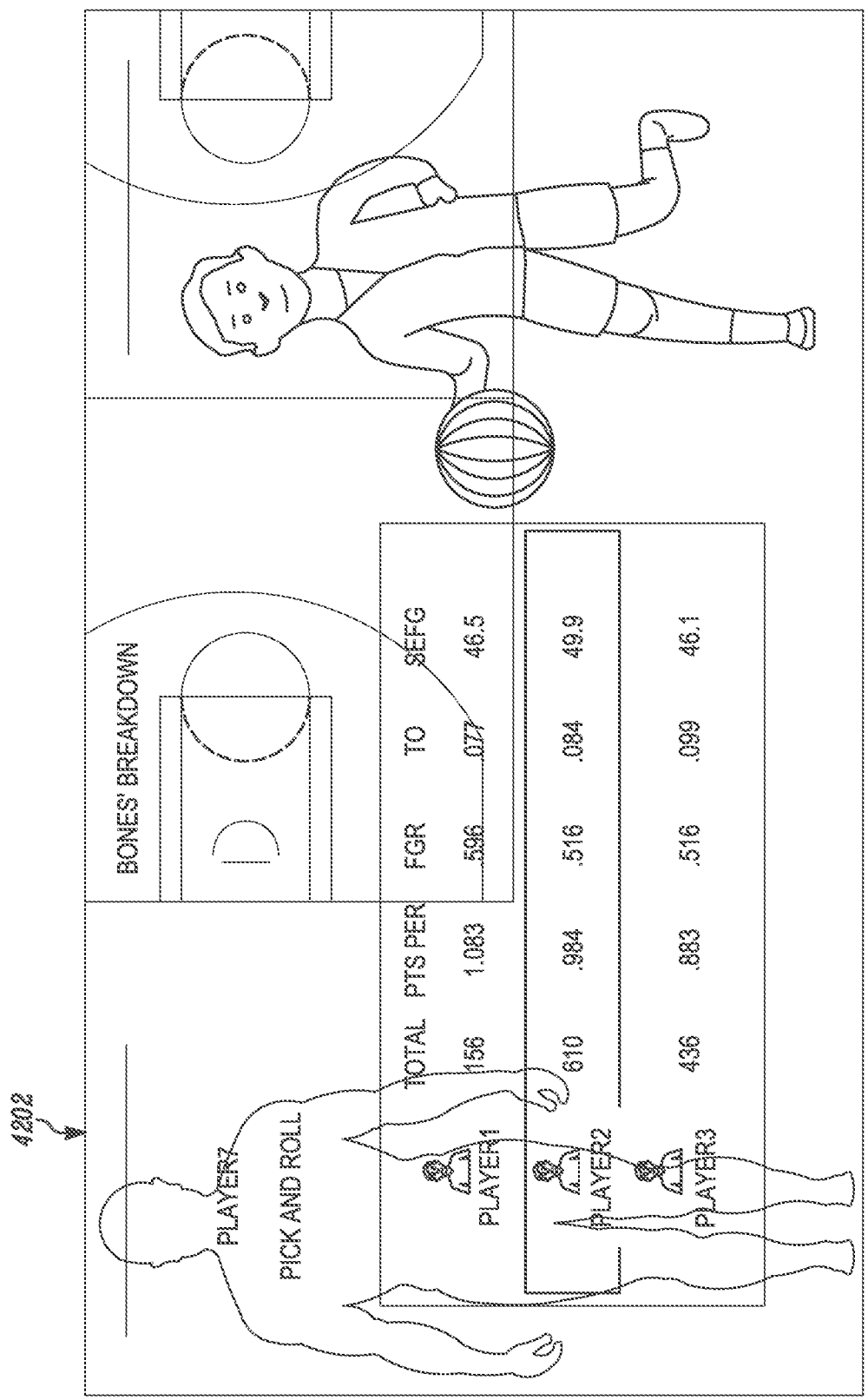
FIGS. 42A, 42B, and 42C illustrate a screen shot according to an exemplary and non-limiting embodiment.
Figure 42B:
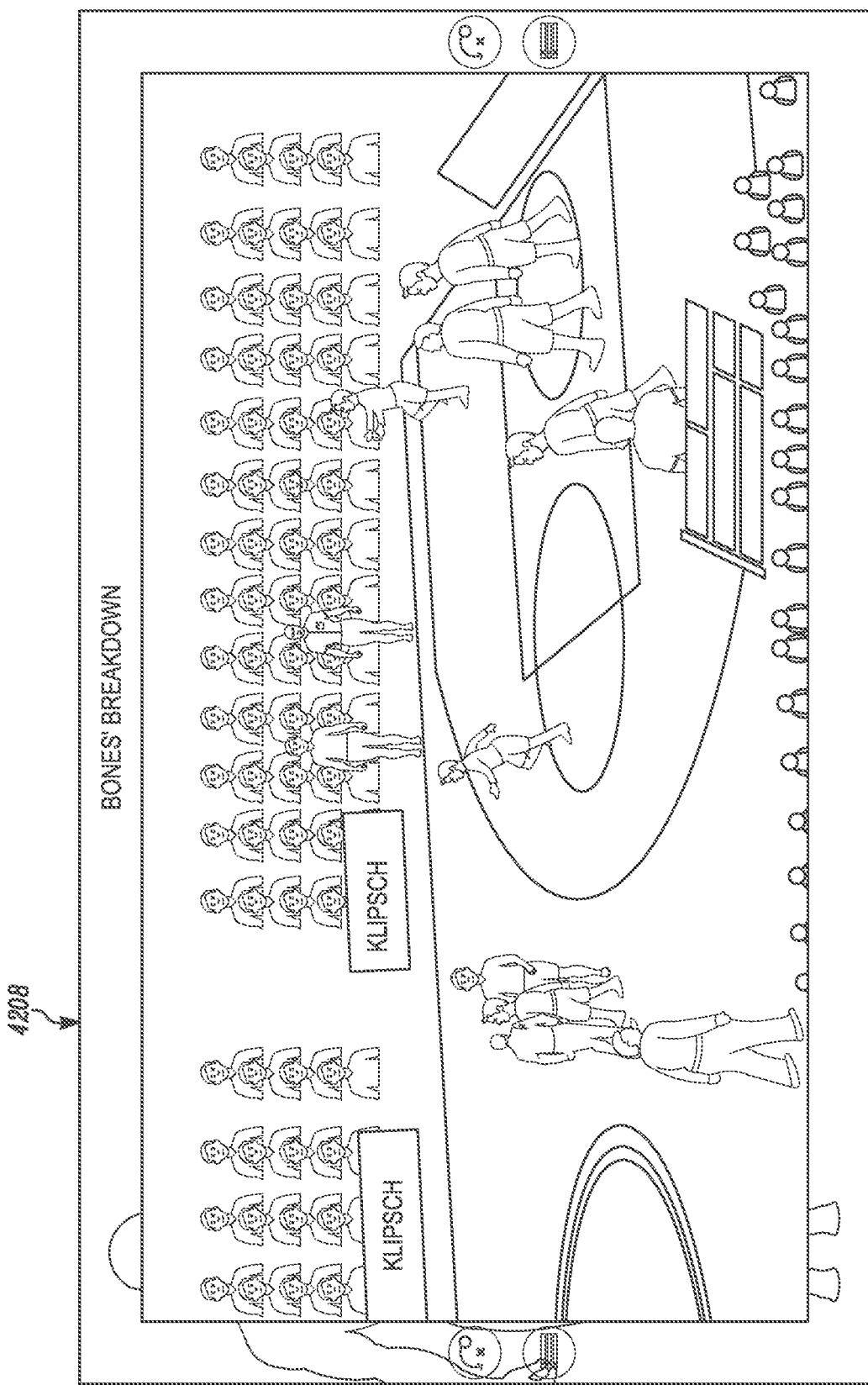
Figure 42C:
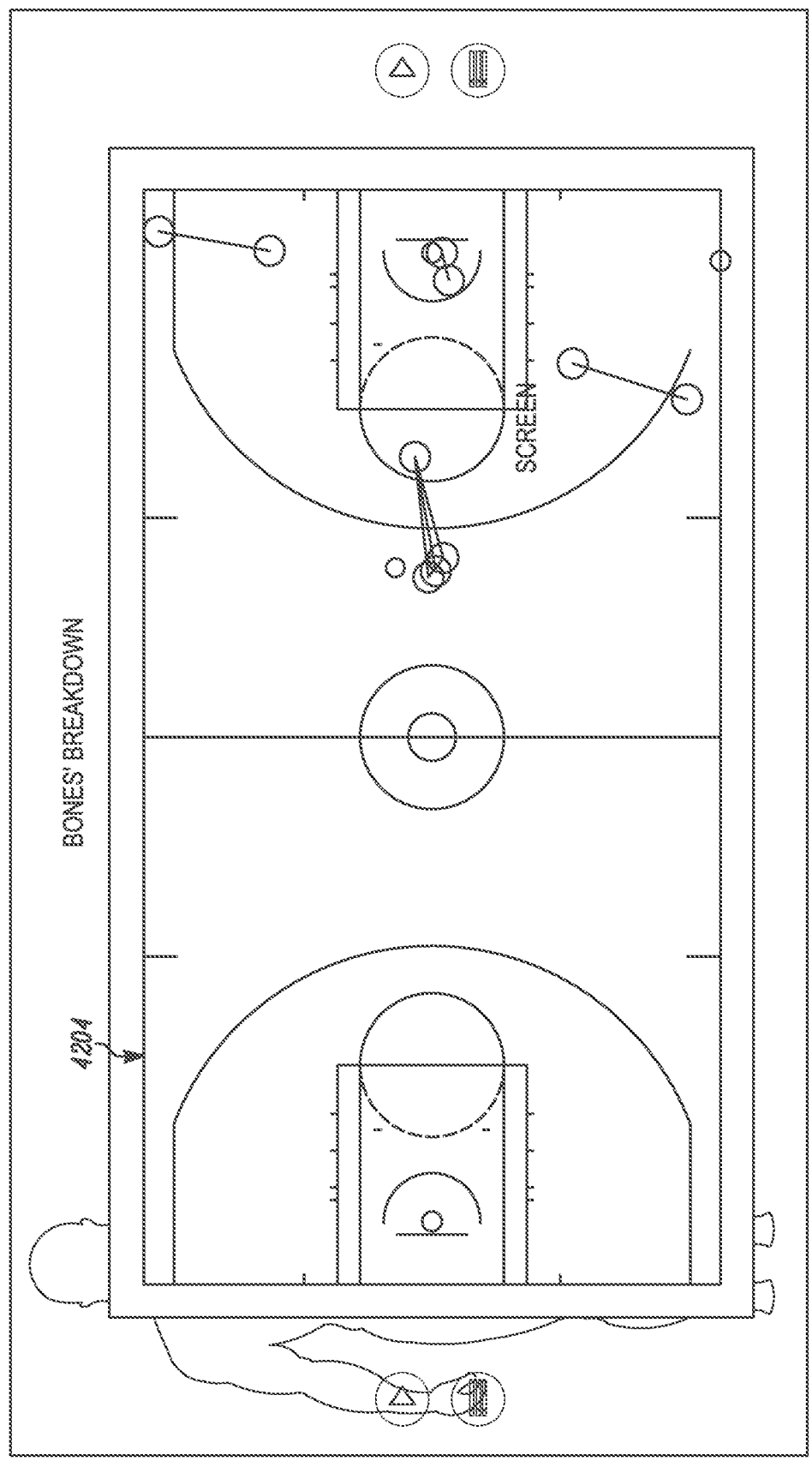
Figure 43:
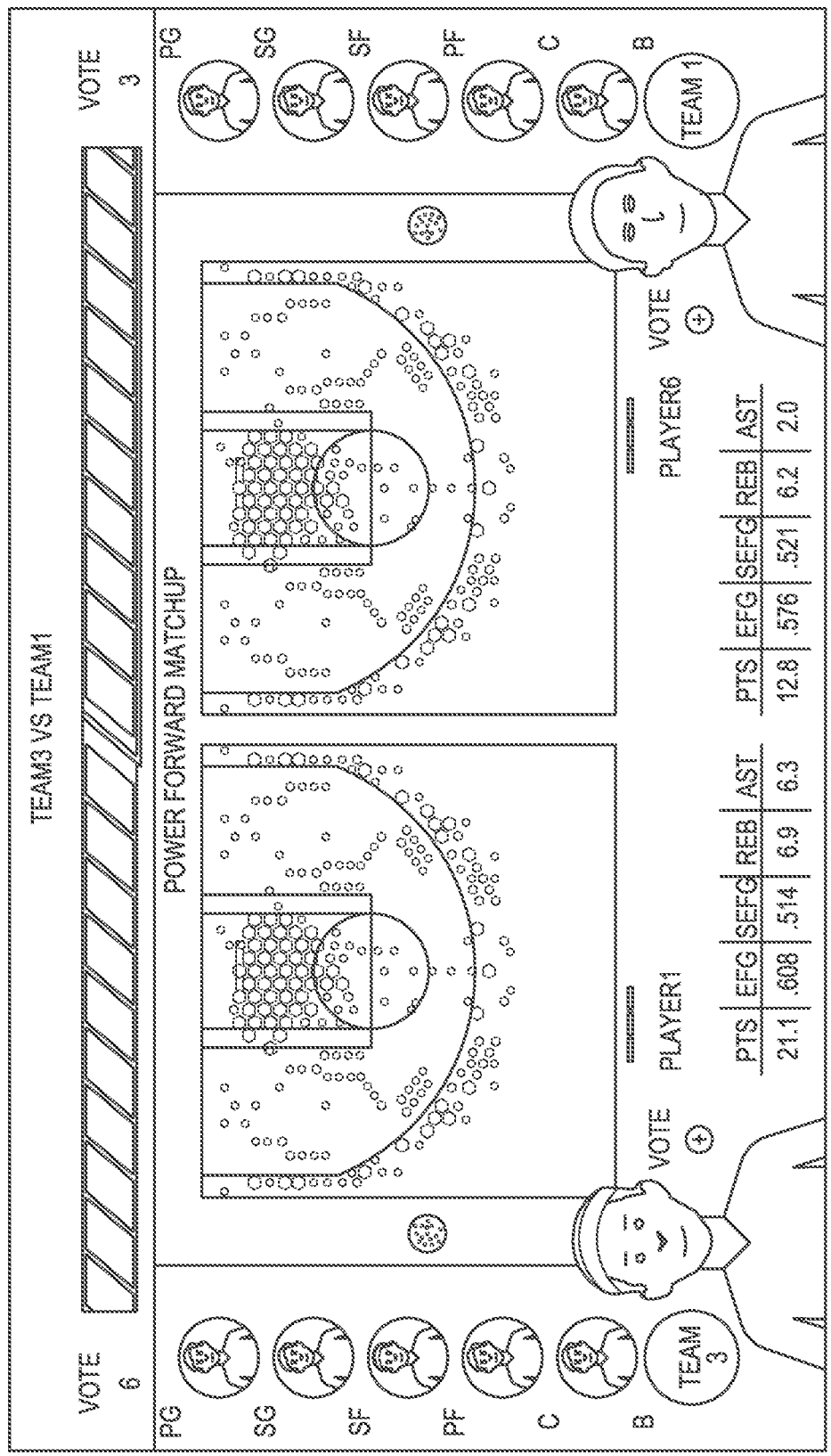
FIG. 43 illustrates a screen shot according to an exemplary and non-limiting embodiment.

FIGS. 41A-41B relates to an offering referred to as "inSight." This offering allows pushing of relevant stats to fans' mobile devices 4104. For example, if player X just made a three-point shot from the wing, this would show statistics about how often he made those types of shots 4108, versus other types of shots, and what types of play actions he typically made these shots off of. inSight does for hardcore fans what Eagle (the system described above) does for team analysts and coaches. Information, insights, and intelligence may be delivered to fans' mobile devices while they are seated in the arena. This data is not only beautiful and entertaining but is also tuned into the action on the court. For example, after a seemingly improbable corner three by a power forward, the fan is immediately pushed information that shows the shot's frequency, difficulty, and the likelihood of being made. In embodiments, the platform features described above as "Eagle," or a subset thereof may be provided, such as in a mobile phone form factor for the fan. An embodiment may include a storyboard stripped down, such as from a format for an 82" touch screen to a small 4" screen. Content may be pushed to a device that corresponds to the real time events happening in the game. Fans may be provided access to various effects (e.g., DataFX features described herein) and to the other features of the methods and systems disclosed herein.

FIGS. 42A-42C and FIG. 43 show touchscreen product interface elements 4202, 4204, 4208, 4302 and 4304. These are essentially many different skins and designs on the same basic functionality described throughout this disclosure. Advanced stats are shown in an intuitive large-format touch screen interface. A touchscreen may act as a storyboard for showing various visualizations, metric and effects that conform to an understanding of a game or element thereof. Embodiments include a large format touch screen for commentators to use during a broadcast. While InSight serves up content to a fan, the Storyboard enables commentators on TV to access content in a way that helps them tell the most compelling story to audiences.

Features include providing a court view, a hexagonal Frequency+Efficiency View, a "City/Matrix" View with grids of events, a Face/Histogram View, Animated intro sequences that communicate to a viewer that each head's position means that player's relative ranking, an Animated face shuttle that shows re-ranking when metric is switched, a ScatterRank View, a ranking using two variables (one on each axis), a Trends View, integration of metrics with on-demand video and the ability to r-skin or simplify for varying levels of commentator ability.

In embodiments, new metrics can be used for other activities, such as driving new types of fantasy games, e.g., point scoring in fantasy leagues could be based on new metrics.

In embodiments, DataFX can show the player how his points were scored, e.g., overlay that runs a counter over an RB's head showing yards rushed while the video shows RB going down the field. In embodiments, one can deliver, for example, video clips (possibly enhanced by DataFX effects) corresponding to plays that scored points for a fantasy user's team for that night or week.

Using an inSight-like mobile interface, a social game can be made so that much of the game play occurs in real time while the fan is watching the game.

Using Insight-like mobile device features, a social game can be managed so that game play occurs in real time while a fan is watching the game, experiencing various DataFX effects and seeing fantasy scoring-relevant metrics on screen during the game. In embodiments, the methods and systems may include a fantasy advice or drafting tool for fans, presenting rankings and other metrics that aid in player selection.

Just as Eagle enables teams to get more wins by devising better tactics and strategy, we could provide an Eagle-like service for fantasy players that gives the players a winning edge. The service/tool would enable fans to research all the possible players, and help them execute a better draft or select a better lineup for an upcoming week/game.

DataFX can also be used for instant replays with DataFX optimized so that it can produce "instant replays" with DataFX overlays. This relies on a completely automated solution for court detection, camera pose solving, player tracking, and player roto-scoping.

Interactive DataFX may also be adapted for display on a second screen, such as a tablet, while a user watches a main screen. Real time or instant replay viewing and interaction may be used to enable such effects. On a second screen-type viewing experience, the fan could interactively toggle on and off various elements of DataFX. This enables the fan to customize the experience and to explore many different metrics. Rather than only DataFX-enabled replays, the system could be further optimized so that DataFX is overlaid in true real time, enabling the user to toggle between a live video feed and a live video feed that is overlaid with DataFX. The user would then also be able to choose the type of DataFX to overlay, or which player(s) to overlay it on.

A touch screen UI may be established for interaction with DataFX.

Many of the above embodiments may be used for basketball, as well as for other sports and for other items that are captured in video, such as TV shows, movies, or live video (e.g., news feeds). For sports, a player tracking data layer may be employed to enable the computer to "understand" every second of every game. This enables the computer to deliver content that is extracting from portions of the game and to augment that content with relevant story-telling elements. The computer thus delivers personalized interactive augmented experiences to the end user.

For non-sports domains, such as TV shows or movies, there is no player tracking data layer that assists the computer in understanding the event, Rather, in this case, the computer derives, in some other way, an understanding of each scene in a TV show or movie. For example, the computer might use speech recognition to extract the dialogue throughout a show. In further examples, the computer might use computer vision to recognize objects in each scene, such as robots in the Transformer movie. In further examples, the computer might use combinations of these inputs and others to recognize things like explosions. In further examples, the sound track could also provide clues.

The resulting system would use this understanding to deliver the same kind of personalized interactive augmented experience as we have described for the sports domain. For example, a user could request to see the Transformer movie series, but only a compilation of the scenes where there are robots fighting and no human dialogue. This enables "short form binge watching," where users can watch content created by chopping up and recombining bits of content from original video. The original video could be sporting events, other events TV shows, movies, and other sources, Users can thus gorge on video compilations that target their individual preferences. This also enables a summary form of watching, suitable for catching up with current events or currently trending video, without having to watch entire episodes or movies.

Figure 44:
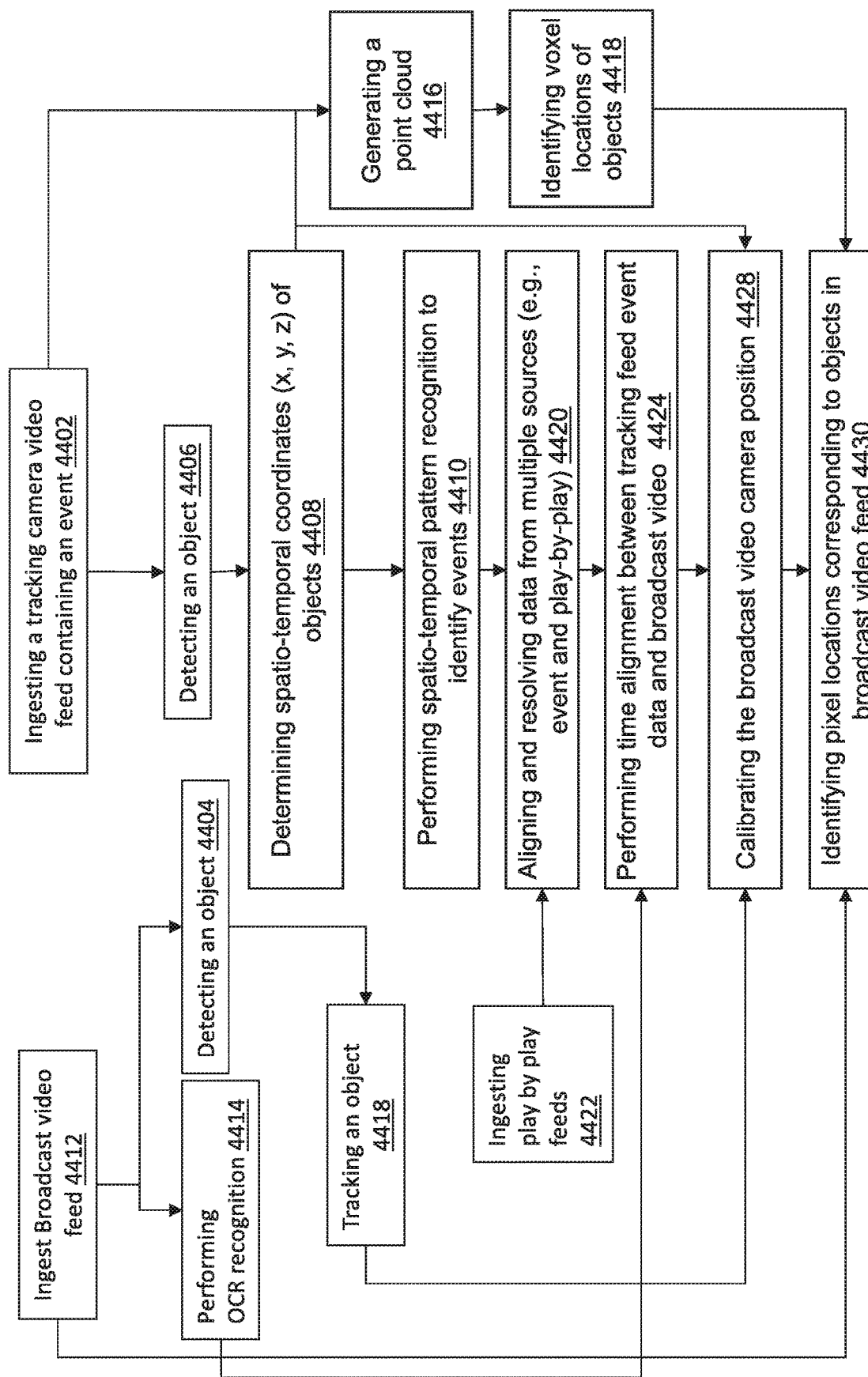
FIG. 44 illustrates a process flow according to an exemplary and non-limiting embodiment.

FIG. 44 provides a flow under which the platform may ingest and align the content of one or more broadcast video feeds and one or more tracking camera video feeds. At a step 4412, a broadcast video feed may be ingested, which may consist of an un-calibrated and un-synchronized video feed. The ingested broadcast video feed may be processed by performing optical character recognition at a step 4414, such as to extract information from the broadcast video feed that may assist with aligning events within the feed with events identified in other sources of video for the same event. This may include recognizing text and numerical elements in the broadcast video feed, such as game scores, the game clock, player numbers, player names, text feeds displayed on the video, and the like. For example, the time on the game clock, or the score of a game, may assist with time-alignment of a broadcast feed with another video feed. At a step 4404 objects may be detected within the broadcast video feed, such as using machine-based object-recognition technologies. Objects may include players (including based on recognizing player numbers), body parts of players (e.g., heads of players, torsos of players, etc.) equipment (such as the ball in a basketball game), and many others. Once detected at the step 4404, objects may be tracked over time in a step 4418, such as in progressive frames of the broadcast video feed. Tracked objects may be used to assist in calibrating the broadcast video intrinsic and extrinsic camera parameters by associating the tracked objects with the same objects as identified in another source, such as a tracking camera video feed.

At a step 4402, in parallel with the steps involved in ingesting and processing a broadcast video feed, video feeds from tracking cameras, such as tracking cameras for capturing 3D motion in a venue (like a sports arena), may be ingested. The tracking camera video feeds may be calibrated and synchronized to a frame of reference, such as one defined by the locations of a set of cameras that are disposed at known locations within the venue where the tracking camera system is positioned. At a step 4406, one or more objects may be detected within the tracking camera video feed, including various objects of the types noted above, such as players, numbers, items of equipment, and the like. In embodiments, spatiotemporal coordinates of the objects may be determined by processing the information from the tracking camera video feed, the coordinates being determined for the recognized objects based on the frame of reference defined by the camera positions of the tracking system. In embodiments, the coordinates being determined for the recognized objects can be based on the court or the field on which the game is played. In embodiments, the coordinates being determined for the recognized objects are based on the boundaries, lines, markers, indications, and the like associated with the court or the field on which the game is played. The video feed from the tracking camera system and the information about spatiotemporal object positions may be used to generate a point cloud at a step 4416, within which voxel locations of the objects detected at the step 4406 may be identified at a step 4418. The tracking camera video feed that was processed to detect and track objects may be further processed at a step 4410 by using spatiotemporal pattern recognition (such as machine-based spatiotemporal pattern recognition as described throughout this disclosure) to identify one or more events, which may be a wide range of events as described throughout this disclosure, such as events that correspond to patterns in a game or sport.

In embodiments, other feeds may be available that may contain additional information about events that are contained in the tracking camera video feed. For example, a data feed, such as a play-by-play feed, for a game may be ingested at a step 4422. At a step 4420, the information from multiple sources may be aligned, such as aligning the play-by-play data feed from the step 4422 with events recognized at the step 4410. Similarly, at a step 4424 the recognized event data in the tracking camera video feed at the step 4410 may be aligned with events recognized in the broadcast video feed at the step 4414, resulting in time-aligned broadcast video, tracking camera, and other (e.g., play-by-play) feeds. Once the tracking camera video feed and the broadcast video feed are time-aligned for an event, objects detected at the step 4404 in the broadcast video feed and tracked at the step 4418 (e.g., players' heads) may be used at a step 4428 to calibrate the broadcast video camera position, such as by identifying the broadcast video camera position within the frame of reference of the tracking camera system used to capture the tracking camera video feed. This may include comparing sizes and orientations of the same object as it was detected at the step 4404 in the broadcast video feed and at the step 4406 in the tracking camera system video feed. In embodiments, calibration parameters of the broadcast camera can be determined by, among other things, comparing positions of detected objects in the video with detected three-dimensional positions of the corresponding objects that can be obtained using the calibrated tracking system. In embodiments, heads of the players in the game can be suitable objects because the heads of the players can be precisely located relative to other portions of the bodies of the players. Once calibrated, the broadcast video camera information can be processed as another source just like any of the tracking cameras. This may include re-calibrating the broadcast video camera position for each of a series of subsequent events, as the broadcast video camera may move or change zoom between events. Once the broadcast video camera position is calibrated to the frame of reference of the tracking camera system, at a step 4430 pixel locations in the broadcast video feed may be identified, corresponding to objects in the broadcast video feed, which may include using information about voxel locations of objects in the point cloud generated from the motion tracking camera feed at the step 4418 and/or using image segmentation techniques on the broadcast video feed. The process of FIG. 44 thus provides time-aligned broadcast video feeds, tracking camera event feeds, and play-by-play feeds, where within each feed pixel locations or voxel locations of objects and backgrounds are known, so that various activities can be undertaken to process the feeds, such as for augmenting the feeds, performing pattern recognition on objects and events within them (such as to find plays following particular patterns), automatically clipping or cutting them to produce content (such as capturing a reaction in broadcast video to an event displayed in or detected by the tracking camera feeds based on a time sequence of time-aligned events), and many others as described throughout this disclosure.

In some embodiments, the platform may use stationary features on a playing surface (e.g., a basketball court) to calibrate the broadcast video camera parameters and to time align two or more video feeds, For example, the platform may utilize stationary lines (e.g., yard lines, top of the three point line, a half court line, a center field line, side lines, intersections between half court or field lines and side lines, logos, goal posts, and the like) to calibrate the broadcast video camera parameters, In these embodiments, the stationary features may be detected in the broadcast video feed and in the tracking video feed, In embodiments, the platform may determine the x, y, and z locations of the stationary features in the tracking video feed, and may calibrate the broadcast video camera parameters based on the x, y, z coordinates of the stationary features or voxel coordinates, For example, in embodiments, the platform may cross-reference the pixel locations of a stationary feature in the broadcast video feed with the x, y, z coordinates of the stationary feature in the tracking camera feeds, Once the broadcast video feed is calibrated with respect to one or more tracking camera feeds, moving objects tracked in the broadcast video can be cross-referenced against the locations of the respective moving objects from the tracking camera video feeds, In some of these embodiments, the platform may track moving objects in the broadcast video feed and the tracking camera feed(s) with respect to the locations of the stationary features in the respective broadcast video feed and tracking camera feeds to time align the broadcast video feed and tracking camera feeds, For example, the platform may time align one or more broadcast video feeds and one or more tracking camera feeds at respective time slices where a player crosses a logo or other stationary features on the playing surface in each of the respective feeds (broadcast video and tracking camera feeds).

Figure 45:
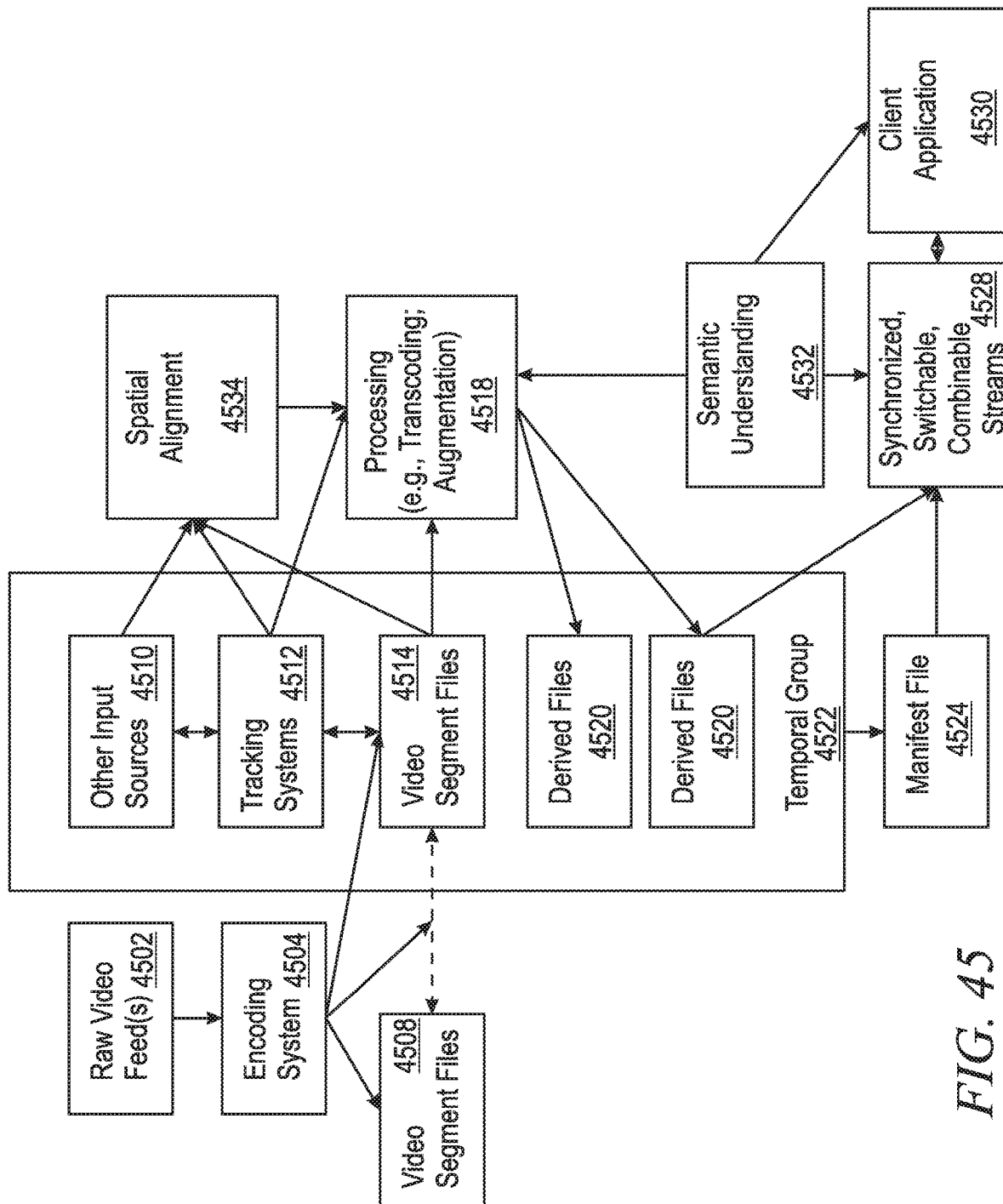
FIG. 45 illustrates systems and methods for parallel processing, synchronization, and failover across multiple streams of a live event according to an exemplary and non-limiting embodiment.

Referring to FIG. 45, embodiments of the methods and systems disclosed herein may involve handling multiple video input feeds 4502, information from one or more tracking systems 4512 (such as player tracking systems that may provide time-stamped location data and other information, such as physiological monitoring information, activity type information, etc.), and one or more other input sources 4510 (such as sources of audio information, play-by-play information, statistical information, event information, etc.). In embodiments, live video input feeds 4502 are encoded by one or more encoding systems 4504 to produce a series of video segment files 4508, each consisting of a video chunk, optionally of short duration, e.g., four seconds. Video segment files 4514 from different input feeds corresponding to the same time interval are considered as part of a temporal group 4522 associated with that time interval. The temporal group 4522 may also include information and other content from tracking systems 4512 and other input sources 4510.

In embodiments, each video segment file 4508 may independently and in parallel undergo various processing operations 4518 in one or more processing systems, such as transcoding to various file formats, streaming protocols, and the like. The derived video files 4520 output from the processing operations 4518 may be associated with the same temporal group 4522. Temporal grouping 4522 enables time synchronization among the original and derived files without having to further maintain or track timing or synchronization information. Such processing operations 4518 may include, without limitation, standard video on demand (VOD) transcoding, such as into lower bit rate video files. Processing operations 4518 may also include augmentation, such as with graphics, audio overlays, or data, producing augmented derived video files 4520. Other data derived from the video streams or obtained from other input sources 4510 (e.g., coordinate positions of players and objects obtained via optical or chip tracking systems 4512), which may typically become available with a small time delay relative to the live video input streams 4502, may also be synchronized to the video segment files 4508 in a temporal group 4522, such as by adding them as metadata files to the corresponding temporal group or by binding them to the video segment files 4514. In embodiments, a manifest file 4524 based on these temporal groups 4522 may be created to enable streaming of the original video input feed 4502, the video segment files 4514 and/or derived video files 4520 as a live, delayed or on-demand stream. Synchronization among the output streams may enable combining and/or switching 4528 seamlessly among alternative video feeds (e.g., different angles, encoding, augmentations or the like) and data feeds of a live streamed event.

Among other benefits, synchronization across original video input feeds 4502, video segment files 4508, derived video files 4520 with encoded, augmented or otherwise processed content, and backup video feeds, described by a manifest file 4524, may allow client-side failover from one stream to another without time discontinuity in the viewing of the event. For instance, if an augmented video stream resulting from processing operations 4518 is temporarily unavailable within the time offset at which the live stream is being viewed or falls below a specified buffering amount, a client application 4530 consuming the video feed may temporarily fail over to an un-augmented video input feed 4502 or encoded video segment file 4508.

In embodiments, the granularity with which the client application 4530 switches back to the augmented stream 4528 when available may depend on semantically defined boundaries in the video feed, which in embodiments may be based on a semantic understanding of events within the video feed, such as achieved by the various methods and systems described in connection with the technology stack 100 and the processes described throughout this disclosure. For example, a switch back to derived video file 4520 with various augmentations added in processing operations 4518 may be timed to occur after a change of possession, a timeout, a change in camera angle, a change in point-of-view, or other appropriate points in the action, so that the switching occurs while minimizing disruption of the viewing experience. Switching may also be controlled by semantic understanding 4532 of the content of different video input feeds 4502 at each time instant; for example, if a camera is not pointing at the current action on the court, an alternative video input feed 4502, video segment file 4514 or derived video file 4520 may be selected.

In embodiments, a "smart pipe" may be provided consisting of multiple aligned content channels (e.g., audio, video, or data channels) that are indexed both temporally and spatially. Spatial indexing and alignment 4534 may include indexing of pixels in 2D streams, voxels in 3D streams, and other objects, such as polygonal meshes used for animation, 3D representation, or the like. In embodiments, a wide variety of elements may be indexed, such as, without limitation, events, and locations of objects (including players, game objects, and objects in the environment, such as a court or arena) involved in those events. In embodiments, a further variety of elements may be indexed including information and statistics related to events and locations. In embodiments, a further variety of elements may be indexed including locations of areas corresponding to floor areas, background areas, signage areas, or the like where information, augmentations, graphics, animations, advertising, or the like may be displayed over a content frame. In embodiments, a further variety of elements may be indexed including indices or indicators of what information, augmentation elements or the like that are available to augment a video feed in a content channel such as ones that may be selected individually or in combination.

In embodiments, a further variety of elements may be indexed including predefined combinations of content (e.g., particular combinations of audio, video, information, augmentation elements, replays, or other content elements), such as constituting channels or variations from which end-users may choose ones that they prefer. Thus, a system for spatial indexing and alignment 4534 may provide spatial indexing and alignment information to the processing operations 4518 (or may be included therein), such that the derived video files 4520 (and optionally various objects therein) that are indexed both temporally and spatially. In such a case, the "smart pipe" for synchronized, switchable and combinable content streams 4528 may contain sufficient indexed and aligned content to allow the creation of derived content, the creation of interactive applications, and the like, each optionally tied to live and recorded events (such as sporting events). In embodiments, the tracking systems 4512, the spatial indexing and alignment 4534 and the semantic understanding 4532 may be part of the larger alignment, tracking, and semantic system included in the systems and methods disclosure herein that may take various inputs including original video feeds and play-by-play feeds, and may produce X, Y, Z tracking data and semantic labels. The X, Y, Z tracking data and semantic labels may be stored as separate metadata files in the temporal group 4522 or used to produce derived video files 4520 in the temporal group 4522.

In embodiments, any combination of inputs such as from a tracking camera system, a 3D camera array, broadcast video, a smartphone video, lidar, and the like may be used to automatically obtain a 3D understanding of a game. The automatically obtained 3D understanding of the game may be used to index voxels of 3D representations (e.g., AR/VR video) or pixels of any 2D video footage (e.g., from tracking cameras, broadcast, smartphones, reconstructed video from any point of view such as first person point of view of players in the game) or alternatively to voxels/pixels, other graphics representations such as polygonal meshes.

In embodiments, a "smart pipe" may consist of multiple aligned content channels (e.g., audio, video, or data channels) that are indexed both temporally and spatially (e.g., indexing of pixels/voxels/polygonal meshes) with events and locations of players/objects involved in those events. By way of this example, the indexing both temporally and spatially with events and locations of players/objects involved in those events may also include information and statistics related to events and locations. The indexing both temporally and spatially with events and locations of players/objects involved in those events may also include locations of areas corresponding to floor or background areas where information, augmentations (e.g., filters that manipulate the look of the ball/players) or advertising may be displayed over each video frame. In embodiments, available pieces of information and augmentation elements may be selected individually or in combination. In embodiments, combinations of audio, video, information, augmentation, replays, and the like may constitute channels for end-users to choose from. The smart pipe may contain sufficient indexed and aligned content to create derived content and interactive apps tied to live and recorded games.

In embodiments, the composition of video via frames, layers and/or tracks may be generated interactively by distributed sources, e.g., base video of the sporting event, augmentation/information layers/frames from different providers, audio tracks from alternative providers, advertising layers/frames from other providers, leveraging indexing and synchronization concepts, and the like. By way of this example, the base layers and/or tracks may be streamed to the various providers as well as to the clients. In embodiments, additional layers and/or tracks may be streamed directly from the providers to the clients and combined at the client. In embodiments, the composition of video via frames, layers and/or tracks and combinations thereof may be generated interactively by distributed sources and may be based on user personalizations.

In embodiments, the systems and methods described herein may include a software development kit (SDK) 4804 that enables content being played at a client media player 4808 to dynamically incorporate data or content from at least one separate content feed 4802, In these embodiments, the SDK 4804 may use timecodes or other timing information in the video to align the client's current video playout time with data or content from the at least one separate content feed 4802, in order to supply the video player with relevant synchronized media content 4810.

Figure 48:
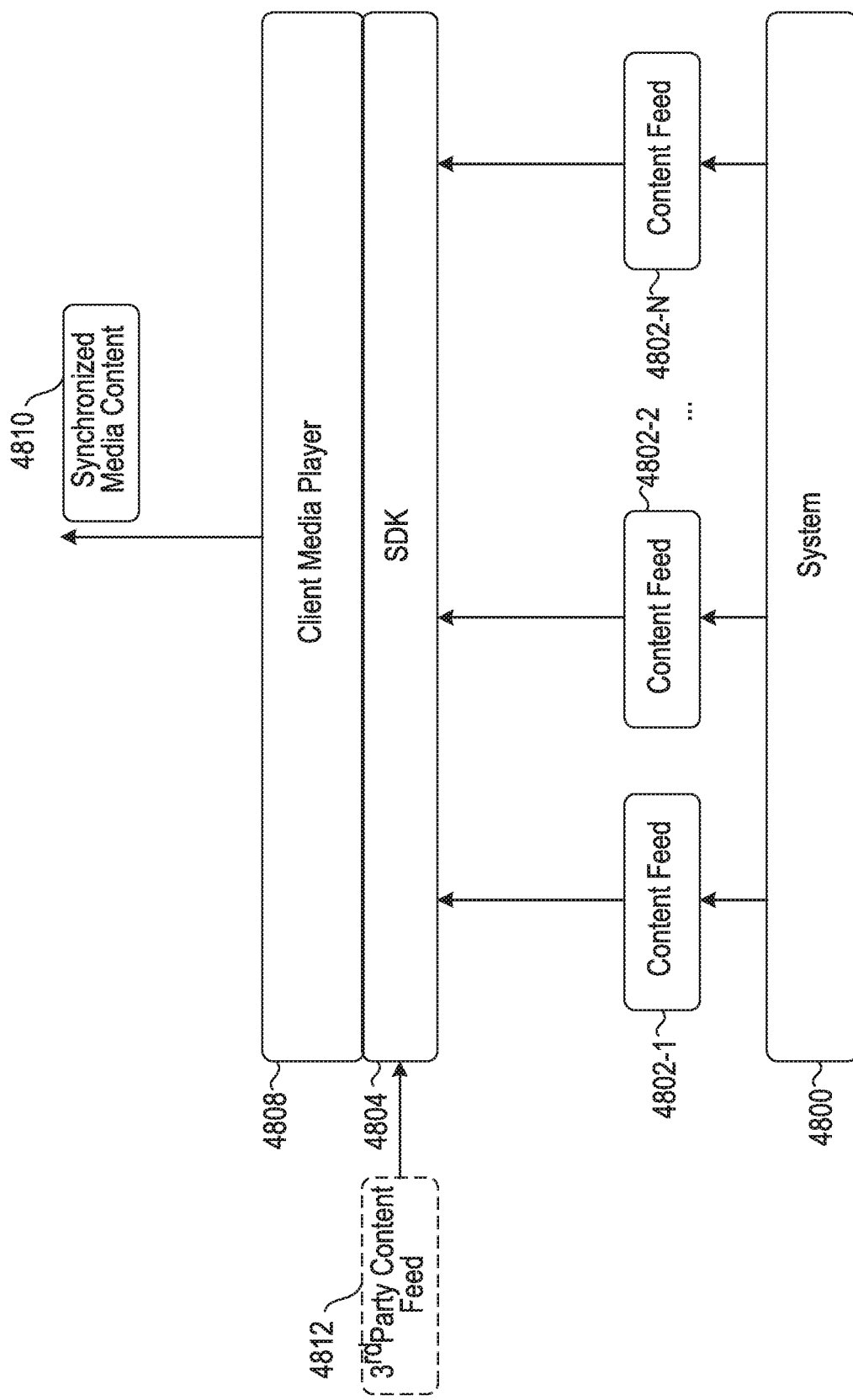
FIG. 48 illustrates systems and methods for dynamic incorporation of data or content using a software development kit (SDK) according to an exemplary and non-limiting embodiment.

In operation, as shown in FIG. 48, a system 4800 (e.g., the system described herein) may output one or more content feeds 4802-1, 4802-2 . . . 4802-N. The content feeds may include video, audio, text, and/or data (e.g., statistics of a game, player names). In some embodiments, the system 4800 may output a first content feed 4802-1 that includes a video and/or audio that is to be output (e.g., displayed) by a client media player 4808. The client media player 4808 may be executed by a user device (e.g., a mobile device, a personal computing device, a tablet computing device, and the like). The client media player 4808 is configured to receive the first content feed 4802 and to output the content feed 4802 via a user interface (e.g., display device and/or speakers) of the user device. Additionally or alternatively, the client media player 4808 may receive a third-party content feed 4812 from a third-party data source (not shown). For example, the client media player 4808 may receive a live-game video stream from the operator of an arena. Regardless of the source, a content feed 4802-2 or 4812 may include timestamps or other suitable temporal indicia to identify different positions (e.g., frames or chunks) in the content feed. The client media player 4808 may incorporate the SDK 4804. The SDK 4804 may be configured to receive additional content feeds 4802-2 . . . 4802-N to supplement the outputted media content. For example, a content feed 4802-2 may include additional video (e.g., a highlight or alternative camera angle). In another example, a content feed 4802-2 may include data (e.g., statistics or commentary relating to particular game events). Each additional content feed 4802-2 . . . 4802-N may include timestamps or other suitable temporal indicia as well. The SDK 4804 may receive the additional content feed(s) 4802-2 . . . 4802-N and may augment the content feed being output by the media player with the one or more additional content feeds 4802-2 . . . 4802-N based on the timestamps of the respective content feeds 4802-1, 4802-2, . . . 4802-N to obtain dynamic synchronized media content 4810. For example, while playing a live feed (with a slight lag) or a video-on-demand (VOD) feed of a basketball game, the SDK 4804 may receive a first additional content feed 4802 containing a graphical augmentation of a dunk in the game and a second additional content feed 4802 indicating the statistics of the player who performed the dunk. The SDK 4804 may incorporate the additional content feeds into the synchronized media content 4810, by augmenting the dunk in the live or VOD feed with the graphical augmentation and the statistics. In some embodiments, a client app using the SDK may allow client-side selection or modification of which subset of the available additional content feeds to incorporate. In some implementations, the SDK 4804 may include one or more templates that define a manner by which the different content feeds 4802 may be laid out. Furthermore, the SDK 4804 may include instructions that define a manner by which the additional content feeds 4802 are to be synchronized with the original content feed.

In embodiments, the systems and methods disclosed herein may include joint compression of channel streams such as successive refinement source coding to reduce streaming bandwidth and/or reduce channel switching time, and the like.

In embodiments, the systems and methods disclosed herein may include event analytics and/or location-based games including meta-games, quizzes, fantasy league and sport, betting, and other gaming options that may be interactive with many of the users at and connected to the event such as identity-based user input, e.g., touching or clicking a player predicted to score next. In embodiments, the event analytics and/or location-based games may include location-based user input such as touching or clicking a location where a rebound or other play or activity is expected to be caught, to be executed, and the like. In embodiments, the event analytics and/or location-based games may include timing-based user input such clicking or pressing a key to indicate when a user thinks a shot should be taken, a defensive play should be initiated, a time-out should be requested, and the like. In embodiments, the event analytics and/or location-based games may include prediction-based scoring including generating or contributing to a user score based on the accuracy of an outcome prediction associated with the user. By way of this example, the outcome prediction may be associated with outcomes of individual offensive and defensive plays in the games and/or may be associated with scoring and/or individual player statistics at predetermined time intervals (e.g., quarters, halves, whole games, portions of seasons, and the like). In embodiments, the event analytics and/or location-based games may include game state-based scoring including generating or contributing to a user score based on expected value of user decision calculated using analysis of instantaneous game state and/or comparison with evolution of game state such as maximum value or realized value of the game state in a given chance or possession.

In embodiments, the systems and methods disclosed herein may include interactive and immersive reality games based on actual game replays. By way of this example, the interactive and immersive reality games may include the use of one or more simulations to diverge from actual game events (partially or in their entirety) based on user input or a collection of user input. In embodiments, the interactive and immersive reality games may include an action-time resolution engine that may be configured to determine a plausible sequence of events to rejoin the actual game timeline relative to, in some examples, the one or more simulations to diverge from actual game events (partially or in their entirety) based on user input or a collection of user input. In embodiments, the interactive and immersive reality games may include augmented reality simulations that may integrate game event sequences, using cameras on located on one or more backboards and/or along locations adjacent to the playing court. In embodiments, the systems and methods disclosed herein may include simulated sports games that may be based on detailed player behavior models. By way of this example, the detailed player behavior models may include tendencies to take different actions and associated probabilities of success of different actions under different scenarios including teammate/opponent identities, locations, score differential, period number, game clock, shot clock, and the like.

In embodiments, the systems and methods disclosed herein may include social chat functions and social comment functions that may be inserted into a three-dimensional scene of a live event. By way of this example, the social chat and comment functions that may be inserted into the three-dimensional scene of the live event may include avatars inserted into the crowd that may display comments within speech bubbles above the avatars. In other examples, the social chat and comment functions may be inserted into a three-dimensional scene of the live event as a running commentary adjacent to other graphics or legends associated with the event.

In embodiments, the systems and methods disclosed herein may include the automating of elements of broadcast production such as automatic control of camera pan, tilt, and zoom. By way of this example, the automating of elements of broadcast production may also include automatic switching between camera views. In embodiments, the automating of elements of broadcast production may include automatic live and color commentary generation and automatic placement and content from synthetic commentators in the form of audio or in the form of one or more audio and video avatars with audio content that may be mixed with semantic and contextual based reactions from the live event and/or from other users. By way of this example, the automated elements of broadcast production may include automated generation of commentary in audio only or audio and video form including AR augmentation and associated content by, for example, combining semantic machine understanding of events in the game and semantic machine understanding of camera views, camera cuts, and camera close-ups in broadcast or another video.

In embodiments, the automated generation of commentary may also be based on semantic machine understanding of broadcaster/game audio, statistics from semantic machine understanding of past games, information/statistics from other sources, and combinations thereof. In embodiments, a ranking of potential content items may be based on at least one of the rarity of events, comparison against the rest of the league, diversity with respect to previously shown content, personalization based on channel characteristics, explicit user preferences, inferred user preferences, the like, or combinations thereof. In embodiments, the automated generation of commentary may include the automatic selection of top-ranked content items or a short list of top-ranked content items shown to a human operator for selection.

Figure 49:
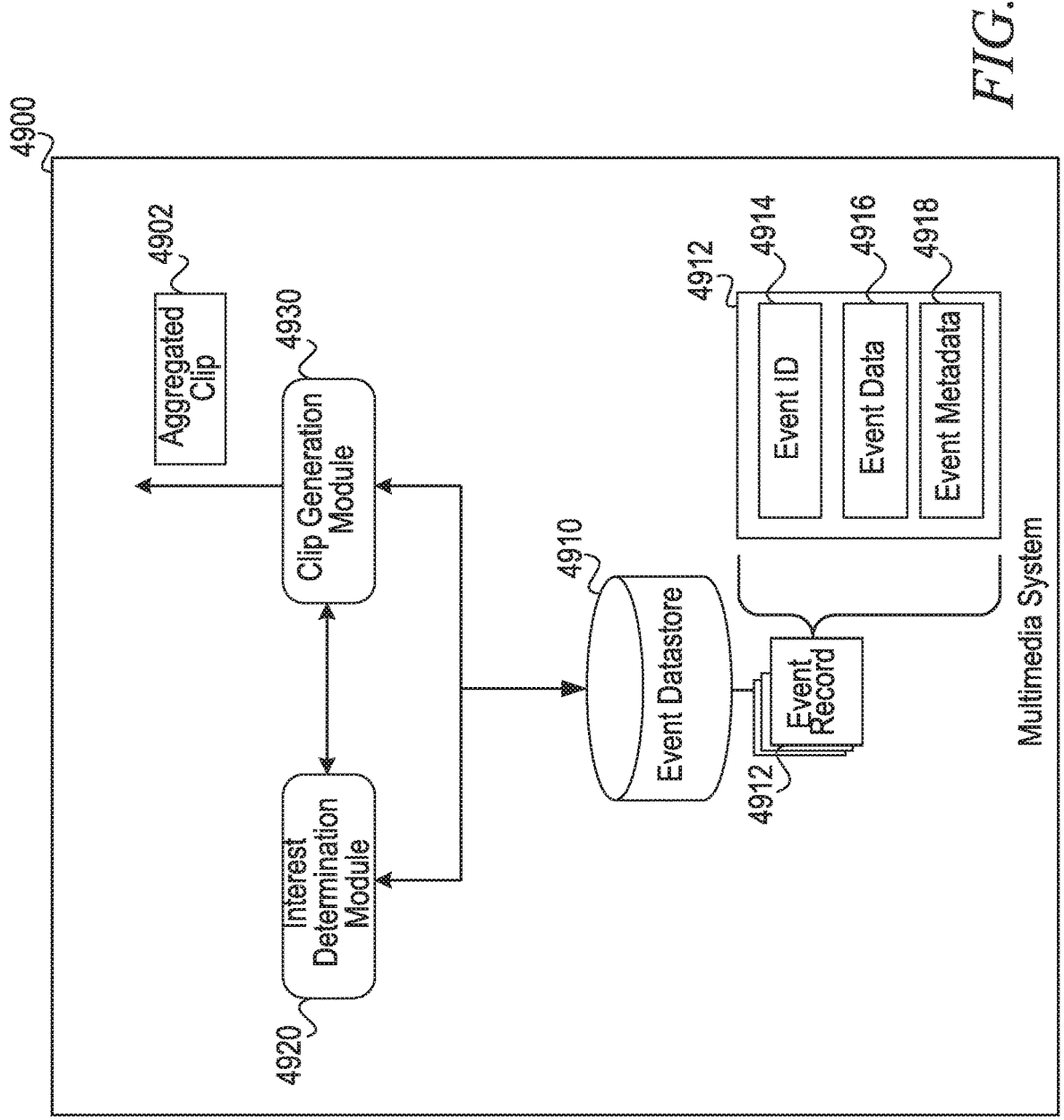
FIG. 49 illustrates systems and methods of machine-automated or machine-assisted generation of aggregated media clips according to an exemplary and non-limiting embodiment.

In embodiments, and as shown in FIG. 49, the systems and methods disclosed herein may include machine-automated or machine-assisted generation of aggregated clips 4902. Examples of aggregated clips 4902 include highlights and/or condensed games. The aggregated clip may be comprised of one or more selected media segments (e.g., video and/or audio segments). In the example of FIG. 49, a multimedia system 4900 may include an event datastore 4910, an interest determination module 4920, and a clip generation module 4930. The event datastore 4910 may store event records 4912. Each event records 4912 may correspond to a respective event (e.g., an offensive possession, a shot, a dunk, a defensive play, a blitz, a touchdown pass). An event record 4912 may include an event ID 4914 that uniquely identifies the event. An event record 4912 may also include event data 4916 that corresponds to the event. For example, event data 4916 may include a media segment (e.g., video and/or audio) that captures the event or a memory address that points to the media segment that captures the event. The event record 4912 may further include event metadata 4918. Event metadata 4918 may include any data that is pertinent to the event. Examples of event metadata 4918 may include, but is not limited to, an event type (e.g., a basketball shot, a dunk, a football blitz, a touchdown, a soccer goal), a list of relevant players (e.g., the shooter and defender, the quarterback, the goal scorer), a time corresponding to the event (e.g., when during the game did the event occur), a length of the event (e.g., how many seconds is the media segment that captures the event), a semantic understanding of the event, the potential impact event on win probability (e.g., a delta of win probability from before and after the event), references (e.g., event IDs) to other events that are pertinent to event (e.g., other events during a run made by a team, and/or any other suitable types of metadata. In some embodiments, the event metadata 4918 may further include an interest score of the event, where the interest score of an event may be a numerical value indicating a degree of likelihood that a user would find the event interesting (e.g., worthy of watching).

In embodiments, an interest determination module 4920 determines an interest level of an event or group of related events. In some of these embodiments, the interest determination module 4920 determines an interest score of an event or group of related events. The interest score may be relative to other events in a particular game or relative to events spanning multiple games and/or sports. In some embodiments, the interest determination module 4920 may determine the interest score of a particular event or group of events based on the event metadata 4918 of the respective event(s). In some embodiments, the interest determination module 4920 may incorporate one or more machine-learned models that receive event metadata 4918 of an event or group of related events and outputs a score based on the event metadata 4918. A machine-learned model may, for example, receive an event type, and other relevant features (e.g., time, impact on win probability, relevant player) and may determine the score based thereon. The machine-learned models may be trained in a supervised, semi-supervised manner, or unsupervised manner. The interest determination module 4920 may determine the interest score of an event or group of related events in other manners as well. For example, the interest determination module 4920 may utilize rules-based scoring techniques to score an event or group of related events, In some embodiments, the interest determination module 4920 is configured to determine an interest score for a particular user. In these embodiments, the interest scores may be used to generate personalized aggregated clips 4902 for a user. In these embodiments, the interest determination module 4920 may receive user-specific data that may be indicative of a user's personal biases. For example, the interest determination module 4920 may receive user-specific data that may include, but is not limited to, a user's favorite sport, the user's favorite team, the user's list of favorite players, a list of events recently watched by the user, a list of events recently skipped by the user, and the like. In some of these embodiments, the interest determination module 4920 may feed the user-specific data into machine-learned models along with event metadata 4818 of an event to determine an interest score that is specific to a particular user. In these embodiments, the interest determination module 4920 may output the user-specific interest score to the clip generation module 4930.

In some embodiments, one or more humans may assign interest levels to various events. In these embodiments, the human-assigned interest levels may be used to determine which events to include in an aggregated clip 4902. Furthermore, the human-assigned interest levels may be used to train a model used to determine interest scores of respective events.

The clip generation module 4930 generates aggregated clips 4902 based on one or more identified events. The clip generation module 4930 may determine one or more events to include in an aggregated clip based on the interest level of the events relating to a game or collection of games. In some embodiments, the clip generation module 4930 determines the events to include in an aggregated clip 4902 based on the interest level of the respective events. The clip generation module 4930 may implement optimization or reinforcement learning to determine which events (depicted in media segments) to include in an aggregated clip 4902. For instance, the clip generation module 4930 may include media segments depicting events having the highest relative interest scores and media segments of additional events that may be relevant to the high scoring events. In embodiments, the clip generation module 4930 may determine how many events to include in the aggregated clip 4902 depending on the intended purpose of the aggregated clip 4902. For example, a highlight may be shorter in duration than a condensed game. In embodiments, the length of an aggregated clip 4902 may be a predetermined parameter (e.g., three minutes). In these embodiments, the clip generation module 4930 may select a sufficient number of events to span the predetermined duration. For example, the clip generation module 4930 may identify a set of media segments of events having requisite interest scores, where the aggregated duration of the set of media segments is approximately equal to the predetermined duration.

In embodiments, the clip generation module 4930 may be configured to generate personalized aggregated clips. In these embodiments, the clip generation module 4930 may receive user-specific interest scores corresponding to events of a particular game or time period (e.g., "today's personalized highlights), The clip generation module 4930 may utilize the user-specific interest scores of the events, a user's history (e.g., videos watched or skipped), and/or user profile data (e.g., location, favorite teams, favorite sports, favorite players) to determine which events to include in a personalized aggregated clip 4902. In embodiments, the clip generation module 4930 may determine how many events to include in the personalized aggregated clip 4902 depending on the intended purpose of the aggregated clip 4902 and/or the preferences of the user. For example, if a user prefers to have longer condensed games (i.e., more events in the aggregated clip), the clip generation module 4930 may include more media segments in the aggregated clip. In some embodiments, the length of an aggregated clip 4902 may be a predetermined parameter (e.g., three minutes) that may be explicitly set by the user. In these embodiments, the clip generation module 4930 may select a sufficient number of events to span the predetermined duration set by the user. For example, the clip generation module 4930 may identify a set of media segments of events having requisite interest scores, where the aggregated duration of the set of media segments is approximately equal to the predetermined duration.

In embodiments, the clip generation module 4930 requests the scores of one or more events from the interest determination module 4920 when the clip generation module 4930 is tasked with generating aggregated clips 4902. Alternatively, the interest determination module 4920 may score each event defined in the event datastore 4910. Upon determining which events to include in an aggregated clip 4902, the clip generation module 4930 may retrieve the media segments corresponding to the identified events. For example, the clip generation module 4930 may retrieve the event records 4912 of the identified events using the event IDs 4914 of the identified events. The clip generation module 4930 may then generate the aggregated clip based on the event data 4916 contained in the retrieved event records 4912. The sequence of events depicted in the aggregated clip 4902 may be generated in any suitable manner. For example, the events may be depicted sequentially as they occurred or in order of ascending or descending interest score. The clip generation module 4930 may transmit the aggregated clip 4902 to a user device and/or store the aggregated clip 4902 in memory.

Figure 50:
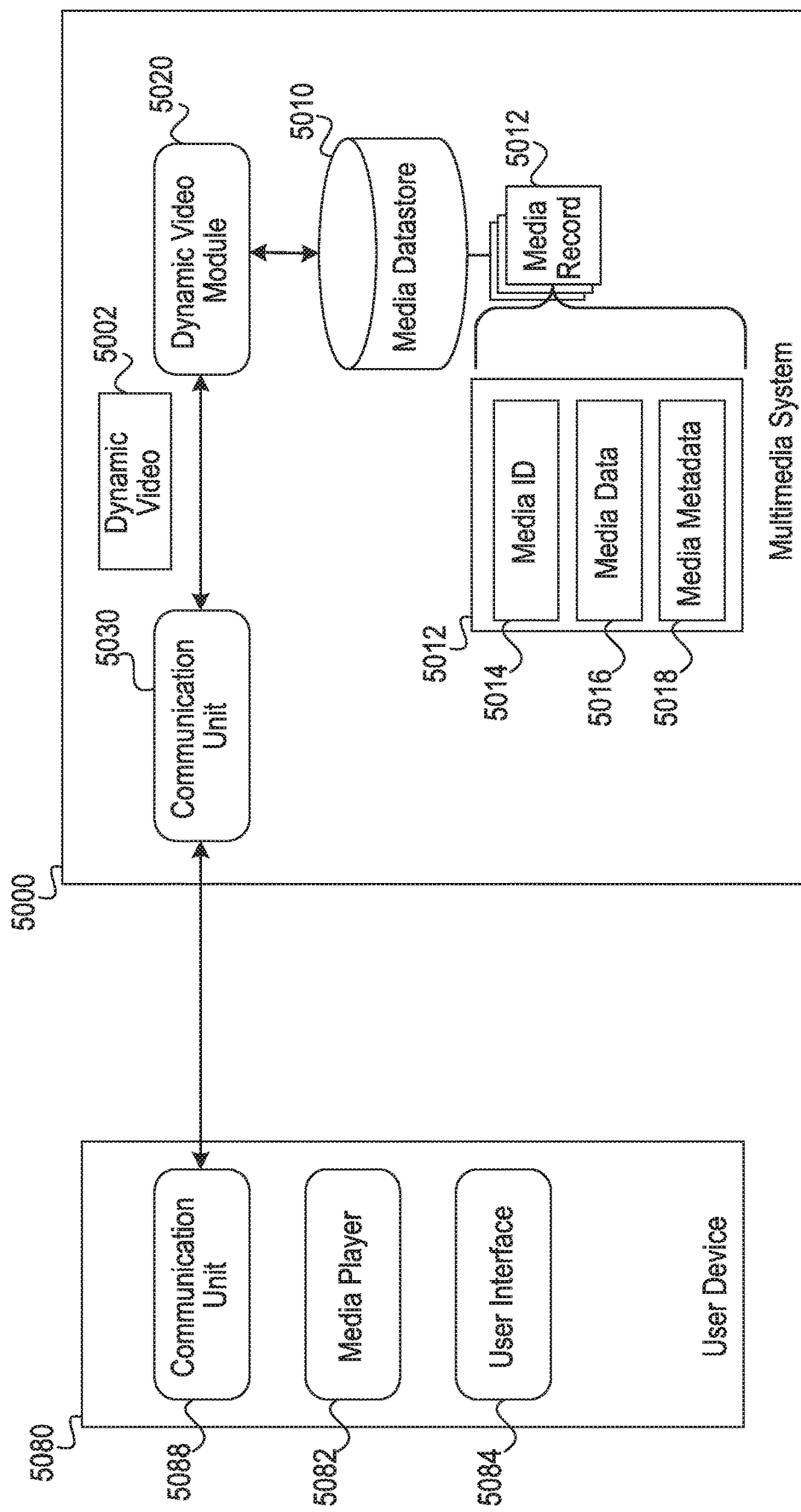
FIG. 50 illustrates systems and methods for generation of dynamic video according to an exemplary and non-limiting embodiment.

In embodiments, and in the example of FIG. 50, the systems and methods disclosed herein may be configured to provide "dynamic videos" 5002. A dynamic video 5002 may refer to the concatenated display of media segments (e.g., video and/or audio) that can be dynamically selected with short time granularity (e.g., frame-level or chunk-level granularity). A dynamic video 5002 may be comprised of one or more constituent media segments of dynamically determined length, content, and sequencing. The dynamic video 5002 may include constituent media segments that are stitched together in a single file or a collection of separate files that may each contain a respective constituent media segment. The constituent media segments of a dynamic video 5002 may be related based on one or more suitable relationships. For example, the constituent media segments may be of a same event taken from different camera angles, of different events of a same game, of different events from different games but of the same sport and on the same day, of different events relating to the same player or team, and/or of different events but the same subject, topic, or sentiment. Additionally, in some embodiments, the constituent media segments may be supplemented or augmented with graphical and/or text overlays. The graphical and/or text overlays may be confined to a single media segment or may span across multiple constituent media segments.

In the illustrated example, a multimedia system 5000 provides the dynamic videos 5002 to a user device 5080. The user device 5080 may be a mobile device (e.g., smartphone), a personal digital assistant, a laptop computing device, a personal computer, a tablet computing device, a gaming device, a smart television, and/or any other suitable electronic device with the capability to present the dynamic videos. The user device 5080 may include a media player 5082 that outputs the dynamic video 5002 via a user interface 5084. The media player 5082 may also receive user commands via the user interface 5084. The user interface 5084 may include a display device (e.g., an LED screen or a touchscreen), a physical keyboard (e.g., a qwerty keyboard), an input device (e.g., a mouse), an audio device (e.g., speakers), and the like. The user device 5080 may further include a communication unit 5088 that effectuates communication with external devices directly and/or via a network. For example, the communication unit 5088 may include one or more wireless and/or wired transceivers that communicate using any suitable communication protocol.

The multimedia system 5000 may include a media datastore 5010, a communication unit 5030, and a dynamic video module 5020. The media datastore 5010 may store media records 5012. A media record 5012 may correspond to a media segment that captures one or more events. A media record may include a media ID 5014 that uniquely identifies the media record 5012. A media record 5012 may include media data 5016. The media data 5016 may include the media segment itself or a memory address of the media segment. The media record 5012 may further include media metadata 5018. The media metadata 5018 may include any data that is pertinent to the media segment. Examples of media metadata 5018 may include, but is not limited to, one or more event identifiers the identify one or more events depicted in the media segment, one or more event types that describe the one or more events depicted in the media segment, a list of relevant players depicted in the multimedia segment, a time corresponding to the media segment (e.g., a starting time of the media segment with respect to a game), a time length of the media segment, a semantic understanding of the media segment, the potential impact of the events depicted in the media segment on win probability (e.g., a delta of win probability from before and after the event), references (e.g., media IDs) to other media segments that are pertinent to the media segment (e.g., other angles of the same events depicted in the media segment), and/or any other suitable types of metadata. In embodiments, the media records 5012 may further reference entire content feeds (e.g., an entire game or a livestream of a game). In these embodiments, the media metadata 5018 of a media record may include any suitable information relating to the content feed. For example, the media metadata 5018 may include an identifier of the game to which the content feed corresponds, an indicator whether the content feed is live or recorded, identifiers of the teams playing in the game, identifiers of players playing in the game, and the like.

The dynamic video module 5020 is configured to generate dynamic videos and to deliver dynamic videos to a user device 5080. The dynamic video module 5020 may select the media segments to include in the dynamic video 5002 in any suitable manner. In some embodiments, the dynamic video module 5020 may implement optimization and/or reinforcement learning-based approaches to determine the selection, length, and/or sequence of the constituent media segments. In these embodiments, the dynamic video module 5020 may utilize the media metadata 5018 of the media records 5012 stored in the media datastore 5010 to determine the selection, length, and/or sequence of the constituent media segments. The dynamic video module 5020 may additionally or alternatively implement a rules based approach to determine which media segments to include in the dynamic video. For example, the dynamic video module 5020 may be configured to include alternative camera angles of an event if multiple media segments depicting the same event exist. In this example, the dynamic video module 5020 may be further configured to designate media clips taken from alternative camera angles as supplementary media segments (i.e., media segments that can be switched to at the user device) rather than sequential media segments. In embodiments, the dynamic video module 5020 may be configured to generate dynamic video clips from any suitable sources, including content feeds. In these embodiments, the dynamic video module 5020 may generate dynamic videos 5002 having any variety of constituent media segments by cutting media segments from one or more content feeds and/or previously cut media segments. Furthermore, the dynamic video module 5020 may add any combination of augmentations, graphics, audio, statistics, text, and the like to the dynamic video, In some embodiments, the dynamic video module 5020 is configured to provide personalized dynamic videos 5002. The dynamic video module 5020 may utilize user preferences (either predicted, indicated, or inferred) to customize the dynamic video. The dynamic video 5002 may utilize a user's profile, location, and/or history to determine the user preferences. A user profile may indicate a user's favorite teams, players, sports, and the like. In another example, the dynamic video module 5020 may be able to predict a user's favorite teams and players based on the location of the user. In yet another example, the dynamic video module 5020 may be configured to infer user viewing preferences based on the viewing history of the user (e.g., telemetry data reported by the media player of the user). For example, if the user history indicates that the user routinely skips over media segments that are longer than 30 seconds, the dynamic video module 5020 may infer that the user prefers media segments that are less than 30 seconds long. In another example, the dynamic video module 5020 may determine that the user typically "shares" media segments that include reactions of players or spectators to a notable play. In this example, the dynamic video module 5020 may infer that the user prefers videos that include reactions of players or spectators, and therefore, media segments that tend to be longer in duration. In another example, the user history may indicate that the user watches media segments of a particular type of event (e.g., dunks), but skips over other types of events (e.g., blocked shots). In this example, the dynamic video module 5020 may infer that the user prefers to consume media segments of dunks over media segments of blocked shots. In operation, the dynamic video module 5020 can utilize the indicated, predicted, and/or inferred user preferences to determine which media segments to include in the dynamic video and/or the duration of the media segments (e.g., should the media segment be shorter or longer). The dynamic video module 5020 may utilize an optimization and/or reinforcement-based learning approach to determine which media segments to include in the dynamic video 5002, the duration of the dynamic video 5002, and the sequence of the media segments in the dynamic video 5002.

The multimedia system 5000 may transmit a dynamic video 5002 to a user device 5080. The media player 5082 receives the dynamic video 5002 via the communication unit 5088 and outputs one or more of the media segments contained in the dynamic video 5002 via the user interface 5084. The media player 5082 may be configured to record user telemetry data (e.g., which media segments the user consumes, which media segments the user skips, and/or terms that the user searches for) and to report the telemetry data to the multimedia system 5000. The media player 5082 may be configured to receive commands from a user via the user interface 5084. The commands may be executed locally by the media player 5082 and/or may be communicated to the multimedia system 5000, In some embodiments, the media player 5082 may be configured to allow selection of the media segments that are displayed based on user input and/or AI-controls. In the former scenario, the media player 5082 may be configured to receive user commands via the user interface 5084, For example, the media player 5082 may allow a user to enter search terms or to choose from a displayed set of suggestions. In response to the search terms or the user selections, the media player 5082 may initialize (e.g., request and begin outputting) a dynamic video 5002, in which the media player 5082 displays a machine-controlled sequence of media segments related to the search terms/user selection. A user may issue additional commands via the user interface 5084 (e.g., via the keyboard or by touching or directional swiping on a touchscreen) to request media segments related in different ways to the current media segment, to indicate when to move on to the next media segment, and/or to interactively pull up statistics and other information. For example, swiping upwards may indicate that the user wishes to see a different camera angle of the same event, swiping downwards may indicate that the user wishes to see an augmented replay of the same event, and swiping right may indicate that the user wishes to move on to the next clip. A set of keyword tags corresponding to each clip may be shown to facilitate the user adding one or more of the displayed tags to the set of search terms that determines potentially relevant media segments to display. The media player 5082 may report the user's inputs or interactions with the media player 5082, if any, to the multimedia system 5000. In response to such commands, the multimedia system 500 may use such data to adapt subsequent machine-controlled choices of media segment duration, content type, and/or sequencing in the dynamic video. For example, the user's inputs or interactions may be used to adjust the parameters and/or reinforcement signals of an optimization or reinforcement learning-based approach for making machine-controlled choices in the dynamic video 5002.

In embodiments, the dynamic video module 5020 may be configured to generate the dynamic video in real time. In these embodiments, the dynamic video module 5020 may begin generating and transmitting the dynamic video 5002. During display of the dynamic video 5002 by the media player 5082, the dynamic video module 5020 may determine how to sequence/curate the dynamic video. For instance, the dynamic video module 5020 may determine (either based on a machine-learning-based decision or from explicit instruction from the user) that the angle of a live feed should be switched to a different angle. In this situation, the dynamic video module 5020 may update the dynamic video 5002 with a different video feed that is taken from an alternative angle. In another example, a user may indicate (either explicitly or implicitly) that she is uninterested in a type of video being shown (e.g., baseball highlights). In response to the determination that the user is uninterested, the dynamic video module 5020 may retrieve media segments relating to another topic (e.g., basketball) and may begin stitching those media segments into the dynamic video 5002. In this example, the dynamic video module 5020 may be configured to cut out any media segments that are no longer relevant (e.g., additional baseball highlights). It is noted that in some embodiments, the dynamic video module 5020 may transmit alternative content feeds and/or media segments in the dynamic video 5002. In these embodiments, the media player 5082 may be configured to switch between feeds and/or media segments.

In embodiments, the automating of elements of broadcast production may include automatic live commentary generation that may be used to assist referees for in situ evaluation or post-mortem evaluation. The automatic live commentary generation that may be used to assist referees may also be used to train referees in unusual situations that may be seen infrequently in actual games but may be reproduced or formed from AR content based on or purposefully deviated from live game events. By way of the above examples, the referee assistance, evaluation, training, and the like associated with the improvement of referee decisions may be based on semantic machine understanding of game events.

In embodiments, the systems and methods disclosed herein may include the use of player-specific information in three-dimensional position identification and reconstruction to improve trade-offs among camera requirements. Toward that end, fewer or lower resolution cameras may be used, computational complexity/delay may be reduced and output quality/accuracy may be increased when compared to typical methods. With reference to FIG. 46, the player-specific information in three-dimensional position identification and reconstruction 4600 may be shown to improve the balance in trade-offs of camera requirements including improved localization of keypoints 4602 such as a head, joints, and the like, by using player models 4604 of specific players in conjunction with player identification 4608 such as identifying a jersey number or automatically recognizing a face and remote sensing technology to capture the players such as one or more video cameras, lidar, ultrasound, Wi-Fi visualization, and the like. By way of this example, the improved localization of keypoints may include optimizing over constraints on distances between keypoints from player models combined with triangulation measurements from multiple cameras.

In embodiments, the improved localization of keypoints may also include using the player models 4604 to enable 3D localization with a single camera. In embodiments, the system and methods disclosed herein may also include the use of the player models 4604 fitted to detected keypoints to create 3D reconstructions 4620 or to improve 3D reconstructions in combination with point cloud techniques. Point cloud techniques may include a hybrid system including the player models 4604 that may be used to replace areas where the point cloud reconstruction does not conform adequately to the model. In further examples, the point cloud techniques may include supplementing the point cloud in scenarios where the point cloud may have a low density of points. In embodiments, the improved localization of keypoints may include the use of player height information combined with face detection, gaze detection, posture detection, or the like to locate the point of view of players.

In embodiments, the improved localization of keypoints may also include the use of camera calibration 4630 receiving one or more video feeds 4632, the 3D reconstruction 4610 and projection onto video in order to improve player segmentation for broadcast video 4640.

In embodiments, the systems and methods disclosed herein may include using a state-based machine learning model with hierarchical states. By way of this example, the state-based machine learning model with hierarchical states may include input training state labels at the finest granularity. In embodiments, the machine learning model may be trained at the finest level of granularity as well as at intermediate levels of aggregated states. In embodiments, the output and cost function optimization may be at the highest level of state aggregation. In embodiments, the machine learning model may be trained using an ensemble of active learning methods for multiclass classification including weighting of methods based on a confusion matrix and a cost function that may be used to optimize the distribution of qualitatively varied instances for active learning.

Figure 51:
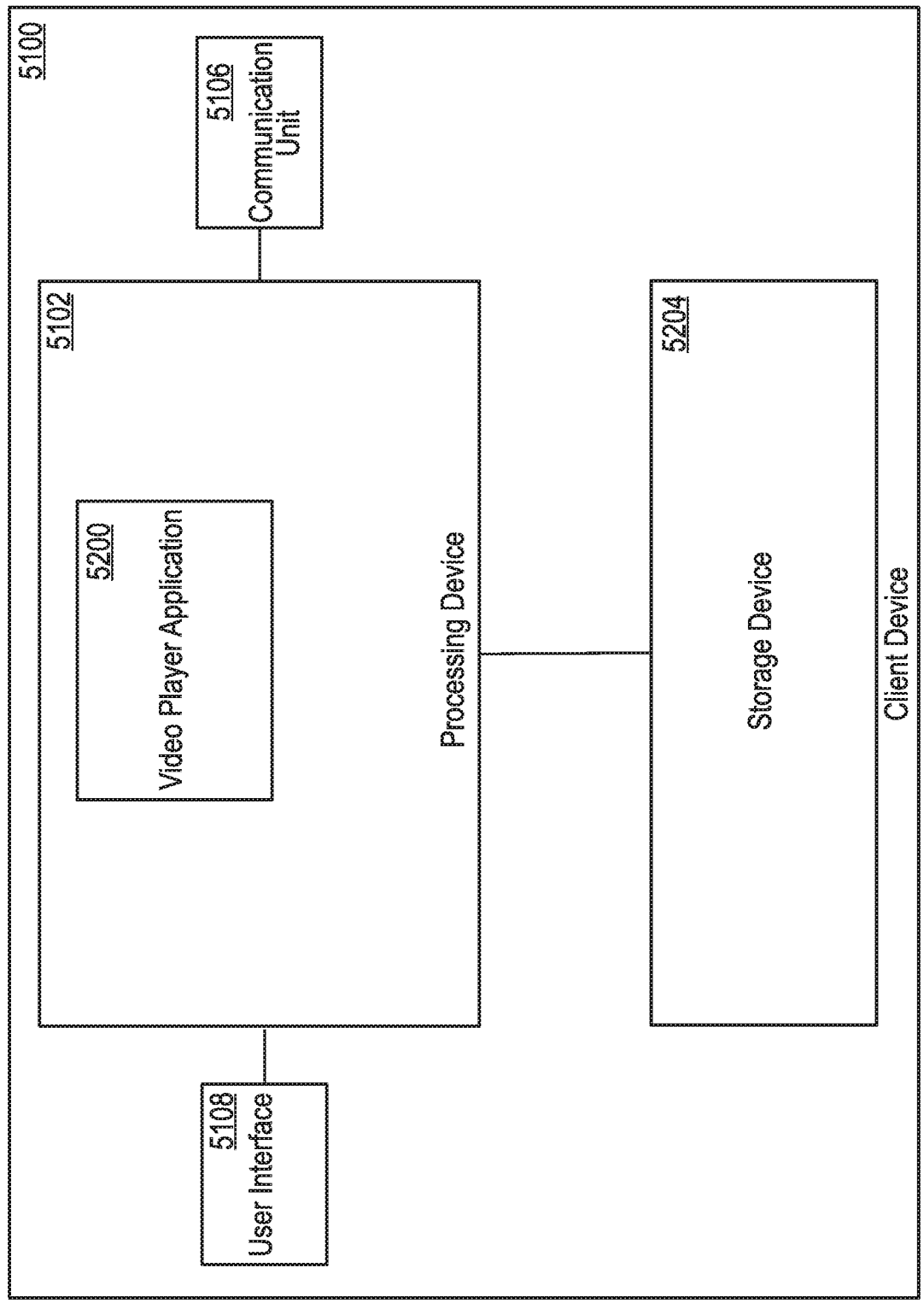
FIG. 51 illustrates an example client device configured with a video player application according to an exemplary and non-limiting embodiment.

FIG. 51 illustrates an example of a client device 5100 configured to display augmented content to a user according to some embodiments of the present disclosure, In the illustrated example, the client device 5100 may include a processing device 5102, a storage device 5104, a communication unit 5106 that effectuates communication between the client device and other devices via one or more communication networks (e.g., the Internet and/or a cellular network), and a user interface 5108 (e.g., a touchscreen, a monitor, a mouse, a keyboard, and the like), The processing device 5102 may include one or more processors and memory that stores computer-executable instructions that are executed by the one or more processors, The processing device 5102 may execute a video player application 5200, In embodiments, the video player application 5200 is configured to allow a user to consume video and related content from different content channels (e.g., audio, video, and/or data channels), In some of the embodiments, the video and related content may be delivered in time-aligned content channels (e.g., a "smart pipe"), where the content may be indexed temporally and/or spatially, In embodiments, the spatial indexing may include indexing the pixels or groups of pixels of multiple streams, 3D pixels (e.g., voxels) or groups of 3D pixels, and/or objects (e.g., polygonal meshes used for animation, overlay graphics, and the like), In these embodiments, a wide variety of elements may be indexed temporally (e.g., in relation to individual video frames) and/or spatially (e.g., in relation to pixels, groups of pixels, or "real world" locations depicted in the video frames), Examples of elements that may be indexed include events (match/game identifier), objects (players, game objects, objects in the environment such as court or playing field) involved in an event, information and statistics relating to the event and locations, locations of areas corresponding to the environment (e.g., floor areas, background areas, signage areas) where information, augmentations, graphics, animations, and advertising can be displayed in a frame, indicia of what information, augmentation elements, and the like that are available to augment a video feed in a content channel, combinations of content (e.g., particular combinations of audio, video, information, augmentation elements, replays, or other suitable elements), and/or references to other content channels corresponding to the event (such that end-users can select between streams), In this way, the video player may allow a user to interact with the video, such that the user can request the video player to display information relating to a time and/or location in the video feed, display relevant information relating to the event, switch between video feeds of the event, view advertisements, and the like, In these embodiments, the smart pipe may allow the video player application 5200 to create dynamic content at the client device 5100.

Figure 52:
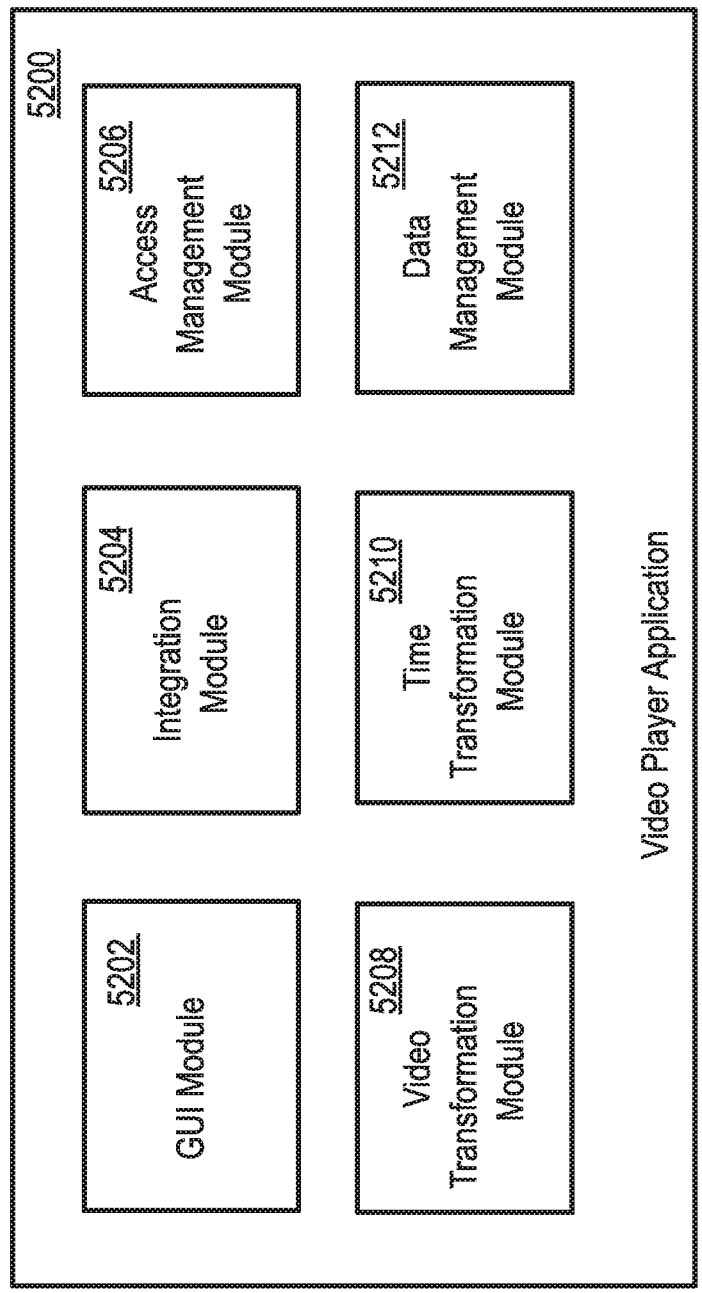
FIG. 52 illustrates an example configuration of a video player application according to an exemplary and non-limiting embodiment.

FIG. 52 illustrates an example implementation of the video player application 5200 according to some embodiments of the present disclosure. The video player application 5200 may include a GUI module 5202, an integration module 5204, an access management module 5206, a video transformation module 5208, a time transformation module 5210, and a data management module 5212, The video player application 5200 may include additional or alternative modules not discussed herein without departing from the scope of the disclosure, In embodiments, the GUI module 5202 receives commands from a user and displays video content, including augmented video content, to the user via the user interface 5108, In embodiments, the GUI module 5202 displays a menu/selection screen (e.g., drop down menus, selection elements, and/or search bars) and receives commands from a user corresponding to the available menus/selection items via a user via the user interface 5108, For example, the GUI module 5202 may receive an event selection via a drop down menu and/or a search bar/results page, In embodiments, an event selection may be indicative of a particular sport and/or a particular match, In response to an event selection, the GUI module 5202 may provide the event selection to the integration module 5204, In response, the GUI module 5202 may receive a video stream (of one or more video streams capturing the selected event) from the video transformation module 5208 and may output a video corresponding to the video feed via the user interface 5112, The GUI module 5202 may allow a user to provide commands with respect to the video content, including commands such as pause, fast forward, and rewind, The GUI module 5202 may receive additional or alternative commands, such as "make a clip," drill down commands (e.g., provide stats with respect to a player, display players on the playing surface, show statistics corresponding to a particular location, and the like), switch feed commands (e.g., switch to a different viewing angle), zoom in/zoom out commands, select link commands (e.g., selection of an advertisement), and the like.

The integration module 5204 receives an initial user command to view a particular sport or game and instantiates an instance of a video player (also referred to as a "video player instance"), In embodiments, the integration module 5204 receives a source event identifier (ID), an access token, and/or a domain ID, The source event ID may indicate a particular game (e.g., MLB: Detroit Tigers v. Houston Astros), The access token may indicate a particular level of access that a user has with respect to a game or league (e.g., the user may access advanced content or MLB games may include multi-view feed), The domain ID may indicate a league or type of event (e.g., NBA, NFL, FIFA), In embodiments, the integration module may instantiate a video player instance in response to the source event ID, the domain ID, and the access token, The integration module 5204 may output the video player instance to the access management module 5206, In some embodiments, the integration module 5204 may further output a time indicator to the access management module 5206, A time indicator may be indicative of a time corresponding to a particular frame or group of frames within the video content, In some of these embodiments, the time indicator may be a wall time, Other time indicators, such as a relative stream (e.g., 10 seconds from t=0), may be used, however, The access management module 5206 receives the video player instance and manages security and/or access to video content and/or data by the video player from a multimedia system. In embodiments, the access management module 5206 may expose a top layer API to facilitate the ease of access to data by the video player instance. The access management module 5206 may determine the level of access to provide the video player instance based on the access token, In embodiments, the access management module 5206 implements a single exported SDK that allows a data source (e.g., multimedia servers) to manage access to data, In other embodiments, the access management module 5206 implements one or more customized exported SDKs that each contain respective modules for interacting with a respective data source, The access management module 5206 may be a pass through layer, whereby the video player instance is passed to the video transformation module 5208, The video transformation module 5208 receives the video player instance and obtains video feeds and/or additional content provided by a multimedia server (or analogous device) that may be displayed with the video encoded in the video feeds. In embodiments, the video transformation module 5208 receives the video content and/or additional content from the data management module 5212, In some of these embodiments, the video transformation module 5208 may receive a smart pipe that contains one or more video feeds, audio feeds, data feeds, and/or an index, In embodiments, the video feeds may be time-aligned video feeds, such that the video feeds offer different viewing angles or perspectives of the event to be displayed. In embodiments, the index may be a spatio-temporal index. In these embodiments, the spatio-temporal index identifies information associated with particular video frames of a video and/or particular locations depicted in the video frames, In some of these embodiments, the locations may be locations in relation to a playing surface (e.g., at the fifty yard line or at the free throw line) or defined in relation to individual pixels or groups of pixels, It is noted that the pixels may be two-dimensional pixels or three-dimensional pixels (e.g., voxels), The spatio-temporal index may index participants on a playing surface (e.g., players on a basketball court), statistics relating to the participants (e.g., Player A has scored 32 points), statistics relating to a location on the playing surface (e.g., Team A has made 30% of three-pointers from a particular area on a basketball court), advertisements, score bugs, graphics, and the like, In some embodiments, the spatio-temporal index may index wall times corresponding to various frames, For example, the spatio-temporal index may indicate a respective wall time for each video frame in a video feed (e.g., a real time at which the frame was captured/initially streamed), The video transformation module 5208 receives the video feeds and the index and may output a video to the GUI module 5202, In embodiments, the video transformation module 5208 is configured to generate augmented video content and/or switch between different video feeds of the same event (e.g., different camera angles of the event). In embodiments, the video transformation module 5208 may overlay one or more GUI elements that receive user selections into the video being output, For example, the video transformation module 5208 may overlay one or more visual selection elements over the video feed currently being output by the GUI module 5202, The visual selection elements may allow a user to view information relating to the event depicted in the video feed, to switch views, or to view a recent highlight, In response to the user providing a command via the user interface of the client device 5100, the video transformation module 5208 may augment the currently displayed video feed with augmentation content, switch the video feed to another video feed, or perform other video transformation related operations.

The video transformation module 5208 may receive a command to display augmentation content, For example, the video transformation module 5208 may receive a command to display information corresponding to a particular location (e.g., a pixel or group of pixels) and a particular frame, In response to the command, the video transformation module 5208 may reference the spatio-temporal index to determine an object (e.g., a player) that is located at the particular location in the particular frame, The video transformation module 5208 may retrieve information relating to the object, For example, the video transformation module 5208 may retrieve a name of a player or statistics relating to a player or a location on the playing surface, The video transformation module 5208 may augment the current video feed with the retrieved content, In embodiments, the video transformation module 5208 may request the content (e.g., information) from the multimedia server via the data management module 5212, In other embodiments, the content may be transmitted in a data feed with the video feeds and the spatio-temporal index, In response to receiving the requested content (which may be textual or graphical), the video transformation module 5208 may overlay the requested content on the output video, The video transformation module 5208 may determine a location in each frame at which to display the requested data, In embodiments, the video transformation module 5208 may utilize the index to determine a location at which the requested content may be displayed, whereby the index may define locations in each frame where specific types of content may be displayed, In response to determining the location at which the requested content may be displayed, the video transformation module 5208 may overlay the content onto the video at the determined location, In another example, the video transformation module 5208 may receive a command to display an advertisement corresponding to a particular frame and location, In response to the command, the video transformation module 5208 determines the advertisement to display from the spatio-temporal index based on the particular frame and location, In embodiments, the video transformation module 5208 may retrieve the advertisement from the multimedia server (or another device), In other embodiments, the advertisement may be transmitted with the video feeds and the spatio-temporal index, In response to obtaining the advertisement, the video transformation module 5208 may determine a location at which the advertisement is to be displayed (e.g., in the manner discussed above), and may overlay the advertisement onto the video at the determined location, In embodiments, the video transformation module 5208 may receive a command to switch between video feeds in response to a user command to switch feeds, In response to such a command, the video transformation module 5208 switches the video feed from the current video feed to a requested video feed, while maintaining time-alignment between the video (i.e., the video continues at the same point in time but from a different feed), For example, in streaming a particular basketball game and receiving a request to change views, the video transformation module 5208 may switch from a sideline view to an under the basket view without interrupting the action of the game, The video transformation module 5208 may time align the video feeds (i.e., the current video feed and the video feed being switched to) in any suitable manner, In some embodiments, the video transformation module 5208 obtains a wall time from the time transformation module 5210 corresponding to a current frame or upcoming frame, The video transformation module 5208 may provide a frame identifier of the current frame or the upcoming frame to the video transformation module 5208, In embodiments, the frame identifier may be represented in block plus offset form (e.g., a block identifier and a number of frames within the block), In response to the frame identifier, the time transformation module 5210 may return a wall time corresponding to the frame identifier, The video transformation module 5208 may switch to the requested video feed, whereby the video transformation module 5208 begins playback at a frame corresponding to the received wall time, In these embodiments, the video transformation module 5208 may obtain the wall time corresponding to the current or upcoming frame from the time transformation module 5210, and may obtain a frame identifier of a corresponding frame in the video feed being switched to based on the received wall time, In some embodiments, the video transformation module 5208 may obtain a "block plus offset" of a frame in the video feed being switched to based on the wall time, The block plus offset may identify a particular frame within a video stream as a block identifier of a particular video frame and an offset indicating a number of frames into the block where the particular video frame is sequenced, In some of these embodiments, the video transformation module 5208 may provide the video transformation module 5208 with the wall time and an identifier of the video feed being switched, and may receive a frame identifier in block plus offset format from the time transformation module 5210, In some embodiments, the video transformation module 5208 may reference the index using a frame identifier of a current or upcoming frame in the current video feed to determine a time aligned video frame in the requested video feed, It is noted that while the "block plus offset" format is described, other formats of frame identifiers may be used without departing from the scope of the disclosure, In response to obtaining a frame identifier, the video transformation module 5208 may switch to the requested video feed at the determined time aligned video frame, For example, the video transformation module 5208 may queue up the requested video feed at the determined frame identifier, The video transformation module 5208 may then begin outputting video corresponding to the requested video feed at the determined frame identifier, In embodiments, the time transformation module 5210 receives an input time value in a first format and returns an output time value in a second format, For example, the time transformation module 5210 may receive a frame indicator in a particular format (e.g., block plus offset") that indicates a particular frame of a particular video feed (e.g., the currently displayed video feed of an event) and may return a wall time corresponding to the frame identifier (e.g., the time at which the particular frame was captured or was initially broadcast), In another example, the time transformation module 5210 receives a wall time indicating a particular time in a broadcast and a request for a frame identifier of a particular video feed, In response to the wall time and the frame identifier request, the time transformation module 5210 determines a frame identifier of a particular video frame within a particular video feed and may output the frame identifier in response to the request, The time transformation module 5210 may determine the output time in response to the input time in any suitable manner, In embodiments, the time transformation module 5210 may utilize an index corresponding to an event (e.g., the spatio-temporal index corresponding to an event) to determine a wall time in response to a frame identifier and/or a frame identifier in response to a wall time. In these embodiments, the spatio-temporal index may be keyed by frame identifiers and/or wall times, whereby the spatio-temporal index returns a wall time in response to a frame identifier and/or a frame identifier in response to a wall time and a video feed identifier, In other embodiments, the time transformation module 5210 calculates a wall time in response to a frame identifier and/or a frame identifier in response to a wall time, In some of these embodiments, each video feed may include metadata that includes a starting wall time that indicates a wall time at which the respective video feed began being captured/broadcast, a number of frames per block, and a frame rate of the encoding, In these embodiments, the time transformation module 5210 may calculate a wall time in response to a frame identifier based on the starting time of the video feed indicated by the frame identifier, the number of frames per block, and the frame indicated by the frame identifier (e.g., the block identifier and the offset value). Similarly, the time transformation module 5210 may calculate a frame identifier of a requested video feed in response to a wall time based on the starting time of the requested video feed, the received wall time, the number of frames per block, and the encoding rate.

Figure 47:
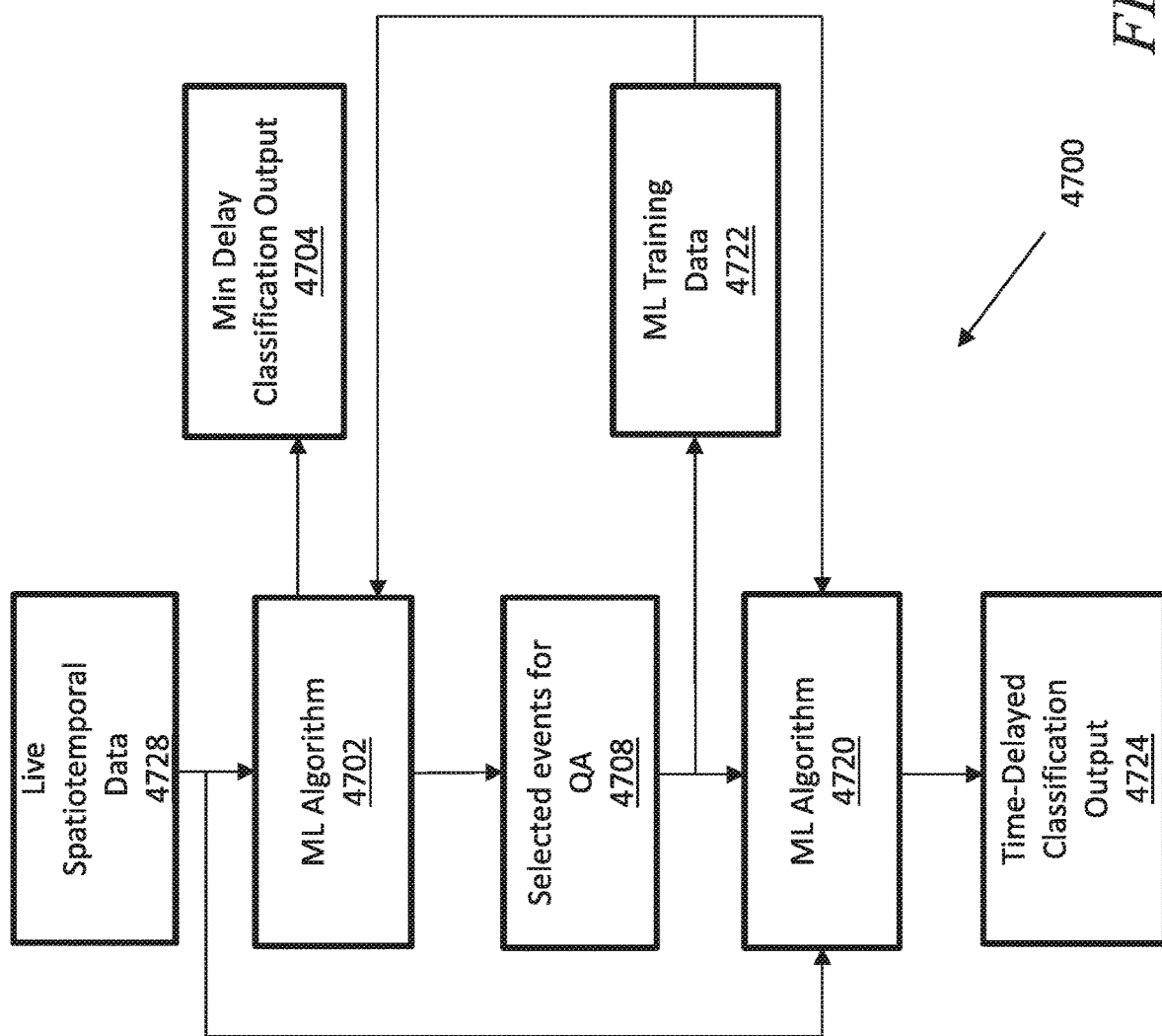
FIG. 47 illustrates systems and methods for a machine learning model including active learning and active quality assurance in accordance with the various embodiments.

In some embodiments, the time transformation module 5210 may be configured to transform a time with respect to first video feed to a time with respect to a second video feed, For example, the time transformation module 5210 may receive a first frame indicator corresponding to a first video feed and may output a second frame indicator corresponding to a second video feed, where the first frame indicator and the second frame indicator respectively indicate time-aligned video frames, In some of these embodiments, the time transformation module 5210 may utilize an index corresponding to an event (e.g., the spatio-temporal index corresponding to an event) to determine the second frame identifier in response to the second frame identifier. In these embodiments, the spatio-temporal index may be keyed by frame identifiers and may index frame identifiers of video frames that are time-aligned with the video frame referenced by each respective frame identifier, In other embodiments, the time transformation module 5210 calculates the second frame identifier in response to the first identifier, In some of these embodiments, the time transformation module 5210 may convert the first frame identifier to a wall time, as discussed above, and then may calculate the second frame identifier based on the wall time, as described above, In embodiments, the data management module 5212 requests and/or receives data from external resources and provides the data to a requesting module, For example, the data management module 5212 may receive the one or more video feeds from a multimedia server, The data management module 5212 may further receive an index (e.g., spatio-temporal index) corresponding to an event being streamed, For example, in some embodiments, the data management module 5212 may receive a smart pipe corresponding to an event. The data management module 5212 may provide the one or more video feeds and the index to the video transformation module 5208, In embodiments, the data management module 5212 may expose one or more APIs of the video player application to external resources, such multimedia servers and/or related data servers (e.g., a server that provides game information such as player names, statistics, and the like), In some embodiments, the external resources may push data to the data management module 5212, Additionally or alternatively, the data management module 5212 may be configured to pull the data from the external resources, In embodiments, the data management module 5212 may receive requests for data from the video transformation module 5208, For example, the data management module 5212 may receive a request for information relating to a particular frame identifier, a location within the frame indicated by a frame identifier, and/or an object depicted in the frame indicated by a frame identifier, In these embodiments, the data management module 5212 may obtain the requested information and may return the requested information to the video transformation module 5208, In some embodiments, the external resource may push any information that is relevant to an event to the data management module 5212, In these embodiments, the data management module 5212 may obtain the requested data from the pushed data, In other embodiments, the data management module 5212 may be configured to pull any requested data from the external resource, In these embodiments, the data management module 5212 may transmit a request to the external resource, whereby the request indicates the information sought, For example, the request may indicate a particular frame identifier, a location within the frame indicated by a frame identifier, or an object (e.g., a player) depicted in the frame indicated by the frame identifier, In response to the request, the data management module 5212 may receive the requested information, which is passed to video transformation module 5208, In embodiments, the data management module 5212 may be configured to obtain individual video feeds corresponding to an event, In some of these embodiments, the data management module 5212 may receive a request from the video transformation module 5208 for a particular video feed corresponding to an event, In response to the request, the data management module 5212 may return the requested video feed to the video transformation module 5208, The video feed may have been pushed to the video application by an external resource (e.g., multimedia platform), or may be requested (pulled) from the external resource in response to the request, With reference to FIG. 47, the machine learning model may include active learning and active quality assurance on a live spatiotemporal machine learning workflow 4700 in accordance with the various embodiments. The machine learning workflow 4700 includes a machine learning (ML) algorithm 4702 that may produce live and automatic machine learning (ML) classification output 4704 (with minimum delay) as well as selected events for human quality assurance (QA) 4708 based on live spatiotemporal data 4710. In embodiments, the live spatiotemporal machine learning workflow 4700 includes the data from the human question and answer sessions that may then be fed back into a machine learning (ML) algorithm 4720 (which may be the same as the ML algorithm 4702), which may be rerun on the corresponding segments of data, to produce a time-delayed classification output 4724 with improved classification accuracy of neighboring events, where the time delay corresponds to the QA process.

In embodiments, the machine learning workflow 4700 includes data from the QA process 4708 being fed into ML training data 4722 to improve the ML algorithm models for subsequent segments such as improving on the ML algorithm 4702 and/or the ML algorithm 4702. Live spatiotemporal data 4730 may be aligned with other imperfect sources of data related to a sequence of spatial-temporal events. In embodiments, the alignment across imperfect sources of data related to a sequence of spatial-temporal events may include alignment using novel generalized distance metrics for spatiotemporal sequences combining event durations, ordering of events, additions/deletions of events, a spatial distance of events, and the like.

In embodiments, the systems and methods disclosed herein may include modeling and dynamically interacting with an n-dimensional point-cloud. By way of this example, each point may be represented as an n-sphere whose radius may be determined by letting each n-sphere grow until it comes into contact with a neighboring n-sphere from a specified subset of the given point-cloud. This method may be similar to a Voronoi diagram in that may allocate a single n-dimensional cell for every point in the given cloud, with two distinct advantages. The first advantage includes that the generative kernel of each cell may also be its centroid. The second advantage includes continuously changing shifts in the resulting model when points are relocated in a continuous fashion (e.g., as a function of time in an animation, or the like). In embodiments, ten basketball players may be represented as ten nodes that are divided into two subsets of five teammates. At any given moment, each player's cell may be included in a circle extending in radius until it comes to be mutually tangent with an opponent's cell. By way of this example, players on the same team will have cells that overlap.

In embodiments, the systems and methods disclosed herein may include a method for modeling locale as a function of time, some other specified or predetermined variable, or the like. In embodiments, coordinates of a given point or plurality of points are repeatedly sampled over a given window of time. By way of this example, the sampled coordinates may then be used to generate a convex hull, and this procedure may be repeated as desired and may yield a plurality of hulls that may be stacked for a discretized view of spatial variability over time. In embodiments, a single soccer player might have their location on a pitch sampled every second over the course of two minutes leading to a point cloud of location data and an associated convex hull. By way of this example, the process may begin anew with each two-minute window and the full assemblage of generated hulls may be, for example, rendered in a translucent fashion and may be layered so as to yield a map of the given player's region of activity.

In embodiments, the systems and methods disclosed herein may include a method for sampling and modeling data by applying the recursive logic of a quadtree to a topologically deformed input or output space. In embodiments, the location of shots in a basketball game may be sampled in arc-shaped bins, which may be partitioned by angle-of-incidence to the basket and the natural logarithm of distance from the basket, and, in turn, yielding bins which may be subdivided and visualized according to the same rules governing a rectilinear quadtree.

In embodiments, the systems and methods disclosed herein may include a method for modeling multivariate point-cloud data such that location coordinates map to the location, while velocity (or some other relevant vector) may be represented as a contour map of potential displacements at various time intervals. In embodiments, a soccer player running down a pitch may be represented by a node surrounded by nested ellipses each indicating a horizon of displacement for a given window of time.

In embodiments, the systems and methods disclosed herein may include a method for modeling and dynamically interacting with a directed acyclic graph such that every node may be rendered along a single line, while the edges connecting nodes may be rendered as curves deviating from this line in accordance with a specified variable. In embodiments, these edges may be visualized as parabolic curves wherein the height of each may correspond to the flow, duration, latency, or the like of the process represented by the given edge.

The methods and systems disclosed herein may include methods and systems for enabling a user to express preferences relating to display of video content and may include using machine learning to develop an understanding of at least one event, one metric related to the event, or relationships between events, metrics, venue, or the like within at least one video feed to determine at least one type for the event; automatically, under computer control, extracting the video content displaying the event and associating the machine learning understanding of the type for the event with the video content in a video content data structure; providing a user interface by which a user can indicate a preference for at least one type of content; and upon receiving an indication of the preference by the user, retrieving at least one video content data structure that was determined by the machine learning to have content of the type preferred by the user and providing the user with a video feed containing the content of the preferred type.

In embodiments, the user interface is of at least one of a mobile application, a browser, a desktop application, a remote control device, a tablet, a touch screen device, a virtual reality or augmented reality headset, and a smart phone. In embodiments, the user interface further comprises an element for allowing a user to indicate a preference as to how content will be presented to the user. In embodiments, the machine learning further comprises determining an understanding of a context for the event and the context is stored with the video content data structure. In embodiments, the user interface further comprises an element for allowing a user to indicate a preference for at least one context. In embodiments, upon receiving an indication of a preference for a context, video content corresponding to the context preference is retrieved and displayed to the user. In embodiments, the context comprises at least one of the presence of a preferred player in the video feed, a preferred matchup of players in the video feed, a preferred team in the video feed, and a preferred matchup of teams in the video feed. In embodiments, the user interface allows a user to select at least one of a metric and a graphic element to be displayed on the video feed, wherein at least one of the metric and the graphic is based at least in part on the machine understanding.

The methods and systems disclosed herein may include methods and systems for enabling a mobile application allowing user interacting with video content method and may include taking a video feed; using machine learning to develop an understanding of an event within the video feed, the understanding including identifying context information relating to the event; automatically, under computer control, extracting the content displaying the event and associating the extracted content with the context information; producing a video content data structure that includes the associated context information; and using the context information for a plurality of such video content data structures to generate, automatically under computer control, producing a story or video clip that includes the video content data structure, wherein the content of the story is based on a user preference. In embodiments, the user preference for a type of content is based on at least one of a user expressed preference and a preference that is inferred based on user interaction with an item of content.

The methods and systems disclosed herein may include methods and systems for enabling a user to express preferences relating to display of video content and may include a machine learning facility for developing an understanding of at least one event within at least one video feed to determine at least one type for the event; a video production facility for automatically, under computer control, extracting the video content displaying the event and associating the machine learning understanding of the type for the event with the video content in a video content data structure; a server for serving data to a user interface by which a user can indicate a preference for at least one type of content; and upon receiving at the server an indication of the preference by the user, retrieving at least one video content data structure that was determined by the machine learning to have content of the type preferred by the user and providing the user with a video feed containing the content of the preferred type.

In embodiments, the user interface is of at least one of a mobile application, a browser, a desktop application, a remote control device, a tablet, and a smart phone. In embodiments, the user interface further comprises an element for allowing a user to indicate a preference as to how content will be presented to the user. In embodiments, the machine learning further comprises determining an understanding of a context for the event and the context is stored with the video content data structure. In embodiments, the user interface further comprises an element for allowing a user to indicate a preference for at least one context. In embodiments, upon receiving an indication of a preference for a context, video content corresponding to the context preference is retrieved and displayed to the user. In embodiments, the context comprises at least one of the presence of a preferred player in the video feed, a preferred matchup of players in the video feed, a preferred team in the video feed, and a preferred matchup of teams in the video feed. In embodiments, the user interface allows a user to select at least one of a metric and a graphic element to be displayed on the video feed, wherein the metric is based at least in part on the machine understanding.

The methods and systems disclosed herein may include methods and systems delivering personalized video content and may include using machine learning to develop an understanding of at least one event within at least one video feed to determine at least one type for the event; automatically, under computer control, extracting the video content displaying the event and associating the machine learning understanding of the type for the event with the video content in a video content data structure; developing a personal profile for a user based on at least one of expressed preferences of the user, information about the user, and information collected about actions taken by the user with respect to at least one type of video content; and upon receiving an indication of the user profile, retrieving at least one video content data structure that was determined by the machine learning to have content of the type likely to be preferred by the user based on the user profile, The methods and systems disclosed herein may include methods and systems for delivering personalized video content and may include using machine learning to develop an understanding of at least one event within at least one video feed to determine at least one type for the event, wherein the video feed is a video feed for a professional game; using machine learning to develop an understanding of at least one event within a data feed relating to the motion of a non-professional player; based on the machine learning understanding of the video feed for the professional game and the data feed of the motion of the non-professional player, automatically, under computer control, providing an enhanced video feed that represents the non-professional player playing within the context of the professional game. In embodiments, the methods and systems may further include providing a facility having cameras for capturing 3D motion data and capturing video of a non-professional player to provide the data feed for the non-professional player. In embodiments, the non-professional player is represented by mixing video of the non-professional player with video of the professional game. In embodiments, the non-professional player is represented as an animation having attributes based on the data feed about the non-professional player.

The methods and systems disclosed herein may also include one or more of the following features and capabilities: spatiotemporal pattern recognition (including active learning of complex patterns and learning of actions such as P&R, postups, play calls); hybrid methods for producing high quality labels, combining automated candidate generation from XYZ data, and manual refinement; indexing of video by automated recognition of game clock; presentation of aligned optical and video; new markings using combined display, both manual and automated (via pose detection etc.); metrics: shot quality, rebounding, defense and the like; visualizations such as Voronoi, heatmap distribution, etc.; embodiment on various devices; video enhancement with metrics & visualizations; interactive display using both animations and video; gesture and touch interactions for sports coaching and commentator displays; and cleaning of XYZ data using, for example, HMM, PBP, video, hybrid validation.

Further details as to data cleaning step 204 are provided herein. Raw input XYZ is frequently noisy, missing, or wrong. XYZ data is also delivered with attached basic events such as possession, pass, dribble, shot. These are frequently incorrect. This is important because event identification further down the process (Spatiotemporal Pattern Recognition) sometimes depends on the correctness of these basic events. As noted above, for example, if two players' XY positions are switched, then "over" vs. "under" defense would be incorrectly switched, since the players' relative positioning is used as a critical feature for the classification. Also, PBP data sources are occasionally incorrect. First, one may use validation algorithms to detect all events, including the basic events such as possession, pass, dribble, shot, and rebound that are provided with the XYZ data. Possession/Non-possession may use a Hidden Markov Model to best fit the data to these states. Shots and rebounds may use the possession model outputs, combined with 1) projected destination of the ball, and 2) PBP information. Dribbles may be identified using a trained ML algorithm and also using the output of the possession model.

Specifically, once possessions are determined, dribbles may be identified with a hidden Markov model. The hidden Markov model consists of three states:

1. Holding the ball while the player is still able to dribble.
2. Dribbling the ball.
3. Holding the ball after the player has already dribbled.

A player starts in State 1 when he gains possession of the ball. At all times players are allowed to transition to either their current state, or the state with a number one higher than their current state, if such a state exists.

The players' likelihood of staying in their current state or transitioning to another state may be determined by the transition probabilities of the model as well as the observations. The transition probabilities may be learned empirically from the training data. The observations of the model consist of the player's speed, which is placed into two categories, one for fast movement, and one for slow movement, as well as the ball's height, which is placed into categories for low and high height. The cross product of these two observations represents the observation space for the model. Similar to the transition probabilities, the observation probabilities, given a particular state, may be learned empirically from the training data. Once these probabilities are known, the model is fully characterized and may be used to classify when the player is dribbling on unknown data.

Once it is known that the player is dribbling, it remains to be determined when the actual dribbles occur. This may be done with a Support Vector Machine that uses domain specific information about the ball and player, such as the height of the ball as a feature to determine whether at that instant the player is dribbling. A filtering pass may also be applied to the resulting dribbles to ensure that they are sensibly separated, so that for instance, two dribbles do not occur within 0.04 seconds of each other.

Returning to the discussion of the algorithms, these algorithms decrease the basic event labeling error rate by a significant factor, such as about 50%. Second, the system has a library of anomaly detection algorithms to identify potential problems in the data. These include temporal discontinuities (intervals of missing data are flagged); spatial discontinuities (objects traveling is a non-smooth motion, "jumping"); interpolation detection (data that is too smooth, indicating that post-processing was done by the data supplier to interpolate between known data points in order to fill in missing data). This problem data is flagged for human review so that events detected during these periods are subject to further scrutiny.

Spatio-player tracking may be undertaken in at least two types, as well as in a hybrid combined type. For tracking with broadcast video, the broadcast video is obtained from multiple broadcast video feeds. Typically, this will include a standard "from the stands view" from the center stands midway-up, a backboard view, a stands view from a lower angle from each corner, and potentially other views. Optionally, PTZ (pan tilt zoom) sensor information from each camera is also returned. An alternative is a Special Camera Setup method. Instead of broadcast feeds, this uses feeds from cameras that are mounted specifically for the purposes of player tracking. The cameras are typically fixed in terms of their location, pan, tilt, zoom. These cameras are typically mounted at high overhead angles; in the current instantiation, typically along the overhead catwalks above the court. A Hybrid/Combined System may be used. This system would use both broadcast feeds and feeds from the purpose-mounted cameras. By combining both input systems, accuracy is improved. Also, the outputs are ready to be passed on to the DataFX pipeline for immediate processing, since the DataFX will be painting graphics on top of the already-processed broadcast feeds. Where broadcast video is used, the camera pose is solved in each frame, since the PTZ may change from frame to frame. Optionally, cameras that have PTZ sensors may return this info to the system, and the PTZ inputs are used as initial solutions for the camera pose solver. If this initialization is deemed correct by the algorithm, it will be used as the final result; otherwise, refinement will occur until the system receives a usable solution. As described above, players may be identified by patches of color on the court. The corresponding positions are known since the camera pose is known, and we can perform the proper projections between 3D space and pixel space.

Where purpose mounted cameras are used, multiple levels of resolution may be involved. Certain areas of the court or field require more sensitivity, e.g., on some courts, the color of the "paint" area makes it difficult to track players when they are in the paint. Extra cameras with higher dynamic range and higher zoom are focused on these areas. The extra sensitivity enables the computer vision techniques to train separate algorithms for different portions of the court, tuning each algorithm to its type of inputs and the difficulty of that task.

In a combination system, by combining the fixed and broadcast video feeds, the outputs of a player tracking system can feed directly into the DataFX production, enabling near-real-time DataFX. Broadcast video may also produce high-definition samples that can be used to increase accuracy.

The methods and systems disclosed herein may include methods and systems for enabling interaction with a broadcast video content stream and may include a machine learning facility for developing an understanding of at least one event within a video feed for a video broadcast, the understanding including identifying context information relating to the event; and a touch screen user interface by which a broadcaster can interact with the video feed, wherein the options for broadcaster interaction are based on the context information, wherein the interaction with the touch screen controls the content of the broadcast video event. In embodiments, the touch screen interface is a large screen adapted to be seen by viewers of the video broadcast as the broadcaster uses the touch screen. In embodiments, a smaller touch screen is used by a commentator on air to control the information content being displayed, and the images/video on the touch screen is simultaneously displayed on a larger screen that is filmed and broadcast or is simultaneously displayed directly in the broadcast feed. In embodiments, the broadcaster can select from a plurality of context-relevant metrics, graphics, or combinations thereof to be displayed on the screen. In embodiments, the broadcaster can display a plurality of video feeds that have similar contexts as determined by the machine learning facility. In embodiments, the similarity of contexts is determined by comparing events within the video feeds. In embodiments, the broadcaster can display a superimposed view of at least two video feeds to facilitate a comparison of events from a plurality of video feeds. In embodiments, the comparison is of similar players from different, similar, or identical time periods. In embodiments, a similarity of players is determined by machine understanding of the characteristics of the players from the different time periods. In embodiments, the broadcaster can display a plurality of highlights that are automatically determined by a machine understanding of a live sports event that is the subject of the video feed. In embodiments, the highlights are determined based on similarity to highlights that have been identified for other events.

The methods and systems disclosed herein may include methods and systems for enabling interaction with a broadcast video content stream and may include developing a machine learning understanding of at least one event within a video feed for a video broadcast, the understanding including identifying context information relating to the event; and providing a touch screen user interface by which a broadcaster can interact with the video feed, wherein the options for broadcaster interaction are based on the context information, wherein the interaction with the touch screen controls the content of the broadcast video event. In embodiments, the touch screen interface is a large screen adapted to be seen by viewers of the video broadcast as the broadcaster uses the touch screen. In embodiments, the broadcaster can select from a plurality of context-relevant metrics to be displayed on the screen. In embodiments, the broadcaster can display a plurality of video feeds that have similar contexts as determined by the machine learning facility. In embodiments, the similarity of contexts is determined by comparing events within the video feeds. In embodiments, the broadcaster can display a superimposed view of at least two video feeds to facilitate a comparison of events from a plurality of video feeds. In embodiments, the comparison is of similar players from different time periods.

In embodiments, a similarity of players is determined by the machine understanding of the characteristics of the players from the different time periods. In embodiments, the broadcaster can display a plurality of highlights that are automatically determined by a machine understanding of a live sports event that is the subject of the video feed. In embodiments, the highlights are determined based on similarity to highlights that have been identified for other events.

The methods and systems disclosed herein may include methods and systems for enabling interaction with a broadcast video content stream and may include taking a video feed; using machine learning to develop an understanding of an event within the video feed, the understanding including identifying context information relating to the event; automatically, under computer control, extracting the content displaying the event and associating the extracted content with the context information; producing a video content data structure that includes the associated context information; and providing an application by which a user can interact with the video content data structure, wherein the options for user interaction are based on the context information, wherein the interaction with the video content data structure controls the presentation of a broadcast video event on a display screen.

Methods and systems disclosed herein may include tracklet stitching. Optical player tracking results in short to medium length tracklets, which typically end when the system loses track of a player or the player collides (or passes close to) with another player. Using team identification and other attributes, algorithms can stitch these tracklets together.

Where a human being is in the loop, systems may be designed for rapid interaction and for disambiguation and error handling. Such a system is designed to optimize human interaction with the system. Novel interfaces may be provided to specify the motion of multiple moving actors simultaneously, without having to match up movements frame by frame.

In embodiments, custom clipping is used for content creation, such as involving OCR. Machine vision techniques may be used to automatically locate the "score bug" and determine the location of the game clock, score, and quarter information. This information is read and recognized by OCR algorithms. Post-processing algorithms using various filtering techniques are used to resolve issues in the OCR. Kalman filtering/HMMs may be used to detect errors and correct them. Probabilistic outputs (which measure the degree of confidence) assist in this error detection/correction.

Sometimes, a score is nonexistent or cannot be detected automatically (e.g., sometimes during PIP or split screens). In these cases, remaining inconsistencies or missing data is resolved with the assistance of human input. Human input is designed to be sparse so that labelers do not have to provide input at every frame. Interpolation and other heuristics are used to fill in the gaps. Consistency checking is done to verify game clock.

For alignment 2112, as discussed in connection with FIG. 21, another advance is to use machine vision techniques to verify some of the events. For example, video of a made shot will typically show the score being increased or will show a ball going through a hoop. Either kind of automatic observation serves to help the alignment process result in the correct video frames being shown to the end user.

In accordance with an exemplary and non-limiting embodiment, augmented or enhanced video with extracted semantics-based experience is provided based, at least in part, on 3D position/motion data. In accordance with other exemplary embodiments, there is provided embeddable app content for augmented video with an extracted semantics-based experience. In yet another exemplary embodiment, there is provided the ability to automatically detect the court/field, and relative positioning of the camera, in (near) real time using computer vision techniques. This may be combined with automatic rotoscoping of the players in order to produce dynamic augmented video content.

The methods and systems disclosed herein may include methods and systems for embedding video content in an application and may include taking a video feed; using machine learning to develop an understanding of an event within the video feed, the understanding including identifying context information relating to the event; automatically, under computer control, extracting the content displaying the event and associating the extracted content with the context information; producing a video content data structure that includes the associated context information; taking an application that displays video content; and embedding the video content data structure in the application. In embodiments, the user interface of the application offers the user the option to control the presentation of the video content from the video content data structure in the application. In embodiments, the control of the presentation is based on at least one of a user preference and a user profile. In embodiments, the application is a mobile application that provides a story about an event and wherein the video content data structure comprises at least one of a content card and a digital still image.

The methods and systems disclosed herein may include methods and systems for enabling a mobile application that allows user interaction with video content and may include a video ingestion facility for taking a video feed; a machine learning facility for developing an understanding of an event within the video feed, the understanding including identifying context information relating to the event; and a video production facility for automatically, under computer control, extracting the content displaying the event, associating the extracted content with the context information and producing a video content data structure that includes the associated context information; and using the context information for a plurality of such video content data structures to generate, automatically under computer control, a story that includes a sequence of the video content data structures. In embodiments, the content of the story is based on a user profile that is based on at least one of an expressed user preference, information about a user interaction with video content, and demographic information about the user. In embodiments, the methods and systems may further include determining a pattern relating to a plurality of events in the video feed and associating the determined pattern with the video content data structure as additional context information. In embodiments, the pattern relates to a highlight event within the video feed. In embodiments, the highlight event is associated with at least one of a player and a team. In embodiments, the embedded application allows a user to indicate at least one of a player and a team for which the user wishes to obtain video feeds containing the highlight events. In embodiments, the pattern relates to a comparison of events occurring at least one of within the video feed or within a plurality of video feeds. In embodiments, the comparison is between events occurring over time. In embodiments, the embedded application allows a user to select at least one player to obtain a video providing a comparison between the player and at least one of a past representation of the same player and a representation of another player. In embodiments, the pattern is a cause-and-effect pattern related to the occurrence of a following type of event after the occurrence of a pre-cursor type of event. In embodiments, the embedded application allows the user to review video cuts in a sequence that demonstrate the cause-and-effect pattern. In embodiments, the application provides a user interface for allowing a user to enter at least one of text and audio input to provide a narrative for a sequence of events within the video feed. In embodiments, the user may select a sequence of video events from within the feed for display in the application. In embodiments, upon accepting the user narrative, the system automatically generates an electronic story containing the events from the video feed and the narrative.

The methods and systems disclosed herein may include methods and systems for enabling a mobile application that allows user interaction with video content and may include taking a video feed; using a machine learning facility to develop an understanding of an event within the video feed, the understanding including identifying context information relating to the event; and automatically, under computer control, extracting the content displaying the event, associating the extracted content with the context information and producing a video content data structure that includes the associated context information. In embodiments, the methods and systems may further include using the context information for a plurality of such video content data structures to generate, automatically under computer control, a story that includes a sequence of the video content data structures.

In embodiments, the user may interact with an application, such as on a phone, laptop, or desktop, or with a remote control, to control the display of broadcast video. As noted above in connection with interaction with a mobile application, options for user interaction may be customized based on the context of an event, such as by offering options to display context-relevant metrics for the event. These selections may be used to control the display of broadcast video by the user, such as by selecting preferred, context-relevant metrics that appear as overlays, sidebars, scrolling information, or the like on the video display as various types of events take place in the video stream. For example, a user may select settings for a context like a three point shot attempt, so that when the video displays three point shot attempts, particular metrics (e.g., the average success percentage of the shooter) are shown as overlays above the head of the shooter in the video, The methods and systems disclosed herein may include methods and systems for personalizing content for each type of user based on determining the context of the content through machine analysis of the content and based on an indication by the user of a preference for a type of presentation of the content.

The methods and systems disclosed herein may include methods and systems for enabling a user to express preferences relating to display of video content and may include: taking a video feed; using machine learning to develop an understanding of an event within the video feed, the understanding including identifying context information relating to the event; automatically, under computer control, extracting the content displaying the event and associating the extracted content with the context information; producing a video content data structure that includes the associated context information; and providing a user interface by which a user can indicate a preference for how content that is associated with a particular type of context will be presented to the user.

In embodiments, a user may be presented with an interface element for a mobile application, browser, desktop application, remote control, tablet, smart phone, or the like, for indicating a preference as to how content will be presented to the user. In embodiments, the preference may be indicated for a particular context, such a context determined by a machine understanding of an event. In embodiments, a user may select to see certain metrics, graphics or additional information overlaid on top of the existing broadcast for certain types of semantic events such as players expected field goal percentage when they possess the ball or the type and effectiveness of defense being played on a pick and roll.

The methods and systems disclosed herein may include methods and systems for automatically generating stories/content based on the personal profile of a viewer and their preferences or selections of contextualized content, The methods and systems disclosed herein may include methods and systems for enabling a mobile application allowing user interacting with video content method and may include taking a video feed; using machine learning to develop an understanding of an event within the video feed, the understanding including identifying context information relating to the event; automatically, under computer control, extracting the content displaying the event and associating the extracted content with the context information; producing a video content data structure that includes the associated context information; and using the context information for a plurality of such video content data structures to generate, automatically under computer control, a story that includes the video content data structures, wherein the content of the story is based on a user preference. In embodiments, the user preference for a type of content is based on at least one of a user expressed preference and a preference that is inferred based on user interaction with an item of content.

In embodiments, items of content that are associated, based on machine understanding, with particular events in particular contexts can be linked together, or linked with other content, to produce modified content such as stories, For example, a game summary, such as extracted from an online report about an event, may be augmented with machine-extracted highlight cuts that correspond to elements featured in the game summary, such as highlights of important plays, images of particular players, and the like. These stories can be customized for a user, such as linking a story about a game played by the user's favorite team with video cuts of the user's favorite player that were taken during the game.

The methods and systems disclosed herein may include methods and systems for using machine learning to extract context information and semantically relevant events and situations from a video content stream, such that the events and situations may be presented according to the context of the content.

The methods and systems disclosed herein may include methods and systems for embedding video content in an application and may include taking a video feed; using machine learning to develop an understanding of an event within the video feed, the understanding including identifying context information relating to the event; automatically, under computer control, extracting the content displaying the event and associating the extracted content with the context information; producing a video content data structure that includes the associated context information; taking an application that displays video content; and embedding the video content data structure in the application, wherein the location of the embedded video content in the application is based on the context information.

In embodiments, context-identified video cuts can be used to enrich or enhance applications, such as by embedding the cuts in relevant locations in the applications. For example, a mobile application displaying entertainment content may be automatically populated with video cuts of events that are machine-extracted and determined to be of the appropriate type (based on context), for the application. A video game application can be enhanced, such as by including real video cuts of plays that fit a particular context (e.g., showing a pick-and-roll play where players A and B are matched up against players C and D in a real game, and the same matchup is determined to occur in the video game).

To facilitate embedding the application, a set of protocols, such as APIs, may be defined, by which available categories (such as semantic categories, types of contexts, types of events, and the like) are specified, such that an application may call for particular types of events, which can, in turn, be embedded in the application. Similarly, an application may be constructed with appropriate pointers, calls, objects, or the like, that allow a designer to specify, and call for, particular types of events, which may be automatically extracted from a library of machine-extracted, context-identified events and then embedded where appropriate into the application code.

In embodiments, an application may provide stories about events, such as sporting events, and the machine-extracted content may include content cards or digital stills that are tagged by context so that they can be placed in appropriate locations in a story. The application can provide automatically generated content and stories, enhanced by content from a live game. In embodiments, an application may recommend video clips based on the use of keywords that match machine learned semantics that enable users to post or share video clips automatically tailored to text that they are writing. For example, clips may be recommended that include the presence of a particular player, that include a particular type of play (e.g., "dunks") and/or that are from a particular time period (e.g., "last night," etc.), In accordance with an exemplary and non-limiting embodiment, there is described a method for the extraction of events and situations corresponding to semantically relevant concepts. In yet other embodiments, semantic events may be translated and cataloged into data and patterns.

The methods and systems disclosed herein may include methods and systems for embedding content cards or digital stills with contextualized content stories/visualizations into a mobile application. They may include automatically generated content, such as stories, extracted from a live game delivered to users via an application, such as a mobile application, an augmented reality glasses application, a virtual reality glasses application, or the like. In embodiments, the application is a mobile application that provides a story about an event and wherein the video content data structure comprises at least one of a content card and a digital still image.

The methods and systems disclosed herein may include methods and systems for applying contextualized content from actual sporting events to video games to improve the reality of the game play.

The methods and systems disclosed herein may include methods and systems for improving a video game and may include taking a video feed; using machine learning to develop an understanding of at least one first real event within the video feed, the understanding including identifying context information relating to the first real event; taking a game event coded for display within a video game; matching the context information for the real event with the context of the game event in the video game; comparing the display of the game event to the video for the real event; and modifying the coding of the game event based on the comparison.

In embodiments, context information can be used to identify video cuts that can be used to improve video games, such as by matching the context of a real event with a similar context in a coded video game event, comparing the video for the real event with the video game display of a similar event, and modifying the video event to provide a more faithful simulation of the real event. The methods and systems disclosed herein may include methods and systems for taking the characteristics of a user either from a video capture of their recreational play or through user generated features and importing the user's avatar into a video game. The methods and systems disclosed herein may include methods and systems for interactive contextualized content that can be filtered and adjusted via a touch screen interface. In embodiments, the user interface is a touch screen interface.

The methods and systems disclosed herein may include methods and systems for real time display of relevant fantasy and betting metrics overlaid on a live game feed. The methods and systems disclosed herein may include methods and systems for real time adjustment of betting lines and/or additional betting option creation based on in-game contextual content.

The methods and systems disclosed herein may include methods and systems for taking a video feed and using machine learning to develop an understanding of at least one first event within the video feed. The understanding includes identifying context information relating to the first event. The methods and systems also include determining a metric based on the machine understanding. The metric is relevant to at least one of a wager and a fantasy sports outcome. The methods and systems include presenting the metric as an overlay for an enhanced video feed.

In embodiments, the metrics described throughout this disclosure may be placed as overlays on video feeds. For example, metrics calculated based on machine-extracted events that are relevant to betting lines, fantasy sports outcomes, or the like, can be presented as overlays, scrolling elements, or the like on a video feed. The metrics to be presented can be selected based on context information, such as showing fantasy metrics for players who are on screen at the time or showing the betting line where a scoring play impacts the outcome of a bet. As noted above, the displays may be customized and personalized for a user, such as based on that user's fantasy team for a given week or that user's wagers for the week.

The methods and systems disclosed herein may include methods and systems for taking a video feed of a recreational event; using machine learning to develop an understanding of at least one event within the video feed, the understanding including identifying context information relating to the event; and based on the machine understanding, providing content including information about a player in the recreational event based on the machine understanding and the context. The methods and systems may further include providing a comparison of the player to at least one professional player according to at least one metric that is based on the machine understanding.

In embodiments, machine understanding can be applied to recreational venues, such as for capturing video feeds of recreational games, practices, and the like. Based on machine understanding, highlight clips, metrics, and the like, as disclosed throughout this disclosure, may be extracted by processing the video feeds, including machine understanding of the context of various events within the video. In embodiments, metrics, video, and the like can be used to provide players with personalized content, such as a highlight reel of good plays, or a comparison to one or more professional players (in video cuts, or with semantically relevant metrics). Context information can allow identification of similar contexts between recreational and professional events, so that a player can see how a professional acted in a context that is similar to one faced by the recreational player. The methods and systems may enable the ability to use metrics and events recorded from a video stream to enable the creation of a recreational fantasy sports game with which users can interact. The methods and systems may enable the ability for to recognize specific events or metrics from a recreational game and compare them to similar or parallel events from a professional game to help coach a recreational player or team or for the creation of a highlight reel that features both recreational and professional video cuts.

The methods and systems disclosed herein may include methods and systems for providing enhanced video content and may include using machine learning to develop an understanding of a plurality of events within at least one video feed to determine at least one type for each of the plurality of events; extracting a plurality of video cuts from the video feed and indexing the plurality of video cuts based on at least one type of event determined by the understanding developed by machine learning; and making the indexed and extracted video cuts available to a user. In embodiments, the user is enabled to at least one of edit, cut, and mix the video cuts to provide an enhanced video containing at least one of the video cuts. In embodiments, the user is enabled to share the enhanced video. In embodiments, the methods and systems may further include indexing at least one shared, enhanced video with the semantic understanding of the type of events in that was determined by machine learning. In embodiments, the methods and systems may further include using the index information for the shared, enhanced video to determine a similarity between the shared, enhanced video and at least one other video content item. In embodiments, the similarity is used to identify additional extracted, indexed video cuts that may be of interest to the user. In embodiments, the similarity is used to identify other users who have shared similarly enhanced video. In embodiments, the similarity is used to identify other users who are likely to have an interest in the shared, enhanced video. In embodiments, the methods and systems may further include recommending at least one of the shared, enhanced video and one of the video cuts based on an understanding of the preferences of the other users. In embodiments, the similarity is based at least in part on user profile information for users who have indicated an interest in the video cut and the other video content item.

The methods and systems disclosed herein may include methods and systems for providing enhanced video content and may include using machine learning to develop an understanding of a plurality of events within at least one video feed to determine at least one type for each of the plurality of events; extracting a plurality of video cuts from the video feed and indexing the plurality of video cuts to form an indexed set of extracted video cuts, wherein the indexing is based on at least one type of event determined by the understanding developed by machine learning; determining at least one pattern relating to a plurality of events in the video feed; adding the determined pattern information to the index for the indexed set of video cuts; and making the indexed and extracted video cuts available to a user. In embodiments, the user is enabled to at least one of edit, cut, and mix the video cuts to provide an enhanced video containing at least one of the video cuts. In embodiments, the user is enabled to share the enhanced video. In embodiments, the video cuts are clustered based on the patterns that exist within the video cuts. In embodiments, the pattern is determined automatically using machine learning and based on the machine understanding of the events in the video feed. In embodiments, the pattern is a highlight event within the video feed. In embodiments, the highlight event is presented to the user when the indexed and extracted video cut is made available to the user. In embodiments, the user is prompted to watch a longer video feed upon viewing the indexed and extracted video cut.

In accordance with an exemplary and non-limiting embodiment, there is provided a touch screen or other gesture-based interface experience based, at least in part, on extracted semantic events.

The methods and systems disclosed herein may include methods and systems for machine extracting semantically relevant events from 3D motion/position data captured at a venue, calculating a plurality of metrics relating to the events, and presenting the metrics in a video stream based on the context of the video stream.

The methods and systems disclosed herein may include methods and systems for producing machine-enhanced video streams and may include taking a video feed from 3D motion and position data from a venue; using machine learning to develop an understanding of at least one first event within the video feed, the understanding including identifying context information relating to the first event; calculating a plurality of metrics relating to the events; and producing an enhanced video stream that presents the metrics in the video stream, wherein the presentation of at least one metric is based on the context information for the event with which the metric is associated in the video stream.

In embodiments, semantically relevant events determined by machine understanding of 3D motion/position data for an event from a venue can be used to calculate various metrics, which may be displayed in the video stream of the event. Context information, which may be determined based on the types and sequences of events, can be used to determine what metrics should be displayed at a given position within the video stream. These metrics may also be used to create new options for users to place wagers on or be integrated into a fantasy sports environment.

The methods and systems disclosed herein may include methods and systems enabling a user to cut or edit video based on machine learned context and share the video clips. These may further include allowing a user to interact with the video data structure to produce an edited video data stream that includes the video data structure. In embodiments, the interaction includes at least one of editing, cutting, and sharing a video clip that includes the video data structure. The methods and systems may enable the ability for users to interact with video cuts through an interface to enhance the content with graphics or metrics based on a pre-set set of options, and then share a custom cut and enhanced clip. The methods and systems may include the ability to automatically find similarity in different video clips based on semantic context contained in the clips, and then cluster clips together or to recommend additional clips for viewing. The methods and systems may include the ability to extract contextualized content from a feed of a recreational event to immediately deliver content to players, including comparing a recreational player to a professional player based on machine learned understanding of player types.

In accordance with an exemplary and non-limiting embodiment, there is described a second screen interface unique to extracted semantic events and user selected augmentations. In yet other embodiments, the second screen may display real-time, or near real time, contextualized content.

In accordance with further exemplary and non-limiting embodiments, the methods and systems disclosed herein may include methods and systems for taking a video feed; using machine learning to develop an understanding of an event within the video feed, the understanding including identifying context information relating to the event; automatically, under computer control, extracting the content displaying the event and associating the extracted content with the context information; and producing a video content data structure that includes the associated context information. In embodiments, the methods and systems may further include determining a plurality of semantic categories for the context information and filtering a plurality of such video content data structures based on the semantic categories. In embodiments, the methods and systems may further include matching the events that occur in one video feed to those that occur in a separate video feed such that the semantic understanding captured in the first video feed can be used to at least one of filter and cut a separate second video feed based on the same events. In embodiments, the methods and systems may further include determining a pattern relating to a plurality of the events and providing a content data structure based on the pattern. In embodiments, the pattern comprises a plurality of important plays in a sports event that are identified based on comparison to similar plays from previous sports events. In embodiments, the pattern comprises a plurality of plays in a sports event that is determined to be unusual based on comparison to video feeds from other sports events. In embodiments, the methods and systems may further include extracting semantic events over time to draw a comparison of at least one of a player and a team over time.

In embodiments, the methods and systems may further include superimposing video of events extracted from video feeds from at least two different time periods to illustrate the comparison. In embodiments, the methods and systems may further include allowing a user to interact with the video data structure to produce an edited video data stream that includes the video data structure. In embodiments, the interaction includes at least one of editing, mixing, cutting, and sharing a video clip that includes the video data structure. In embodiments, the methods and systems may further include enabling users to interact with the video cuts through a user interface to enhance the video content with at least one graphic element selected from a menu of options.

In embodiments, the methods and systems may further include enabling a user to share the enhanced video content. In embodiments, the methods and systems may further include enabling a user to find similar video clips based on the semantic context identified in the clips. In embodiments, the methods and systems may further include using the video data structure and the context information to construct modified video content for a second screen that includes the video data structure. In embodiments, the content for the second screen correlates to the timing of an event displayed on a first screen. In embodiments, the content for the second screen includes a metric determined based on the machine understanding, wherein the metric is selected based on the context information.

The methods and systems disclosed herein may include methods and systems for displaying contextualized content of a live event on a second screen that correlates to the timing of the live event on the first screen. These may include using the video data structure and the context information to construct modified video content for a second screen that includes the video data structure. In embodiments, the content for the second screen correlates to the timing of an event displayed on a first screen. In embodiments, the content for the second screen includes a metric determined based on the machine understanding, wherein the metric is selected based on the context information.

In embodiments, machine extracted metrics and video cuts can be displayed on a second screen, such as a tablet, smart phone, or smart remote control screen, such as showing metrics that are relevant to what is happening, in context, on a main screen.

The methods and systems disclosed herein may include methods and systems for an ingestion facility adapted or configured to ingest a plurality of video feeds; a machine learning system adapted or configured to apply machine learning on a series of events in a plurality of video feeds in order to develop an understanding of an event within the video feed, the understanding including identifying context information relating to the event; an extraction facility adapted or configured to automatically, under computer control, extract the content displaying the event and associate the extracted content with the context information; and a video publishing facility for producing a video content data structure that includes the associated context information. In embodiments, the methods and systems may further include an analytic facility adapted or configured to determine a plurality of semantic categories for the context information and filter a plurality of such video content data structures based on the semantic categories. In embodiments, the methods and systems may further include a matching engine adapted or configured to match the events that occur in one video feed to those that occur in a separate video feed such that the semantic understanding captured in the first video feed can be used to at least one of filter and cut a separate second video feed based on the same events. In embodiments, the methods and systems may further include a pattern recognition facility adapted or configured to determine a pattern relating to a plurality of the events and providing a content data structure based on the pattern.

The methods and systems disclosed herein may include methods and systems for displaying machine extracted, real time, contextualized content based on machine identification of a type of event occurring in a live video stream.

The methods and systems disclosed herein may include methods and systems for taking a video feed; using machine learning to develop an understanding of an event within the video feed, the understanding including identifying context information relating to the event; automatically, under computer control, extracting the content displaying the event and associating the extracted content with the context information; and producing a video content data structure that includes the associated context information. The methods and systems disclosed herein may include methods and systems for providing context information in video cuts that are generated based on machine extracted cuts that are filtered by semantic categories.

The methods and systems disclosed herein may include methods and systems for determining a plurality of semantic categories for the context information and filtering a plurality of the video content data structures based on the semantic categories. The methods and systems disclosed herein may include methods and systems for matching the events that occur in one video feed to those that occur in a separate video feed such that the semantic understanding captured in the first video feed can be used to filter and cut a separate second video feed based on these same events.

The methods and systems disclosed herein may include methods and systems for enabling user interaction with a mobile application that displays extracted content, where the user interaction is modified based on the context of the content (e.g., the menu is determined by context).

The methods and systems disclosed herein may include methods and systems for enabling an application allowing user interaction with video content and may include an ingestion facility adapted or configured to access at least one video feed, wherein the ingestion facility may be executing on at least one processor; a machine learning facility operating on the at least one video feed to develop an understanding of an event within the video feed, the understanding including identifying context information relating to the event; an extraction facility adapted or configured to automatically, under computer control, extract the content displaying the event and associate the extracted content with the context information; a video production facility adapted or configured to produce a video content data structure that includes the associated context information; and an application having a user interface by which a user can interact with the video content data structure, wherein the options for user interaction are based on the context information. In embodiments, the application is a mobile application. In embodiments, the application is at least one of a smart television application, a virtual reality headset application and an augmented reality application. In embodiments, the user interface is a touch screen interface. In embodiments, the user interface allows a user to enhance the video feed by selecting a content element to be added to the video feed. In embodiments, the content element is at least one of a metric and a graphic element that is based on the machine understanding. In embodiments, the user interface allows the user to select content for a particular player of a sports event. In embodiments, the user interface allows the user to select content relating to a context involving the matchup of two particular players in a sports event.

In embodiments, the system takes at least two video feeds from different time periods, the machine learning facility determines a context the includes a similarity between at least one of a plurality of players and a plurality of plays in the two feeds and the user interface allows the user to select at least one of the players and the plays to obtain a video feed that illustrates a comparison. In embodiments, the user interface includes options for at least one of editing, cutting, and sharing a video clip that includes the video data structure.

In embodiments, the video feed comprises 3D motion camera data captured from a live sports venue. In embodiments, the ability of the machine learning facility to develop the understanding is developed by feeding the machine learning facility a plurality of events for which context has already been identified.

The methods and systems disclosed herein may include methods and systems for enabling a mobile application allowing user interaction with video content and may include taking at least one video feed; applying machine learning on the at least one video feed to develop an understanding of an event within the video feed, the understanding including identifying context information relating to the event; automatically, under computer control, extracting the content displaying the event and associating the extracted content with the context information; producing a video content data structure that includes the associated context information; and providing a mobile application having a user interface by which a user can interact with the video content data structure, wherein the options for user interaction are based on the context information. In embodiments, the user interface is a touch screen interface. In embodiments, the user interface allows a user to enhance the video feed by selecting a content element to be added to the video feed. In embodiments, the content element is at least one of a metric and a graphic element that is based on the machine understanding. In embodiments, the user interface allows the user to select content for a particular player of a sports event. In embodiments, the user interface allows the user to select content relating to a context involving the matchup of two particular players in a sports event.

In embodiments, the system takes at least two video feeds from different time periods, the machine learning facility determines a context the includes a similarity between at least one of a plurality of players and a plurality of plays in the two feeds and the user interface allows the user to select at least one of the players and the plays to obtain a video feed that illustrates a comparison. In embodiments, the user interface includes options for at least one of editing, cutting, and sharing a video clip that includes the video data structure. In embodiments, the video feed comprises 3D motion camera data captured from a live sports venue. In embodiments, the ability of the machine learning facility to develop the understanding is developed by feeding the machine learning facility a plurality of events for which context has already been identified.

The methods and systems disclosed herein may include methods and systems for enabling a mobile application allowing user interacting with video content and may include taking a video feed; using machine learning to develop an understanding of an event within the video feed, the understanding including identifying context information relating to the event; automatically, under computer control, extracting the content displaying the event and associating the extracted content with the context information; producing a video content data structure that includes the associated context information; and providing a mobile application by which a user can interact with the video content data structure, wherein the options for user interaction are based on the context information.

In embodiments, machine extracted content, with associated context information, may be provided to users via a mobile application, through which the users may display and interact with the content, such as by selecting particular types of content based on a desired semantic category (such as by selecting the category in list, menu, or the like), playing content (including pausing, rewinding, fast forwarding, and the like), and manipulating content (such as positioning content within a display window, zooming, panning, and the like). In embodiments, the nature of the permitted interaction may be governed by the context information associated with the content, where the context information is based on a machine understanding of the content and its associated context. For example, where the content is related to a particular type of play within a context of an event like a game, such as rebounding opportunities in basketball, the user may be permitted to select from a set of metrics that are relevant to rebounding, so that the selected metrics from a context-relevant set are displayed on the screen with the content. If the context is different, such as if the content relates to a series of pick-and-roll plays by a particular player, different metrics may be made available for selection by the user, such as statistics for that player, or metrics appropriate for pick-and-rolls. Thus, the machine-extracted understanding of an event, including context information, can be used to customize the content displayed to the user, including to allow the user to select context-relevant information for display.

The methods and systems disclosed herein may include methods and systems for allowing a user to control a presentation of a broadcast video event, where the options for control are based on a context of the content as determined by machine extraction of semantically relevant events from the content.

In accordance with an exemplary and non-limiting embodiment, there is described a method for "painting" translated semantic data onto an interface.

In accordance with an exemplary and non-limiting embodiment, there is described spatiotemporal pattern recognition based, at least in part, on optical XYZ alignment for semantic events. In yet other embodiments, there is described the verification and refinement of spatiotemporal semantic pattern recognition based, at least in part, on hybrid validation from multiple sources.

In accordance with an exemplary and non-limiting embodiment, there is described human identified video alignment labels and markings for semantic events. In yet other embodiments, there is described machine learning algorithms for spatiotemporal pattern recognition based, at least in part, on human identified video alignment labels for semantic events.

In accordance with an exemplary and non-limiting embodiment, there is described automatic game clock indexing of video from sporting events using machine vision techniques, and cross-referencing this index with a semantic layer that indexes game events. The product is the ability to query for highly detailed events and return the corresponding video in near real-time.

In accordance with an exemplary and non-limiting embodiment, there is described unique metrics based, at least in part, on spatiotemporal patterns including, for example, shot quality, rebound ratings (positioning, attack, conversion) and the like.

In accordance with an exemplary and non-limiting embodiment, there is described player tracking using broadcast video feeds.

In accordance with an exemplary and non-limiting embodiment, there is described player tracking using a multi-camera system.

In accordance with an exemplary and non-limiting embodiment, there is described video cut-up based on extracted semantics. A video cut-up is a remix made up of small clips of video that are related to each other in some meaningful way. The semantic layer enables real-time discovery and delivery of custom cut-ups. The semantic layer may be produced in one of two ways: (1) Video combined with data produces a semantic layer, or (2) video directly to a semantic layer, Extraction may be through ML or human tagging. In some exemplary embodiments, video cut-up may be based, at least in part, on extracted semantics, controlled by users in a stadium and displayed on a Jumbotron. In other embodiments, video cut-up may be based, at least in part, on extracted semantics, controlled by users at home and displayed on broadcast TV. In yet other embodiments, video cut-up may be based, at least in part, on extracted semantics, controlled by individual users and displayed on the web, tablet, or mobile for that user. In yet other embodiments, video cut-up may be based, at least in part, on extracted semantics, created by an individual user, and shared with others. Sharing could be through inter-tablet/inter-device communication, or via mobile sharing sites.

In accordance with further exemplary and non-limiting embodiments, the methods and systems disclosed herein may include methods and systems for enabling an application allowing user interaction with video content and may include an ingestion facility for taking at least one video feed; a machine learning facility operating on the at least one video feed to develop an understanding of an event within the video feed, the understanding including identifying context information relating to the event; an extraction facility for automatically, under computer control, extracting the content displaying the event and associating the extracted content with the context information; a video production facility for producing a video content data structure that includes the associated context information; and an application having a user interface by which a user can interact with the video content data structure, wherein the options for user interaction are based on the context information. In embodiments, the application is a mobile application. In embodiments, the application is at least one of a smart television application, a virtual reality headset application and an augmented reality application. In embodiments, the user interface is a touch screen interface. In embodiments, the user interface allows a user to enhance the video feed by selecting a content element to be added to the video feed. In embodiments, the content element is at least one of a metric and a graphic element that is based on the machine understanding. In embodiments, the user interface allows the user to select content for a particular player of a sports event. In embodiments, the user interface allows the user to select content relating to a context involving the matchup of two particular players in a sports event.

In embodiments, the system takes at least two video feeds from different time periods, the machine learning facility determines a context the includes a similarity between at least one of a plurality of players and a plurality of plays in the two feeds and the user interface allows the user to select at least one of the players and the plays to obtain a video feed that illustrates a comparison. In embodiments, the user interface includes options for at least one of editing, cutting, and sharing a video clip that includes the video data structure.

In embodiments, the video feed comprises 3D motion camera data captured from a live sports venue. In embodiments, the ability of the machine learning facility to develop the understanding is developed by feeding the machine learning facility a plurality of events for which context has already been identified.

The methods and systems disclosed herein may include methods and systems for enabling a mobile application allowing user interaction with video content and may include taking at least one video feed; applying machine learning on the at least one video feed to develop an understanding of an event within the video feed, the understanding including identifying context information relating to the event; automatically, under computer control, extracting the content displaying the event and associating the extracted content with the context information; producing a video content data structure that includes the associated context information; and providing a mobile application having a user interface by which a user can interact with the video content data structure, wherein the options for user interaction are based on the context information. In embodiments, the user interface is a touch screen interface. In embodiments, the user interface allows a user to enhance the video feed by selecting a content element to be added to the video feed. In embodiments, the content element is at least one of a metric and a graphic element that is based on the machine understanding. In embodiments, the user interface allows the user to select content for a particular player of a sports event. In embodiments, the user interface allows the user to select content relating to a context involving the matchup of two particular players in a sports event.

In embodiments, the system takes at least two video feeds from different time periods, the machine learning facility determines a context the includes a similarity between at least one of a plurality of players and a plurality of plays in the two feeds and the user interface allows the user to select at least one of the players and the plays to obtain a video feed that illustrates a comparison. In embodiments, the user interface includes options for at least one of editing, cutting, and sharing a video clip that includes the video data structure.

In embodiments, the video feed comprises 3D motion camera data captured from a live sports venue. In embodiments, the ability of the machine learning facility to develop the understanding is developed by feeding the machine learning facility a plurality of events for which context has already been identified.

The methods and systems disclosed herein may include methods and systems for an analytic system and may include a video ingestion facility for ingesting at least one video feed; a machine learning facility that develops an understanding of at least one event within the video feed, wherein the understanding identifies at least a type of the event and a time of the event in an event data structure; a computing architecture enabling a model that takes one or more event data structures as input and applies at least one calculation to transform the one or more event data structures into an output data structure; and a data transport layer of the computing architecture for populating the model with the event data structures as input to the model. In embodiments, the output data structure includes at least one prediction. In embodiments, the prediction is of an outcome of at least one of a sporting event and at least one second event occurring within a sporting event. In embodiments, the video feed is of a live sporting event, wherein the prediction is made during the live sporting event, and wherein the prediction relates to the same sporting event. In embodiments, the prediction is based on event data structures from a plurality of video feeds.

In embodiments, the prediction is used for at least one of placing a wager, setting a line for a wager, interacting with a fantasy program, setting a parameter of a fantasy program, providing insight to a coach and providing information to a fan. In embodiments, the model takes inputs from a plurality of data sources in addition to the event data structures obtained from the video feed. In embodiments, the methods and systems may further include a pattern analysis facility that takes a plurality of the event data structures and enables analysis of patterns among the event data structures. In embodiments, the pattern analysis facility includes at least one tool selected from the group consisting of a pattern visualization tool, a statistical analysis tool, a machine learning tool, and a simulation tool. In embodiments, the methods and systems may further include a second machine learning facility for refining the model based on outcomes of a plurality of predictions made using the model.

The methods and systems disclosed herein may include methods and systems for an analytic method and may include ingesting at least one video feed in a computing platform capable of handling video data; developing an understanding of at least one event within the video feed using machine learning, wherein the understanding identifies at least a type of the event and a time of the event in an event data structure; providing a computing architecture that enables a model that takes one or more event data structures as input and applies at least one calculation to transform the one or more event data structures into an output data structure; and populating the model with the event data structures as input to the model. In embodiments, the output data structure includes at least one prediction. In embodiments, the prediction is of an outcome of at least one of a sporting event and at least one-second event occurring within a sporting event. In embodiments, the video feed is of a live sporting event, wherein the prediction is made during the live sporting event, and wherein the prediction relates to the same sporting event. In embodiments, the prediction is based on event data structures from a plurality of video feeds. In embodiments, the prediction is used for at least one of placing a wager, setting a line for a wager, interacting with a fantasy program, setting a parameter of a fantasy program, providing insight to a coach and providing information to a fan. In embodiments, the model takes inputs from a plurality of data sources in addition to the event data structures obtained from the video feed. In embodiments, the methods and systems may further include providing a pattern analysis facility that takes a plurality of the event data structures and enables analysis of patterns among the event data structures. In embodiments, the pattern analysis facility includes at least one tool selected from the group consisting of a pattern visualization tool, a statistical analysis tool, a machine learning tool, and a simulation tool. In embodiments, the methods and systems may further include at least one of providing and using a second machine learning facility to refine the model based on outcomes of a plurality of predictions made using the model.

The methods and systems disclosed herein may include methods and systems for taking a video feed; using machine learning to develop an understanding of a semantically relevant event within the video feed; indexing video segments of the video feed with information indicating the semantically relevant events identified within the feed by the machine learning; and applying machine learning to a plurality of the semantically relevant events to determine a pattern of events. In embodiments, the pattern is within a video feed. In embodiments, the pattern is across a plurality of video feeds. In embodiments, the pattern corresponds to a narrative structure. In embodiments, the narrative structure corresponds to a recurring pattern of events. In embodiments, the narrative structure relates to a sporting event and wherein the pattern relates to at least one of a blow-out victory pattern, a comeback win pattern, a near comeback pattern, a back-and-forth game pattern, an individual achievement pattern, an injury pattern, a turning point moment pattern, a close game pattern, and a team achievement pattern.

In embodiments, the indexed video segments are arranged to support the narrative structure. In embodiments, the arranged segments are provided in an interface for developing a story using the segments that follow the narrative structure and wherein a user may at least one of edit and enter additional content for the story. In embodiments, summary content for the narrative structure is automatically generated, under computer control, to provide a story that includes the video sequences. In embodiments, the methods and systems may further include delivering a plurality of the automatically generated stories at least one of from a defined time period and of a defined type, allowing a user to indicate whether they like or dislike the delivered stories, and using the indications to inform later delivery of at least one additional story. In embodiments, the pattern is relevant to a prediction. In embodiments, the prediction is related to a wager, and the pattern corresponds to similar patterns that were used to make predictions that resulted in successful wagers in other situations.

The methods and systems disclosed herein may include methods and systems for machine-extracting semantically relevant events from a video content stream and determining a pattern relating to the events. The methods and systems also include providing a content stream based on the pattern. In embodiments, the content stream is used to provide coaching information based on the pattern. In embodiments, the content stream is used to assist the prediction of an outcome in a fantasy sports contest. In embodiments, the pattern is used to provide content for a viewer of a sporting event.

The methods and systems disclosed herein may include methods and systems for machine-extracting semantically relevant events from a video content stream; determining a pattern relating to the events; storing the pattern information with the extracted events; and providing a user with the option to view and interact with the patterns, wherein at least one of the patterns and the interaction options are personalized based on a profile of the user. In embodiments, the profile is based on at least one of user indication of a preference, information about actions of the user, and demographic information about the user. In embodiments, the pattern comprises at least one of a trend and a statistic that is curated to correspond with the user profile. In embodiments, the pattern relates to a comparison of a professional athlete to another athlete. In embodiments, the other athlete is the user and the comparison are based on a playing style of the user as determined by at least one of information indicated by the user and a video feed of the user. In embodiments, the pattern relates to an occurrence of an injury. In embodiments, the pattern information is used to provide coaching to prevent an injury. In embodiments, the methods and systems may further include automatically generating, under computer control, an injury prevention regimen based on the pattern and based on information about the user.

The methods and systems disclosed herein may include methods and systems for machine-extracting semantically relevant events from a video content stream, determining a pattern relating to the events, and providing a content stream based on the pattern. The methods and systems may further include determining a pattern relating to a plurality of the events and providing a content data structure based on the pattern.

In embodiments, machine-extracted information about events and contexts may be used to determine one or more patterns, such as by analyzing time series, correlations, and the like in the machine-extracted events and contexts. For example, tendencies of a team to follow running a certain play with a particular play may be determined by comparing instances of the two plays over time. Embodiments may include extracting particularly interesting or potential "game changing" plays by understanding the context of an individual event and comparing it to similar events from previous games. Embodiments may include extracting situations or plays that are particularly rare or unique by understanding the context of an individual event and comparing it to similar events from previous games. Embodiments may include extracting semantic events over time to draw a comparison of a player's or team's trajectory over time and superimposing video to draw out this comparison.

The methods and systems disclosed herein may include methods and systems for a model to predict the outcome of a game or events within a game based on a contextualized understanding of a live event for use in betting/fantasy, coaching, augmented fan experiences, or the like.

The methods and systems disclosed herein may include methods and systems for an analytic system and may include taking a video feed; using machine learning to develop an understanding of at least one first event within the video feed, the understanding including identifying context information relating to the first event; taking a model used to predict the outcome of at least one of a live game and at least one second event within a live game; and populating the model with the machine understanding of the first event and the context information to produce a prediction of an outcome of at least one of the game and the second event. In embodiments, the model is used for at least one of placing a wager, setting a line for a wager, interacting with a fantasy program, setting a parameter of a fantasy program, providing insight to a coach and providing information to a fan.

In embodiments, machine-extracted event and context information can be used to populate one or more predictive models, such as models used for betting, fantasy sports, coaching, and entertainment. The machine understanding, including various metrics described throughout this disclosure, can provide or augment other factors that are used to predict an outcome. For example, outcomes from particular matchups can be machine extracted and used to predict outcomes from similar matchups in the future. For example, based on the machine understood context of a moment in an individual game, and the machine understanding of similar moments from previous games, a model can be created to predict the outcome of an individual play or a series of plays on which an individual can place a bet or on which a betting line may be set.

In embodiments, the methods and systems disclosed herein may include methods and systems for suggestions of bets to make based on patterns of previously successful bets. For example, a user may be prompted with an option to place a bet based on previous betting history on similar events or because a particular moment is an opportunistic time to place a bet based on the context of a game and other user generated preferences or risk tolerances.

The methods and systems disclosed herein may include methods and systems for automated storytelling, such as the ability to use patterns extracted from semantic events, metrics derived from tracking data, and combinations thereof to populate interesting stories about the content.

The methods and systems disclosed herein may include methods and systems for enabling automated generation of stories and may include taking a video feed; using machine learning to develop an understanding of a semantically relevant event within the video feed, the understanding including identifying context information relating to the event; providing a narrative structure for a story, wherein the narrative structure is arranged based on the presence of semantic types of events and the context of those events; and automatically, under computer control, generating a story following the narrative structure, wherein the story is populated based on a sequence of the machine-understood events and the context information.

In embodiments, patterns from semantic events may be used to populate stories. Various narrative structures can be developed, corresponding to common patterns of events (e.g., stories about blow-out victories, comeback wins, back-and-forth games, games that turned on big moments, or the like). Machine extracting of events and contexts can allow identification of patterns in the events and contexts that allow matching to one or more of the narrative structures, as well as population of the story with content for the events, such as video cuts or short written summaries that are determined by the machine extraction (e.g., "in the first quarter, Team A took the lead, scoring five times on the pick-and-roll.").

The methods and systems disclosed herein may include methods and systems for enabling a mobile application allowing user interacting with video content and may include taking a video feed; using machine learning to develop an understanding of an event within the video feed, the understanding including identifying context information relating to the event; automatically, under computer control, extracting the content displaying the event and associating the extracted content with the context information; producing a video content data structure that includes the associated context information; and providing a mobile application by which a user can interact with the video content data structure, wherein the options for user interaction are based on the context information.

In embodiments, machine extracted content, with associated context information, may be provided to users via a mobile application, through which the users may display and interact with the content, such as by selecting particular types of content based on a desired semantic category (such as by selecting the category in list, menu, or the like), playing content (including pausing, rewinding, fast forwarding, and the like), and manipulating content (such as positioning content within a display window, zooming, panning, and the like). In embodiments, the nature of the permitted interaction may be governed by the context information associated with the content, where the context information is based on a machine understanding of the content and its associated context. For example, where the content is related to a particular type of play within a context of an event like a game, such as rebounding opportunities in basketball, the user may be permitted to select from a set of metrics that are relevant to rebounding, so that the selected metrics from a context-relevant set are displayed on the screen with the content. If the context is different, such as if the content relates to a series of pick-and-roll plays by a particular player, different metrics may be made available for selection by the user, such as statistics for that player, or metrics appropriate for pick-and-rolls. Thus, the machine-extracted understanding of an event, including context information, can be used to customize the content displayed to the user, including to allow the user to select context-relevant information for display.

The methods and systems disclosed herein may include methods and systems for allowing a user to control the presentation of a broadcast video event, where the options for control are based on a context of the content as determined by machine extraction of semantically relevant events from the content.

In accordance with an exemplary and non-limiting embodiment, X, Y, and Z data may be collected for purposes of inferring player actions that have a vertical component.

The methods and systems disclosed herein may employ a variety of computer vision, machine learning, and/or active learning techniques and tools to extract, analyze and process data elements originating from sources, such as, but not limited to, input data sources relating to sporting events and items in them, such as players, venues, items used in sports (such as balls, pucks, and equipment), and the like. These data elements may be available as video feeds in an example, such that the video feeds may be captured by image recognition devices, video recognition devices, image and video capture devices, audio recognition devices, and the like, including by use of various devices and components such as a camera (such as a tracking camera or broadcast camera), a microphone, an image sensor, or the like. Audio feeds may be captured by microphones and similar devices, such as integrated on or with cameras or associated with independent audio capture systems. Input feeds may also include tracking data from chips or sensors (such as wearable tracking devices using accelerometers and other motion sensors), as well as data feeds about an event, such as a play-by-play data feed, a game clock data feed, and the like. In the case of input feeds, facial recognition systems may be used to capture facial images of players, such as to assist in recognition of players (such as in cases where player numbers are absent or obscured) and to capture and process expressions of players, such as emotional expressions, micro-expressions, or the like. These expressions may be associated with events, such as to assist in machine understanding (e.g., an expression may convey that the event was exciting, meaningful, the like, that it was disappointing to one constituency, that it was not important, or the like). Machine understanding may thus be trained to recognize expressions and provide an expression-based understanding of events, such as to augment one or more data structures associated with an event for further use in the various embodiments described herein. For example, a video feed may be processed based on a machine understanding of expressions to extract cuts that made players of one team happy. As another example, a cut showing an emotional reaction (such as by a player, fan, teammate, or coach) to an event may be associated with a cut of the event itself, providing a combined cut that shows the event and the reaction it caused. The various embodiments described throughout this disclosure the involve machine understanding, extraction of cuts, creation of data structures that are used or processed for various purposes, combining cuts, augmenting data feeds, producing stories, personalizing content, and the like should all be understood to encompass, where appropriate, use of machine understanding of emotional expression within a video feed, including based on use of computer vision techniques, including facial recognition techniques and expression recognition techniques.

The computer vision, machine learning and/or active learning tools and techniques (together referred to as computer-controlled intelligent systems for simplicity herein) may receive the data elements from various input feeds and devices as a set of inputs either in real-time (such as in case of a live feed or broadcast) or at a different time (such as in case of a delayed broadcast of the sporting or any other event) without limitations. The computer-controlled intelligent systems may process the set of inputs, apply machine learning and natural language processing using artificial intelligence (AI) and natural language processing (NLP) capabilities to produce a set of services and outputs.

In an example, the set of services and outputs may signify spatial-temporal positions of the players and sports accessories/objects such as a bat, ball, football, and the like. In an example, the set of services and outputs may represent spatial-temporal alignments of the inputs such as the video feeds, etc. For example, a broadcast video feed may be aligned in time with another input feed, such as input from one or more motion tracking cameras, inputs from player tracking systems (such as wearable devices), and the like. The set of services and outputs may include machine understood contextual outputs involving machine learning or understanding that may be built using various levels of artificial intelligence, algorithmic processes, computer-controlled tasks, custom rules, and the like, such as described throughout this disclosure. The machine understanding may include various levels of semantic identification, as well as information of position and speed information for various items or elements, identification of basic events such as various types of shots and screens during a sporting event, and identification of complex events or a sequence of events such as various types of plays, higher level metrics and patterns involving such as game trajectory, style of play, strengths and weaknesses of teams and team members/players from each team, and the like. The machine learning tools and input feed alignment may allow automatic generation of content and information such as statistics, predictions, comparisons, and analysis. The machine learning tools may further allow to generate outputs based on a user query input such as to determine various predictive analytics for a particular team player in view of historical shots and screens in a particular context, determine possibilities of success and failures in particular zones and game scenarios conditioned to particular user inputs, and the like. The machine understanding tools may simulate entire aspects of real-life sporting events on a computer screen utilizing visualization and modeling examples. The services and outputs generated by the intelligent computer-controlled systems may be used in a variety of ways such as generation of a live feed or a delayed feed during a sporting event in real time or at a later broadcasting time after the sporting event. The services and outputs may allow generating various analyses of statistics, trends, and strategy before events or across multiple events. The services and outputs may facilitate an interactive user session to extract contextual details relating to instantaneous sporting sessions of the sporting events in association with user defined queries, constraints, and rules.

In an example, the services and outputs generated by the computer-controlled intelligent systems may enable spatiotemporal analysis of various game attributes and elements for exploring, learning, analyzing such sporting events and utilize analytics results to generate predictive models and predictive analytics for gaming strategy. These services and outputs may provide valuable insights and learnings that are otherwise not visible.

The methods and systems disclosed herein may employ delay-dependent computer vision and machine learning systems (or the intelligent computer-controlled systems) for providing delay-dependent services and outputs with respect to the occurrence of a sporting event. The services and outputs as discussed herein may be employed in different applications with varying time delays relative to the actual occurrence of the sporting event. For example, the actual event may occur at a time T1 and the content feeding or broadcasting may occur at a time T2 with a time delay of T2-T1. The time delay may be small such as of a few seconds so as the content is useful in a live commentary or augmentation of a live video. In such cases, the machine learning tools may for example utilize real-time services and outputs and benefit from the spatiotemporal features and attributes to generate game patterns and automatic validations during the event itself such as to highlight certain event aspects in the commentary and/or validate momentary sessions when there are confusions during the event for decision making. The time delay may be longer in certain situations such as for replays, post-event analysis, predictive modeling, and future strategies, and the like.

The methods and systems disclosed herein may support the provisioning of the services and outputs at various time delays by determining processing steps and their order of execution according to delay requirements. The system may be configured to operate such that the services and outputs may be obtained at arbitrary times with an increasing accuracy or time resolution or such that the system targets specific delay requirements as specified by users or defined in accordance with intended applications. For example, if in an application, computational resources are insufficient to process all frames originating from input devices such as cameras etc. at maximum accuracy at a video frame rate within a desired delay, then instead of processing the input video frames in sequential orders, processing may be ordered in such a way that at any time there is a uniform or approximately uniform distribution of processed frames. In some cases, processing decisions may also be influenced by other computational efficiency considerations for certain tasks that operate on video segments, such as an opportunity to reuse certain computations across successive frames in tracking algorithms. In some examples, processing techniques such as inference and interpolation over processed frames may be used to provide a tracking output whose accuracy and time resolution improves with delay as more frames are processed. If a target delay is specified, each component of processing application (such as background subtraction, detection of various elements) may be assigned an execution time budget within which to compute its output, such that the specified delay is met by a combination of the components. In some examples, the specified time delays may also consider video qualities needed at sending destinations so as to ensure that enough computation resources are allocated for appropriate resolutions and transmission rates at the destinations during broadcasting of the content. In certain cases, a normal resolution may be sufficient while in other cases a higher resolution may be needed. In various embodiments, the intelligent computer-controlled systems may be capable of defining appropriate resolutions, data transmission rates, and computation resources allocation in view of the delay requirements.

The methods and systems disclosed herein may facilitate enabling calibration of a moving camera or any other image recognition device via tracking of moving points in a sporting event. Existing techniques for finding unknown camera calibration parameters from captured images or videos of sporting events rely on identifying a set of known locations, such as intersections of lines on the court or field. In accordance with such techniques, calibrating the moving camera as it changes its position or zooms across frames is challenging since there may be only a few of such known locations in the frames. The methods and systems disclosed herein may enable finding the calibration parameters of the moving or operator-controlled camera by using positions of moving points located by an associated tracking system. In an example, these positions may represent locations and spatial coordinates of a player's or a referee's head or hand or legs in the sporting event which may be identified by the tracking system. The tracking system may be an optical tracking system or a chip-based tracking system, which may be configured to determine positions of locations tags. In various examples, several other types of camera control, calibration, and position determining systems may be employed along with the tracking systems. For example, a fixed spotting camera may be used to capture a view and a moving camera contained within the tracking system may be used to capture the positions of the moving points in the frames. The moving camera may be configured to perform several functions such as zoom, tilt, pan, and the like. The tracking system may be configured to perform calibration and identification of the positions based on a tracking algorithm that may execute pre-defined instructions to compute relevant information necessary to drive the tracking system across the frames.

The methods and systems disclosed herein may facilitate enabling pre-processing of images from calibrated cameras to improve object detection and recognition. The methods and systems disclosed herein may enable providing for accurate detection and recognition of humans, such as players or referees, and objects, such as a ball, a game clock, jersey numbers and the like with better performance and lower complexity. In embodiments, the tasks of object detection and recognition may be performed on the basis of knowledge of known calibration parameters of the cameras in the tracking system and known properties of the objects being detected such as their size, orientation, or positions etc. For example, perspectives and distortions introduced by the cameras can be undone by applying a transformation such that the objects being detected may have a consistent scale and orientation in transformed images. The transformed images may be used as inputs to detection and recognition algorithms by image processing devices so as to enable faster and more accurate object detection and recognition performance with lower complexity as compared to performing object detection and recognition directly on original images. In such cases, an output generated by the image processing devices may be used as inputs, along with other inputs described herein, to enable or refine the various machine learning and algorithmic capabilities described throughout this disclosure. In some embodiments, machine learning capabilities may be introduced to build improved processing utilizing machine learning tools as discussed above in the document.

In many sports, analyzing and understanding offensive and defensive tactics associated with plays is relevant and interesting to coaches, players and fans. A play may include a sequence of actions taken by one or more players in certain locations on the playing field/court. A simple example of a play in basketball could include the following actions: a screener sets a pick at the top of the key, the pick is taken, the screener rolls to the basket, receives a pass and shoots.

A number of sports leagues, including at least the National Basketball Association, National Football League and English Premier League, have tracking systems that produce spatiotemporal coordinate sequences for the players and ball in each game. Using this spatiotemporal data to analyze the tactics employed by different teams is of much interest to teams, fans and media. Using low-level spatiotemporal coordinate sequences directly for finding similar sequences does not perform well in identifying plays that are the most similar from a tactical standpoint. Therefore, while any two actions/events/plays may be determined to be spatiotemporally similar (through position and movement of players, for example); they may not be tactically similar. On the other hand, any two actions/events/plays may be tactically similar while being spatiotemporally distinct. For example, some players might be more important to the play than others, so only looking at player positions assumes that only the positions of players are important, rather than which player is at which position. In an example, a play may have a substantively different tactical value when a position of two of the players is transposed, resulting in a more important player being positioned to take an action, such as a scoring chance. In addition, using spatiotemporal coordinate sequences directly is not robust to changes in the speed of portions of the play. Certain actions in the play can vary in duration, having a substantive impact on the tactical importance of the play; for example the ball handler might wait a long time before passing, or might pass immediately. Changes in duration of actions in a play may indicate tactical significance. Therefore, only matching on player locations over time would not robustly handle changes in how quickly the play develops.

Methods, systems, algorithms, and techniques for determining if a target sequence is tactically similar to another sequence, such as a sequence in a library of tactically relevant sequences are described herein.

In embodiments, a degree of tactical similarity for sequences, each of which may be a time-limited portion (e.g., a contiguous time-limited portion) of a video, and the spatiotemporal similarity of which may optionally be inconclusive (or merely non-existent), may be determined through multi-level tactical relevance and similarity computing that may include recursively sharing information between levels, such as using information output(s) from one level to derive data for use as input to another level. Optionally, the output of one level may be applied as input to another level. In embodiments, a first level of tactical relevance and similarity computing for determining tactical similarity may include determining spatiotemporal similarity of a plurality of sequences and assigning one or more labels that indicate at least one of a sequence representing a game chance (optionally referred to herein as "chance" or "chances") and a sequence representing a tactical chance, and a second level of tactical relevance and similarity computing that determines tactical similarity of a plurality of sequences, which may optionally include the plurality of sequences to which the first level of tactical relevance and similarity computing was applied. The second level of tactical relevance and similarity computing may rely on labels of sequences indicating tactical chances as a factor in determining sequence-to-sequence tactical meaning. In embodiments, tactically similar sequences may include similar tactical chance labels but may be differentiated by at least one of movement of elements in the sequence, time duration of movement of elements in the sequence, total time duration of a sequence, relative position of elements at one or more times in the sequence, and the like.

In embodiments, a chance, such as a game chance, a tactical chance and the like may indicate a type of chance or may indicate the presence of a chance in a given sequence. A label, such as a game chance label or a tactical label may be syntactically similar (e.g., a given chance label may convey one or more of a game chance meaning and a tactical chance meaning), depending on the processing function (e.g., a tactical relevance and similarity computing algorithm and the like) to which such a label is applied. In embodiments, a chance label "pick" in an exemplary basketball application, may be useful for determining spatiotemporally similar sequences (or portions thereof, such as actions, events and the like) and may facilitate classifying such similar sequences as a "pick". Whereas a sequence label with the same value "pick" may indicate a sequence that has a tactical meaning to a function, for example that seeks to match sequences from different sources that are tactically similar. Sequences, events, actions and the like so labeled may be deemed to have tactical significance when determining tactical similarity of sequences as described herein. While the label value "pick" is used herein and may convey a meaning that is commonly understood in the sport of basketball, for example, any computer readable label value for a game chance and/or tactical sequence may be used without limitation.

A labelled sequence may be referred to herein as an event, a chance, a play, drive, and the like. Likewise, any portion of a sequence, such as an action, subset, grouping of sequences, movement, arrangement of players in a frame of video, and the like, similarly may be referred to herein as an event. Therefore, the methods and systems for developing event understanding and the like described herein, including without limitation semantic understanding and the like may be applied when determining a degree of tactical similarity as described herein, such as when applying either or both of the first and second levels of tactical relevance and similarity computing and the like. The methods and systems for developing an understanding of an event may be used to facilitate labeling sequences and the like as game chances, tactical chances, and the like. In embodiments, tactical relevance and similarity computing may include machine learning, (e.g., supervised and/or unsupervised) and the like.

In embodiments, tactically similar sequences, as determined by at least one of the first and second level of tactical relevance and similarity computing described herein, may include spatiotemporally similar time-limited portions, such as an initial position of a portion of elements in the sequence, a final position of a portion of elements in the sequence, movement of at least one of the elements in an action portion (e.g., a time-limited subset) of the sequence, timing of or between multiple action portions (e.g., total duration of the multiple action portions, duration of time between an ending time of a first action portion and a beginning, ending, or other time there between of a second action portion, etcetera), and the like.

As described herein, determining tactical similarity may include among other things, a first level of tactical relevance and similarity computing, and may include the methods and systems for developing an understanding of events and the like described herein. Such first level of tactical relevance and similarity computing may include, without limitation, processing video sequences, audio sequences, element tracking data (e.g., XYZ data from a chip-based or other system that tracks activity of detectable elements in a video sequence, as described herein), play-by-play (PBP) data and the like with spatiotemporal pattern detection, tactical relevance and similarity computing algorithms, and optionally machine learning to produce a first level of understanding of events (e.g., actions, sequences and the like) of a video sequence. Such an exemplary first level of tactical relevance and similarity computing may include detecting events, labelling such events with labels that convey at least a portion of the understanding, such as a semantic label and the like. Event labels may include, without limitation terms that are found in an ontology of an activity occurring in the video, such as a basketball game and the like. Such event labels may be applied to convey a range of meanings or context about a given event, such as if the event occurs within a play, if the event exhibits tactical qualities and the like.

In embodiments, a first level of tactical relevance and similarity computing may facilitate determining events and/or actions that may occur during or between sequences, such as tactically relevant sequences and the like. Such actions may include events that occur between plays of a game, such as when a game clock is stopped, when a shot attempt is made, when the ball is deflected by an opponent, when the ball is in a certain region of the court, when the ball is out of bounds, when activity occurs out of the field of play (out of bounds), and the like. By facilitating detection of such actions, a sequence may be partitioned into one or more subsequences that may contain tactically relevant plays, called tactical chances.

In embodiments, the second level of tactical relevance and similarity computing may facilitate determining a degree of tactical effect of a sequence or portion thereof through use of algorithms that incorporate aspects of events, including aspects derived from the first level of tactical relevance and similarity computing, such as an understanding of an event, sequence, action and the like. An understanding derived from a first level of tactical relevance and similarity computing may be indicated by, among other things, a label associated with the event resulting from the first level of tactical relevance and similarity computing. While a second level of tactical relevance and similarity computing may include spatiotemporal aspects, such as timing of action(s) of events, timing of actions and/or events within sequences, and timing of sequences, spatiotemporal pattern detection and similarity function, and the like, use of results of the first level of tactical relevance and similarity computing facilitates rapid determination of tactical relevance, which leads to faster determination of tactically similar sequences, even when such similar sequences are not spatiotemporally similar. Further, a result of a first level of tactical relevance and similarity computing may comprise information descriptive of a tactical sequence. While the tactical sequence may occur anywhere in the field of play, a location of an event in the sequence in that field of play may be useful in determining to which, if any other, sequence a target sequence is tactically similar. Therefore, a result of performing the first level of tactical relevance and similarity computing on a target sequence may be combined with a field of play location of events in the sequence to facilitate second level tactical relevance and similarity processing, such as for determining which tactical sequence is most similar to a sequence that is detectable in the target sequence. A location of an event may be a specific point, such as an (x, y) coordinate pair; a gross level designation on the field of play, such as right wing, fore court or back court and the like. A location characteristic of the sequence may be determined by the first level of tactical relevance and similarity computing based on, for example a portion of the field of play over which events in the sequence takes place, such as left court, in the paint, along the sideline, and the like. A location characteristic may be a relative location characteristic, such as a location relative to a source of a video sequence, such as a location of a camera that is used to capture the sequence. Camera location, disposition, orientation, pose (whether preconfigured, dynamically determined, variable, such as a camera on a moveable gantry, etc.) and the like may similarly be used as a basis, at least in part, of a tactical similarity location characteristic. A location characteristic that may be used, such as location-event data described elsewhere herein may be characterized as relative to a feature in the video sequence, such as a ball, a field demarcation, another player, a referee and the like. Additionally, location-event data may include location-in-time, such as time measured by a game clock, a shot clock, a video timer, a real-time clock and the like. In an example, a sequence may be determined to be tactically relevant if it occurs within the last two minutes of game time, or if it occurs after a change in lead for a scored game, or if it occurs relative to another event in the video, such as a timeout, a player substitution, and the like. In this way, location may be a location-in-time of a sequence of video frames. Location may further be determined as a two-dimensional or three-dimensional location within one or more video frames.

In embodiments, tactical relevance may be characterized by aspects other than those detectable by and useful in determining spatiotemporal patterns and the like. In embodiments, tactical relevance and/or similarity may be based at least in part on an event's contribution (or portion thereof) to a future outcome, such as a scoring try, defensive success and the like in activities, such as sporting events. Developing an understanding of one or more events, such as its contribution to an outcome, may provide insight into the tactical relevance and/or similarity thereof. In embodiments, use of an understanding of one or more events developed through the methods and systems described herein may lead to improved detection of sequences with tactical relevance and/or similarity. Algorithms that facilitate such use of a developed understanding may include, among other techniques, search techniques that are optimized for distinguishing tactical similarity or differences among events. In embodiments, an algorithm that learns tactically significant characteristics of an event through, for example, applying many examples of tactically similar events to a machine learning process may be used to look for these characteristics in one or more target sequences. Based on which tactical characteristics are found in the target sequences, a search may be conducted of a library of sequences for sequences with similar characteristics. This search may be based on labels as described elsewhere herein and may include, among other things use of a VP tree with a distance metric based at least in part on the tactical characteristics and the like.

Some outcomes, such as a scoring shot in hockey and the like, may be based on opportunity that has no short-term basis in a tactical approach, such as when a defensive player falls, leaving the player with the puck one-on-one with the goalie. However, tactically relevant sequences may produce opportunities for outcomes and therefore may contribute to formation of such opportunities. Spatiotemporal analysis (e.g., pattern recognition, machine learning, and the like) alone leaves out potentially important information about events, actions, sequences and the like, such as participants in an event, results of an event, and the like. Likewise, while two sequences may appear to be spatiotemporally distinct, they may have a high degree of tactical similarity. Therefore, applying an outcome of a first level of tactical relevance and similarity computing, that may among other things, facilitate determining a degree of tactical relevance for chance events supports detection of tactically similar sequences that may not be, per conventional approaches, spatiotemporally similar. This may be due, in part to pre-event activity, variation in event activity and the like that results in a target sequence and a reference sequence being determined to be spatiotemporally distinct. This can occur when, for example, players, represented as elements in the sequence suitable for spatiotemporal analysis, appear to be substantively farther apart or moving substantively faster/slower and/or taking substantively longer for making a movement in comparable sequences.

Spatiotemporally, two such sequences may be deemed to not be similar within some constraints that may be user defined and the like. Thus, spatiotemporal analysis itself may not be sufficient to determine when a sequence of actions amounts to something tactical in nature. Additionally, unless there is some use of an understanding of a sequence, such as a degree of tactical relevance of a sequence, or portion thereof, finding a tactically similar sequence is not readily achievable from spatiotemporal analysis alone. In embodiments, a nearly identical alignment and time-based change of players in two sequences with (substantively) different distances between the players may be tactically similar, but not spatiotemporally similar. Likewise, two sequences that are spatiotemporally similar (or even identical) may not be tactically relevant, such as when a basketball team first positions itself around the opponent's basket after a rebound.

Further by determining characteristics of tactically significant sequences, such as through unsupervised and/or supervised machine learning and the like may lead to understanding an underlying nature of some types of tactical activity in sports. With this deeper understanding, that may be informed by but separate from spatiotemporal pattern detection and analysis, sequences from other sports may be processed with the methods and systems described herein to determine at least a type of tactical sequence present. In a simple example, while the majority of rules and context of the games of professional basketball for men and women and college basketball for men and women may be the same, scoring may be significantly different. However, tactics used may be similar, even if the outcomes (scores) may not be comparable. Therefore, characteristics of sequences that are tactical in college basketball for men may be used, optionally with some contextual adaptation, to determine tactically similar sequences in a professional basketball game for women.

In embodiments, determining tactical similarity of a sequence to at least one other sequence may include determining tactical similarity of a plurality of actions/events (e.g., subsets of a sequence and the like) that make up at least a portion of a sequence. A sequence may include one or more actions that are determined to have some degree of tactical relevance, but the sequence itself may be unclassified as far as its tactical relevance. In embodiments, a sequence may have no classification but may comprise one or more tactically-classified events/actions that may facilitate determining, using one or more similarity detection algorithms described herein, tactical similarity of the sequence with at least one other sequence. In embodiments, two sequences may be deemed to be tactically similar based on a similarity of tactical chance label(s) associated with actions/events that occur within the sequences. In this way, longer or shorter sequences can be found and analyzed for tactical similarity. In embodiments, a target sequence that includes all action from a point of rebound to a point of scoring may be matched tactically with a shorter sequence that covers, for example a pick-and-roll sequence.

In embodiments, elements that are visible in a sequence, such as players in a game, may contribute to at least one of tactical relevance and tactical similarity. In embodiments, each element that is uniquely distinguishable for a given activity, such as data structures representing players in a portion of a basketball game and the like (e.g., by various means described elsewhere herein) may include attributes and/or features that facilitate determining a tactical similarity thereof. In an example, a third-string player may be ranked low on a tactical relevance scale, whereas a star starting player may be ranked (e.g., his representative data structure may be weighted) high on a tactical relevance scale. Therefore, analysis, such as the first level and/or the second level of tactical relevance and similarity computing for determining tactical similarity and the like as described herein, may include as an input to tactical relevance determination element tactical rank/weighting. In embodiments, a sequence that includes a small percentage (e.g., less than 50%, less than 20%, less than 10% and the like) players that are ranked tactically relevant may be deemed to have little tactical relevance. Whereas, a sequence that includes at least one player with a high tactical relevance ranking may be deemed to have a greater likelihood of being tactically relevant. Such information may be captured and associated with sequences, actions, events and the like and made available to one or more of a first level and a second level of tactical relevance and similarity computing for determining tactical relevance and/or similarity of a sequence. In this way, while spatiotemporal aspects of two sequences may substantively differ, sequences with tactically significant elements may be tactically relevant and/or similar. Similarly, players found to be closely involved in a tactical action/event/sequence may be marked as tactically relevant. Therefore, characteristics that may be learned from sequences that are deemed to be tactically significant (e.g., during machine learning training and the like), may include aspects of the elements in the sequence (e.g., players, score, game time, shot/play clock value, game score, count of fouls for players, injury reports, and the like).

In embodiments, determining a relevance of an element in a sequence to an outcome resulting from a tactically relevant event may be based on information about the relevant activity. Here are just a few examples to provide context for some factors that may determine tactical relevance of a player to an event. In basketball, players of a team in possession of a ball that remain behind a center court demarcation during an offensive drive may be deemed to be tactically non-relevant. In hockey, players that take up defensive positions during their team's offensive drive may be deemed to be tactically non-relevant. In football, a player positioned and active on a portion of the field that is well away from movement of the football may be deemed to be tactically non-relevant. These examples appear to be simple to determine using spatiotemporal analysis and the like. Other examples may be more difficult and therefore may require further analysis of a tactically relevant action/event/sequence. Returning to an example of basketball as the activity captured in the sequence, a player who boxes out a potential rebounder may be deemed to be tactically significant even though me may not make any attempt at the ball, whereas a player who attempts rebounding the ball may be deemed to be tactically insignificant if his role in action(s) (or the actions themselves) leading up to the rebound attempt were deemed non-tactical. There are many such examples and the methods of tactical relevance and similarity computing may be adapted (manually or through use of automated techniques) for differing sports (basketball, hockey, football, soccer, rugby, lacrosse, and the like), differing levels of experience (e.g., high school, college, professional) and differing rules (regulation time versus overtime) and the like. In embodiments, player involvement in an action, tactically relevant or otherwise, may be based on a range of factors that may be automatically detected through the various video, audio, XYZ, and PBP analysis methods and systems described herein. Player involvement factors may include proximity to a game ball, visibility of the player with in a field of view that is smaller than the entire field of play, proximity to a feature in the sequence (e.g., a backboard, a basket, an end line, a free throw line, a 3-point line, and the like), contact with the game ball, contact with other players, such as opponents (recall the boxing out rebound example) and the like. In embodiments, players that are determined, such as through spatiotemporal analysis algorithms and the like, to be located similarly in a target sequence to tactically relevant players in a reference sequence, may be deemed tactically relevant in the target sequence. Such designation may be used by either the first or second level of tactical relevance and similarity computing to facilitate determining at least one of tactical relevance and/or tactically similarity of a sequence. Tactically similar sequences may have various characteristics in common, such as similar chance labels (also referred to herein as semantic labels and the like), similar player tactical relevance weighting, similar timing of movement of elements or timing of aggregated actions/events and the like, players positioned and moving similarly in the two sequences independent of their absolute position(s) and independent of the overall timing, and the like.

In embodiments, determining tactically similar sequences may be based at least in part of information accessible in a tactical similarity support data structure, which may be populated with one or more results of the first and/or the second level of tactical relevance and similarity computing. Among other things, the tactical similarity support data structure may be used to provide rapid similarity comparison of sequences. By facilitating rapid assessment of similarity of sequence attributes, such as tactical chance labels, spatiotemporal analysis results, sequence-element tactical relevance weighting and the like with known sequence attributes, sequences that are similar to an arbitrary sequence processed through one or more of the levels of tactical relevance and similarity computing may be determined. Such a data structure may capture any portion of information associated with an event/action/sequence and the like, including without limitation one or more chance labels, element (e.g., player and the like) tactical relevance rate/rank/weighting, metadata associated with an element, team, player, a game score, game clock (e.g., time left in a game period and the like), activity clock (e.g., shot clock in basketball and the like), location of game (e.g., home or away), participation status of one or more players (e.g., injury data, foul status, and the like), statistics associated with a success/failure of a given tactical sequence (e.g., a previously successful offensive tactical sequence may have a high failure rate in a given game due to an adjustment by the opposing team, and the like), and many others that may be understood by one knowledgeable in the art.

In embodiments, one or more pieces of information in the tactical similarity support data structure may be used to determine a tactical distance metric that may be calculated by a tactical similarity algorithm, such as one or more of the levels of tactical relevance and similarity computing. A tactical distance metric may be based on a plurality of pieces or dimensions of information, thereby representing a plurality of dimensions of potential tactical relevance and/or similarity. One such embodiment of a tactical similarity support data structure may include a Vantage Point (VP) Tree that may be adapted to facilitate access to historical sequences through use of a distance metric that may reflect tactical distance/similarity for a plurality of dimensions. When an input query, such as one or more tactical chance labels, spatiotemporal analysis data, player tactical metadata, and the like as described herein without limitation is submitted to a VP Tree adapted for a given activity type, an output of such an exemplary tactical similarity support data structure may be an indication of one or more historical sequences that may be tactically similar to a sequence represented by the input query. The VP Tree query response may alternatively indicate a type of sequence that may have tactical similarity and the like.

In embodiments, adapting a tactical similarity support data structure, such as a VP Tree may include use of expected alignment distance techniques, such as, for example, techniques associated with Deep ExpeCted Alignment DistancE (DECADE) algorithms and the like. In embodiments, DECADE may be applied to an optimization or tuning operation that may facilitate tuning a heuristic definition for similarity of sequences, such as sequences that are of different durations. Such tuning may produce a distance metric that satisfies the triangle inequality for any three sequences.

In embodiments, a tactical similarity support data structure may also facilitate ordering sequences that are determined to be tactically similar to a target sequence. As an example, a sequence that is logically closer to the target sequence (e.g., high compliance of aspects of the sequence that appear on in a tactical distance metric with a tactical distance metric of the target sequence) may be ordered above sequences with less compliance. Ordering of sequences determined to be tactically similar may be adapted based on a range of ordering factors, some of which are described above and include factors, such as time of game, shot clock, player participation status and the like. In embodiments, ordering of sequences may be based on changes in weighting of elements that contribute to a distance metric, so that a sequence search query function may, based on a given adapted weighting produce a different order of or even different sequences based thereon. In an example, a tactical similarity support data structure may reply on a distance metric that includes presence of a specific player for a given type of tactical event. However, such a factor might not be suitable to be applied universally to determining tactical relevance since the player only appears on a specific team. Therefore, sequence queries that rely on the specific player will produce different results for sequences that include the player and those that do not. However, by adapting the sequence similarity criteria to include a player tactical similarity, sequences that do not include the player but include another player with similar tactical features may be ordered above sequences that do not.

In embodiments, a distance metric may be defined/determined as a distance between two given sequences that are represented as an average, over a number of random alignments of the two sequences, of the distance between the two sequences in each alignment, where the distance between two aligned sequences is a suitable function (e.g., based on the Gaussian kernel and the like) of the distance between the locations of players involved in aligned portions of sequences (e.g., events) that are substantially similar or that match in event type, and the number of matching and nonmatching event types in the alignment.

The methods and systems of tactical relevance and similarity computing may facilitate determining, from a set of existing sequences, which one(s) of the existing sequences are tactically similar to a target sequence provided thereto. These methods and systems may facilitate the determining independent of any indication of a category of such sequences. The methods and systems may facilitate the determining without first determining a category of a target sequence, such as a type of tactical event and the like.

Figure 53:
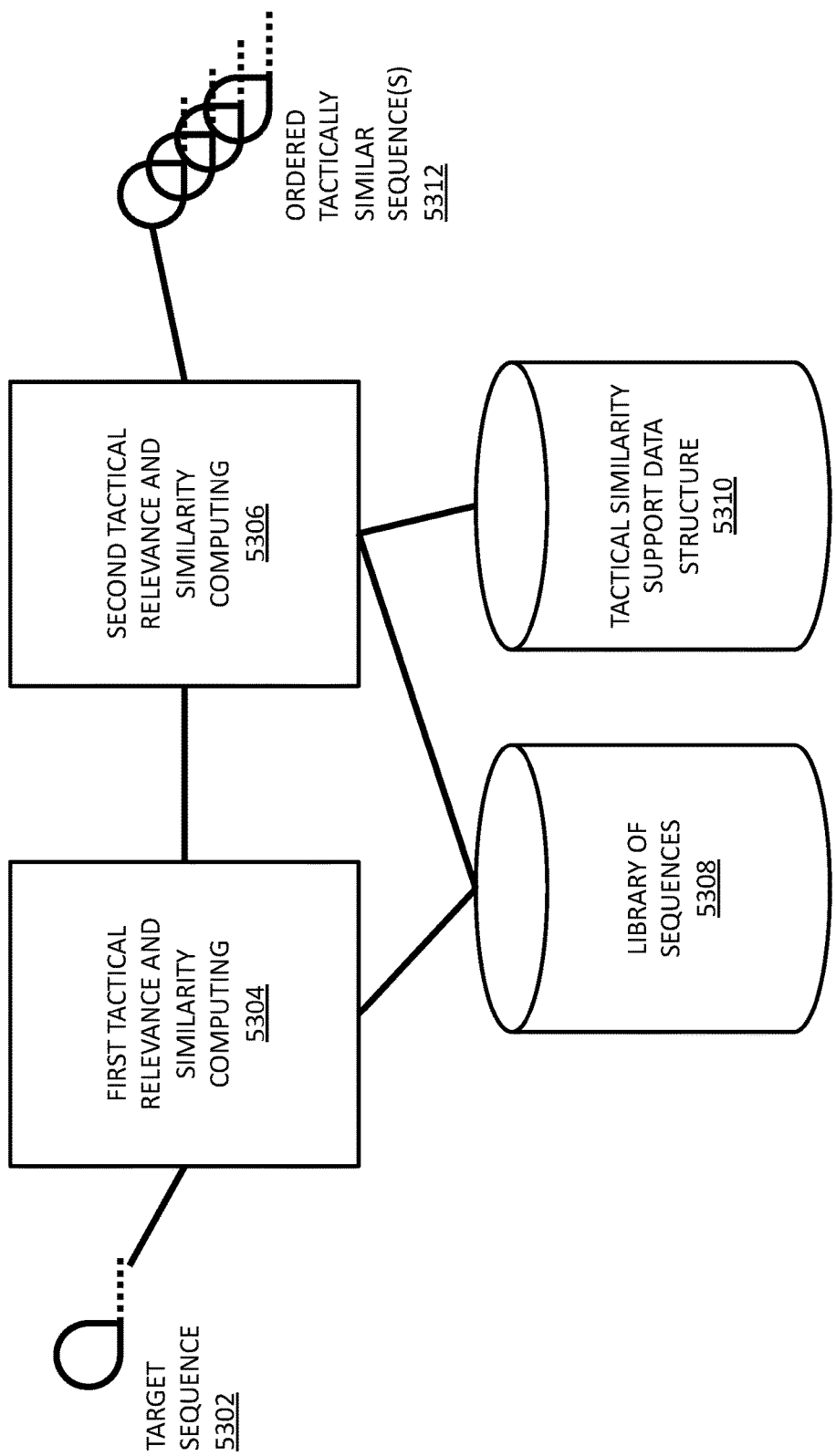
FIG. 53 depicts a diagram of a system for tactical relevance and similarity computation of video sequences.

Referring to FIG. 53, that depicts a diagram of a system for tactical relevance and similarity computation of video sequences, an ordered set of sequences 5312 that are tactically similar to a target sequence 5302 may be retrieved. A target sequence 5302 may be input to a first tactical relevance and similarity computing circuit 5304 that may process the target sequence 5302 to determine portions of the target sequence 5302 that comprises location-event data for one or more events, such as one or more semantic events as described and referenced herein. Additionally, each location-event may be determined to be part of a play, part of a chance, an event, a chance demarcation, and the like.

A result of computing on the target sequence 5302 by the first tactical relevance and similarity computing circuit 5304 may be delivered to a second tactical relevance and similarity. computing circuit 5306. Functions performed for determining at least one of tactical relevance and tactical similarity by the second tactical relevance and similarity computing circuit 5306 may be based on information not available to but produced by the first tactical relevance and similarity computing circuit 5304, such as processing a tactical chance label for a portion of the sequence and the like. The second tactical relevance and similarity computing circuit 5306 may store a result in a library of sequences 5308. Additionally the second tactical relevance and similarity computing circuit 5306 may access and/or operate a tactical similarity support data structure 5310 (e.g., a flat file, a structured file, a hierarchical file, a database, a VP Tree and the like) to, among other things, facilitate determining tactical similarity of the target sequence 5312 with at least one other sequence, such as a sequence from the library of sequences 5308 based on a tactical similarity distance metric and the like.

Figure 54:
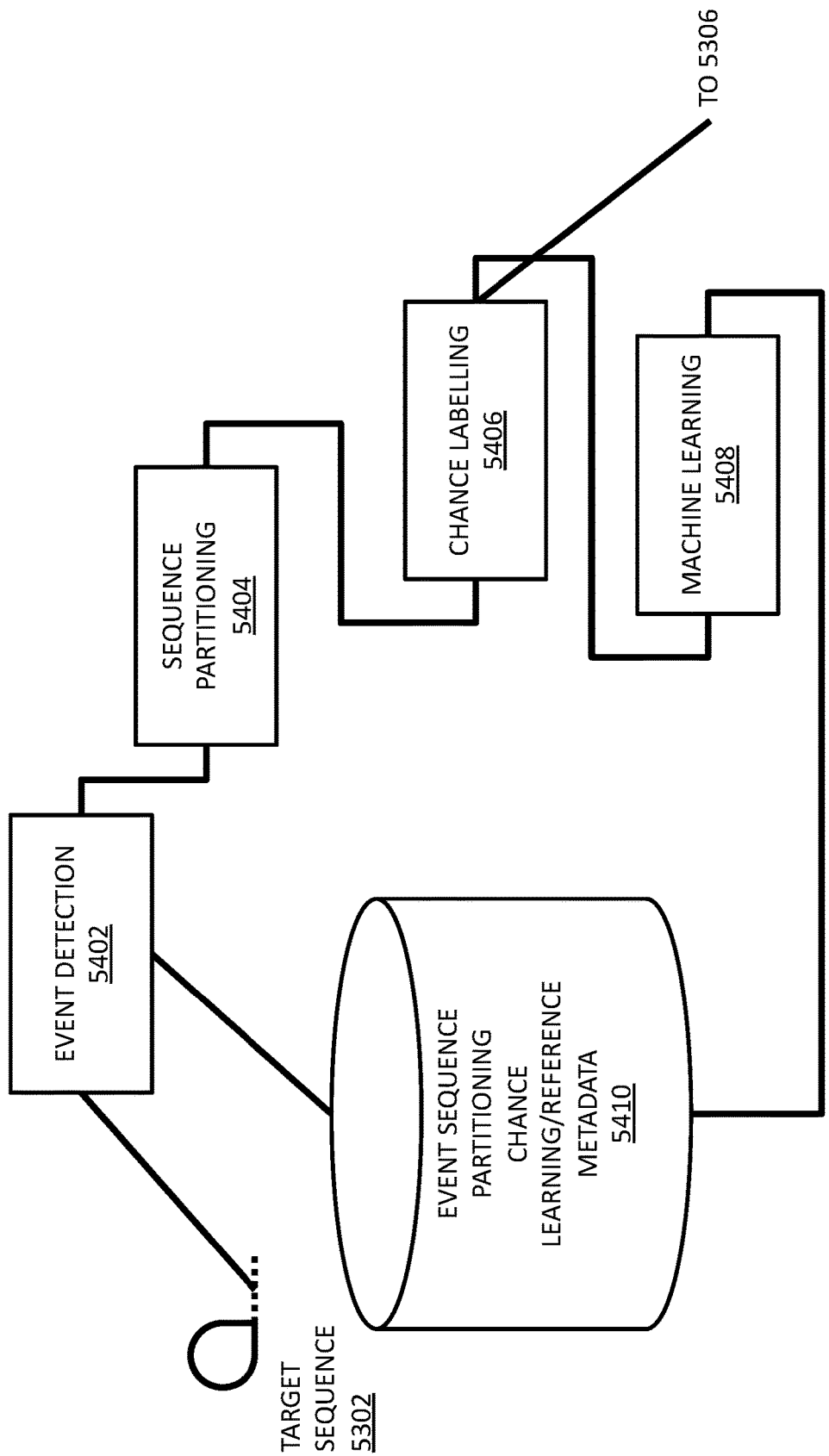
FIG. 54 depicts a diagram of a first level of tactical relevance and similarity computation.

Referring to FIG. 54 that depicts a diagram of a first level of tactical relevance and similarity computation, a target sequence 5302 may be processed to determine at least one of a chance label therefore. In embodiments, a target sequence 5302 may be processed by an event detection circuit 5402 that may reference a data set of information that facilitates detection of an event, a sequence, partitioning thereof, a play, a chance, and the like that may be found or used to process the target sequence 5302. Event detection by event detection circuit 5402 may be followed by sequence partitioning circuit 5404 that may determine location-event data that indicates a point in time within a sequence for partitioning the sequence into one or more chances as described herein. A result of partitioning the target sequence 5302 with the sequence partitioning circuit 5404 may be used by a chance labelling circuit 5406 to facilitate adding semantic-like labels to one or more portions of a sequence, such as to one or more actions, events and the like detectable through processing the target sequence 5302. The result of event detection, partitioning, and labelling may be forwarded onto a second tactical relevance and similarity computation circuit 5306. The circuits 5402, 5404 and 5406 may use machine learning methods and systems, some of which are described herein for developing an understanding of an event in a video sequence.

Figure 55:
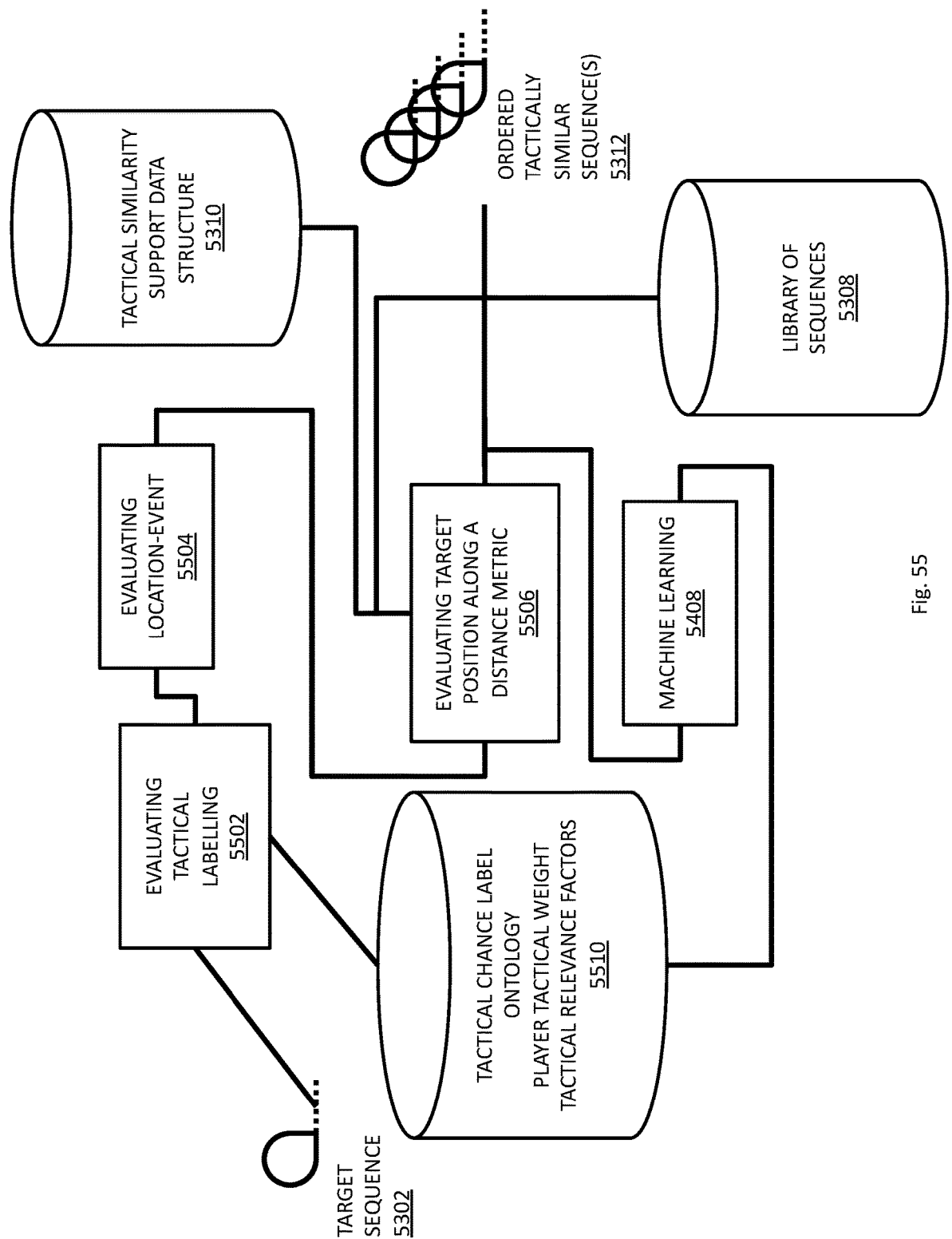
FIG. 55 depicts a diagram of a second level of tactical relevance and similarity computation.

Referring to FIG. 55, that depicts a diagram of a second level of tactical relevance and similarity computation, a target sequence 5302 may be further processed based on, among other things, results of processing the target sequence 5302 with the first tactical relevance and similarity computing circuit 5304, such as one or more semantic labels that may convey an understanding of the target sequence 5302 as tactically relevant and the like. The target sequence 5302 may be processed by a circuit for evaluating tactical labelling 5502 that may capture tactical label meaning and develop a further understanding thereof using a reference data set 5510 that includes tactical chance label ontologies, player tactical weighting factors and the like, and other tactical similarity factors.

In addition to evaluating tactical labelling, the target sequence 5302 may be processed with a location-event evaluation circuit 5504 that may factor into a determination of tactical similarity aspects of spatiotemporal analysis and the like, such as determining if locations of players in the target sequence 5302 are comparable to a location of players (e.g., tactically significant players) in one or more reference sequences that may be sourced from, among other places, a library of sequences 5308.

Additional processing of the target sequence 5302, based at least in part on result of evaluating tactical labelling 5502 and evaluating location-event data 5504 may be performed by distance metric determination and positioning circuit 5506 that may, among other things, determine a position for the target sequence 5302 within the distance metric. This evaluation may be multi-dimensional due to the distance metric capturing tactical similarity from a plurality of perspectives, wherein each perspective may contribute a distinct dimension to the metric. This evaluation circuit 5506 may reference the tactical similarity support data structure 5310 and/or the library of sequences 5308 to facilitate identifying one or more reference sequences (e.g., from the library of sequences 5308) that are tactically similar to the target reference 5302. Such a circuit 5506 may produce an ordered set of one or more tactically similar sequences 5312.

A result of operation of at least the distance metric evaluating circuit 5506 (although results of any other circuit operated to facilitate tactical relevance and/or similarity) may be processed through a feedback loop that may optionally include machine learning to, for example enhance the second tactical relevance and similarity computing circuit 5306, details of which are depicted in this FIG. 55, such as through use of machine learning methods and systems, some of which are described herein for developing an understanding of an event in a video sequence and the like.

Referring to FIG. 56, which depicts a flow diagram of embodiments of methods and systems for determining tactical relevance of a sequence, a target sequence 5302 may be processed through computing circuits that reference tactical relevance and similarity data sets to produce an ordered set of at least one tactically similar sequences. The target sequence 5302 may be processed by applying first tactical relevance and similarity computing algorithms 5604 that may determine one or more aspects of the target sequence 5302, such as a correlation with a chance, events, actions, and the like that may convey tactical significance of the sequence or portions thereof. Results from the first tactical relevance and similarity computing algorithms 5604 may be further processed, along with the target sequence 5302, a library of sequences 5308 and a tactical similarity support data structure 5310, by a second tactical relevance and similarity computing set of algorithms 5606 that may facilitate determining, among other things, one or more sequences in a library of sequences 5308 that are tactically similar thereto. A result of processing with the second tactical relevance and similarity computing algorithms may include an ordered set of tactically similar sequences 5312 and the like. Each of the first and second tactical relevance and similarity computing algorithms may include machine learning or other such automated results-improving functionality to facilitate enhancing results therefrom.

The methods and systems described herein may be deployed in part or in whole through a machine that executes computer software, program codes, and/or instructions on a processor. The processor may be part of a server, client, network infrastructure, mobile computing platform, stationary computing platform, or other computing platforms. A processor may be any kind of computational or processing device capable of executing program instructions, codes, binary instructions, and the like. The processor may be or include a signal processor, digital processor, embedded processor, microprocessor, or any variant such as a co-processor (math co-processor, graphic co-processor, communication co-processor and the like) and the like that may directly or indirectly facilitate execution of program code or program instructions stored thereon. In addition, the processor may enable the execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions, and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, Internet server, intranet server and other variants such as secondary server, host server, distributed server, and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, and the like. Additionally, this coupling and/or connection may facilitate remote execution of program across the network. The networking of some or all of these devices may facilitate parallel processing of a program or method at one or more location without deviating from the scope. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, Internet client, intranet client and other variants such as secondary client, host client, distributed client, and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers, and the like. Additionally, this coupling and/or connection may facilitate remote execution of program across the network. The networking of some or all of these devices may facilitate parallel processing of a program or method at one or more location without deviating from the scope. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM, and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications networks. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers, and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it may be appreciated that the various steps identified and described above may be varied and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It may further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the methods and systems described herein have been disclosed in connection with certain preferred embodiments shown and described in detail, various modifications and improvements thereon may become readily apparent to those skilled in the art. Accordingly, the spirit and scope of the methods and systems described herein are not to be limited by the foregoing examples but is to be understood in the broadest sense allowable by law.

All documents referenced herein are hereby incorporated by reference in their entirety as if they were fully set forth herein.

What is claimed is:

1. A method comprising:
    receiving a first video feed, capturing a first filmed occurrence, the first video feed comprising a sequence of video frames captured by a camera, wherein the first video feed is a video feed that is consumable by a client device;
    detecting at least one game chance sequence from the sequence of video frames based on spatiotemporal analysis that identifies game chance boundary events;
    determining at least one semantic label and associated location data of at least one tactically relevant event in the at least one game chance sequence;
    concatenating the at least one semantic label and the associated location data as a first labeled tactical sequence; and
    identifying from a library of stored game chance sequences at least one stored game chance sequence that is similar to the at least one game chance sequence from the first video feed based on a tactical similarity of a stored labeled tactical sequence of the at least one stored game chance sequence with the first labeled tactical sequence.

2. The method of claim 1, wherein the tactical similarity is further based on similarity of a semantic label for the stored labeled tactical sequence and the associated location data with the at least one semantic label and the associated location data of the first labeled tactical sequence.

3. The method of claim 1, wherein a spatiotemporal pattern analysis of the at least one game chance sequence from the sequence of video frames and of the at least one stored game chance sequence indicates a substantive difference in spatiotemporal patterns therein.

4. The method of claim 1, wherein identifying the game chance boundary events includes detecting actions that occur between labeled tactical sequences.

5. The method of claim 4, wherein a game chance boundary event includes at least one of a game dock stoppage, a scoring attempt, a scoring deflection, an event occurring in a region of a field of play, or an event occurring outside of a field of play.

6. The method of claim 1, wherein the game change boundary events facilitate partitioning the first video feed into one or more labeled tactical subsequences.

7. The method of claim 1, wherein the tactical similarity of two sequences comprises each of the two sequences occurring proximal to a common location.

8. The method of claim 1, wherein a location characteristic of a first sequence that is determined by a first level of tactical relevance and similarity computing informs a second level of tactical relevance and similarity computing performing tactical similarity comparison of the first sequence with at least one other sequence.

9. The method of claim 1, wherein the tactical similarity of two sequences is responsive to outcomes of the two sequences.

10. The method of claim 9, wherein the two sequences that produce different outcomes are not tactically similar.

11. The method of claim 1, wherein the tactical similarity is determined by use of a Vantage Point (VP) tree algorithm that applies a distance metric based at least in part on one or more tactical characteristics of the first labeled tactical sequence and of the stored labeled tactical sequence.

12. The method of claim 1, wherein the tactical similarity is determined by use of multi-dimensional distance metric that is based on a plurality of tactical characteristics of the first labeled tactical sequence and of the stored labeled tactical sequence.

13. The method of claim 1, wherein the tactical similarity is determined by application of distance metric values for a plurality of tactical sequence characteristics via a Vantage Point (VP) tree algorithm.

14. The method of claim 13, wherein the plurality of tactical sequence characteristics includes a player identity characteristic.

15. A method comprising:
- receiving a first video feed capturing a first filmed occurrence, the first video feed comprising a sequence of video frames captured by a camera, wherein the first video feed is a video feed that is consumable by a client device;
- processing the captured first video feed with a first tactical relevance and similarity computing circuit, wherein the first tactical relevance and similarity computing circuit determines, during processing, portions of the video feed that comprise location-event data for one or more semantic events;
- accessing with a second tactical relevance and similarity computing circuit a tactical similarity support data structure; and
- determining similarity of the one or more semantic events with tactical video sequences in a library of video sequences by determining for a plurality of tactical similarity characteristic types accessed in the tactical similarity support data structure a concurrence of instances of each of the plurality of tactical similarity characteristic types associated with at least one semantic event of the one or more semantic events and corresponding instances of tactical similarity characteristics associated with the tactical video sequences in the library of video sequences.

16. The method of claim 15, wherein the location-event data indicates at least one of a play, a part of a chance, an event, or a chance demarcation.

\* \* \* \* \*

UNITED STATES PATENT AND TRADEMARK OFFICE
CERTIFICATE OF CORRECTION

| | |
|---|---|
| PATENT NO. | : 11,113,535 B2 |
| APPLICATION NO. | : 16/678520 |
| DATED | : September 7, 2021 |
| INVENTOR(S) | : Vivek Jayaram et al. |

It is certified that error appears in the above-identified patent and that said Letters Patent is hereby corrected as shown below:

In the Claims

Column 96, Line 29, in Claim 5, delete "dock" and insert -- clock --, therefor.

Column 96, Line 33, in Claim 6, delete "change" and insert -- chance --, therefor.

Signed and Sealed this
Thirty-first Day of January, 2023

Katherine Kelly Vidal
*Director of the United States Patent and Trademark Office*